(12) United States Patent
Akcasu

(10) Patent No.: US 11,224,675 B1
(45) Date of Patent: Jan. 18, 2022

(54) ULTRAVIOLET-C (UV-C) MERCURY DISCHARGE TUBE IRRADIATED FORCED AIRFLOW FACE SHIELD

(71) Applicant: Akcasu Airborne Virus Protection Systems, Inc., Austin, TX (US)

(72) Inventor: Osman Ersed Akcasu, San Diego, CA (US)

(73) Assignee: Akcasu Airborne Virus Protection Systems, Inc., Austin, TX (US)

( * ) Notice: Subject to any disclaimer, the term of this patent is extended or adjusted under 35 U.S.C. 154(b) by 0 days.

(21) Appl. No.: 17/353,518

(22) Filed: Jun. 21, 2021

(51) Int. Cl.
*A61L 9/20* (2006.01)

(52) U.S. Cl.
CPC ............ *A61L 9/20* (2013.01); *A61L 2209/12* (2013.01)

(58) Field of Classification Search
USPC ........................................................ 250/435
See application file for complete search history.

(56) References Cited

U.S. PATENT DOCUMENTS

| | | | |
|---|---|---|---|
| 7,658,891 B1 | 2/2010 | Barnes | |
| 8,925,548 B2 | 1/2015 | Pierro et al. | |
| 9,700,642 B2 | 7/2017 | Neister | |
| 9,927,097 B2 | 3/2018 | Lalicki et al. | |
| 9,974,873 B2 | 5/2018 | Cole | |
| 10,245,340 B2 * | 4/2019 | Stibich | A61L 2/24 |
| 10,369,379 B2 * | 8/2019 | Randers-Pehrson | A61N 5/0601 |
| 10,376,604 B2 | 8/2019 | Romo et al. | |
| 10,426,852 B2 | 10/2019 | Dobrinsky et al. | |
| 10,786,691 B2 | 9/2020 | Kao et al. | |
| 10,850,000 B2 | 12/2020 | Lewis | |
| 10,866,484 B2 * | 12/2020 | Lin | G02B 26/101 |
| 10,987,440 B1 | 4/2021 | Sood et al. | |
| 11,007,292 B1 | 5/2021 | Grenon et al. | |
| 2006/0283786 A1 * | 12/2006 | Harbers | B01J 19/123 210/85 |
| 2009/0004047 A1 | 1/2009 | Hunter et al. | |
| 2011/0011400 A1 | 1/2011 | Gentner et al. | |
| 2012/0315184 A1 * | 12/2012 | Clark | A61L 9/20 422/4 |
| 2015/0336809 A1 | 11/2015 | Leonard et al. | |
| 2018/0169279 A1 | 6/2018 | Randers-Pehrson | |

FOREIGN PATENT DOCUMENTS

CA 2545168 10/2007

OTHER PUBLICATIONS

W. Kowalski, "Ultraviolet Germicidal Irradiation Handbook", Springer-Verlag Berlin Heidelberg 2009, pp. 160-210. (Year: 2009).*
M. Buonanno et al., "Far-UVC light (222 nm) efficiently and safely inactivates airborne human coronaviruses", Scientific Reports, Nature Portfolio, Jun. 2020, pp. 1-6. (Year: 2020).*

* cited by examiner

*Primary Examiner* — Phillip A Johnston
(74) *Attorney, Agent, or Firm* — Law Office of Gerald Maliszewski; Gerald Maliszewski

(57) ABSTRACT

Disclosed herein is a forced irradiated air shielding mechanism that is an effective protective measure against Covid-19. The UV-C irradiated forced air flow face shield described herein is compact enough to be camouflaged under a cap. In this work it is mathematically proven that the described UV-C irradiated forced air flow face shield by itself provides more effective protection against the Covid-19 or similar airborne pathogens. The shield can be enabled using a mercury discharge tube or light emitting diode (LED) irradiator. Computational fluid dynamics is presented to show that positive irradiated air pressure ensures that the only air breathed by the wearer is irradiated. Also presented is a face shield testing apparatus.

30 Claims, 62 Drawing Sheets

REFLECTIVE AND NON-TRANSPARENT
WALLS TO UV-C RADIATION
POLISHED AI OR POREX VIRTEX

ULTRAVIOLET-C (UV-C) MERCURY DISCHARGE TUBE IRRADIATED FORCED AIRFLOW FACE SHIELD

BACKGROUND OF THE INVENTION

1. Field of the Invention

This invention generally relates to respirator masks and, more particularly, to a face shield using irradiated forced air to provide protection against airborne disease.

2. Description of the Related Art 1.0. Introduction

Respiratory infections can be transmitted through droplets of different sizes. When the droplet particles are greater than 5-10 microns rpm) m diameter they are referred to as respiratory droplets, and when then are less than 5 pan in diameter, they are referred to as droplet nuclei or microdroplas. According to current evidence, the COVID-19 virus, which is also referred to as the SARS CoV-2 virus, is primarily transmitted between people through respiratory droplets and contact routes. Droplet transmission occurs when a person is in close contact (within 1 meter (m)) with someone who has respiratory symptoms (e.g., coughing or sneezing) and is therefore at risk of having their mucosae (mouth and nose) or conjunctiva (eyes) exposed to potentially infective respiratory droplets. Transmission may also occur through fomites in the immediate environment around the infected person. Therefore, transmission of the COVID-19 virus can occur by direct contact with infected people and indirect contact with surfaces in the immediate environment or with objects used by the infected person. The latter having a much less probability in spreading COVID-19.

Airborne transmission is different from droplet transmission as it refers to the presence of microbes or viruses within droplet nuclei or microdroplets, which are generally considered to be particles less than 5 μm in diameter. These microbes or viruses can remain in the air ha: long periods of time, more than 15-20 minutes, and can be transmitted to others over distances greater than 1 meter.

Viruses are between 20-400 nanometers (nm) in size and Covid-19, commonly known as the "Coronavirus", is 80-160 nm in diameter with 9-12 nm S-Protein spikes giving it a solar corona appearance. There are 7 types of known Coronaviruses which infect humans. The official name of the virus Severe Acute Respiratory Syndrome, or SARS CoV-2, is the cause of the pandemic referred to as the Covid-19 outbreak in 2019. It is the successor of the SARS CoV-1 virus that caused the 2002-2004 SARS outbreak. Another type of Coronavirus is the Middle East Respiratory Syndrome (MERS), commonly known as the Camel Flue of 2012 or MERS-CoV virus, was first identified in the Arabian Peninsula in 2012 with later outbreaks in Korea in 2015 and Saudi Arabia in 2018 and 2020, with mortality rates as high as 35%. The Coronavirus family of viruses is very small, but there are even smaller viruses, such as West Nile (WNV) and the Dengue (DENV) viruses, which are on the order of 50 nm in diameter. There are even smaller Adeno associated viruses and which are 20 nm in diameter. These are very small dimension by any means and some examples of things smaller can add some perspective to these dimensions. For example, Oxygen ($O_2$) and Nitrogen molecules ($N_2$), making 99% of air that we breathe, are 0.299 nm and 0.305 nm respectively, 260-530 times smaller than coronavirus. Sodium (Na) and Potassium (K) atoms, a key for proper functioning of our nervous system, are 0.157 nm and 0.203 nm, respectively. Water molecule is a V shaped molecule with a 105.95° angle between its legs and can fit in a sphere with a radius of 0.275 nm (2.75 Angstroms). A cell membrane is on the order of 7.5-10 nm, slightly larger than the S-Protein spikes of SARS CoV-2.

Similar in size to the Coronavirus (SARS CoV-2) are the particulate matter (PM) diameters of oil mist and cigarette smoke, which are on the order of 100 nm in size. There are many larger size examples, such as the *bacillus* bacteria, a very common rod shape bacteria which is 500 nm long, with an inhalable particle size of 1 μm, and one of the smallest human cells, the red blood cell, a disc shape cell with a diameter of 6-8 μm and a thickness of 2-2.5 μm at its edges, thinning down to 0.8-1 μm at the center. The *Tuberculosis bacillus* is rod shape bacterium 2-4 μm in length and 200-500 nm in width. Some other PM which can be commonly found in air include mold spores and cinders in the 10 μm range. Human hair is 17-180 μm and industrial particles can be on the order of 1,000 μm.

It is also worthwhile to mention the size of some man-made objects. At the time of writing, semiconductor processing technologies in several places work with minimum geometries of 7 nm, and even as small as 4 nm, 20-40 times smaller than Coronavirus (SARS CoV-2), as used in almost every processor, memory or flash memory integrated circuits, or cell phone.

FIG. 1 is a diagram comparing various sized air pollutants with their conventional filtration methods (prior art). One way of avoiding the spread of any airborne disease like Covid-19 is by filtering the air that is breathed in, by letting the air in and straining the Covid-19 viruses out. There are many types of filtering techniques, as shown, that can be employed based on particulate size, going all the way from molecular size to dust.

Gas phase filters use chemical adsorption employing chemicals like Potassium Hydroxide (KOH), Potassium Iodure, Sodium Thiosulfate, Potassium Permanganate, or Activated Carbon, utilizing their extremely large surface area for their filtering function. As an example, 1 gram of activated carbon, due to its high degree of micro-porosity, has a surface area of 3,000 $m^2$ available for adsorption or surface chemical reactions. The main application of these filters is to filter gases like gas phase hydrocarbons ($C_xH_y$), chlorine ($Cl_2$), hydrogen sulfide ($H_2S$), silicon dioxide ($SO_2$), nitrous oxide ($NO_2$), hydrogen chloride (HCl), and mercury (Hg), which are much smaller in size than Coronavirus.

N95 mask and HEPA (High Efficiency Particulate Air) filters assert that they are capable of filtering 99.95% of the particulate matter in air down to 300 nm in size. HEPA filter technology was developed in 1940's during atomic bomb research to filter radioactive dust and hazardous materials from air. They are made by randomly aligned high density very thin fibers made of glass (silica, alumina, calcium oxide, boron oxide, magnesium oxide, sodium oxide, etc.) or synthetic materials. The HEPA filter four primary filtering mechanisms are known as diffusion, interception, inertial impaction, and electrostatic. To really understand the HEPA filter filtration function the "collection efficiency curve" must be checked, which gives the fractional collection efficiency vs. particulate matter (PM) size compared to the target PM dimension.

FIG. 2 is a diagram depicting a typical HEPA filter collection efficiency curve (prior art). Many of the HEPA filters in the market filter air with a 10-100 nm PM size at a better than 80% efficiency, where diffusion mechanism becomes the major filtering mechanism. For a PM size in the range of 100-1,000 nm, which covers the coronavirus size range (80-160 nm), the diffusion-interception filtration mechanism takes over, with a collection efficiency no better than 65%.

Recent studies show that water droplets injected into air by coughing or sneezing potentially have viruses in them and can be significant in the spread the coronavirus. These droplet sizes are roughly 0.1 to 1 micron in diameter and they can stay floating in air for up to 20 minutes, potentially infecting other people who breathe them in. Almost any filter in the market can block micro droplets that are 100 nm in diameter, but of concern is what happens to the virus after the water evaporates.

FIG. 3 is an N95 surgical mask (prior art). The simplest and cheapest form of filtering the air which we breathe can be done through a surgical mask made from nonwoven fabric using the melt blowing process. The physical microscopic structure of a surgical mask can be represented by very high-density thin fibers randomly oriented in a small thickness like in the HEPA filters. The air must pass through these randomly oriented fibers, rather than going in a straight path, in the process of going from one side of the surgical mask thickness to the other. In the process of air movement through the surgical mask the particulates in the air gets stuck between the randomly oriented fibers. The denser the fibers, the better the filtration that can performed for smaller size particulates in air. Similarly, the thicker the surgical mask or the larger the number of layers, even with the same random fiber density, the better the filtration performs. Surgical masks were originally designed to protect medical personnel from splashes or sprays of bodily fluids. They were intended to prevent infections in patients and treating personnel by catching bacteria shed in liquid droplets and aerosols from the wearer's mouth and nose. They were not designed to protect the wearer from breathing in airborne bacteria or viruses whose particles are smaller, but potentially they are effective protection because viruses are generally carried through in droplets and are in the filtering range of any properly wore surgical mask. Surgical masks in use in USA and European community must have a Bacterial Filtration Efficiency (BFE) of more than 95%, simulated with particles of size 3.0 µm. Their effectiveness against Coronavirus is a subject of heated debate. The consensus today is they are a must, and they are effective if used properly.

In general, people don't like to wear masks. There are several reasons discouraging people from wearing a mask and they can be listed as:

i) Masks make breathing difficult. Many health workers complain of headaches after wearing surgical masks for a long period of time. This is mainly due to rebreathing the exhaled air rich with carbon dioxide ($CO_2$), ii) Masks do not allow for eating or drinking, iii) Conversation through a mask can be difficult to understand and is tiring, iv) If glasses are worn, masks can cause the glasses to become fogged, which is a nuisance, v) Masks make recognition and non-verbal communication difficult. Seeing facial expressions during conversation is a part of the effective communication. Communication between people wearing masks is not as exciting and pleasant, vi) Masks degrade the personal appearance of a person, and it is not comfortable to have something covering the mouth and the nose for long periods of time, vii) Masks may be a difficult proposition for a claustrophobic person.

On the other hand, the scientific studies and the data show that wearing a mask is very important in bringing Covid-19 under control. The CDC director Dr. Robert Redfield, on Sep. 16, 2020, at a Senate Appropriations Committee Hearings on Covid-19 said, "(w)e have clear scientific evidence they work, and they are our best defense. I might even go so far as to say that this face mask is more guaranteed to protect me against Covid than when I take a Covid vaccine".

Technically any kind of mask will filter the air and reduce the number of pathogens inhaled. On the other hand, pandemics can be mathematically modeled with some observable parameters. The original work goes all the way back to 1927 in a series of mathematical papers published by Kermack and McKendrick [43]. This process involves solving a system of three coupled differential equations. One of the key parameters in the models relates to how fast one can infect another. The reduction in the number of pathogens inhaled by wearing a mask or having a face shield, or the reduction in airborne pathogens by any means reduces the chance of getting infected, and its contribution to the spread can be modeled using the SIR model (Susceptible-Infected-Removed).

From December of 2019 to $25^{th}$ of January 2021, just in nearly a year, the worldwide number of reported Covid-19 cases exceeded 99,814,781, with Covid-19 related deaths being 2,140,088. This amounts to a worldwide mortality rate of 2.144%. In the same period the number of Covid-19 cases in the United States was 25,702,125 with related number of deaths reaching 429,490, giving a 1.67% mortality rate. Tables 1.1 through 1.3 summarize the Covid-19 pandemic progressed through 14 countries to give an idea of the seriousness of the pandemic worldwide.

It is difficult to comprehend the significance of a number by itself. It is easier to comprehend the significance of a number if it can be compared to the numbers from other events. Table 1.4. lists the 12 deadliest events in US history, putting Covid-19 in the number two position, only ranking less than the Civil war which lasted for 4 years. In terms of the yearly toll on human life per year, Covid-19 is at least three times deadlier than the Civil War.

TABLE 1.1

Number of Covid49 Cases, deaths percentage of case/death ratio and population. Worldometers.info 20th of Oct. 2020.
https://www.worldometers.info/coronavirus/

| Country | Number of Cases | Number of Deaths | Case/death % | Population |
|---|---|---|---|---|
| USA | 8,459,041 | 225,241 | 2.26 | 331,589,937 |
| Brazil | 5,251,127 | 154,226 | 2.93 | 231,015,720 |
| India | 7,600,125 | 115,267 | 1.52 | 1,384,085,979 |

TABLE 1.1-continued

Number of Covid49 Cases, deaths percentage of case/death ratio and population. Worldometers.info 20th of Oct. 2020.
https://www.worldometers.info/coronavirus/

| Country | Number of Cases | Number of Deaths | Case/death % | Population |
|---|---|---|---|---|
| Russia | 1,431,635 | 24,635 | 1.72 | 145,953,533 |
| Italy | 423,578 | 36,616 | 8.64 | 60,434,663 |
| UK | 741,212 | 43,726 | 5.89 | 67,993,982 |
| Belgium | 230,480 | 10,443 | 4.53 | 11,604,914 |
| France | 910,277 | 33,623 | 3.69 | 65,317,424 |
| Spain | 1,015,795 | 33,992 | 3.34 | 46,760297 |
| Holland | 236,226 | 6,768 | 2.86 | 17,146,399 |
| Germany | 374,734 | 9,910 | 2.64 | 83,865285 |
| South Africa | 705,254 | 18,492 | 2.62 | 59,532,742 |
| Switzerland | 86,167 | 2,144 | 2.48 | 8,673,730 |
| China | 85,704 | 4,634 | 5.4 | 1,439,323776 |
| World | 40,720,262 | 1,124,213 | 2.76 | 7,819,802,200 |

TABLE 1.2

Number of Covid49 Cases, deaths percentage of case/death ratio and population. Worldometers.info 25th of Nov. 2020.
https://www.worldometers.info/coronavirus/

| Country | Number of Cases | Number of Deaths | Case/death % | Population |
|---|---|---|---|---|
| USA | 12,955,007 | 265,891 | 2.05 | 331,589,937 |
| Brazil | 6,121,449 | 170,179 | 2.78 | 231,015,720 |
| India | 9,222,216 | 134,743 | 1.46 | 1,384,085,979 |
| Russia | 2,138,828 | 37,031 | 1.73 | 145,953,533 |
| Italy | 1,455,022 | 51,306 | 3.53 | 60,434,663 |
| UK | 1,538,794 | 55,838 | 3.63 | 67,993,982 |
| Belgium | 561,803 | 15,938 | 2.83 | 11,604,914 |
| France | 2,153,815 | 50,237 | 3.69 | 65,317,424 |
| Spain | 1,614,126 | 50,237 | 3.11 | 46,760297 |
| Holland. | 493,744 | 9,035 | 1.83 | 17,146,399 |
| Germany | 964,909 | 15,007 | 1.56 | 83,865285 |
| South Africa | 772,252 | 21,083 | 2.73 | 59,532,742 |
| Switzerland | 304,593 | 4,308 | 1.41 | 8,673,730 |
| China | 86,469 | 4,634 | 5.36 | 1,439,323776 |
| World | 60,197,077 | 1,417,003 | 2.35 | 7,819,802,200 |

TABLE 1.3

Number of Covid49 Cases, deaths percentage of case/death ratio and population. Worldometers.info 25th of Jan. 2020.
https://www.worldometers.info/coronavirus/

| Country | Number of Cases | Number of Deaths | Case/death % | Population |
|---|---|---|---|---|
| USA | 25,702,125 | 429,490 | 1.67 | 331,589,937 |
| Brazil | 8,844,600 | 217,081 | 2.45 | 231,015,720 |
| India | 10,668,674 | 153,508 | 1.438 | 1,384,085,979 |
| Russia | 3,738,690 | 69,918 | 1.87 | 145,953,533 |
| Italy | 2,466,813 | 85,461 | 3.46 | 60,434,663 |
| UK | 3,647,463 | 97,939 | 2.685 | 67,993,982 |
| Belgium | 693,666 | 20,779 | 2.995 | 11,604,914 |
| France | 3,738,690 | 73,049 | 1.953 | 65,317,424 |
| Spain | 2,603,472 | 55,441 | 2.129 | 46,760297 |
| Netherlands | 948,933 | 13,540 | 1.426 | 17,146,399 |
| Germany | 2,147,740 | 52,777 | 2.457 | 83,865285 |
| South Africa | 1,412,986 | 40,874 | 2.892 | 59,532,742 |
| Switzerland | 509,279 | 9,065 | 1.779 | 8,673,730 |
| China | 89,115 | 4,635 | 5.20 | 1,439,323,776 |
| World | 99,814,781 | 2,140,088 | 2.144 | 7,819,802,200 |

TABLE 1.4

Some of the major deadly events in US History

| Event | Years | Deaths |
|---|---|---|
| Revolutionary War | 1775-1783 | 4,435 |
| Civil War | 1861-1865 | 620,000 |
| Pearl Harbor | 1941 | 2,403 |
| World War I | 1917-1918 | 116,516 |
| Spanish Hue | 1918-1919 | 675,000 |
| World War IT | 1941-1945 | 405,399 |
| Korean War | 1950-1953 | 36,574 |
| Vietnam War | 1964-1973 | 58,220 |
| September 11 | 2001 | 2,977 |
| 2009 Swine Flue | 2009 | 12,469 |
| H1N1 + H3N2 Flue | 2017-2018 | 61,000 |
| Flu Season of 2018-2019 | 2018-2019 | 34,200 |

The accuracy of the numbers in the Tables above will always be questionable, but even if we take a 2% fatality number, a 10% reduction in the number of cases in the USA would result in 84,590 fewer cases and 22,000 fewer deaths, which shows the significance of any work in disease preventive.

In the course of the Covid-19 pandemic social media was full of false claims regarding the reasons of the pandemic and remedies to it, and included many unfounded non-scientific statements, speculations, and conspiracy theories lacking any supporting proof. Math is the best platform to prove anything and this fact is worded beautifully by Henri Poincaré (1854-1912), without any doubt one of the best mathematicians ever lived as, "(m)athematicians prove, others, argue."

It would be advantageous if a mechanism existed that was more effective in the prevention and spread of airborne pathogens than the conventional HEPA or N95 mask. It would be advantageous if the effectiveness of the new mechanism could be mathematically proved.

SUMMARY OF THE INVENTION

Disclosed herein is a forced irradiated air shielding mechanism that is a more effective protective measure against Covid-19 and other known virus or bacteriological pathogens, as compared to N95 and surgical masks. The shielding mechanism is designed to address the public's objections to wearing conventional masks. Even a small percentage of the public wearing this "safe face shield" will reduce the number of cases and automatically reduce the number of lives lost. One of the key objectives is to mathematically prove the effectiveness of the face shield, rather than simply listing advantageous attributes.

It is known that ultraviolet-C (UV-C), which is the light in the wavelength band of 100-280 nanometers nm, if applied in correct dosages, deactivates the Coronavirus. The UV-C irradiated forced air flow face shield described herein can be camouflaged under a cap, such as a baseball hat or a golf cap. In this work it is mathematically proven that the described UV-C irradiated forced air flow face shield by itself provides a more effective protection against the Covid-19 or similar airborne pathogens, as compared to even most properly worn surgical masks.

The optional cap forms a decorative portion of face shield and may act to encourage the use of the face shield, as opposed to the opposition by many against using any type of protective gear, such as seen with the one-time use surgical masks used in many countries since the pandemic started. In one aspect, a Plexiglas or the polycarbonate transparent face shield is placed at the edge of the sunshade of the cap, leaving just enough space to hold the sunshade with fingertips, e.g., not greater than 1 centimeter (cm). The shield-to-face spacing may be made larger than standard face shields, providing better comfort and minimizing claustrophobic effects. The shield may cover the face with openings at the bottom under the chin and at the left and right sides of the face. A powered air intake and the miniature UV-C irradiator reactor may be placed at the back of the head or cap, not visible from the front. The UV-C air irradiator reactor may be made comparable in size to a smartphone, much smaller than the Powered Air Purifying Respirator (PAPR) side or back packs. UV-C irradiated air may be taken through tubing, in one aspect under a cap, and blown to the area under the cap's sunshield (brim) and discharged downward parallel to the face. Using complex computational fluid dynamics, it can be shown that if the volumetric air flow rate is kept at least three times higher than the volumetric respiratory air-in and ex-flow rate of the persons wearing the shield, there is a positive air pressure maintained in the volume defined by the face and the shield as compared to the outside air. This condition helps ensure that the only air that the wearer of the shield breathes is the filtered and UV-C irradiated air supplied by the UV-C irradiator reactor. The air breathing volumetric rate of an adult is $1.567 \times 10^{-3}$ cubic meters per second (m$^3$/sec) at 1 Bar pressure during exercise. Therefore, in one aspect the filter and the fan supply $(1.567 \times 10^{-3}) \times 3 \cong 4.7 \times 10^{-3}$ m$^3$/sec of air at 1 Bar. In another aspect the UV-C irradiation reactor provides a minimum of 8,000 microwatt-seconds per square cm $\mu$W·sec/cm$^2$ dosage for the complete deactivation of Covid-19 type pathogens at this air flow rate. The fan and all electronics may be powered by a 2500 milliamp-hour (mA·hour) smartphone battery, which may provide on the order of 14 hours of uninterrupted operation designed for the longest intercontinental flight with one full charge.

Support for the effectiveness of the above-described face shield is provided by a mathematical modeling methodology that is presented in detail. Novel fluid dynamics analysis for a given airstream volumetric flow rate in the UV-C reactor is combined with the methodology of calculating UV-C irradiation integral in this air flow volume, for any given UV-C source, which is the basis for the computer aided design software called Ultra-Violet Germicidal Irradiation Designer, or "UVGI Designer". UVGI Designer is a key factor in the design of the safe protection face shield, named the "Safe Face Shield", as described herein. This is a more comfortable and optionally more stylish face shield alternative that provides protection at the same levels as a PAPR with an airtight hood as used in hospitals and special biologic research labs.

The application area of the UVGI Designer is not limited to safe face shield design. It can be used for any UVGI system design needed for large disinfection applications in public transport, planes, trains, busses, or any public transport or crowded places like hotels, shopping malls, and schools by only specifying the desired volumetric air flow rate, deactivation dose needed, and the UV-C source information.

Another feature described herein is an apparatus that quantitatively measures the effectiveness of any filter, surgical mask, or face shield. Using the methodology explained below, various masks, filters, or face shields can be quantitatively compared using more objectively than simple "fit tests".

Accordingly, a personal airflow irradiation system is provided with a face shield having a back surface, a gas cavity formed between the back surface and a human face, a gas input aperture, and a gas exhaust aperture. A fan has an input interface to accept an ambient gas at an ambient pressure and an output interface to supply the ambient gas at a positive pressure. A UV-C irradiator reactor has an input interface to accept the ambient gas and an output interface to supply irradiated gas at a positive pressure. The irradiator reactor may incorporate either a discharge lamp (e.g., mercury) or a UV-C light emitting diode (LED). Typically, the system includes a battery to power the fan and the irradiator reactor.

The gas exhaust aperture emits irradiated gas at a positive pressure greater than the ambient gas pressure. For example, if the fan accepts air at an ambient pressure of 1 Bar, the gas exhaust aperture may emit irradiated air at a positive pressure of greater than about $4.7 \times 10^{-3}$ cubic meters per second (m$^3$/sec). Typically, the irradiator reactor supplies radiation at a dose of at least 8,000 $\mu$W·sec/cm$^2$, capable of deactivating many known pathogens in the air.

In different aspects of the system there exists a radiation dosage control mechanism for adjusting the output interfaces of the fan and the irradiator reactor. The system may also include a particulate filter and/or an electrostatic filter to accept the ambient gas and supply a filtered ambient gas.

To secure the electrical components and shield, the system may include a headband configured to fit around the circumference of a human head with a brim connected between the face shield and a forward section of the headband. The gas input aperture may be formed in or under the brim, with a tubing network to supply the irradiated gas to the gas input aperture. In this case, the fan and the irradiator reactor may be attached to a rear section of the headband. Optionally, a hat may cover the headband.

Also provided is a method for designing a radial UV-C mercury discharge tube airflow irradiator. The method may be enabled as a sequence of processor execution instructions stored in a non-transitory memory. The method selects irradiation reactor unit chamber and mercury discharge tube cross-sectional dimensions. An irradiation integral ($P_I$) is calculated and a deactivation dosage $D_{kill}$ is determined. A maximum airflow velocity ($V_{MAX}$) is calculated in response to the irradiation integral, cross-sectional dimensions, and deactivation dosage. Finally, the irradiation reactor unit chamber length (L) is selected. For example, selecting the irradiation reactor unit chamber and mercury discharge tube cross-sectional dimensions may include the steps of;

selecting a mercury discharge tube radius ($R_1$);

selecting an irradiation reactor unit cylinder interior radius ($R_2$), where the irradiation reactor unit cylinder interior surface is reflective; and, wherein $R_1 \leq r \leq R_2$.

Using a surface irradiation ($I_1$), point irradiation ($I_2$), or view factor model, irradiation is calculated, the number of discharge tube filaments to be modeled is selected, and irradiance is calculated as a function of mercury discharge tube length. From that, the irradiation integral is calculated, followed by the peak airflow velocity.

Also provided is a method for designing a radial UV-C light emitting diode (LED) airflow irradiator. The method selects a plurality of cross-sections ($r_t$) for an airflow guide segment, and selects a plurality of mesh points ($z_i$) along the length of the airflow guide segment. Irradiation calculations ($I(z,r_t)$) are performed for each mesh point, and for each mesh point irradiation calculation, an irradiation integral ($P_I(z,r_t)$) is calculated for each radius. After determining a deactivation dosage ($D_{kill}$), the number of airflow guide segments (n) required to achieve ($D_{kill}$) is calculated at volumetric airflow rate (Q) for each radius. In response to determining the number of airflow guide segments, the total airflow guide length (L) is calculated.

Also provided is a personal airflow irradiation testing apparatus. The apparatus includes a test chamber having an input orifice to accept a first gas and a reservoir having an output orifice to supply a second gas. A mannequin headpiece is located in the test chamber, having an input orifice to accept a mixed gas comprising the first and second gases. A respirator has an input connected to the mannequin headpiece input orifice to apply an oscillating pressure to the mixed gas, and an output to supply the mixed gas. A chemical analyzer has an input connected to the respirator output to measure the contents of the mixed gas and supply a measurement of the first gas content in the mixed gas, as compared to the second gas content. A unit under test (UUT) personal airflow irradiation device is mounted on the mannequin headpiece, with a gas input aperture connected to the reservoir output orifice to accept the second gas, and with a gas exhaust aperture exposed to the test chamber.

Additional details of the above-described systems and methods are provided below.

BRIEF DESCRIPTION OF THE DRAWINGS

FIG. 52 illustrates $I_{1,1FIL}$ and $I_{1,2FIL}$ irradiation integrals as given in (7.16) and (7.17) along the radial direction at z=0, ±a, and ±2a.

FIG. 54 illustrates $I_{2,1FIL}$ and $I_{2,2FIL}$ irradiation integrals as given in (7.26) and (7.27) along the radial direction at z=0, ±a, and ±2a.

Figure 1:
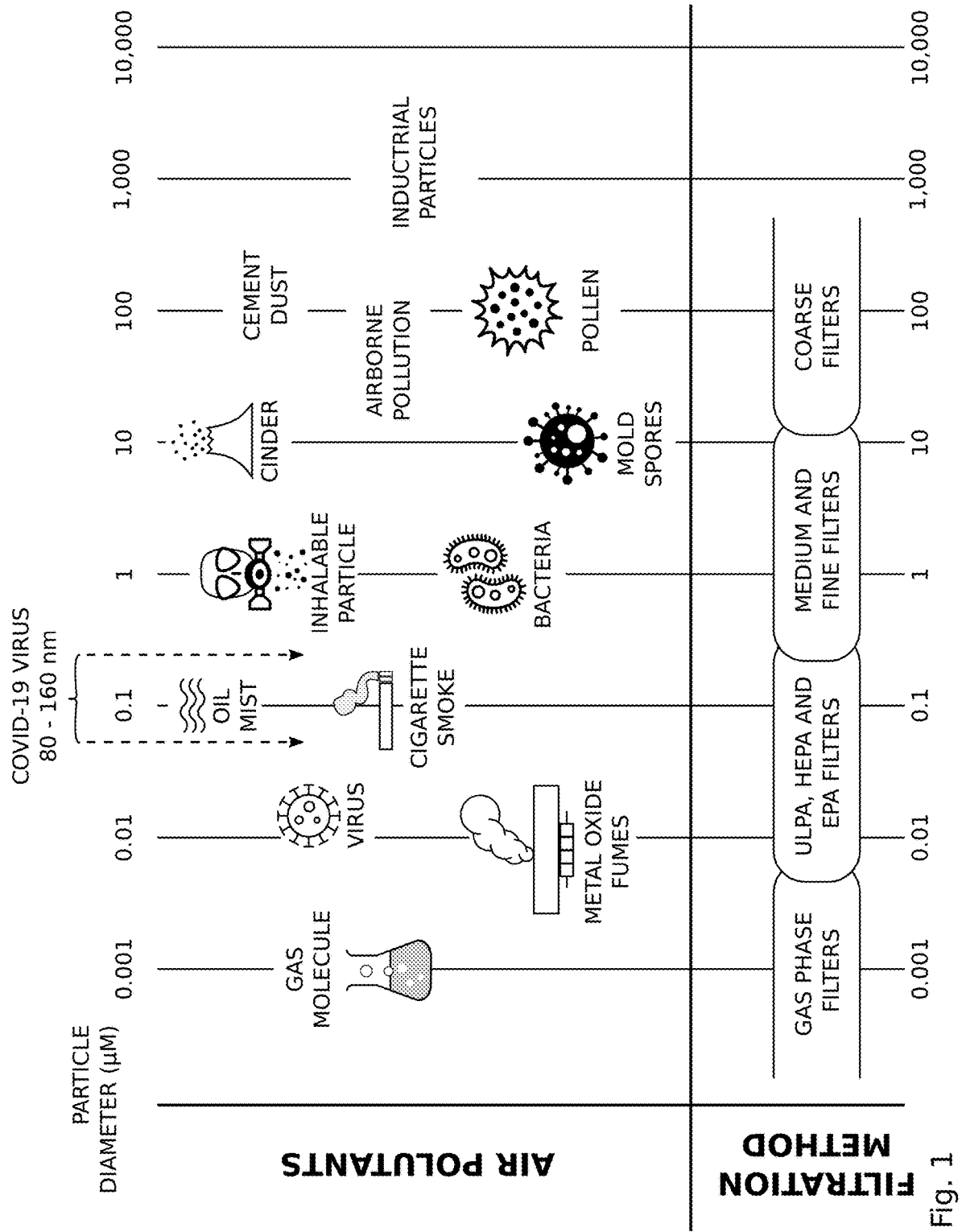
FIG. 1 is a diagram comparing various sized air pollutants with their conventional filtration methods (prior art).
Figure 2:
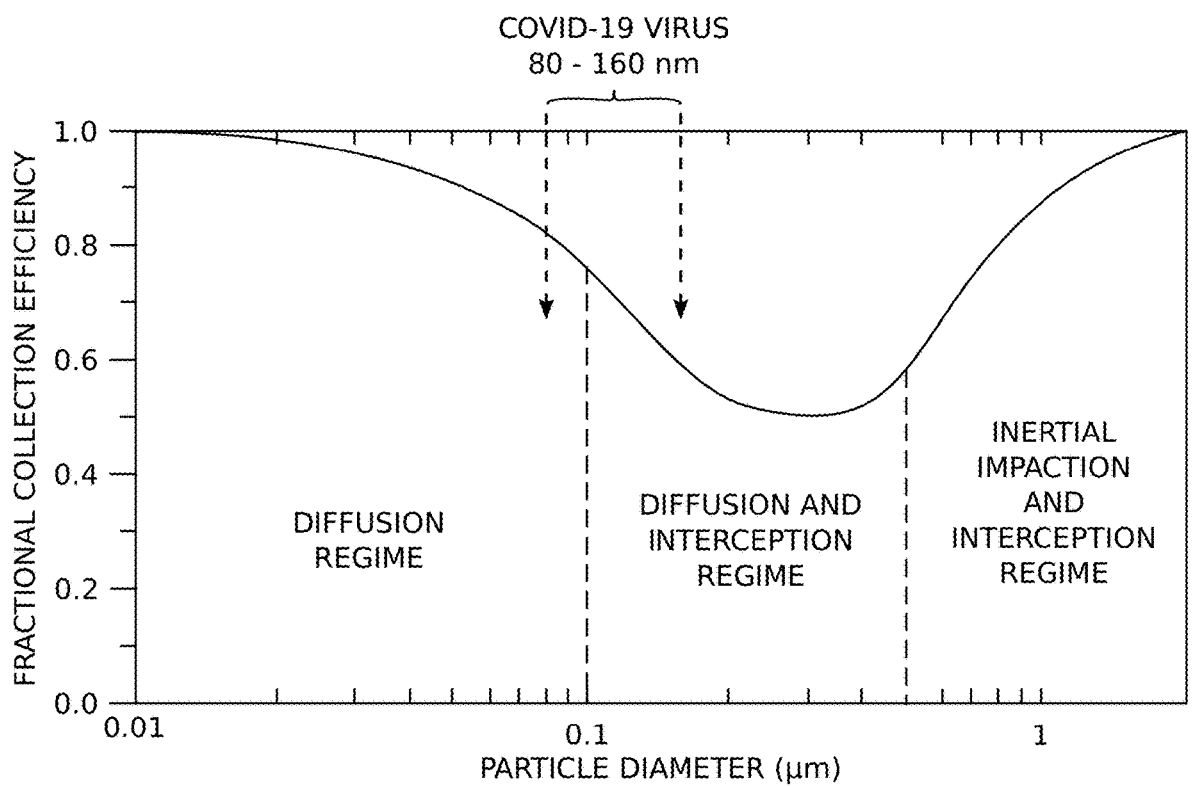
FIG. 2 is a diagram depicting a typical HEPA filter collection efficiency curve (prior art).
Figure 3:
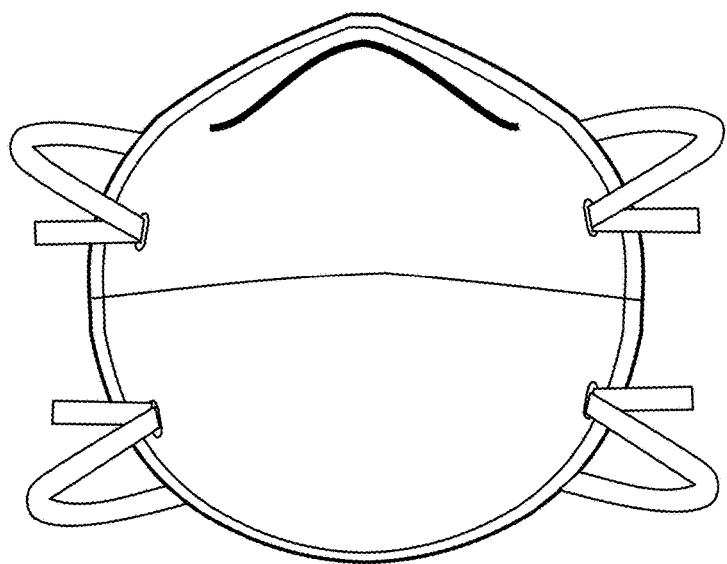
FIG. 3 is an N95 surgical mask (prior art).

Overview of the Fluid Dynamics Background Related to the Safe Face Shield

To formulate the UVGI calculations of air flowing through a tube with a given volumetric flow rate one needs to be able to generate the velocity profile of the airflow in the tube for given geometrical parameters of the tube and the physical parameters of the air flowing in the tube. This can be formulated qualitatively by applying the Poiseuille Law and rudimentary one-page fluid mechanics. Poiseuille Law was experimentally derived independently by Jean Leonard Marie Poiseuille in 1838 and Gotthilf Heinrich Ludwig Hagen and published by Poiseuille in 1840-41 and 1846. Its theoretical derivation was given later by Stokes in 1845 [44].

For incompressible fluids flowing through a pipe under laminar flow condition the Poiseuille-Hagen Law is formulated as, $$Q = \frac{\pi r^4 \Delta p}{8 \mu L} \tag{2.1}$$

Where Q, r, L, $\mu$, and $\Delta p$ are the volumetric flow rate in $m^3/sec$, radius of the pipe in m, the length of the pipe in m, dynamic viscosity in Newton·sec/$m^2$ of the fluid, and the pressure difference in Newton/$m^2$ between the distance L in m along the pipe. Pressure has many units like Standard Atmosphere, mmHg, Pascal, Bar, Torr, and PSI, which can be confusing for many. SI unit of pressure is Pascal [Pa] is equal to Newton/$m^2$. Standard atmosphere is equal to 101,325 Pa, 760 mmHg, 0.98692 Bar, and 760 Torr. In addition to these large number of units of pressure units in physics and engineering, in medicine or human physiology the height of water column is also used as a pressure unit expressed as $cmH_2O$. As an example, 1 $cmH_2O$=98.1 Pa or 0.735 mmHg.

Of interest is the pressure differential between the lungs and ambient during inhale and exhale actions. During inhaling this pressure differential is 8 $cmH_2O$, meaning the ambient air has higher pressure than the interior of the lungs by 8 $cmH_2O$, as a result the ambient air/gases flow into the lungs. During exhale, this differential becomes 5 $cmH_2O$, meaning the gas pressure in the interior of the lungs has a 5 $cmH_2O$ higher pressure than ambient, which results the air/gases in the lungs flowing out of the lungs. The fluid of interest here is air, where the dynamic viscosity of air at sea level conditions is $1.789 \times 10^{-5}$ Newton·sec/$m^2$ or Pa·sec.

The Reynolds Number $R_e$ is a dimensionless quantity in fluid mechanics introduced by George Stokes in 1851, which was popularized by Osborne Reynolds in 1883 and named as "Reynolds Number" by Arnold Sommerfeld in 1908, and is defined as, $$R_e = \frac{\rho v_{AVG} D}{\mu} = \frac{v_{AVG} D}{\nu} \tag{2.2}$$

Where $\rho$, $v_{AVG}$, D, $\mu$, and $\nu$ are density [kg/$m^3$], average flow speed [m/sec], characteristic linear dimension [m], dynamic viscosity [Newton·sec/$m^2$], and kinematic viscosity $m^2$/sec respectively. Laminar flow in a pipe with circular cross-section occurs at low Reynolds numbers, like 2,100-2,300 and below, where fluid flow is constant and smooth which displays smooth streamlines. On the other hand, turbulent flow a pipe with circular cross-section occurs at high Reynolds numbers like 4,000 and higher, where eddy's, vortices, and other flow instabilities occur. The in-between range of Reynolds numbers of 2,100-4,000 is known as the transitional flow range. To calculate the Reynolds number in a pipe or tube, D in (2.2) is replaced by $D_H$ which it stands for hydraulic diameter and is given by, $$D_H = \frac{4A}{W_P} \tag{2.3}$$

Where A and $W_P$ are cross-sectional area and wetted perimeter, which is the total perimeter of all channel walls in contact with fluid flow, respectively. For a circular pipe $D_H$=D, where D is the diameter of the tube. For the laminar flow case the velocity profile in cylindrical tube with a radius of R is a parabolic function of r given as, $$v(r) = v_{MAX} \left[1 - \left(\frac{r}{R}\right)^2\right] \tag{2.4}$$

As can be seen at the center of the tube where r=0 (at its centerline) the velocity becomes maximum and it is twice the average velocity $v_{AVG}$ and has zero velocity at the tube walls. For the turbulent flow case, the simplest and probably the most used form of the velocity profile is represented by the "power law velocity profile" given as, $$v(r) = v_{MAX} \left[1 - \left(\frac{r}{R}\right)\right]^{1/n} \tag{2.5}$$

The exponent n in (2.5) is a function of Reynolds number, increasing with the Reynolds number, being n=7 to 8 for most of practical applications described herein. Relating the fluid velocity profile, both for laminar and turbulent flow conditions to the fluid volumetric flow rate Q, can be done by integrating the radial velocity profile (2.4) or (2.5) in the cross-sectional circular area as, $$Q = \int_0^R v(r) dS = \int_0^R 2\pi r \cdot v(r) dr \tag{2.6}$$

For the laminar flow integral (2.6) becomes, $$Q = 2\pi v_{MAX} \int_0^R r \left[1 - \left(\frac{r}{R}\right)^2\right] dr \tag{2.7}$$

The indefinite integral of (2.7) gives, $$\int r \left[1 - \left(\frac{r}{R}\right)^2\right] dr = \frac{1}{2} r^2 - \frac{1}{4R^2} r^4 \tag{2.8}$$

Applying the integration limits at (2.7) to (2.8) gives the volumetric flow rate Q to $v_{MAX}$ relation as, $$Q = 2\pi v_{MAX} \frac{1}{4} R^2 = \frac{1}{2} \pi v_{MAX} R^2 \quad (2.9)$$

On the other hand, the quantity average fluid flow velocity $v_{AVG}$ for the laminar flow is related to the volumetric flow rate Q and $v_{MAX}$ by, $$v_{AVG} = \frac{Q}{S} = \frac{Q}{\pi r^2} \text{ and } v_{MAX} = 2 v_{AVG} \quad (2.10)$$

The turbulent flow integral (2.6), which relates the velocity profile to the volumetric flow rate Q, leads into a more complex integral as compared to the laminar flow case, $$Q = 2\pi v_{MAX} \int_0^R r \left[1 - \left(\frac{r}{R}\right)\right]^{1/n} dr \quad (2.11)$$

Applying the integration by parts to (2.11) given as [29-31], $$\int u dv = uv - \int v du \quad (2.12)$$

Explicitly U, dv, v, and du in (2.12) becomes, $$u = r \text{ and } dv = \left[1 - \left(\frac{r}{R}\right)\right]^{1/n} dr \quad (2.13)$$

Giving, $$du = dr \text{ and } v = \int \left[1 - \left(\frac{r}{R}\right)\right]^{1/n} dr \quad (2.14)$$

The integral in (2.14) gives, $$v = \int \left[1 - \left(\frac{r}{R}\right)\right]^{1/n} dr = -\frac{nR}{(n+1)} \left[1 - \left(\frac{r}{R}\right)\right]^{\frac{n+1}{n}} \quad (2.15)$$

Substituting (2.15) into the integration by parts relation in (2.12) gives, $$-\frac{nRr}{(n+1)} \left[1 - \left(\frac{r}{R}\right)\right]^{\frac{n+1}{n}} + \frac{nR}{(n+1)} \int \left[1 - \left(\frac{r}{R}\right)\right]^{\frac{n+1}{n}} dr \quad (2.16)$$

Giving, $$-\frac{nRr}{(n+1)} \left[1 - \left(\frac{r}{R}\right)\right]^{\frac{n+1}{n}} - \frac{nR}{(n+1)} \frac{nR}{(2n+1)} \left[1 - \left(\frac{r}{R}\right)\right]^{\frac{2n+1}{n}} \quad (2.17)$$

Applying the integration limits to (2.17) finally gives, $$Q = 2\pi R^2 \frac{n^2}{(n+1)(2n+1)} v_{MAX} \quad (2.18)$$

Substituting (2.18) into (2.10) the average velocity $v_{AVG}$ to $v_{MAX}$ relation for the turbulent flow can be evaluated as, $$v_{AVG} = \frac{Q}{S} = \frac{2n^2}{(n+1)(2n+1)} v_{MAX} \quad (2.19)$$

As can be seen for a given applied pressure difference, using the Poiseuille-Hagen Law one can calculate the volumetric flow rate of a fluid using as a function of radius, length, and physical parameters of a fluid along with velocity profile in a tube along with other parameters for laminar flow, and similar calculations can be extended for turbulent flow conditions.

Figure 4:
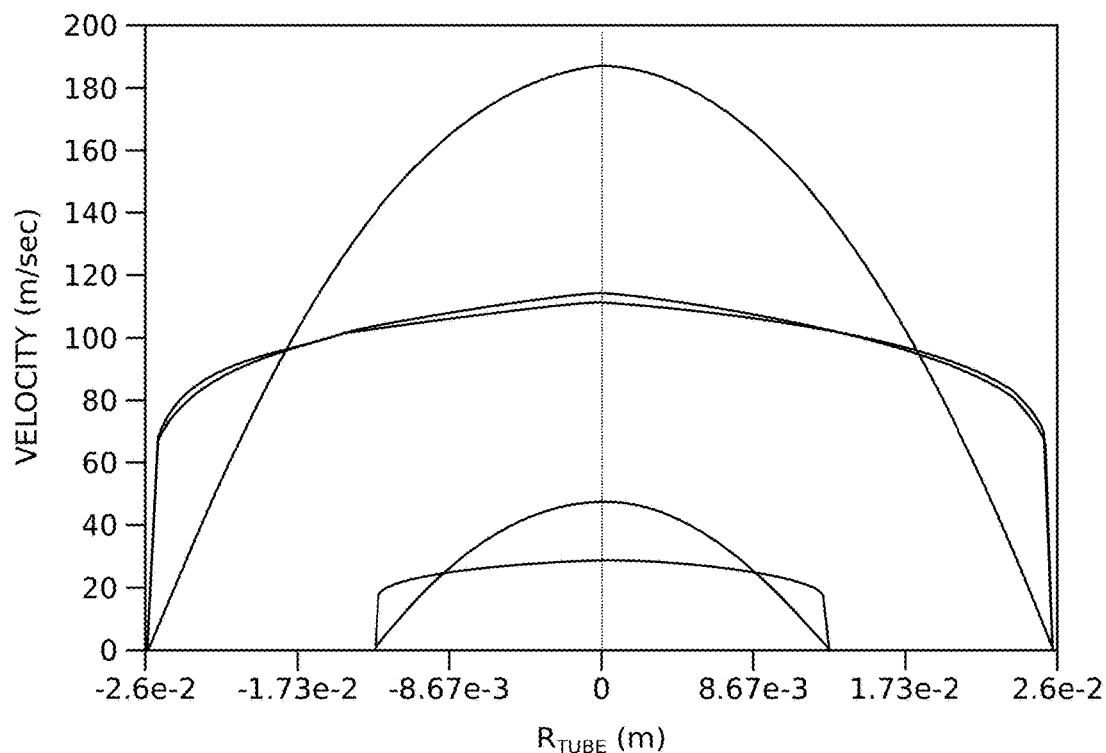
FIG. 4 shows laminar and turbulent velocity profiles for $Q_1=0.01244$ m$^3$/sec and $Q_2=0.199$ m$^3$/sec for tube radii of 1.3 and 2.6 cm with an applied pressure of 2.767 Pa.

FIG. 4 shows laminar and turbulent velocity profiles for $Q_1$=0.01244 [m$^3$/sec] and $Q_2$=0.199 m$^3$/sec for tube radii of 1.3 and 2.6 cm with applied pressure of 2.767 Pa. The exponent n=7 and 8 are characterizing the turbulent power law parameter in (2.5) and (2.18, 2.19).

For a given volume flow rate and pressure one can calculate the required power. Since power is (work/time) and work is (force×distance), the following expression involves a simple chain of substitutions to derive the power as shown below, $$P = \frac{Fd}{t} = \frac{Fd}{t} \frac{A}{A} \quad (2.20)$$

Where P, F, d, A, and t are power in Watt, force in Newton, distance in m, area in m$^2$, and time in seconds, respectively. In the second expression of (2.20) both the dominator (i.e., numerator) and the denominator are multiplied by area A and by the rearrangement of the variables in (2.20) gives, $$P = \left(\frac{F}{A}\right) \frac{(A \cdot d)}{t} = Q \cdot \Delta p \quad (2.21)$$

The first term (F/A) in (2.21) is pressure in Newton/m$^2$, which is equal to Pascal (Pa), and the next parenthesis (A·d) defines a volume, and volume/time is flow rate in m$^3$/sec, which leads the power, becoming (pressure×flow rate).

With these basic fluid dynamics principles (2.1)-(2.21), some facts related to filters can be explained quantitatively. As can be seen in (2.1), the flow rate in a pipe for a given flow rate, for the same pressure difference and pipe length, is inversely proportional to the fourth power of the radius of the pipe for the same length. The power needed to have the same volumetric flow rate obeys the same relation as well. As an example, if we reduce the pore diameter of an air filter from 300 nm to 150 nm, this 2× reduction will result in $2^4$=16 times drop in the flow rate for the same pressure difference Δp and same pore length L. By combining (2.1) with (2.6), a 16× greater pressure difference Δp or power P is needed to maintain the same flow rate Q. Now it is known exactly how many times more difficult it is to breathe from a filter with smaller pore sizes. Similarly reducing the pore diameter from 300 nm to 100 nm, this 3× reduction results in $3^4$=81 times drop in the flow rate for the same pressure difference Δp and same pore length L, or a 81× increase in power or pressure difference is needed to maintain the same flow rate.

It is customary to make an electrical analogy to fluid dynamics with following corresponding variables as listed below in Table 2.

TABLE 2

Corresponding fluid dynamics variables to electrical variables

| Fluid Dynamics Variables | Electrical Network Variables |
|---|---|
| Pressure [Newton/m²] = [Pascal] | Voltage [Volt] |
| Flow Rate [m³/sec] | Current [Ampere] |
| Power [Watt] | Power [Watt] |

Using the correspondence between the electrical and fluid dynamics variables given in Table 2 one can define the fluid dynamic resistance $R_{FD}$ as, $$R_{FD} = \frac{8\mu L}{\pi r^4} \qquad (2.22)$$

Its correspondent variable of electrical resistance is R in Ohms. It is useful to point out that the denominator in (2.22) depends on not only the cross-section area of the flow but also the shape of it, which is different than the direct current (DC) resistance expression. For a circular cross-section (2.22) can be written as, $$R_{FD} = \frac{8\mu L}{\pi r^2 (r^2)} = \frac{8\mu L}{Sr^2} \qquad (2.23)$$

On the other-hand DC resistance of a wire with a circular cross-section is, $$R_{DC} = \frac{\rho L}{S} = \frac{\rho L}{\pi r^2} \qquad (2.24)$$

Where ρ, L, r, and S are resistivity in ohm·m, length of the wire in m, radius, and cross-sectional area of the wire. The radius dependency difference between $R_{FD}$ and $R_{DC}$ is clearly seen by comparing (2.23) and (2.24). The fluid dynamic resistance becomes inversely proportional to $r^4$ instead of $r^2$ dependency in the electrical resistance.

Assume that there are two paths of fluid flow in parallel having different tube radii $r_1$ and $r_2$ and all the remaining variables in (2.22) for each tube remain the same. The calculation of the total flow rate of the combined system and how much fluid will flow in each path can be easily answered by making an electrical analogy. This problem is equivalent to parallel resistance networks in electrical engineering, which makes electrical network analogy very handy. The equivalent resistance R of two parallel resistors $R_1$ and $R_2$ is, $$R = \frac{1}{\frac{1}{R_1} + \frac{1}{R_2}} \qquad (2.25)$$

If there are n resistors in parallel (2.13) simply becomes, $$R = \frac{1}{\sum_{i=1}^{n} \frac{1}{R_i}} \qquad (2.26)$$

The fluid flow problem can be easily solved by replacing $R_1$ in expression (2.26) by $R_{FD}$ in (2.23).

The Simplest Particulate Filter Model Using Rudimentary Fluid Dynamics Principles Under Laminar Flow Conditions The quantitative fluid dynamic analysis of a fluid flowing through a real filter, its physical structure being explained earlier, requires a formidable three-dimensional computational fluid dynamics simulation. This is due to the fact that the fibers that make up the filter are in three-dimensional random arrangement that channels the airflow in a complicated manner. In the end, a simple mathematical relation has been derived to show why it is more difficult to breathe through a filter capable of filtering smaller particulates. This result is very intuitive and almost obvious, but if one can mathematically quantify this fact, the extensions of it will lead to results that are not obvious and lead to the basis of many of the claims presented herein, as well as the formulation of the issues related to improper use of the surgical masks. Instead of analyzing a conventional filter, the above questions can be answered by analyzing a regular structure that can also perform the desired filter function.

Figure 5:
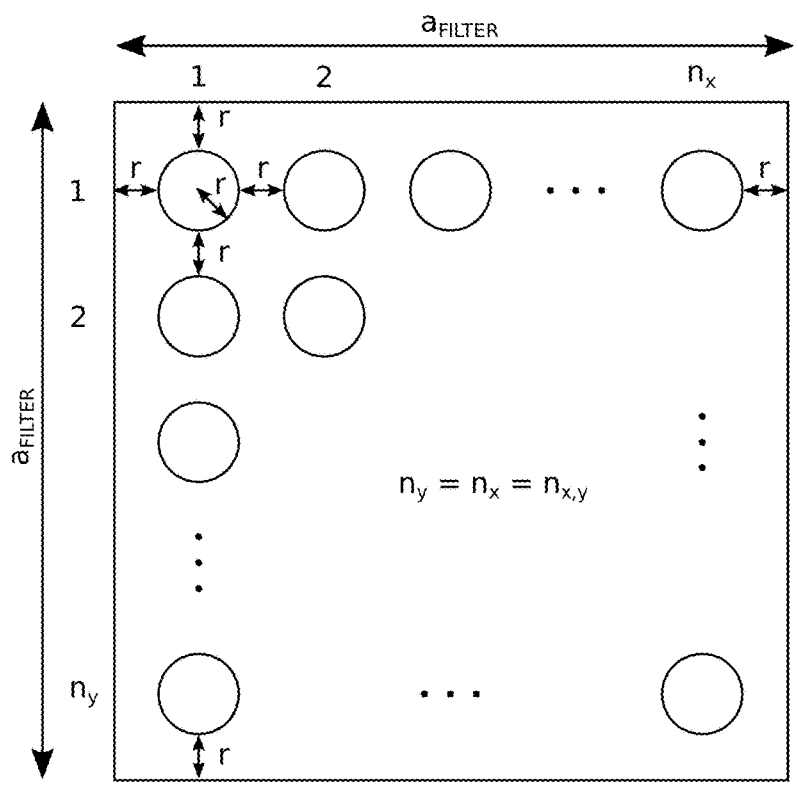
FIG. 5 is a diagram of a square filter structure with regular cylindrical pores.

FIG. 5 is a diagram of a square filter structure with regular cylindrical pores. This simulated filter structure can be a thought of a solid sheet with a thickness of t made from impermeable material to the fluid of interest that needs to be filtered with an array of cylindrical holes drilled as shown. For simplicity, assume the cylindrical holes all have the radius of r and are uniformly spaced by again by the radius r in an array structure, looking like a flat kitchen colander. In this case any particulate with the radius $r_p > r$ cannot pass through the cylindrical holes (pores), which act like a mechanical filter, letting the air or any fluid pass through them and leaving particulates with radii larger than r on the fluid incoming side of the filter. The explained simple filter structure can be produced in several ways but from the fluid dynamic modeling point of view the only work we need to do is characterize the fluid flow from this porous structure. From the fluid dynamics modeling point of view, examining only one pore is a good starting point.

Using Poiseuille-Hagen Law given by (2.1) through (2.7), the following can be formulated: the air volumetric flow rate, average air flow velocity, power, Reynolds number, and velocity profile in a tube versus pore radius for pressure differences on the order of the pressure differential produced by inhale and exhale actions in humans. These pressure differentials are 5 and 8 cmH₂O, respectively. As can be seen in (2.2), fluid flow rate, viscosity, density, and a properly selected critical size determine the Reynolds number. Since we are assuming laminar flow in every tube the Reynolds number must be kept smaller than 2,100. Having a larger Reynolds number does not cause any practical issues, but the fluid flow in the pores would be turbulent instead of being laminar and therefore one cannot relate the fluid velocity profile along the radius r with the parabolic relations as given in (2.4), and the fluid volumetric flow rate to radius relation as given in (2.5) would have to be replaced by its turbulent flow counterpart.

For simplicity, the analysis is restricted to laminar flow case and there are two possibilities of filter thickness that can be enforced. The first assumption of thickness can be made by assuming that the pore length is related to its radius, with the relation, $$L = \beta r \qquad (2.27)$$

This first forces the thickness t of the filter equal to L, being a linear function of pore radius r. The other possible case assumes the filter thickness t being constant, independent of the pore radius r.

Filter Thickness t Linearly Related to the Pore Radius as $t=\beta r$

With (2.15) the volumetric flow rate Q(r) becomes under constant pressure differential applied to the filter becomes, $$Q(r) = \frac{\pi r^4 \Delta p}{8\mu\beta r} = \frac{\pi r^3 \Delta p}{8\mu\beta} \quad (2.28)$$

Figure 6:
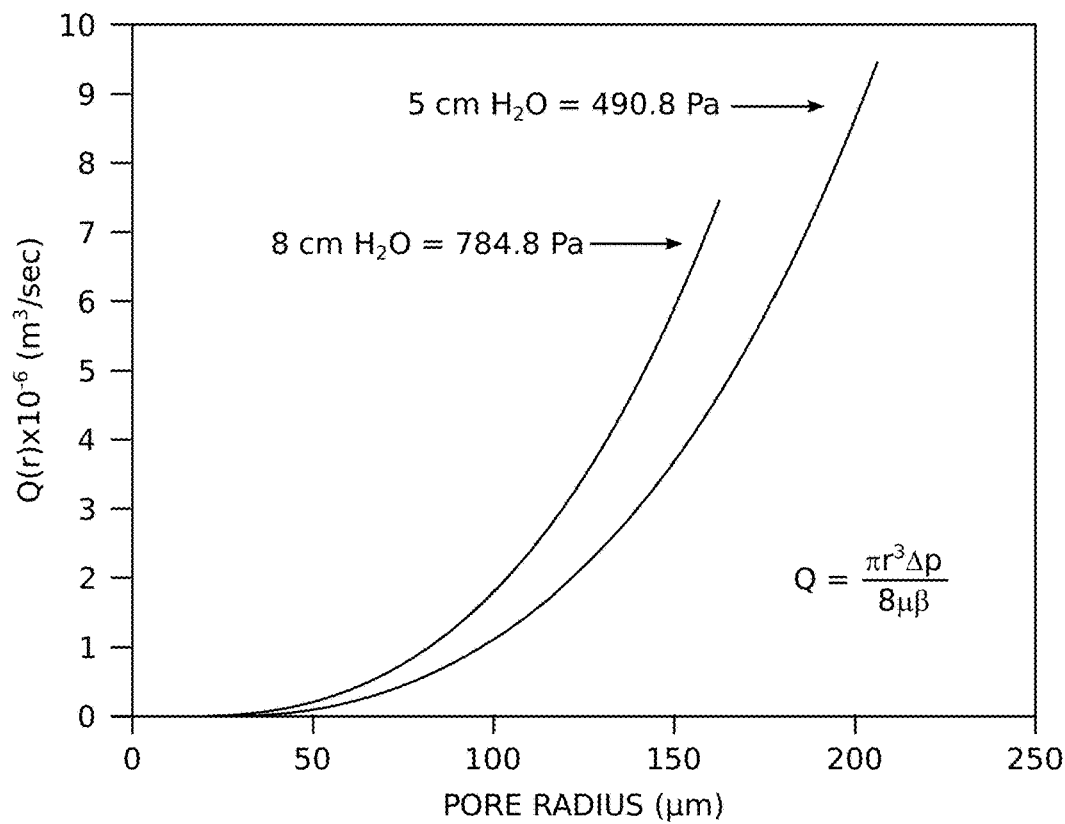
FIG. 6 depicts the volumetric flow rate Q as a function of radius for air having pressure differentials of 5 and 8 cm H$_2$O respectively for $\beta=10$.

FIG. 6 depicts the volumetric flow rate Q as a function of radius for air having pressure differentials of 5 and 8 cmH$_2$O respectively for $\beta=10$. It is important to note that with the substitution of (2.13) the radius dependency of the volumetric flow rate Q(r) turned into $r^3$ dependency. To enforce laminar air flow in the pores the Reynolds number must be less than $R_{eMAX}$ which is given by, $$R_e = \frac{\rho v_{AVG} D}{\mu} = \frac{\rho}{\mu} \frac{Q(r)}{\pi r^2}(2r) = \frac{\rho(2r)}{\mu\pi r^2} \frac{\pi r^4 \Delta p}{8\mu\beta r} \leq R_{eMAX} \quad (2.29)$$

Solving r from (2.29) gives $r_{MAX}$ as, $$r_{MAX} = 2\mu\sqrt{\frac{\beta R_{eMAX}}{\rho \Delta p}} \text{ where } R_{eMAX} = 2000 \quad (2.30)$$

Figure 7:
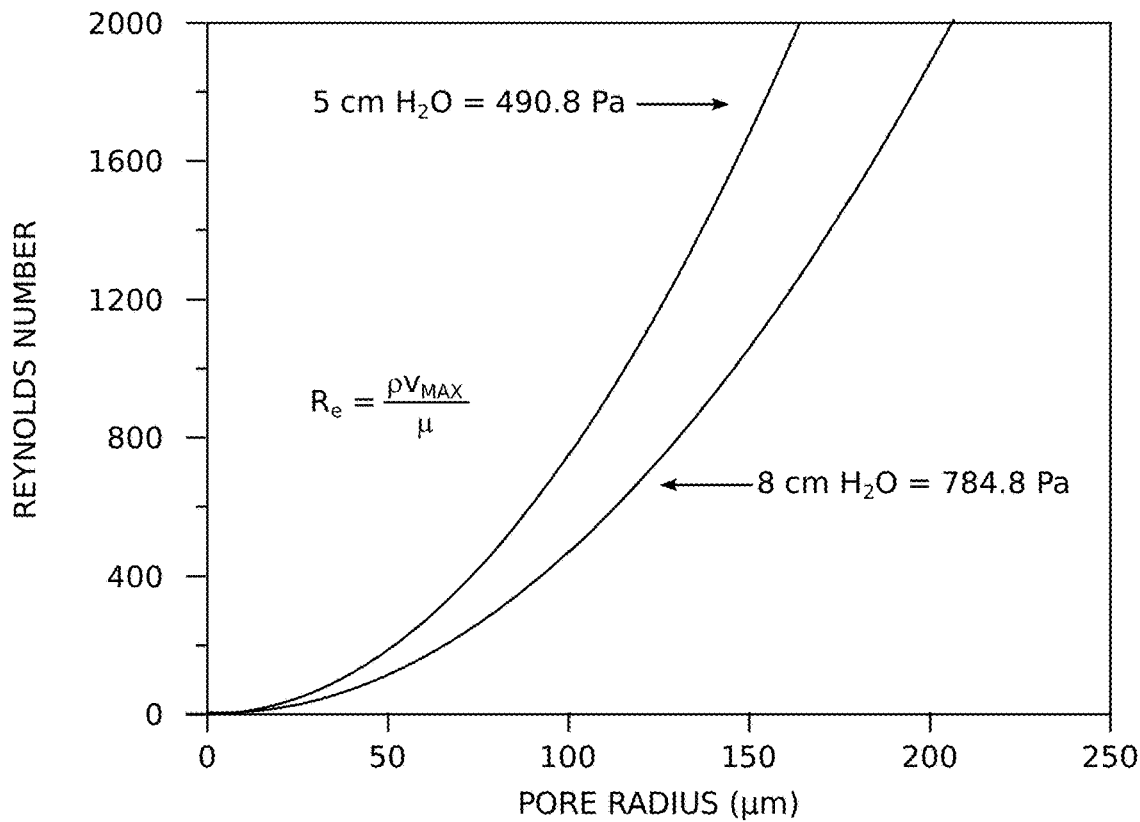
FIG. 7 depicts the Reynolds number as a function of r for $\rho$ and $\mu$ as 1,225 kg/m$^3$ and 1.789×10$^{-5}$ Pa·sec, respectively for $\Delta p=5$ and 8 cm H$_2$O.

FIG. 7 depicts the Reynolds number as a function of r for $\rho$ and $\mu$ as 1,225 kg/m$^3$ and 1.789×10$^{-5}$ Pa·sec, respectively, for $\Delta p=5$ and 8 cmH$_2$O. As can be seen, by having $r \leq r_{MAX}$ given by (2.29) the Reynolds number remains always less than 2000, satisfying the laminar air flow condition for the pores with the interval of r.

Figure 8:
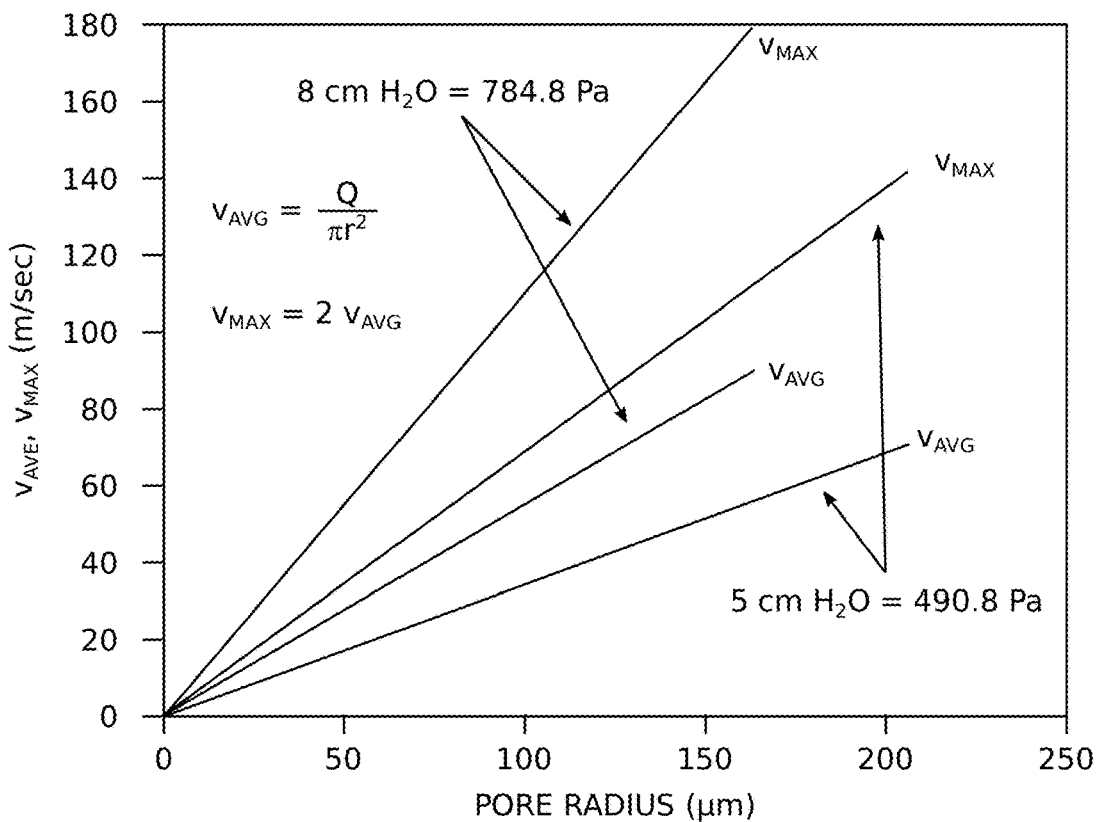
FIG. 8 depicts $V_{AVG}$ and $V_{MAX}$ as a function of r for $\Delta p=5$ and 8 cm H$_2$O.

FIG. 8 depicts $V_{AVG}$ and $V_{MAX}$ as a function of r for $\Delta p=5$ and 8 cmH$_2$O.

Figure 9:
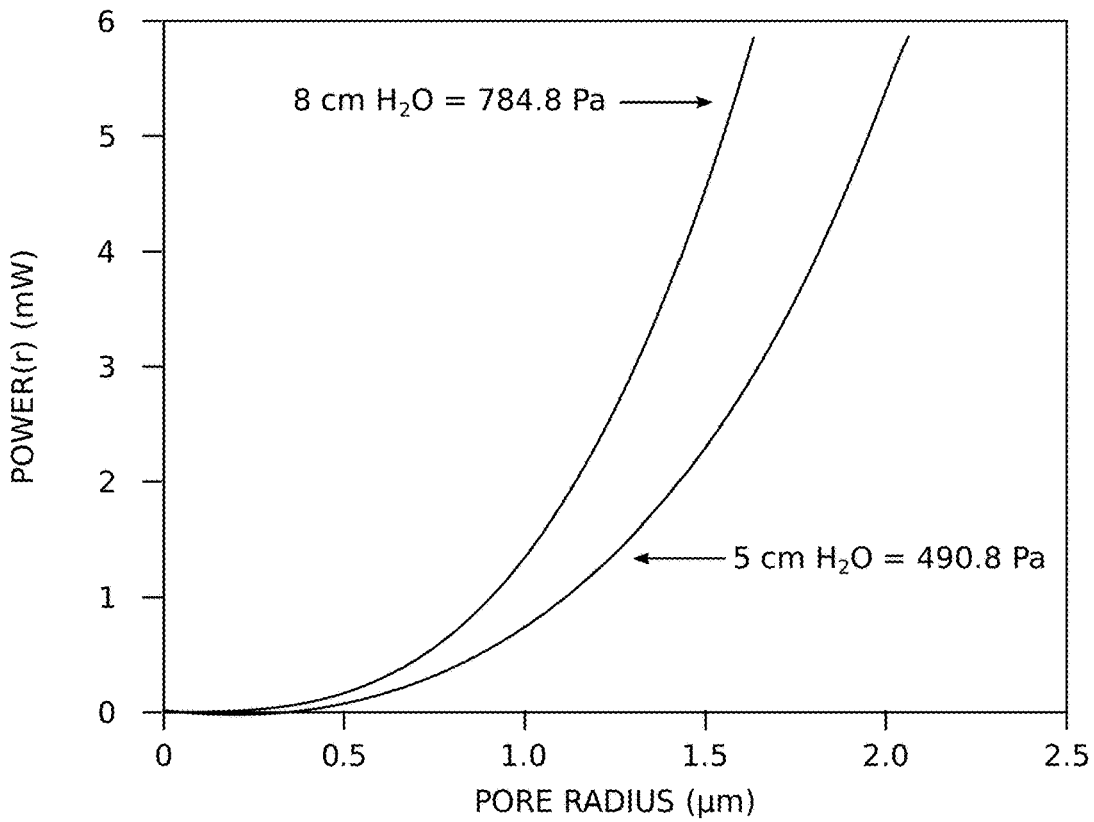
FIG. 9 depicts the power required to move the air in the pores as a function of r for $\Delta p=5$ and 8 cm H$_2$O.

FIG. 9 depicts the power required to move the air in the pores as a function of r for $\Delta p=5$ and 8 cmH$_2$O. As can be seen the power increases as the pore radius increases due to the increase in the volumetric air flow rate through the pores as given in power relation in (2.7). With a given volumetric air flow rate one can calculate how many pores are needed. Since a mask is of interest, the volumetric flow rates for an adult during resting and exercise conditions must be known.

A normal adult at rest will breathe in 2,700 milliliters (ml) of air into their lungs at a rate of 12 breathes per minute. During an exercise, this air intake volume into the lungs can reach 4,700 ml at a rate of 20 breaths per minute. Taking the air density as 1.225 kg/m$^3$ at 25° C. with a normal atmospheric pressure of 1 Bar, along with the conversions giving 1 ml=10$^{-3}$ m$^3$ and 1 minute=60 seconds, one can easily approximate the volumetric air flow rate at rest as $Q_1=5.4 \times 10^{-4}$ m$^3$/sec and airflow mass at rest as 6.615×10$^{-4}$ kg/sec. Similarly, during exercise the volumetric air flow rate becomes $Q_2=1.567 \times 10^{-3}$ m$^3$/sec along with airflow mass during exercise being equal to 1.919×10$^{-3}$ kg/sec.

Figure 10:
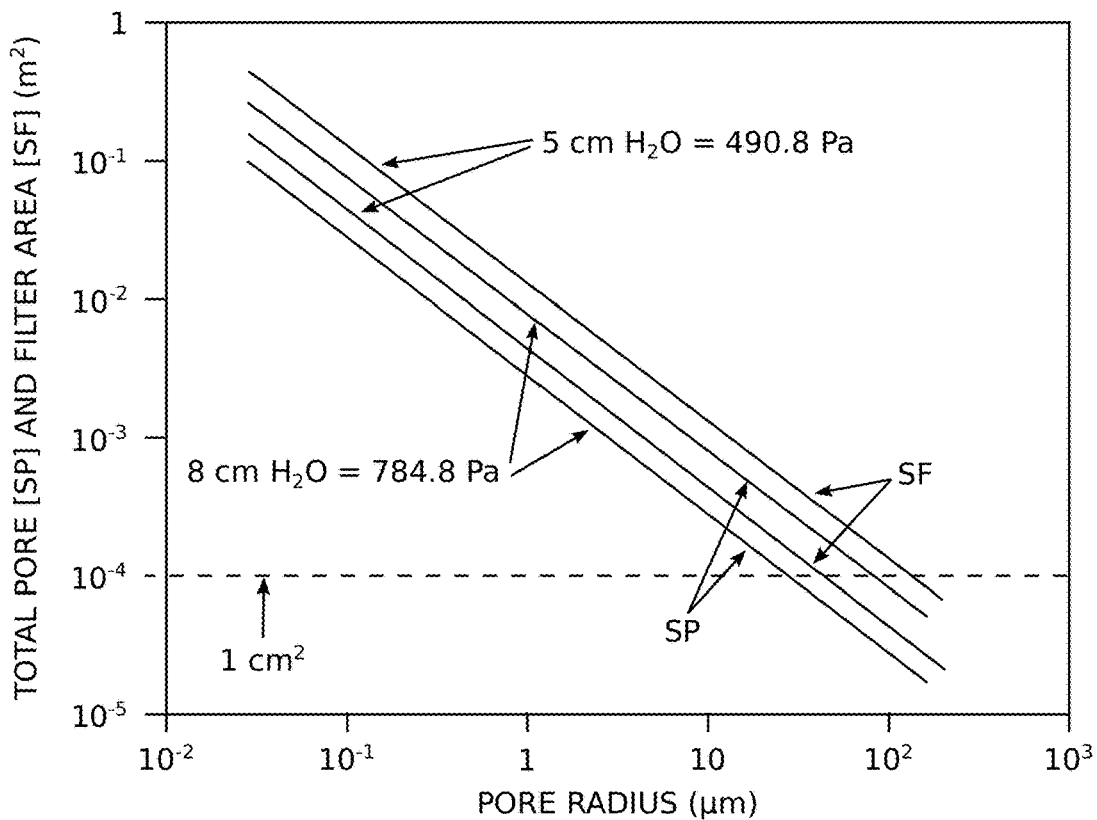
FIG. 10 depicts the total pore area and filter area required for pushing $Q_2=1.567\times10^{-3}$ m$^3$/sec air flow rate, corresponding to the average human air volume for exercising at $\Delta p=5$ and 8 cm H$_2$O.

FIG. 10 depicts the total pore area and filter area required for pushing $Q_2=1.567 \times 10^{-3}$ m$^3$/sec air flow rate, corresponding to the average human air volume for exercising at $\Delta p=5$ and 8 cmH$_2$O. The total pore area versus pore radius calculation is straight forward. It is calculated by dividing $Q_2$ which is the volumetric flow rate during exercise, by Q(r), which is the volumetric flow rate for a single pore with a radius of r as shown in FIG. 4, which gives the number of pores, $\eta_{PORE}(r)$ needed to pass $Q_2=1.567 \times 10^{-3}$ m$^3$/sec air. This number of pores versus radius function is then multiplied by the pore area and is shown in FIG. 10 as SP. FIG. 10 also shows the corresponding filter area shown as SF, which is always larger than corresponding pore area SP. Since the filter in consideration is made of equal radius pores with a radius of r and spaced by the distance of r, in both the x and y dimensions, the number of pores in each direction for a pore array geometry as displayed in FIG. 5 is, $$n_{x,y}(r) = \sqrt{\frac{Q_2}{Q(r)}} \quad (2.31)$$

The total pore area simply becomes, $$SP \to S_{PORE}(r) = \pi r^2 n_{x,y} = \pi r^2 \sqrt{\frac{Q_2}{Q(r)}} \quad (2.32)$$

Since side dimensions are more intuitive than areas, it is useful to give the linear dimension of the filter versus the pore radius. For convenience, assuming the filter is a square, the side dimension a is calculated as a function of number of pores along each direction $n_{x,y}(r)$ as, $$a_{FILTER}(r) = 2rn_{x,y}(r) + r[n_{x,y}(r) + 1] \quad (2.33)$$

The resulting filter area becomes, $$SF \to S_{FILTER}(r) = a_{FILTER}(r)^2 \quad (2.34)$$

FIG. 10 also gives the filter and total pore areas for $Q_1=5.4 \times 10^{-4}$ m$^3$/sec and $Q_2=1.567 \times 10^{-3}$ m$^3$/sec air flow rates, corresponding to the average human air inhale volumetric flow rate numbers for resting and exercising.

For the given side dimension of a square filter as $a_{FILTER}$, the number of pores in x and y direction can be also calculated by solving $n_{x,y}(r)$ from (2.33) giving, $$n_{x,y}(r) = \frac{a_{FILTER}(r) - r}{3r} \quad (2.35)$$

Figure 11:
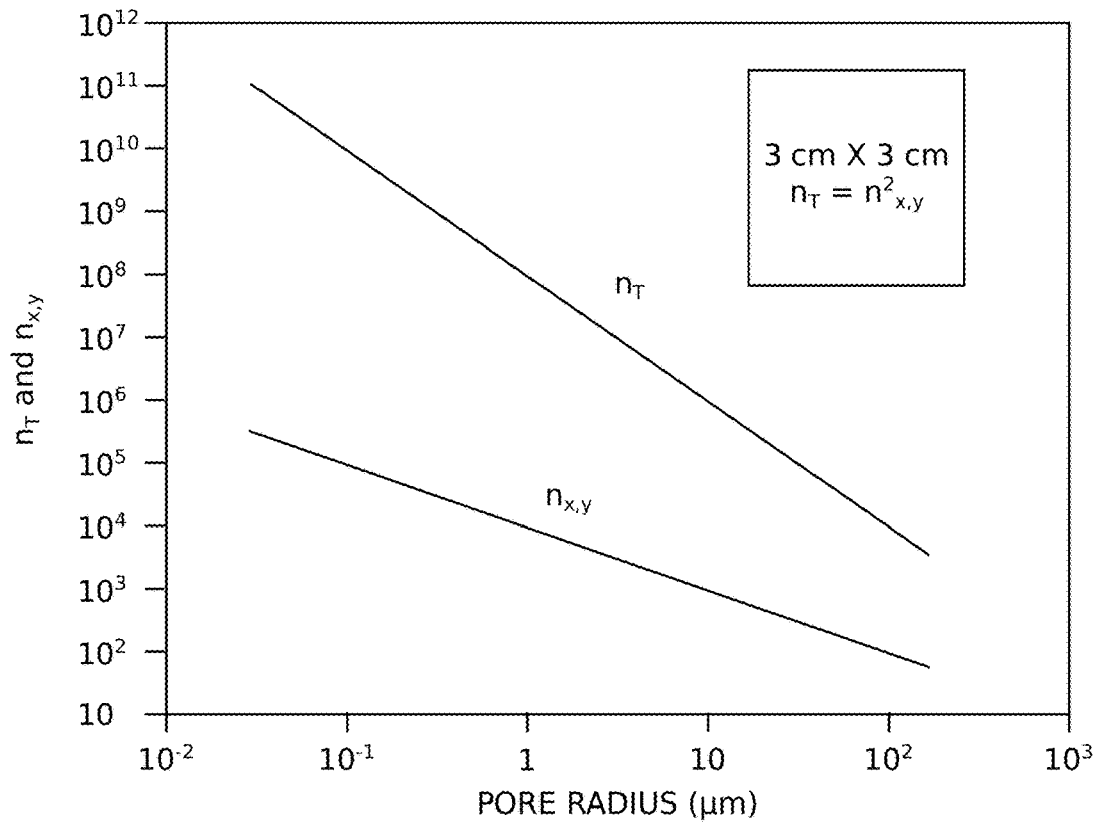
FIG. 11 illustrates the number of pores in x and y sides, $n_{x,y}(r)$ and total number of pores $n_T(r)=n_{x,y}^2(r)$, as a function of r in a 3 cm by 3 cm square filter.

FIG. 11 illustrates the number of pores in x and y sides, $n_{x,y}(r)$ and total number of pores $n_T(r) = n_{x,y}^2(r)$, as a function of r in a 3 cm by 3 cm square filter.

Figure 12:
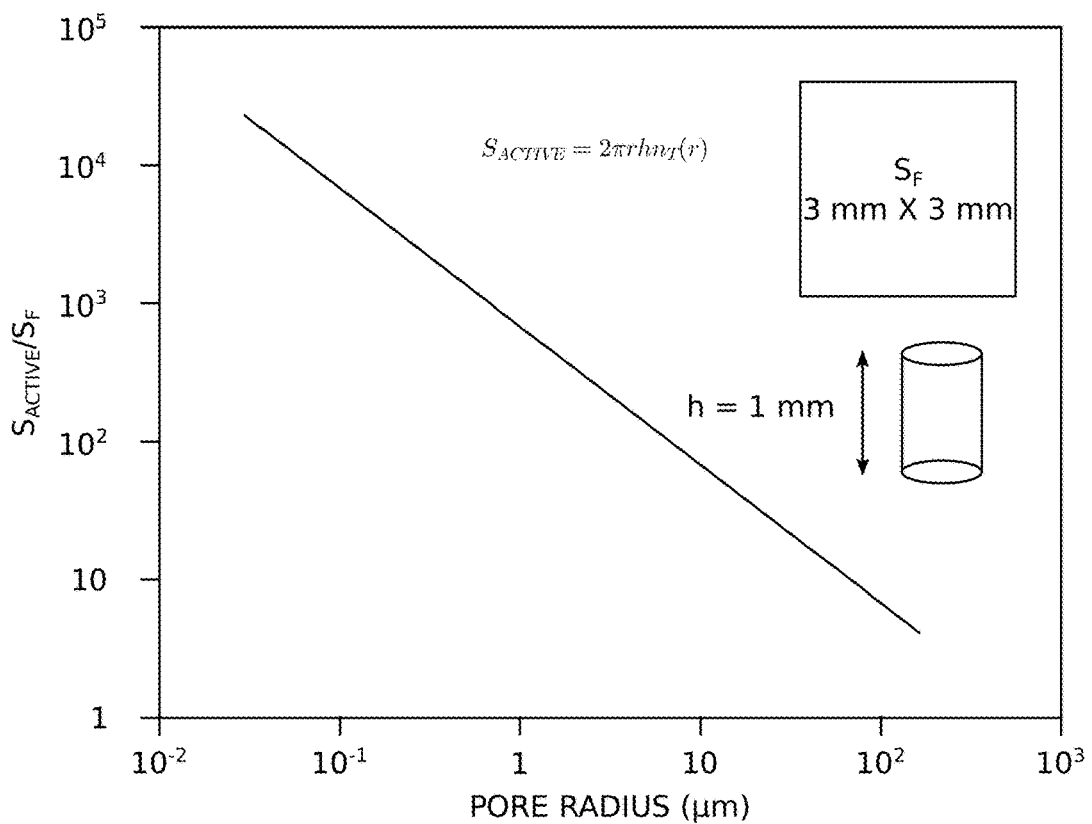
FIG. 12 illustrates the side surface area to flat surface area $S_{ACTIVE}=2\pi r h n_T(r)$ ratio for the filter of FIG. 11 having a thickness of 1 mm.

FIG. 12 illustrates the side surface area to flat surface area $S_{ACTIVE} = 2\pi rh n_T(r)$ ratio for the filter of FIG. 11 having a thickness of 1 mm. As can be seen the area where the air in contact with a surface has increased more than 20,000× for an approximate pore radius of 20 microns.

Another set of calculations can be made for enforcing volumetric air flow rate at rest as $Q_1=5.4 \times 10^{-4}$ m$^3$/sec and $Q_2=1.567 \times 10^{-3}$ m$^3$/sec at exercise versus pore radius, where the Reynolds number is again targeted to be below 2000, giving a laminar flow through the pores in the entire range of r. Solving $\Delta p$ from (2.1) gives, $$\Delta p = \frac{8\mu L Q}{\pi r^4} \quad (2.36)$$

For $L=\beta \cdot r$ (2.36) becomes, $$\Delta p = \frac{8\mu\beta Q}{\pi r^3} \quad (2.37)$$

Figure 13:
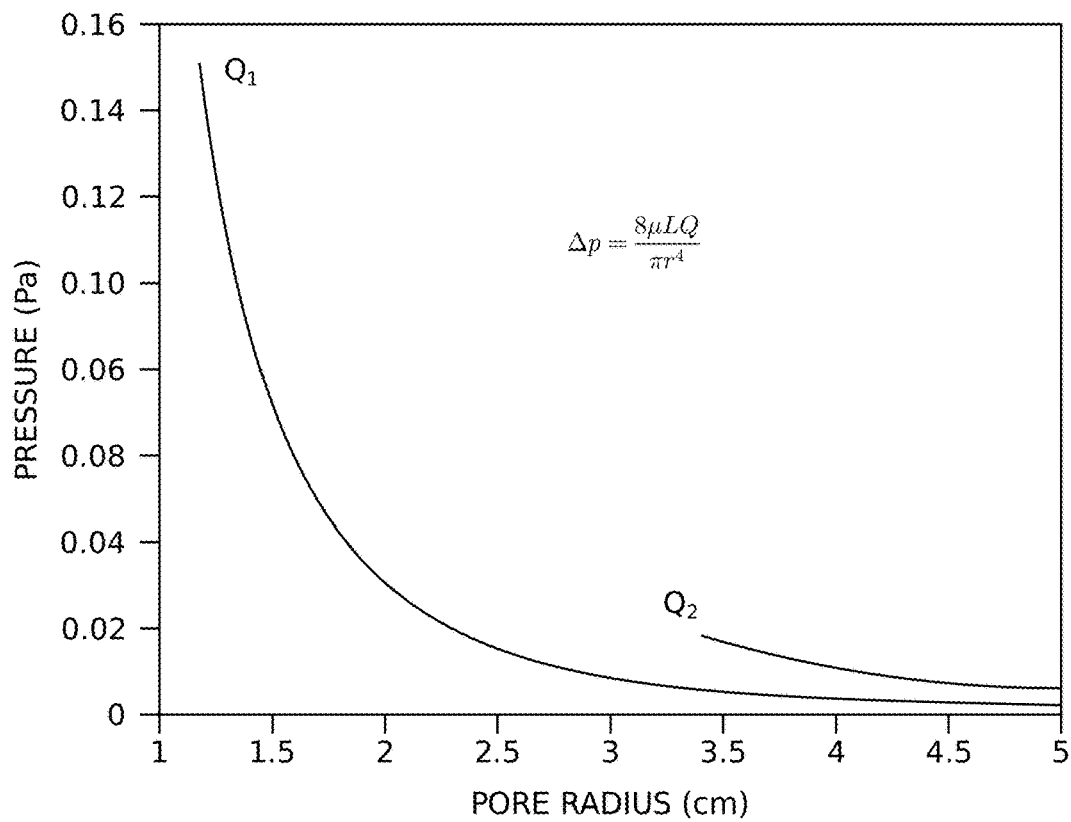
FIG. 13 depicts the pressure versus pore radius for volumetric air flow rates $Q_1=5.4\times10^{-4}$ m$^3$/sec and $Q_2=1.567\times10^{-3}$ m$^3$/sec, having a Reynolds number again below 2000 (L=$\beta$·r for $\beta=10$).

FIG. 13 depicts the pressure versus pore radius for volumetric air flow rates $Q_1=5.4\times10^{-4}$ m³/sec and $Q_2=1.567\times10^{-3}$ m³/sec, having a Reynolds number again below 2000 ($L=\beta \cdot r$ for $\beta=10$). To enforce laminar air flow in the pores the Reynolds number must again be less than $R_{eMAX}$ as done before given by (2.18) with a slight modification.

This time one gets, $$R_{eMAX} = \frac{\rho v_{AVG} D}{\mu} = \rho \frac{Q}{\pi r^2} \frac{(2r)}{\mu} = \frac{2Q\rho}{\pi r \mu} \quad (2.38)$$

Giving, $$r_{MIN} = \frac{2Q\rho}{\pi \mu R_{eMAX}} \text{ where } R_{eMAX} = 2000 \quad (2.39)$$

Figure 14:
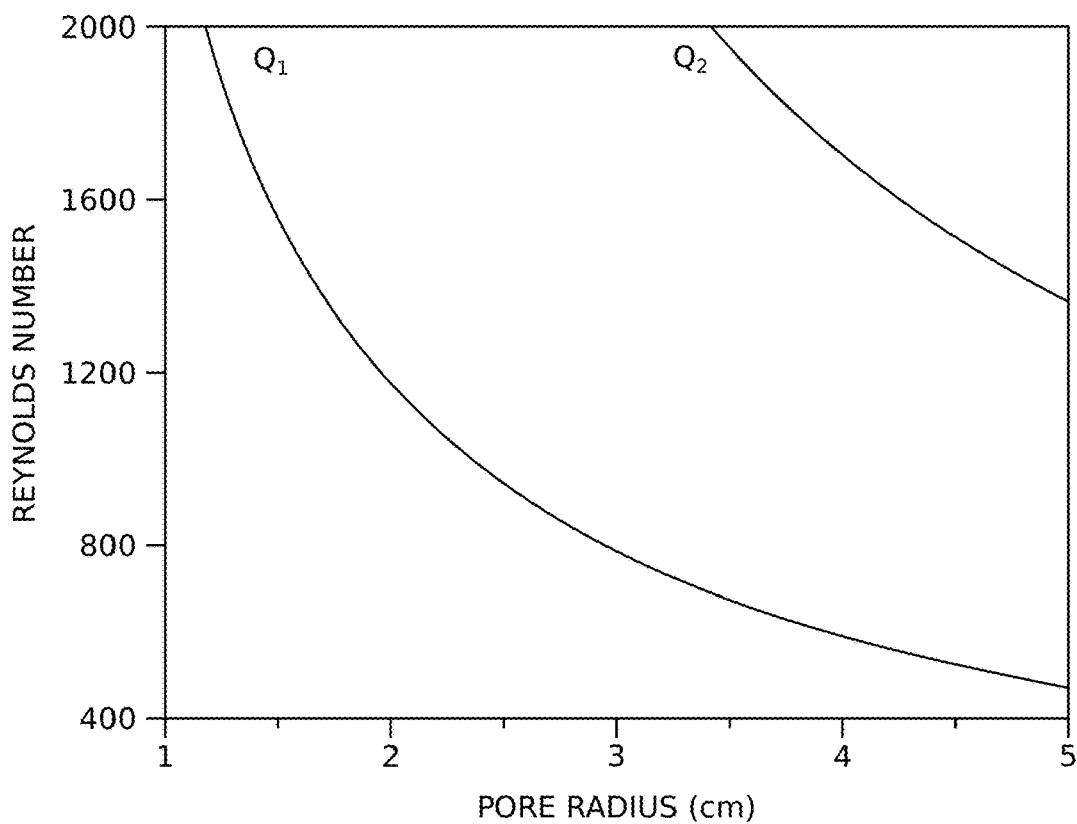
FIG. 14 depicts the Reynolds number versus pore radius for the same volumetric air flow rates $Q_1=5.4\times10^{-4}$ m$^3$/sec and $Q_2=1.567\times10^{-3}$ m$^3$/sec.

FIG. 14 depicts the Reynolds number versus pore radius for the same volumetric air flow rates $Q_1=5.4\times10^{-4}$ m³/sec and $Q_2=1.567\times10^{-3}$ m³/sec.

Figure 15:
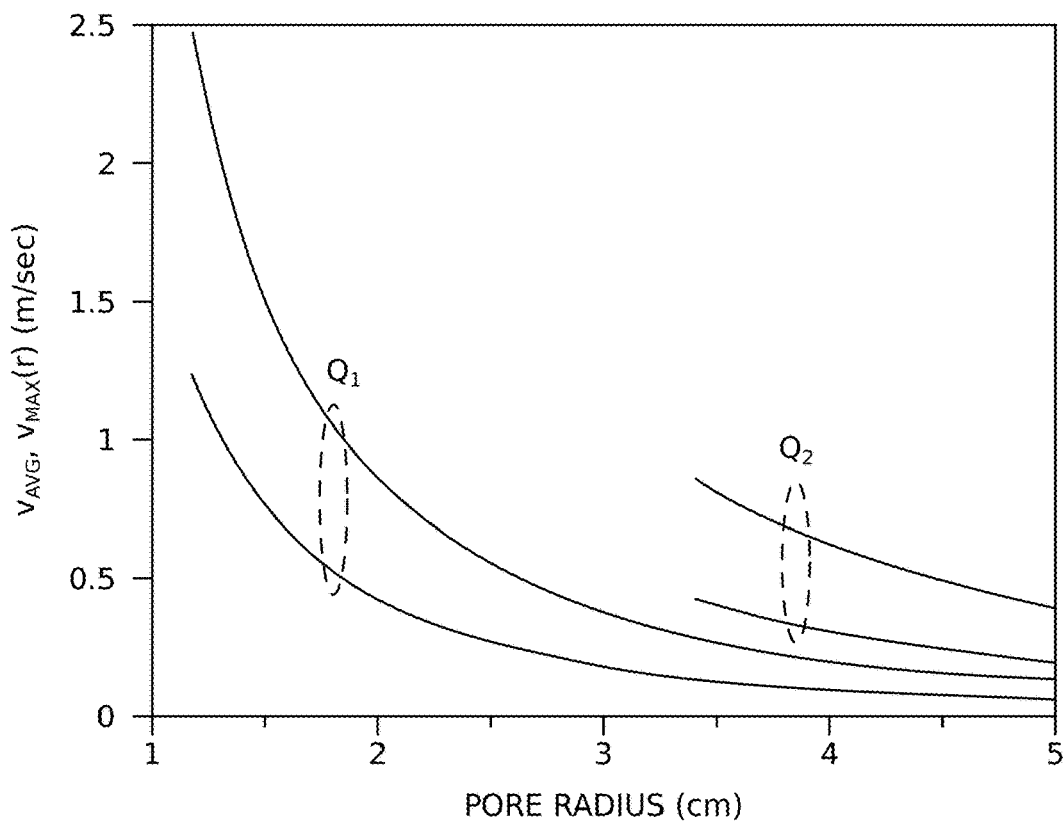
FIG. 15 depicts the $V_{AVG}$ and $V_{MAX}$ as a function of r for the same volumetric air flow rates $Q_1=5.4\times10^{-4}$ m$^3$/sec and $Q_2=1.567\times10^{-3}$ m$^3$/sec.

FIG. 15 depicts the $v_{AVG}$ and $v_{MAX}$ as a function of r for the same volumetric air flow rates $Q_1=5.4\times10^{-4}$ m³/sec and $Q_2=1.567\times10^{-3}$ m³/sec.

Figure 16:
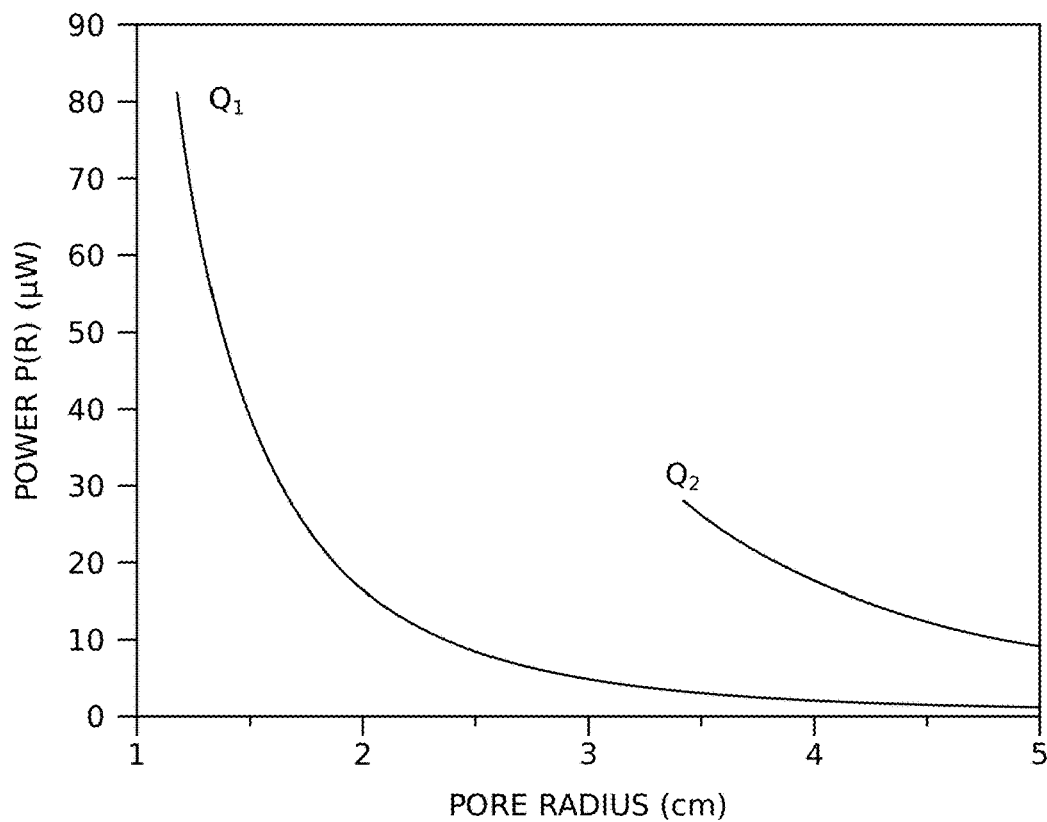
FIG. 16 depicts power vs radius as a function of r for the same volumetric air flow rates $Q_1=Q_1=5.4\times10^{-4}$ m$^3$/sec and $Q_2=1.567\times10^{-3}$ m$^3$/sec.

FIG. 16 depicts power vs radius as a function of r for the same volumetric air flow rates $Q_1=5.4\times10^{-4}$ m³/sec and $Q_2=1.567\times10^{-3}$ m³/sec. The figure shows quantitatively very clearly why it is more difficult to breathe from filters, as it simply requires a lot more power to push the same volume of air through a smaller diameter pore or a filter made a collection of such pores given as, $$P = Q \cdot \Delta p = \frac{8\mu\beta\Delta p^2}{\pi r^3} \quad (2.40)$$

Until now, the analysis has been limited to laminar flow in the pores by limiting the Reynolds number to 2000. One can allow higher Reynolds numbers in the flow and see what can be expected for the power relation for turbulent flow conditions as well. In this condition one should expect inaccuracies in the calculations relating the volumetric air flow rates to the average and maximum air flow velocity given in (2.4) and (2.5).

Figure 17:
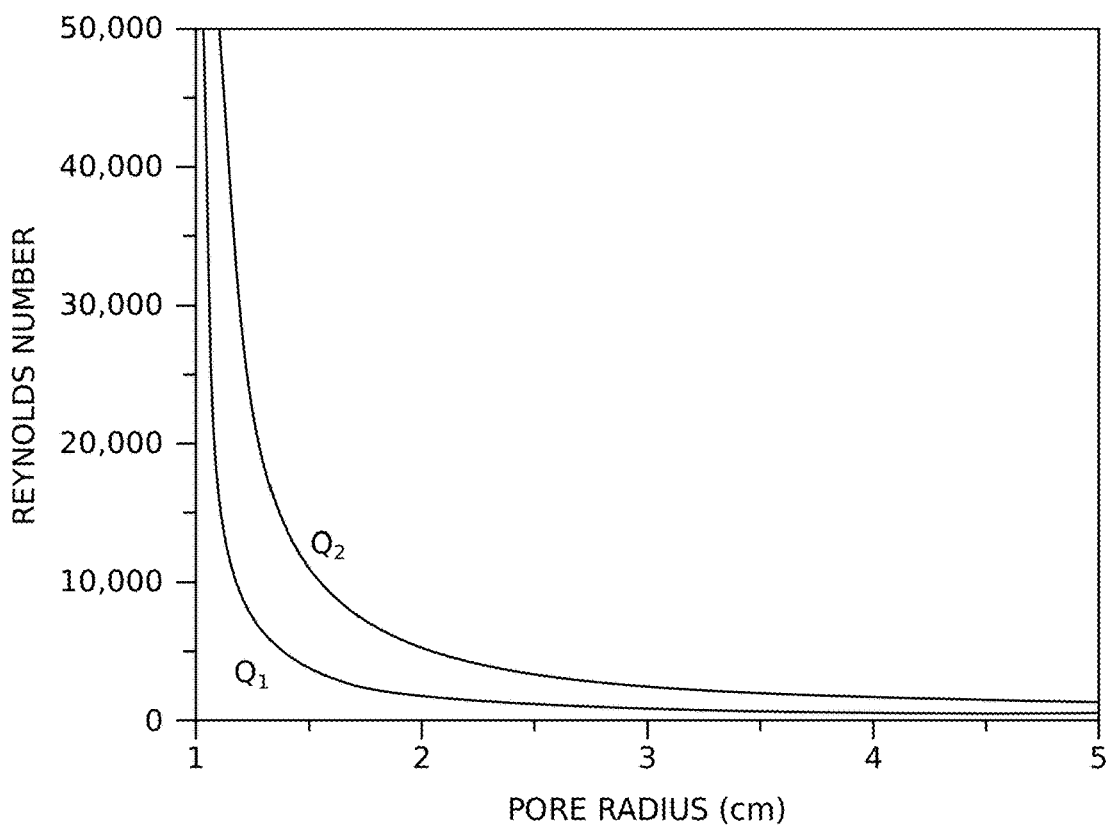
FIG. 17 depicts the Reynolds number versus pore radius for the same volumetric air flow rates $Q_1=5.4\times10^{-4}$ m$^3$/sec and $Q_2=1.567\times10^{-3}$ m$^3$/sec where $R_{EMAX}=50,000$.

FIG. 17 depicts the Reynolds number versus pore radius for the same volumetric air flow rates $Q_1=5.4\times10^{-4}$ m³/sec and $Q_2=1.567\times10^{-3}$ m³/sec where $Re_{MAX}=50,000$. With this condition one can get to smaller pore sizes.

Figure 18:
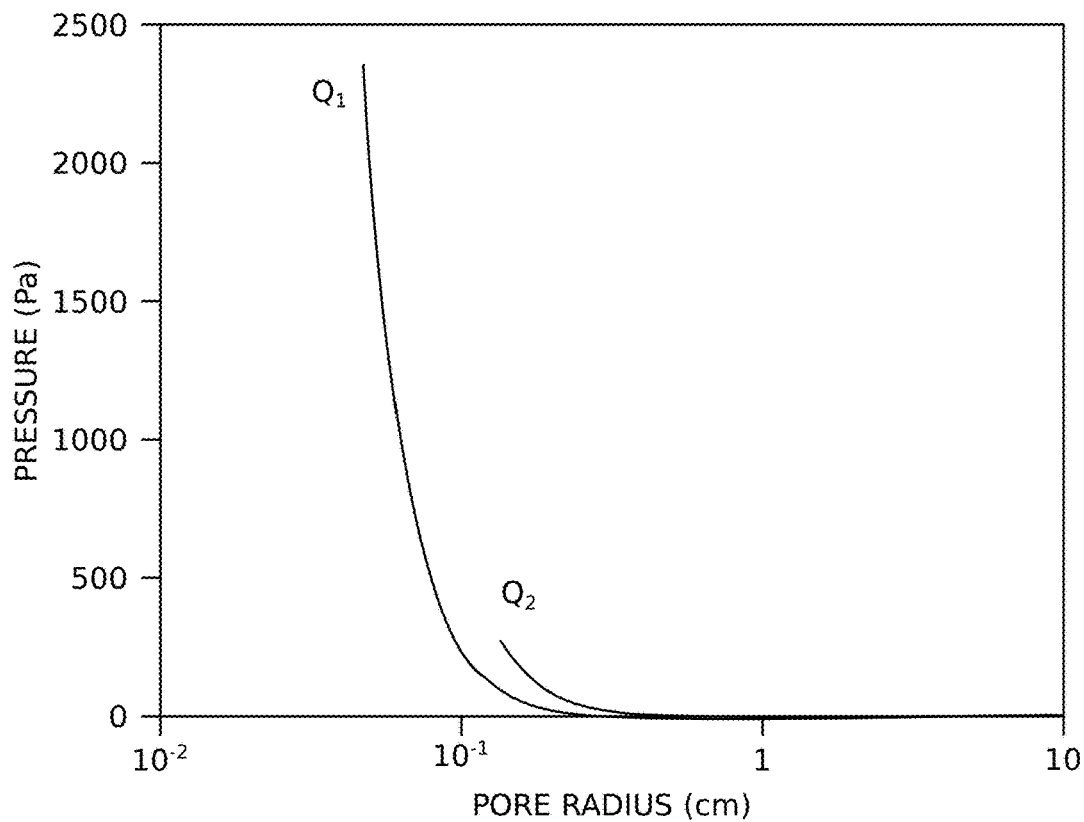
FIG. 18 depicts pressure versus pore radius for volumetric air flow rates $Q_1=5.4\times10^{-4}$ m$^3$/sec and $Q_2=1.567\times10^{-3}$ m$^3$/sec having a Reynolds number below 50,000 in log scale.

FIG. 18 depicts pressure versus pore radius for volumetric air flow rates $Q_1=5.4\times10^{-4}$ m³/sec and $Q_2=1.567\times10^{-3}$ m³/sec having a Reynolds number below 50,000 in log scale.

Figure 19:
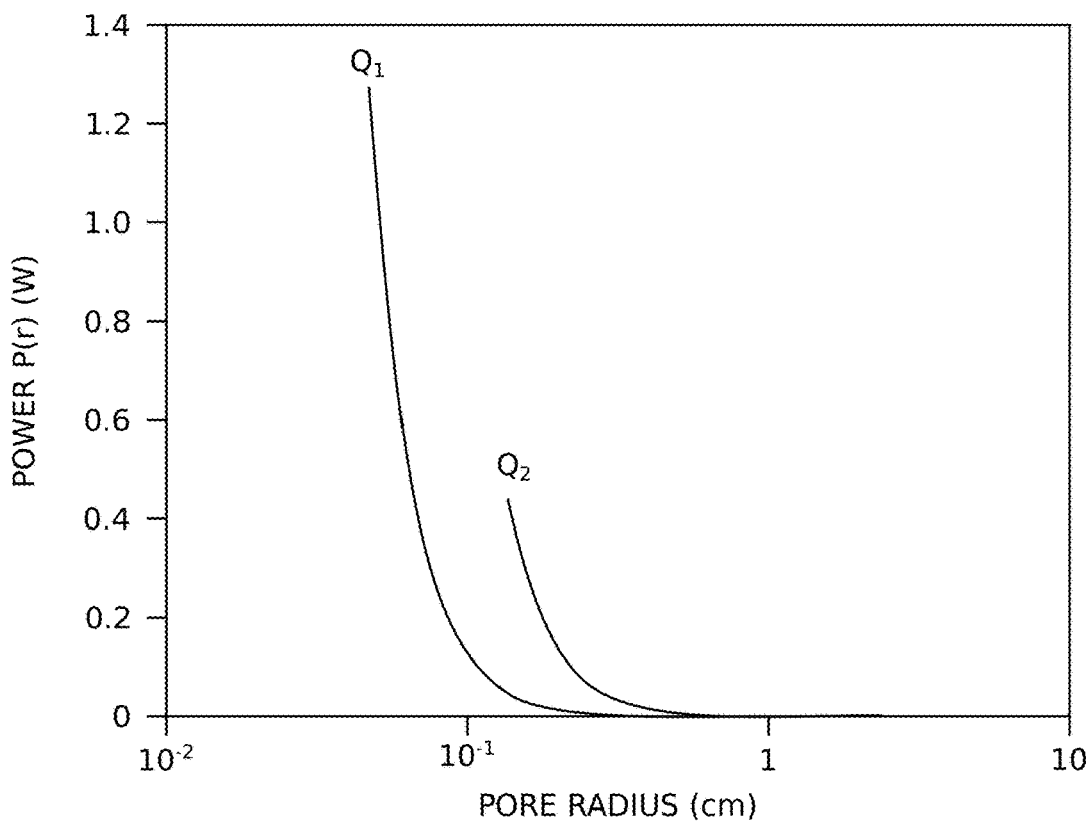
FIG. 19 depicts power versus pore radius for volumetric air flow rates $Q_1=5.4\times10^{-4}$ m$^3$/sec and $Q_2=1.567\times10^{-3}$ m$^3$/sec having a Reynold number below 50,000.

FIG. 19 depicts power versus pore radius for volumetric air flow rates $Q_1=5.4\times10^{-4}$ m³/sec and $Q_2=1.567\times10^{-3}$ m³/sec having a Reynold number below 50,000. As can be seen, the power needed to push the desired airflow increases dramatically with smaller pore sizes in this case.

Constant Filter Thickness, Independent of Pore Radius

Another set of conditions can be given for pores having the same length L, for all the range of pore radii, independent of pore radius r. In practice this length should be equal to the given filter thickness t instead of being a function of their radii given by (2.13). To keep the Reynolds number less than $R_{eMAX}$ for constant pressure condition the equation that needs to be solved becomes, $$R_e = \frac{\rho v_{AVG} D}{\mu} = \frac{\rho}{\mu} \frac{Q(r)}{\pi r^2}(2r) = \frac{2\rho r}{\mu \pi r^2} \frac{\pi r^4 \Delta p}{8\mu t_{Filter}} \leq R_{eMAX} \quad (2.41)$$

Solving r from (2.41) gives, $$r_{MAX} = \left( \frac{4\mu^2 R_{eMAX} t_{Filter}}{\rho \Delta p} \right)^{1/3} \quad (2.42)$$

Figure 20:
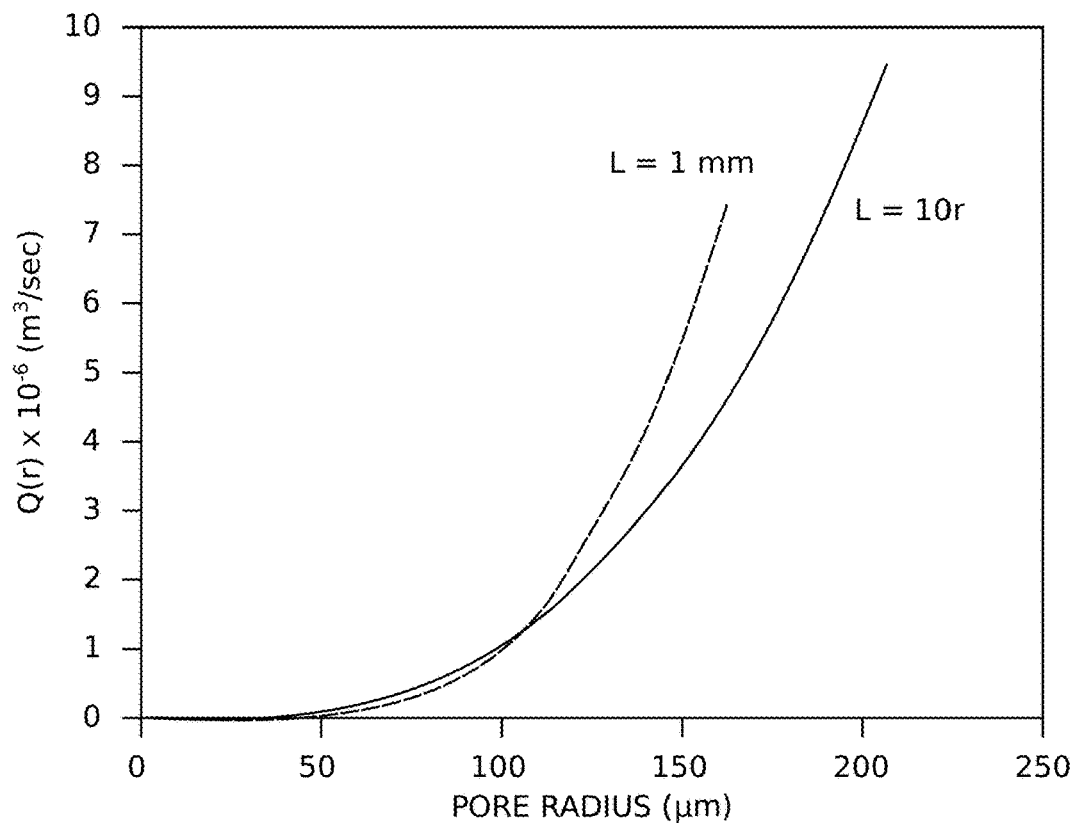
FIGS. 20 and 21 compare volumetric flow rate Q as a function of radius for air pressure differentials of 5 cm H$_2$O for $\beta=10$ and a filter with a thickness of t=1 mm, with FIG. 21 being the log-log representation of FIG. 20.
Figure 21:
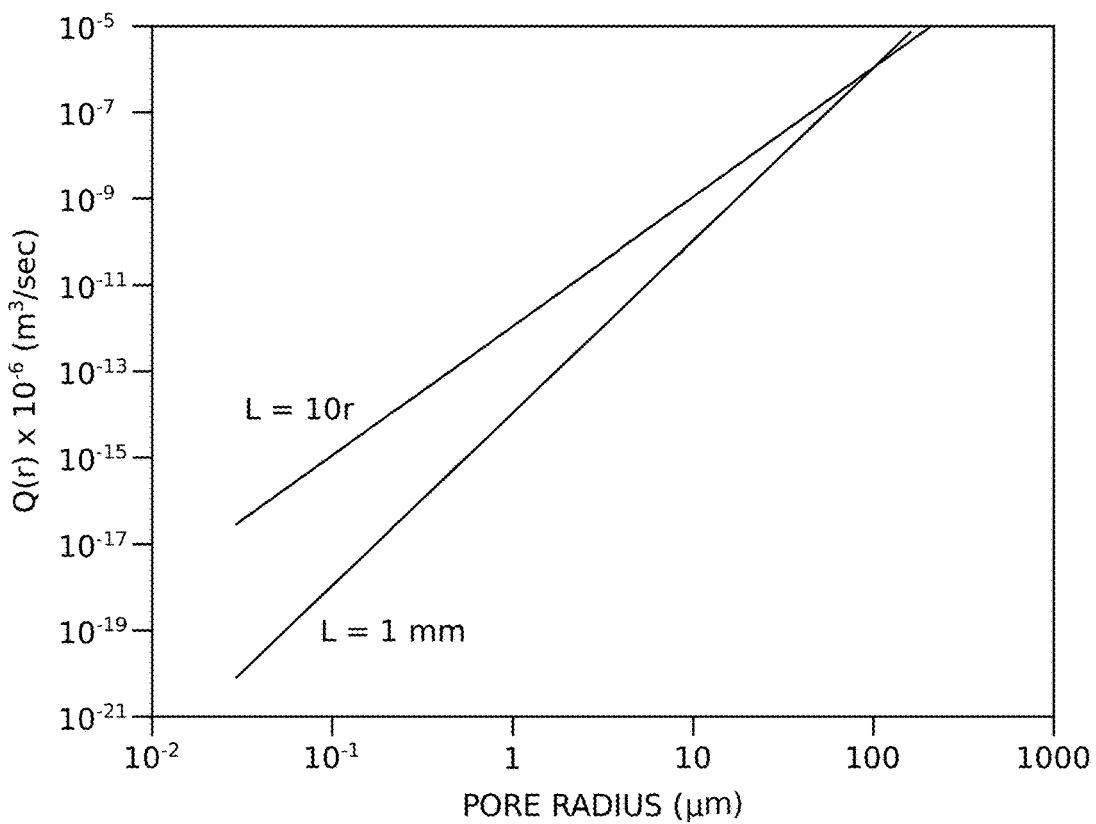

FIGS. 20 and 21 compare volumetric flow rate Q as a function of radius for air pressure differentials of 5 cmH$_2$O for $\beta=10$ and a filter with a thickness of $t=1$ mm, with FIG. 21 being the log-log representation of FIG. 20.

Figure 22:
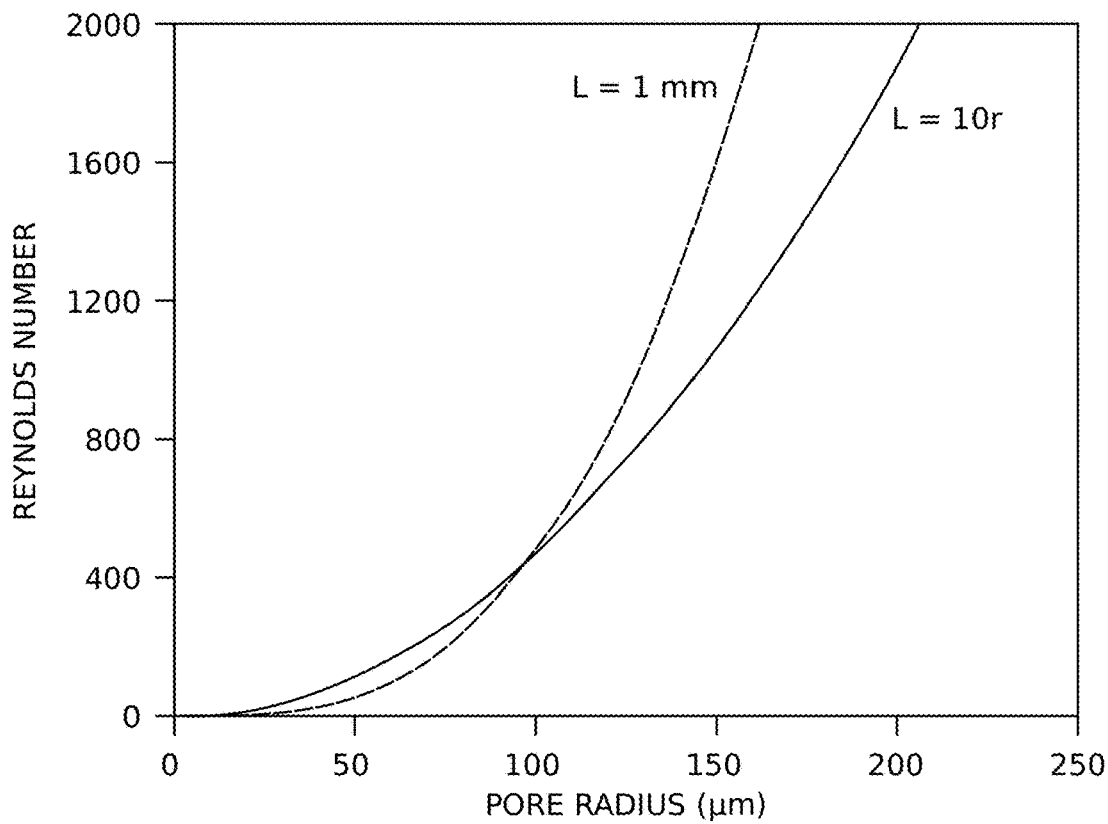
FIG. 22 depicts Reynolds number versus pore radius for air pressure differentials of 5 cm H$_2$O for $\beta=10$ and a filter with a thickness of t=1 mm.

FIG. 22 depicts Reynolds number versus pore radius for air pressure differentials of 5 cmH$_2$O for $\beta=10$ and a filter with a thickness of $t=1$ mm.

Figure 23:
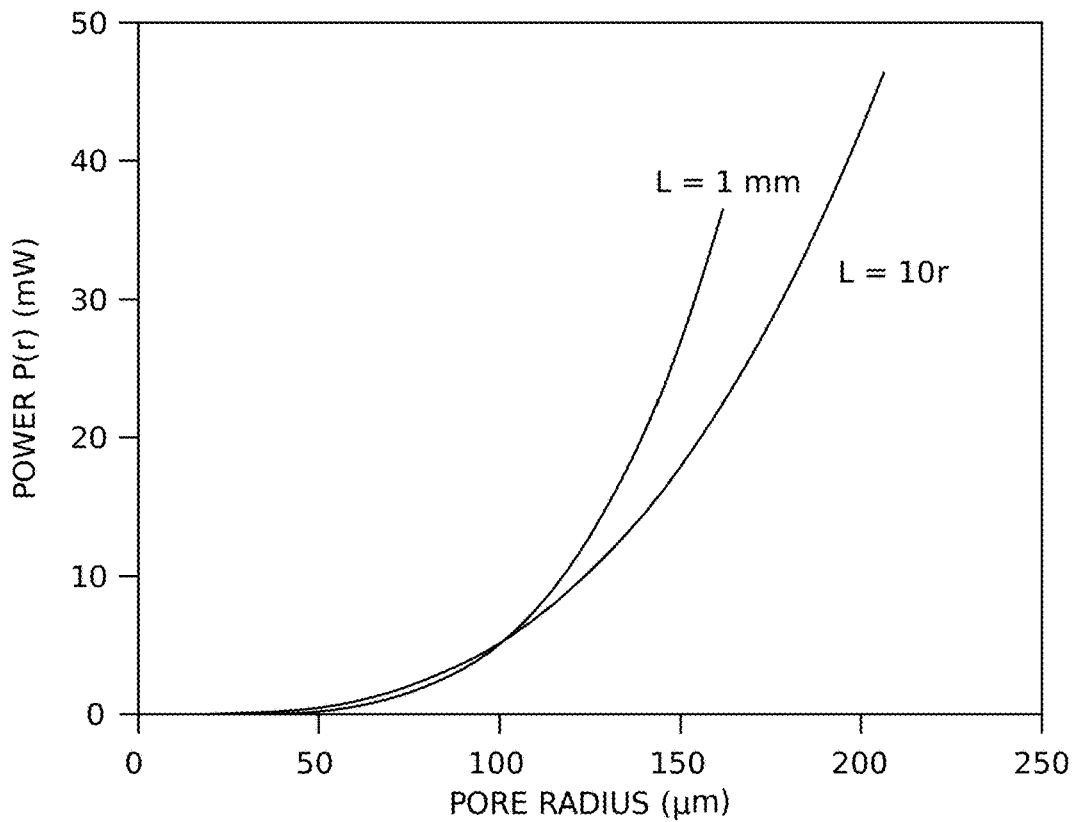
FIG. 23 depicts power versus pore size for 5 cm H$_2$O=490.5 Pa pressure difference in 2 filter cases with $\beta=10$ and a filter thickness of t=1 mm.

FIG. 23 depicts power versus pore size for 5 cmH$_2$O=490.5 Pa pressure difference in 2 filter cases with $\beta=10$ and a filter thickness of $t=1$ mm.

Leaky Filter Analysis, Theoretical "Fit Test"

Figure 24:
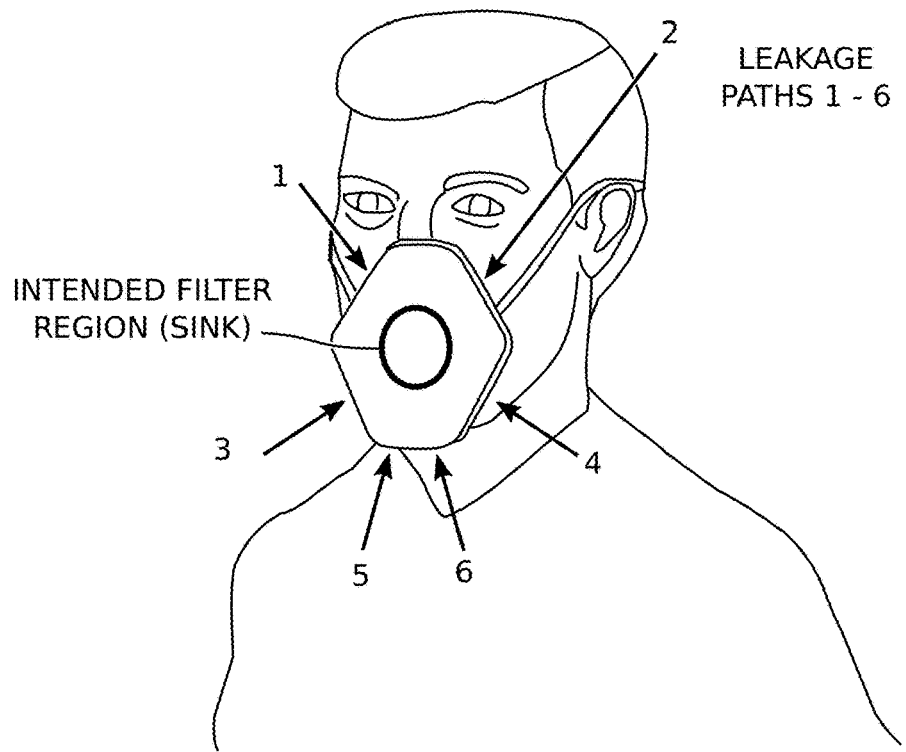
FIG. 24 depicts an exemplary surgical mask (prior art).

FIG. 24 depicts an exemplary surgical mask (prior art). There is no surgical mask on the market that completely hugs the face. Due to the irregularity of the surfaces profile of the face, there will be always irregular gaps left between the face and the mask where the air can pass through without any filtering during inhale action. Even if a mask with perfect fitting was available, it must be properly placed. Many people use a mask to only cover their mouth, leaving their nose uncovered. In most cases these spaces are around the nose towards to the cheeks, side areas of the face, and below the chin. Assume that a surgical face mask covers an area $S_F$ with an average pore radius of $r_P$, and the total area where the mask does not completely hug the face and has an area of $S_L$. Let's also assume that this "leak area" is represented by k irregular regions, like the areas around the nose towards to the cheeks, side areas of the face, and below the chin areas, each having leak areas of $S_{Li}$ Each of the irregular leak areas can be represented with a single effective circular cross section with a radius of $r_{Li}$ calculated as, $$r_{Li} = \sqrt{\frac{S_{Li}}{\pi}} \gg r_P \text{ where } i=1, 2, \ldots k \quad (2.43)$$

This is obviously an over-simplification of the phenomenon. An exact simulation done by complex three-dimensional computational fluid dynamics (CFD) simulations for different leaks and for different face geometries will not give much generality to the solution more than this simple assumption. As can be seen, the equivalent filter geometry becomes n pores, which performs the filtering function by not passing any particulate larger than $r_P$, in parallel to k leak circles each having radiuses of $r_{Li}$ through which particulates can pass.

Figure 25:
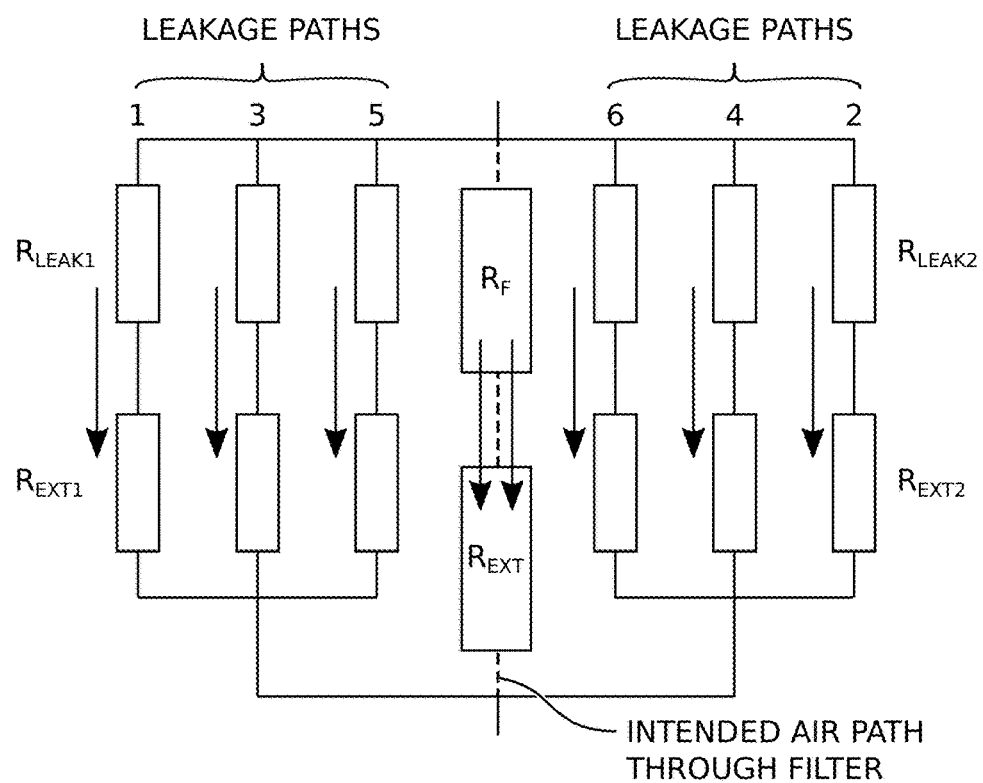
FIG. 25 depicts an electrical parallel resistive network representation of the problem.

FIG. 25 depicts an electrical parallel resistive network representation of the problem. The leaks are represented by resistors and are k=1, 2, 3, 4, 5, and 6. All the leak resistors are connected to the sink region with external series $R_{EXT}$ resistances representing the resistance from the leaks to the sink. The sink is the mouth-nose region where the air is inhaled and exhaled as shown in FIG. 24. We are interested in determining the percentage of particulates that this system can filter with a radius larger than $r_P$. The filter resistance represented with n pores in parallel is $R_F$ and its external series resistance is shown as $R_{EXTF}$. If k or $S_{Li}$ is zero, in other words—if the mask perfectly hugs the face with no leaks, the mask will function perfectly and filter 100% of particulates with radiuses larger than $r_P$ and the entire current in the equivalent circuit would only flow from $R_F$.

To solve this problem one needs to calculate the percentage of air flowing through each possible airflow branch applying Poiseuille-Hagen Law as given in (2.1). Assuming the pressure difference $\Delta p$ is applied to all n pores and k leaks equally, the effective fluid dynamic resistance of the system calculated with the help of the electrical circuit analogy given in (2.26) becomes, $$R = \frac{1}{n\frac{\pi r_P^4}{8\mu L_P} + \sum_{i=1}^{k} \frac{\pi r_{Li}^4}{8\mu L_{Li}}} \tag{2.44}$$

The total volumetric air-flow rate in this combined structure is, $$Q = \Delta p \left( n\frac{\pi r_P^4}{8\mu L_P} + \sum_{i=1}^{k} \frac{\pi r_{Li}^4}{8\mu L_{Li}} \right) \tag{2.45}$$

The ratio of the air flowing through the filter to the total air flow inhaled through the mask is simply, $$\eta = \frac{n\frac{\pi r_P^4}{8\mu L_P}}{\left( n\frac{\pi r_P^4}{8\mu L_P} + \sum_{i=1}^{k} \frac{\pi r_{Li}^4}{8\mu L_{Li}} \right)} \tag{2.46}$$

The leak geometry differs from person to person and is much more variable than the pore geometry variations. To simplify the back of the envelope calculations the ratio $C_i$ is introduced as, $$C_i = \frac{L_{Li}}{L_P} \tag{2.47}$$

Typically, the filter pore geometry doesn't vary as much as the leak geometries. By introducing the ratio $C_i$ (2.47), the efficiency $\eta$ can be written as, $$\eta = \frac{n\frac{r_P^4}{L_P}}{\left( n\frac{r_P^4}{L_P} + \sum_{i=1}^{k} \frac{r_{Li}^4}{C_i L_P} \right)} = \frac{nr_P^4}{\left( nr_P^4 + \sum_{i=1}^{k} \frac{r_{Li}^4}{C_i} \right)} \tag{2.48}$$

Further simplification gives, $$\eta = \frac{1}{\left( 1 + \frac{1}{n}\sum_{i=1}^{k} \frac{r_{Li}^4}{C_i r_P^4} \right)} \tag{2.49}$$

Using the derived simplifications it can be shown that a tiny hole in the mask or a typical gap between the mask and the face in the range of a human hair has a potential to degrade a 100% effective mask down to an efficiency of 78.13%.

Assuming the effective filter area around the mouth is represented by a 3×3 cm square and the thickness of the mask is 1 mm, we can calculate the number of pores in each side and the square of that number giving the total number of pores $n_T$ in this area. Returning to FIG. 11, the number of pores along each 3 cm side of the filter $n_{x,y}$, and total number of pores $n_T$ in the 9 cm² filter area are shown as a function of pore radius.

Returning to FIG. 12, the total pore side area in the 9 cm² filter area to the 9 cm² filter area ratio is illustrated. As can be seen, the total surface area that the air is interacting while passing through the filter is also dramatically increased.

Figure 26:
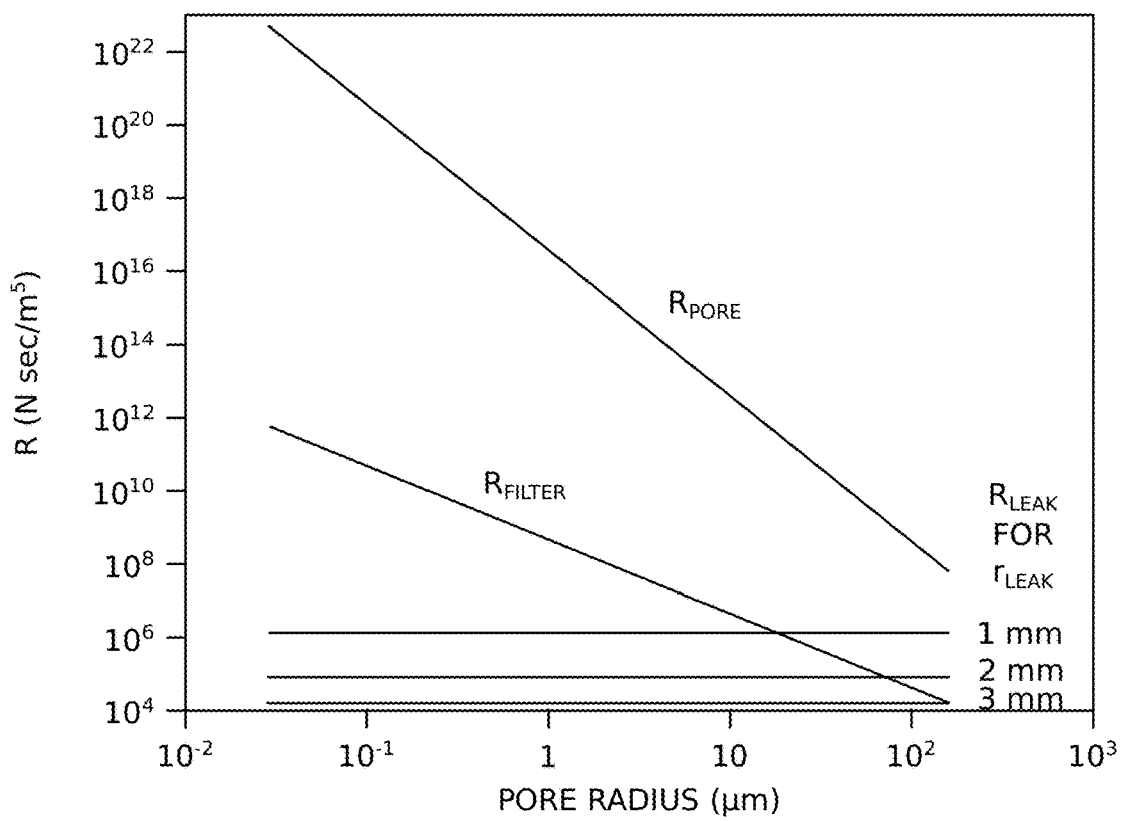
FIG. 26 depicts the pore resistance and $n_t$ number of parallel pores, giving the filter resistance as function of pore size in an effective filter area of 3×3 cm size covering the mouth-nose region.

FIG. 26 depicts the pore resistance and $n_T$ number of parallel pores, giving the filter resistance as function of pore size in an effective filter area of 3×3 cm size covering the mouth-nose region. The leak resistances are circular holes with $R_L$=1, 2, and 3 mm, which are smaller numbers than any practical surgical mask values.

Figure 27:
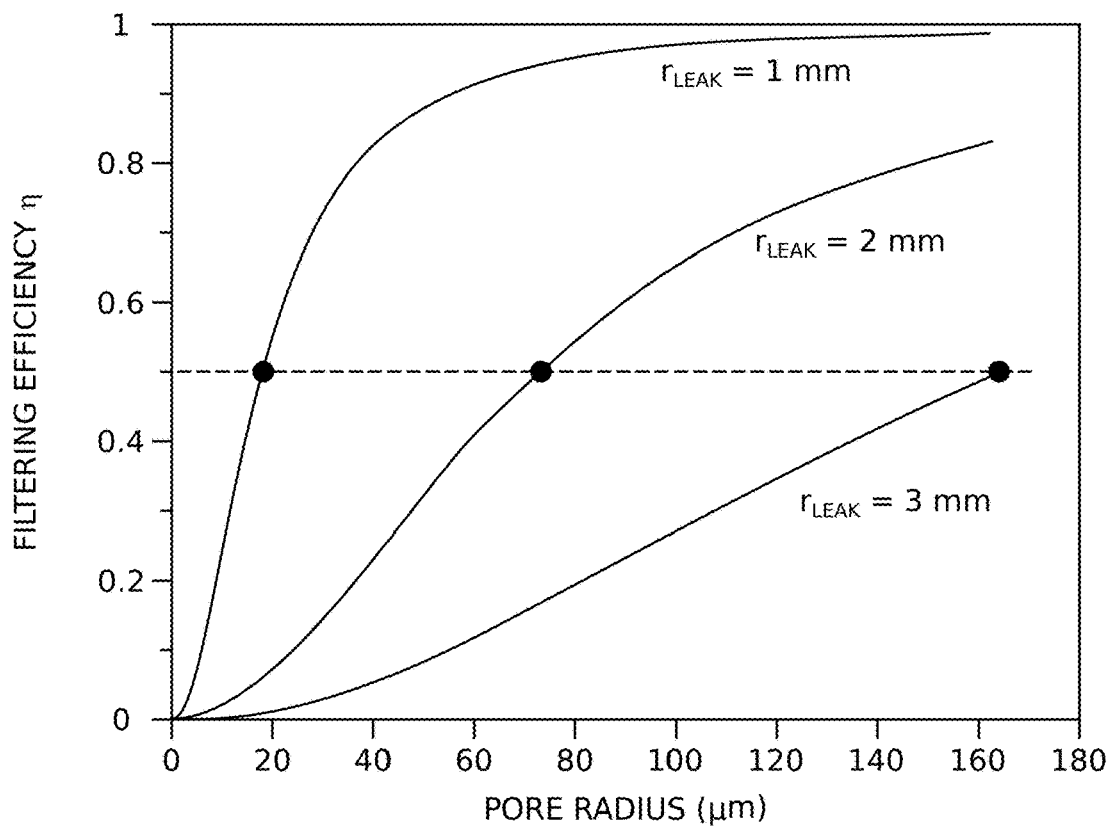
FIG. 27 depicts the significant impact of hole size on filtering efficiency $\eta$.

FIG. 27 depicts the significant impact of hole size on filtering efficiency $\eta$.

Figure 28:
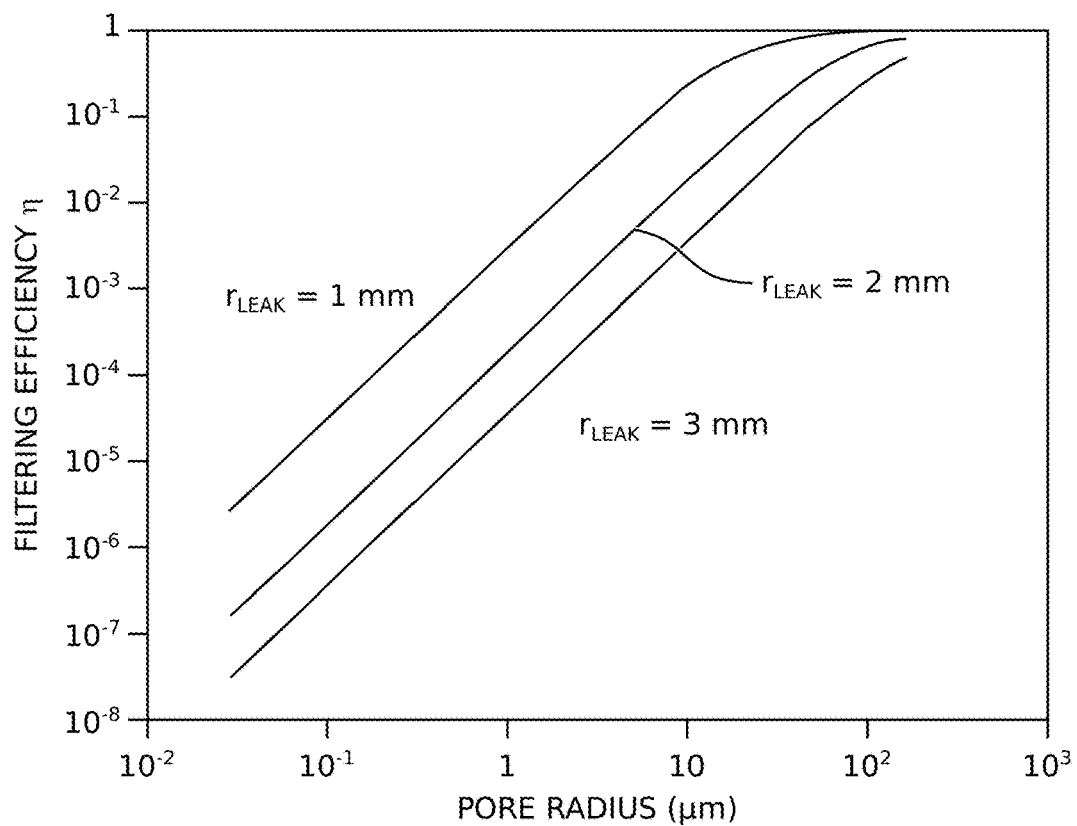
FIG. 28 depicts the filtering efficiency $\eta$ in log scale, showing the lower pore size portion of the curve clearly in the linear scale of FIG. 27.

FIG. 28 depicts the filtering efficiency $\eta$ in log scale, showing the lower pore size portion of the curve clearly in the linear scale of FIG. 27. The $\eta$=0.5 value means that 50% of the air goes through the mask and the remaining air goes through the leaks with no filtration. As can be seen in FIG. 27 and FIG. 28, efficiency degradation is worse for smaller pore size, as should be expected.

The conclusion is that a mask having a pore size less than the particulate size that it is designed to filter, can be ineffective if not properly worn. If the effective pore resistance of the filter becomes comparable or larger than the total leak resistance, the filtering efficiency drops very significantly. Therefore, the proper usage of the surgical mask requires the elimination of leak paths. The largest leak areas are in the nose-cheek areas and this problem is conventionally addressed by inserting a wire to hug the intended side. This helps to reduce the leak area, but not even down to the sub-mm levels, and wearer must keep pressing on it quite frequently to keep the mask where it is intended to be.

If one has a good enough sense of smell, simple scent tests can also show the effectiveness of a mask subjectively. The rule of thumb is that if one can smell cigarette smoke, perfume, or aftershave through a mask, or have eyeglasses that fog in the cold, the filtering efficiency of the mask is minimally degraded by a value of 50%. Another conclusion based on the rudimentary fluid dynamics principles introduced in this work shows that if wearing 2 masks on top of each other does not make it twice as more difficult to breathe, then there is a leak in the airflow path and is not entirely safe.

Another conclusion made through the application of basic fluid dynamics to a mask is that good mask filtering cannot be achieved without making it more difficult to breathe through it. If the goal is to filter the Coronavirus size particulates, what is needed is a filter or mask with Coronavirus size pores. As it is shown mathematically, that makes breathing difficult, which is the main reason why people don't want to wear masks.

It is also mathematically shown that if the mask is not properly worn or if it does not fit to the face properly, there are leaky areas formed reducing the efficiency of the filtering process very significantly, including filters capable of even filtering Coronavirus size particulates. Tight fit masks exist, more for lab use than for everyday use, and they are much harder to wear as compared to surgical masks. Since it is impossible to enforce the proper wearing of a mask, the overall effectiveness of even an improved mask would not reduce the spread of the infections. A more logical solution is protection gear that can stop Coronavirus size particulates from being inhaled, while simultaneous permitting easy breathing. Due to all the reasons explained above and based on physics, it seems that achieving this goal is impossible by improving the mask performance and design.

To achieve a wider social acceptance, as well as better comfort, transparency, and more freedom, a face shield is presented herein as a mask alternative, where UV-C irradiated air is forced downward from the top of the shield and exits through the sides and bottom which are left open. If the forced air volumetric flow rate is three times or higher than the air that is inhaled and exhaled, there is a positive air pressure formed between the shield and the face. Therefore, 100% of the air that is inhaled is UV-C irradiated air, having no active virus or living bacteria in it. As can be seen, the safety is provided by the deactivation of the Coronavirus and all other known pathogens with UV-C irradiated air, as opposed to using conventional filtering techniques (e.g., a mask). The powered UV-C irradiated air fed face shield explained below is typically referred to herein as a "safe face shield".

Face shields have gained some public acceptance throughout the pandemic. Generally, people wear a shield with a surgical mask, as it provides more protection than a mask alone. The safe face shield does not require the use of mask. In one aspect, the safe face shield components can be placed under a cap or hat to make it more fashionable, as cap sales exceed one hundred million every year in the USA. The system typically includes an air blower fan and UV-C irradiation reactor, which both consumes electrical power. Since the volumetric air flow rate is already quantified, the approximate power requirement for the air blower system can be calculated.

The Power Requirement Estimate for the Air Circulation Portion of the System

A normal adult at rest breath is vol_rest=2,700 milliliter (ml) of air at a rate of breath_rest=12 per minute. During an exercise, this air intake volume into the lungs can reach vol_exercise=4,700 ml at a rate of breath_exercise=20 per minute. Exact calculations for the air feed system require complex computational fluid dynamics simulations, which still can be questionable. However, a back of the envelope high school physics level calculation can give an easy and very adequate design information at this preliminary feasibility stage.

Using SI units throughout this work, the air density is 1.225 kg/m³ at 25° C. at a normal atmospheric pressure of 1 Bar, along with the conversions giving 1 ml=$10^{-3}$ m³ and 1 minute=60 seconds, one can easily approximate the powered respirator air pump specifications as, $$vol_{rest} \cdot \text{breath}_{rest} = 2{,}700 \cdot 12 = 32{,}400 \frac{ml}{min} \qquad (3.1)$$

This is equivalent to VOL_air_rest=$5.4 \times 10^{-4}$ m³/sec or M_air_rest=$6.615 \times 10^{-4}$ kg/sec of air flow. Similarly, during an exercise the respirator air pump must supply approximately 2.9 times more air compared to resting, giving, $$vol_{exercise} \cdot \text{breath}_{exercise} = 4{,}700 \cdot 20 = 94{,}000 \frac{ml}{min} \qquad (3.2)$$

This is also equivalent to VOL_air_exercise=$1.567 \times 10^{-3}$ m³/sec or M_air_exercise=$1.919 \times 10^{-3}$ kg/sec of air flow in SI units.

If the mask air inlet has an area of S, assuming an average airflow velocity in this cross-section, the air speed going through the mask air inlet for these volumes of air can be calculated very roughly as, $$v = \frac{VOL_{Air}}{S} \qquad (3.3)$$

For a circular mask air inlet having a radius r=2 cm, the mask air inlet area can be calculated as, $$S = \pi \cdot r^2 = \pi \cdot 0.02 \cdot 0.02 = 1.256 \times 10^{-3} \, m^2 \qquad (3.4)$$

Using (3.3) the average air velocity in the mask air inlet for a person at rest can be approximated as, $$v_{rest} = \frac{VOL_{air_{rest}}}{S} = \frac{5.4 \times 10^{-4}}{1.256 \times 10^{-3}} = 0.5264 \frac{m}{\sec} \qquad (3.5)$$

Similarly, the air velocity in the mask inlet during physical exercise will become, $$v_{exercise} = \frac{VOL_{air_{exercise}}}{S} = \frac{1.567 \times 10^{-3}}{1.256 \times 10^{-3}} = 1.527 \frac{m}{\sec} \qquad (3.6)$$

One might be also interested in the power required in heating the air to a desirable temperature for having comfort in breathing. The needed energy can be easily formulated by, $$Q = m \cdot c \cdot \Delta T \qquad (3.7)$$

Where Q, m, c, and $\Delta T$ are the energy [Joule], mass [kg], specific heat [Joule/kg·K], and temperature difference Kelvin (K) or Centigrade (C) that is desired for this mass respectively. Relations can be written in terms of mass/sec and the left-hand side of (1.7) will be in terms of power Watt giving, $$P = m_{flux} \cdot c \cdot \Delta T \qquad (3.8)$$

Figure 29:
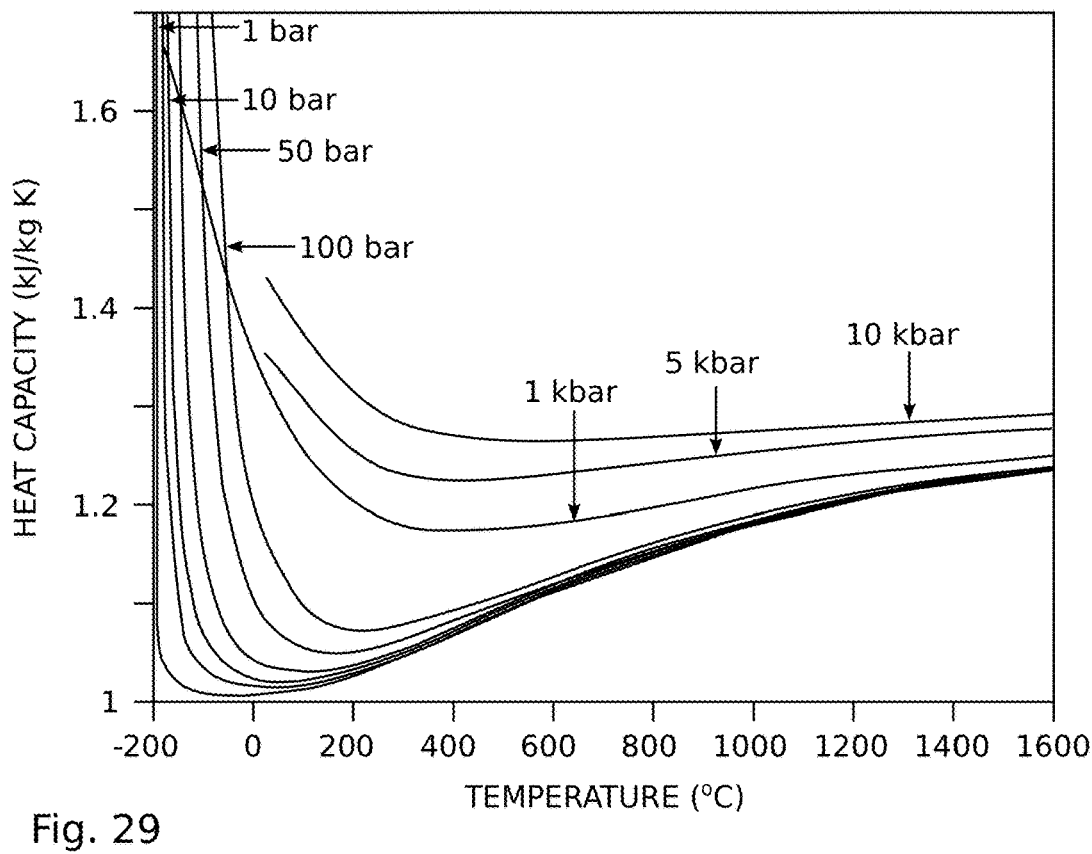
FIG. 29 is a graph depicting the air isobaric heat capacity at varying pressures.

FIG. 29 is a graph depicting the air isobaric heat capacity at varying pressures. The heat capacity for air varies with temperature and pressure as shown. Another factor that affects the heat capacity of air, which is not shown, is humidity. The heat capacity of water is 4.18×10³ joules per kelvin (J/kg·K), 4 times that of air. If we pick 1.006 kJ/kg·K from FIG. 29, for 1 Bar at 25° C., relation (1.7) becomes, $$P_{rest}=6.615\times10^{-4}\cdot1,006\cdot\Delta T=0.6655\cdot\Delta T \text{ [Watts]} \quad (3.9)$$

During resting, the power needed for maintaining a 10° C. change (for heating or cooling) of the air that we breathe will require a power source with a minimum of 6.655 W of power. The heating or cooling power needed in the case of exercising will become, $$P_{exercise}=1.919\times10^{-3}\cdot1,006\cdot\Delta T=1.931\cdot\Delta T \text{ [Watts]} \quad (3.10)$$

Giving 19.31 W of power for a 10° C. change in the air one breathes during exercise.

Another calculation needed is the power required to move the calculated amount of air. In designing commercial systems it is always better to use standard available parts available in the free market if possible. Computer DC motor fans operate with DC or stepper motors, all the way from 24 to 255 m³/hour (6.6×10⁻³-7.1×10⁻² m³/sec) airflow ratings, which is larger than the exercise airflow requirement of 5.4×10⁻⁴ m³/sec. Their power ratings are between 1.9 and 32 Watts operating at 7-15 Volts. Their square frame size varies from 40 to 119 mm. If the 622/2N-RS0 model is chosen, which is a 1.9 Watt fan, delivering 40 m³/hour (0.11×10⁻² m³/sec) of airflow, this is approximately twice the maximum requirement. This fan is in a 60×60 mm square frame and operates with 8-15 VDC. It consumes 0.1266 Amperes. Using a conventional 2500 mA·hour/3.8V fully charged smartphone battery, the fan should last 19+ hours.

There are miniature brushless fans (JDA1504H05S) operating at 5V, 60 mA, fitting in a dimension 15×15×4.5 mm, that provide 4.7×10⁻⁴ m³/sec of airflow, which is just short of 5.4×10⁻⁴ m³/sec exercise airflow requirement, but this could last 30+ hours with a 2500 mA·hour/3.8V fully charged smartphone battery.

On the other hand, heating and cooling functionality can shorten battery operating times. The duration of operation for a person at rest becomes 1.24 hours, and 0.4273 hours for exercising, assuming ΔT=10° C. heating or cooling with 100% efficiency. In practice, heating or cooling typically limits battery efficiency to no better than 30% efficiency. As can be seen, having a battery powered system with heating and cooling functionality becomes unfeasible.

Use of UV-C Radiation for Disinfecting the Air Supply of the Mask

UV-C radiation is an effective means of disinfecting surfaces, air, and water, and it is widely used in germicidal applications [1-10]. Most bottled water is disinfected using UV-C radiation in the wavelengths between 100-280 nm [2, 10]. UV-C irradiation is also used in face mask and air disinfection applications [15-23]. These wavelengths for disinfection purposes can be generated using UV-C LEDs (Light Emitting Diodes) made with semiconductors in a suitable Energy Band Gap [26-28], or mercury vapor UV-C discharge lamps [32, 33, 45, 46].

The photon energy related to these wavelengths can be calculated using the Planck-Einstein relation given as, $$E = h\nu = \frac{hc}{\lambda} \quad (4.1)$$

Where E, h, ν, c, and λ are energy, Planck constant, frequency, speed of light in vacuum, and wavelength, respectively [26-28].

Figure 30:
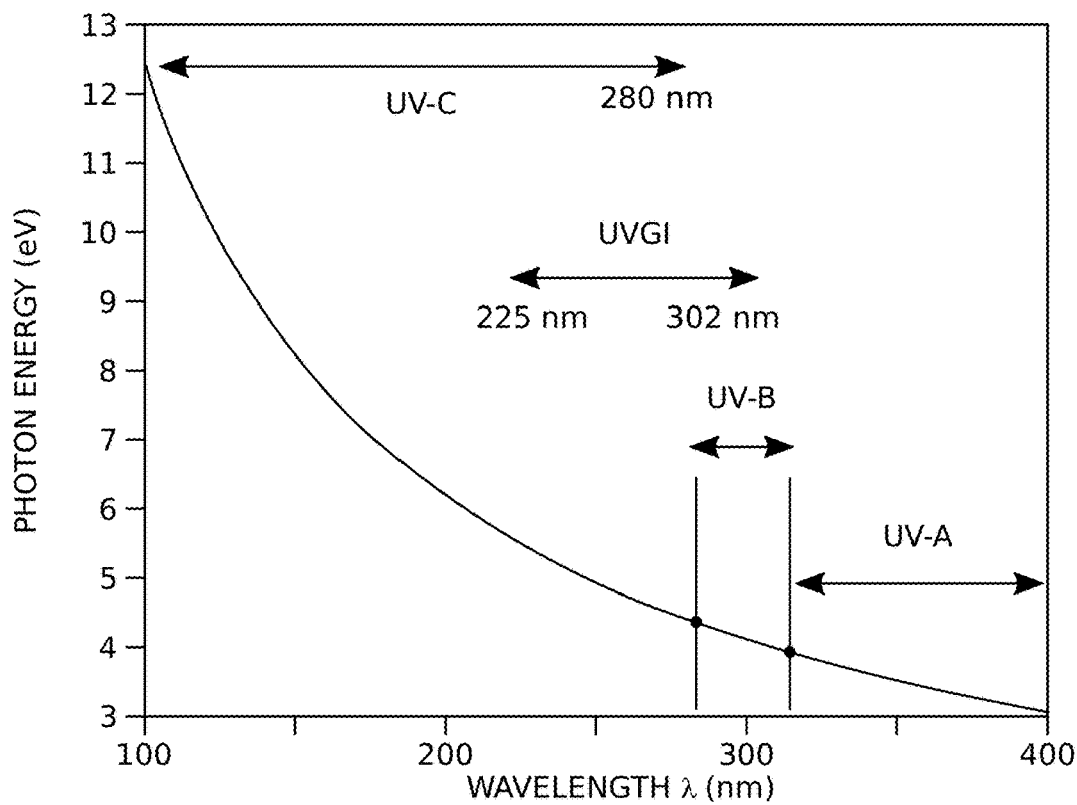
FIG. 30 depicts UV wavelength band photon energy versus wavelength, which is between 100-400 nm wavelength interval, covering UV-A, UV-B, and UV-C.

FIG. 30 depicts UV wavelength band photon energy versus wavelength, which is between 100-400 nm wavelength interval, covering UV-A, UV-B, and UV-C. As can be seen, the UV-C band is particular interest for Covid-19 disinfection purposes in the 100 nm and 280 nm interval, corresponding to photon energies of 12.399 eV and 4.428 eV. The UV wavelength region for germicidal applications is indicated as UVGI (Ultraviolet Germicidal Irradiation), between 225 and 302 nm, which falls in UV-B and UV-C regions. Table 3 summarizes FIG. 30 and includes some important comparative numbers.

TABLE 3

UV Spectrum wavelength and photon energy along with
Mercury vapor discharge lamp and
CL7003C2 UV-C LED of California Eastern Laboratories.

|  | $\lambda_{MIN}$ [nm] | $\lambda_{MAX}$ [nm] | $E_{MIN}$ [eV] | $E_{MAX}$ [eV] |
|---|---|---|---|---|
| UV-A | 315 | 400 | 3.099 | 3.936 |
| UV-B | 280 | 315 | 3.936 | 4.428 |
| UV-C | 100 | 280 | 4.428 | 12.399 |

|  | $\lambda_{PEAK}$ [nm] | $\lambda_{RANGE}$ [nm] | $E_{PEAK}$ [eV] |
|---|---|---|---|
| TUV PL-S | 253.7 | 250-257 | 4.887 |
| CL7003 LED | 275 | 260-300 | 4.509 |

As can be seen, even the lower photon energy limit of 4.428 eV is larger than commonly used semiconductor integrated circuit materials like Si (1.12 eV), Ge (0.67 eV), GaAs (1.44 eV), or SiC (2.99 eV). This simple fact suggests that the UV and UV-C LEDs should be built on a semiconductor material having their energy bandgaps in the UV-C photon energy range, using semiconductors like gallium nitride (GaN), aluminum gallium nitride ($Al_xGa_{1-x}N$), and indium gallium nitride ($In_xGa_{1-x}N$). The bandgap of GaN is 3.4 eV. $Al_xGa_{1-x}N$ and $In_xGa_{1-x}N$ semiconductors have "adjustable" bandgaps as a function of "x" in their symbols, which represent the molar fraction of each element in the compound. Using these semiconductors one can create bandgaps ranging from 3.4 eV to 6.2 eV for $Al_xGa_{1-x}N$ and 0.69 eV to 3.4 eV for $In_xGa_{1-x}N$. As an example, one the most suitable semiconductor for UV-C LED application currently seems to be made of $Al_xGa_{1-x}N$ material where the empirical bandgap formula [27, 28] is given as, $$E_G(x)=xE_G(\text{AlN})+(1-x)E_G(\text{GaN})-bx(1-x) \quad (4.2)$$

Where x, $E_G$(AlN), $E_G$ (GaN), and b are AlN molar fraction, 6.2 eV, 3.4 eV, and the controversial bowing parameter ranging from −0.4 to 1.

As an example, an off the shelf surface mount CL7003C2 UV-C LED from California Eastern Laboratories is 3.5×3.5 mm in size, operates at 5-5.5 Volts of forward bias, drawing 350-600 mA current, giving 30-50 mW of UV-C power with a peak at 275 nm in the 260-300 nm emission range of radiation bandwidth. The peak wavelength of 275 nm corresponds to 4.509 eV of energy. A semiconductor UV-C LED giving this wavelength can be made from $Al_{0.5}Ga_{0.5}N$ material. The data sheet current/voltage figures indicate roughly 10% efficiency in producing UV-C from electricity, which can be considered excellent because the typical efficiency of semiconductor UV-C LEDs are traditionally less than 5%. As can be seen in Table 3 the higher end of the wavelength emission spectrum (300 nm) goes into UV-B range, which is a drawback as far as the Covid-19 disinfection purposes.

The radiation pattern for a UV-C LED is typically represented with a cone having an apex angle of 120°. If one made a UV-C LED source by placing CL7003C2 LEDs side-by-side to create a linear array UV-C LED source, the approximate power density per unit length would be 50/3.5=14.2 mW/mm. This is very comparable to any UV-C mercury discharge lamps as shown in Table 4. This result is very surprising if one looks only to the UV-C radiant power figures at column 5 of Table 4.

Another source of UV-C for disinfection use is mercury vapor compact UV-C lamps, which have efficiencies in the 35% range, significantly higher than UV-C LEDs. Therefore, using a mercury vapor UV-C lamp as a component of the safe face shield appears to support significantly longer operating times with battery power, as compared to LED alternative. Mercury vapor discharge UV-C lamps are not very different than normal fluorescent lamps. The main difference is that the UV non-transparent glass used in normal fluorescent lamps is replaced by the clear quartz glass that is transparent to UV light, and there is no fluorescent coating inside. The electrical circuit requires starter and ballast circuits that can be made with compact solid-state technology.

The example used herein is the Phillips TUV PL-S series, with a radiation spectrum peak at 253.7 nm, which corresponds to 4.887 eV, and which is widely used for disinfection purposes. One specific model in that family of UV-C lamps is the TUV PL-S 13 W/2P. It radiates 3.4 W of UV-C power, consuming 13 W of electrical power, operating at 56 Volts and 0.29 Amperes. This corresponds to approximately a 26% efficiency, much better efficiency of any UV-C LED in the market. A 2500 mA·hour fully charged smartphone battery should last 8.62 hours powering this UV-C lamp. Generating 56 volts from a 3.7 Volt DC smartphone lithium-ion or lithium-polymer battery comes with a small loss in power. Therefore, the system may use 2 re-chargeable lithium smartphone batteries for long lasting functionality exceeding the longest intercontinental flight duration.

Figure 31:
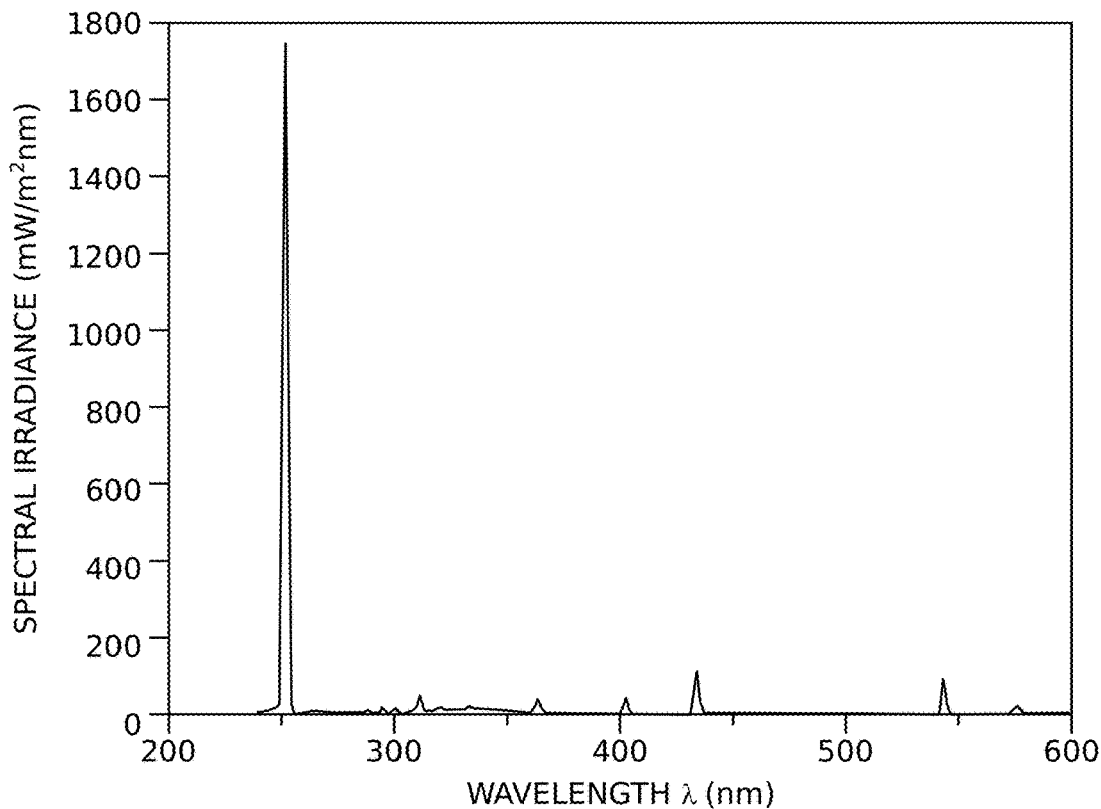
FIG. 31 is a graph depicting the spectral power density characteristics of the Phillips TUV PL-S.

FIG. 31 is a graph depicting the spectral power density characteristics of the Phillips TUV PL-S. As it can be seen it is very narrow emission spectrum centered at 253.7 nm with 7 nm of spread, completely in the UV-C band, which should result in it being efficient in Covid-19 disinfection.

Table 4 lists several Philips mercury discharge UV-C lamp models for comparison to the off-the shelf CL7003C2 UV-C LED from California Eastern Laboratories. Since the focus here is on a face shield design, the size, weight, and power consumption of the irradiation reactor are important design constraints. The two designs based on a UV-C lamp, the TUV PL-S 13 W/2P and CL7003C2 UV-C LEDs are given with general formulations that apply to any UV-C source. Since the TUV PL-S 13 W/2P is 13.95 cm long, the most compact volume, it is likely candidate as the mercury discharge UV-C lamp source for the face shield application.

TABLE 4

Several mercury discharge UV-C lamp models compared to the semiconductor CL7003C2 LED of California Eastern Laboratories [32-34].

| Model Name | Length [mm] | Diameter [mm] | Electrical Power [W] | Radiant Power [W] | Radiant Power Density σ [mW/mm] | Operating Voltage [V] | Current [mA] |
|---|---|---|---|---|---|---|---|
| TUV PL-S 13W/2P (Compact) Twin tube | 139.5 | 2 × 13 Tubes with 2 mm space | 13 | 3.4 | 24.39 (Single filament approx . . .) | 56 | 290 |
| TUV 20W FAM10X25CC | 398 | 16 | 20 | 6 | 15.07 | 45 | 450 |
| TUV 16W FAM10X25CC | 288.3 | 16 | 16 | 4 | 13.87 | 43 | 400 |
| TUV 8W FAM10X25CC | 288.3 | 16 | 8 | 2.4 | 8.32 | 56 | 150 |
| TUV 6W FAM10X25CC | 212.1 | 16 | 6 | 1.7 | 8.01 | 42 | 160 |
| TUV 4W FAM10X25CC | 135.9 | 16 | 4 | 0.9 | 6.6 | 29 | 170 |
| TUV 11W FAM10X25CC | 212.1 | 16 | 11 | 2.6 | 4.71 | 34 | 330 |
| TUV 25W FAM10X25CC | 548.9 | 19.3 | 25 | 8 | 14.57 | 82 | 350 |
| CL7003C2 LED | 3.5 × 3.5 × 1.15 | | 3.3 | 30-50 [mW] | 14.2 | 5.5 | 600 |

Ultraviolet-C(UV-C) Irradiated Forced Air Flow Face Shield

A preliminary first cut at the power requirements of the air circulation and UV-C disinfection system have been investigated above, and it has been shown that it may be feasible to run the UV-C irradiated forced air face shield with a smartphone battery having a 2500 mA·hour capacity for a decent duration of time. A detailed power analysis can be performed after every part is quantified and the entire system is designed.

Figure 32:
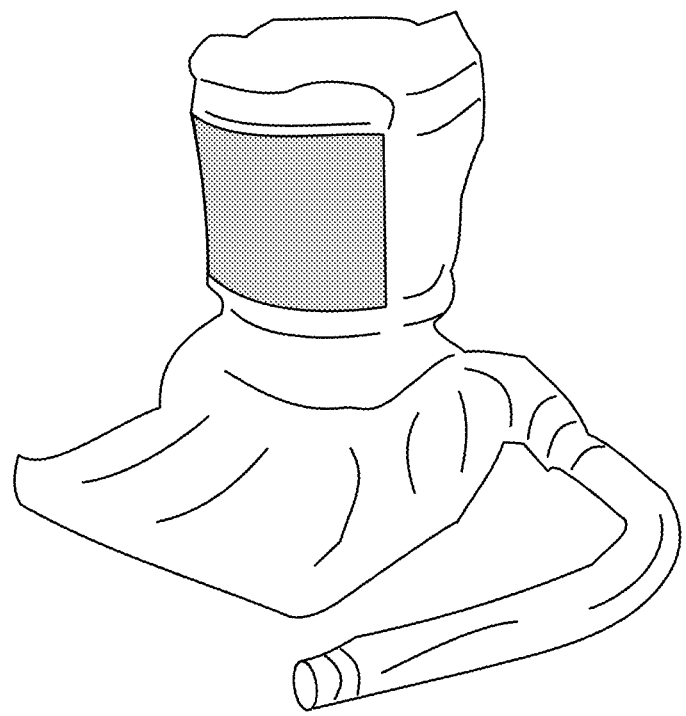
FIG. 32 depicts a conventional face mounted Powered Air Purifying Respirator (PAPR) head piece (prior art).

FIG. 32 depicts a conventional face mounted Powered Air Purifying Respirator (PAPR) head piece (prior art). It is connected to the backpack purification unit with a hose as shown. There are many kinds of different models available in the market ranging from $300-$600 for hospital and lab use. Everyday usage of the PAPR is basically out of the question and would not be accepted by many due to its cost, comfort, and bulk.

UV-C Dose Calculation in an Air Flow Environment, the "Airflow Filament" Concept UV-C dose calculation for a surface is a straight-forward calculation. For this, one needs first to calculate the UV-C irradiance in W/m² produced by the UV-C source at the point of interest on the surface. This calculated UV irradiance is multiplied by the exposure time in seconds to get the dose. This is expressed as, $$\text{Dose [W·sec/m}^2\text{]=UV Irradiance [W/m}^2\text{]×Exposure time[sec]} \quad (6.1)$$

Since [Watt]×[sec] is a Joule, the units of dose can also be written as Joule/m². There are many scientific publications that provide the required UV-C dose for many different bacteria and virus species based on laboratory measurements [4, 6, 8, 23, 39, 40, 41, 45, and 46]. The US Environmental Protection Agency has a UV guidance manual published in 2006, which any product needs to comply with as well [4]. Some of the dose requirements for a 90% kill of most bacteria and viruses range from 2,000 to 8,000 µW·sec/cm². The Covid-19 deactivation (kill) dose is believed to be in the 8,000 µW·sec/cm² range. The preferred unit of dose in the publications is µW·sec/cm², which can be converted to the W·sec/m² standard units by simply dividing it by 100 as, $$1 \, [\mu W \cdot sec/cm^2] = [W \cdot sec/m^2] \times 10^{-2} \quad (6.2)$$

Using the conversion factor given in (6.2), the kill dose of 8,000 µW·sec/cm² becomes 80 W·sec/m². Larger parasites, such as *Cryptosporidium* require a lower dose for inactivation. As a result, the U.S. Environmental Protection Agency has accepted UV disinfection as a method for drinking water plants to obtain *Cryptosporidium*, giardia, or virus deactivation credits. For example, for a 90% reduction of *Cryptosporidium*, a minimum dose of 2,500 µW·s/cm² is required based on the U.S. EPA UV Guidance Manual published in 2006 [4].

Calculations related to disinfecting an airflow, which is defined by an airflow volume with given airflow path and volumetric airflow rate, along with an arbitrary UV-C source geometry, illuminate that this volume is more complicated. The part irradiating air such that the all the pathogens present in the airflow are either killed or deactivated, is referred to herein as the "UV-C irradiation reactor".

First, the UV-C irradiance at every point on the airflow volume is non-uniform and must be calculated from the arbitrary UV-C source geometry provided. The source can be a single UV-C lamp or a UV-C LED, or multiples of them arranged in any configuration, and even with UV-C reflectors in place. This part will be covered in detailed in the next section.

Figure 33:
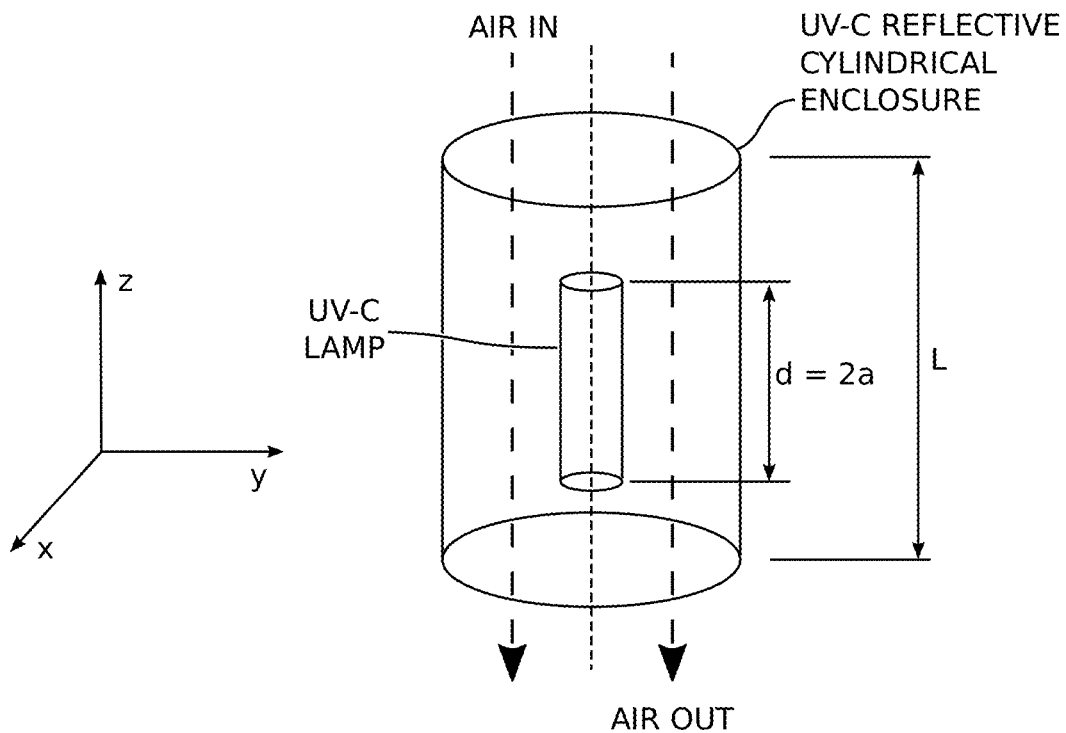
FIG. 33 is a diagram an exemplary UV-C irradiation reactor.

FIG. 33 is a diagram an exemplary UV-C irradiation reactor. The simplest geometrical form of a UV-C irradiation reactor is a single UV-C lamp, like TUV PL-S or any UV-C mercury discharge lamp listed in Table 4, placed in a tube where the forced air enters from one end and exits from the other end flowing parallel to the UV-C lamp as shown. This type of an arrangement may be referred to herein as the "radial UV-C irradiation reactor", having a turbulent flow that is more effective than an axial configuration.

Figure 34:
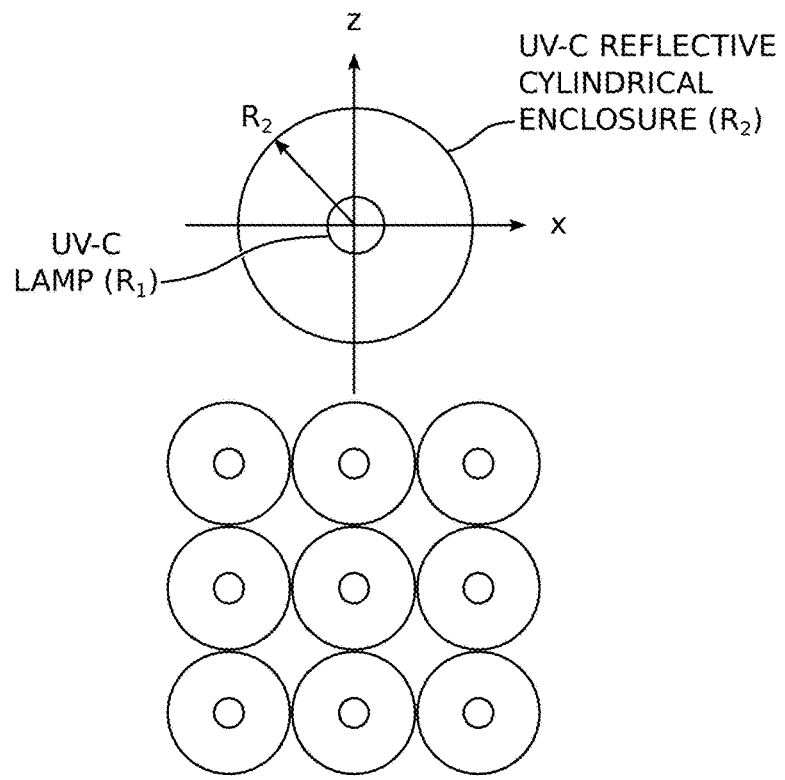
FIG. 34 is a diagram depicting a "radial UV-C irradiation reactor" where the airflow is parallel to the lamp axes.

FIG. 34 is a diagram depicting a "radial UV-C irradiation reactor" where the airflow is parallel to the lamp axes.

Figure 35:
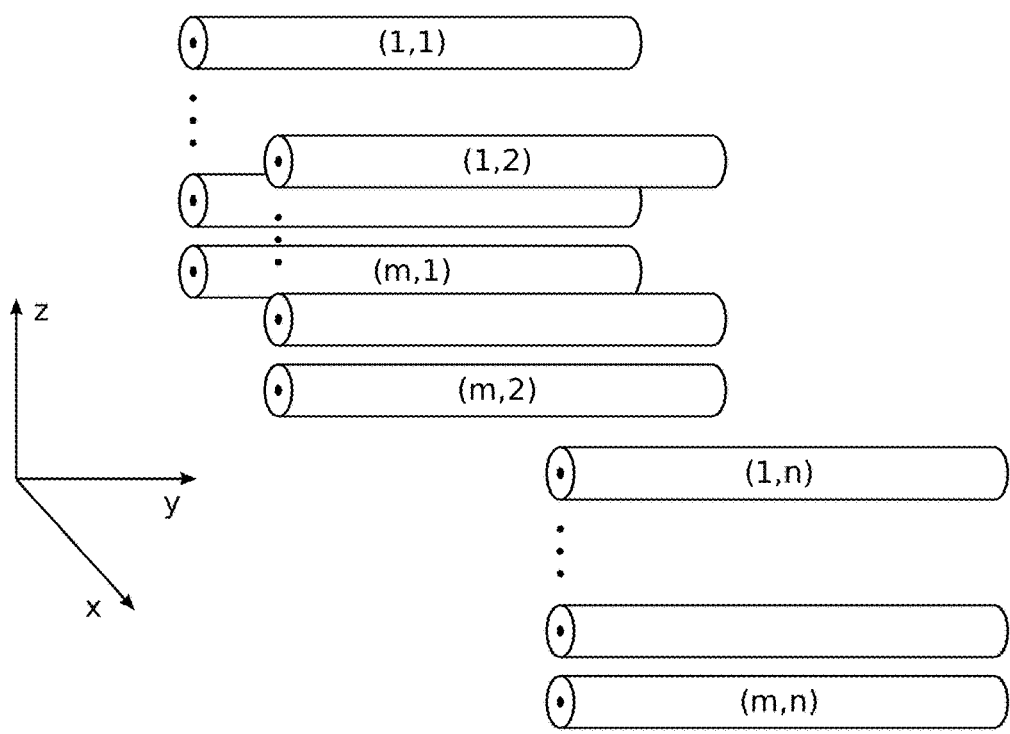
FIGS. 35 and 36 depict an array arrangement, respectively, for the radial UV-C irradiation reactor.
Figure 36:
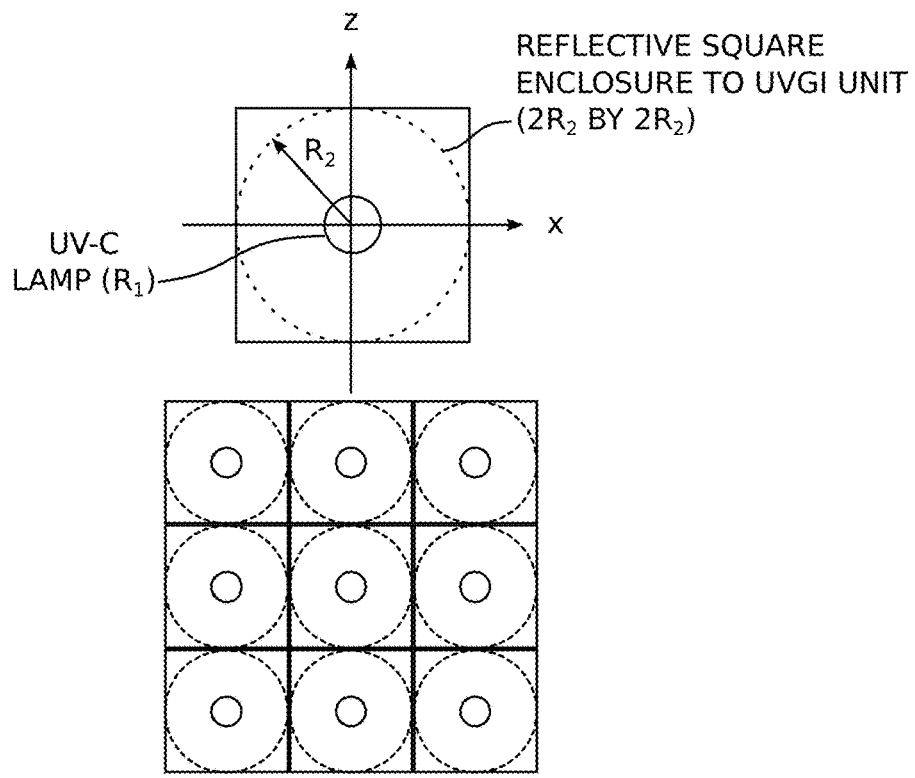

FIGS. 35 and 36 depict an array arrangement, respectively, for the radial UV-C irradiation reactor. The radial UV-C irradiation reactor design concern becomes, for a given UV-C source and required volumetric air-flow rate, the radius and length of the reactor needed to obtain the specified kill dose. A further concern is how the airflow and the reactor can be tailored to have a smaller, lighter, and more power efficient design without sacrificing safety.

It is assumed that the non-uniform UV-C irradiance at every point in the airflow volume is known or can be calculated. To obtain the desired kill dose in every part of the airflow, the UV-C source geometry and the airflow speed must be engineered well. The first step is to accurately calculate the UV-C irradiance (6.1), which any selected UV-C source produces at any coordinate in the airflow path. Then the airflow geometry and flow rate for the designed airflow can be calculated to make sure the system will satisfy 100% kill dose for every volume of air passing through.

The applicable theoretical dose and irradiance calculations are given for two different geometrical approximations of the UV-C mercury discharge lamp TUV PL-S 13 W/2P. The comparative simulation results are given for these two cases, using again 3 different physical models for calculating irradiance.

Figure 37:
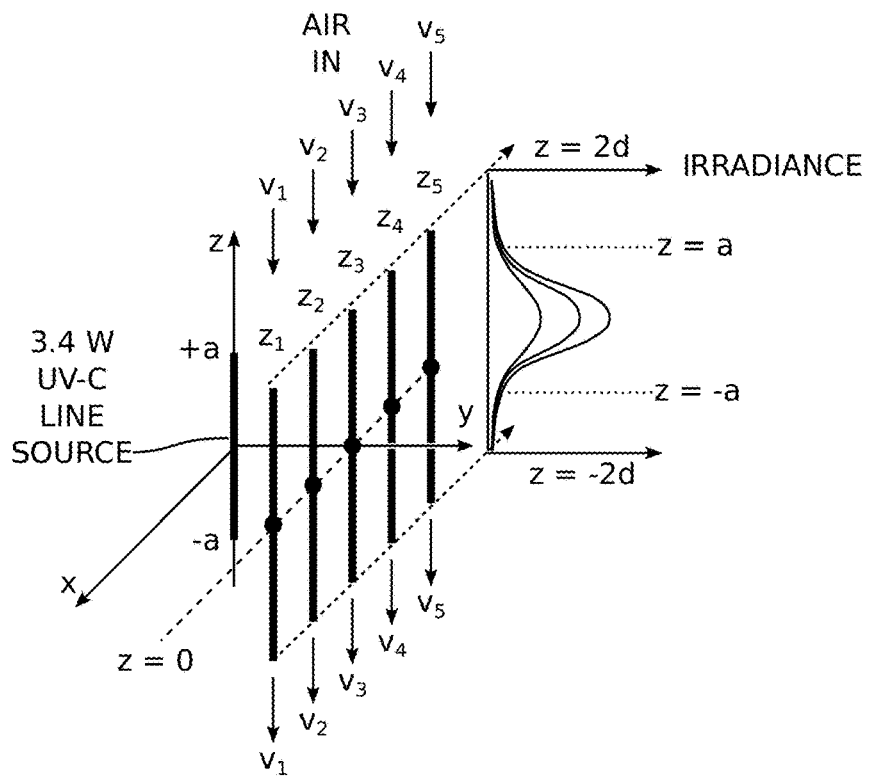
FIG. 37 is a perspective view depicting a one-filament geometric representation of the TUV PL-S 13 W/2P UV-C lamp with 5 air filaments.

FIG. 37 is a perspective view depicting a one-filament geometric representation of the TUV PL-S 13 W/2P UV-C lamp with 5 air filaments.

Figure 38:
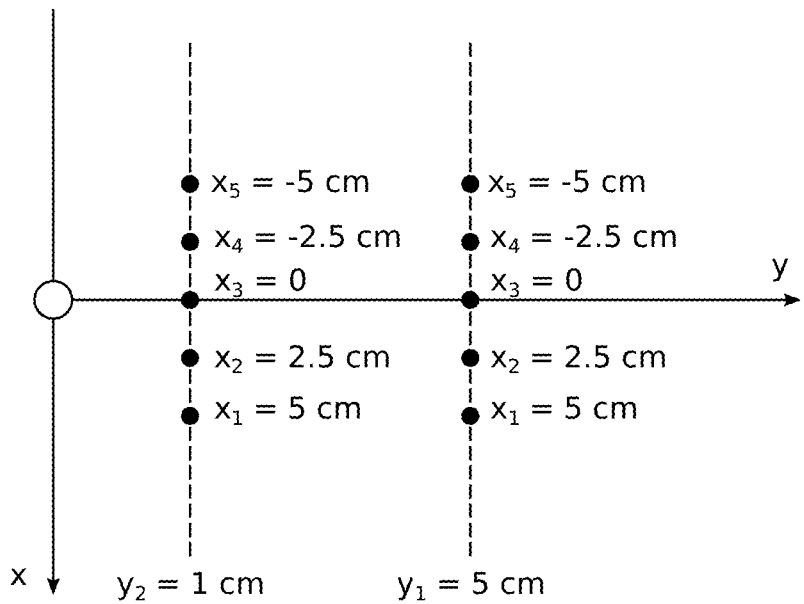
FIG. 38 depicts a xy plane view of the arrangement shown in FIG. 37.

FIG. 38 depicts a xy plane view of the arrangement shown in FIG. 37. All the mercury discharge lamps listed can be represented with a single filament UV-C source as in FIG. 37. A more accurate geometrical representation of the TUV PL-S 13 W/2P UV-C lamp and 5 air filaments can be obtained by representing it with 2 filaments as shown in FIG. 38.

Figure 39:
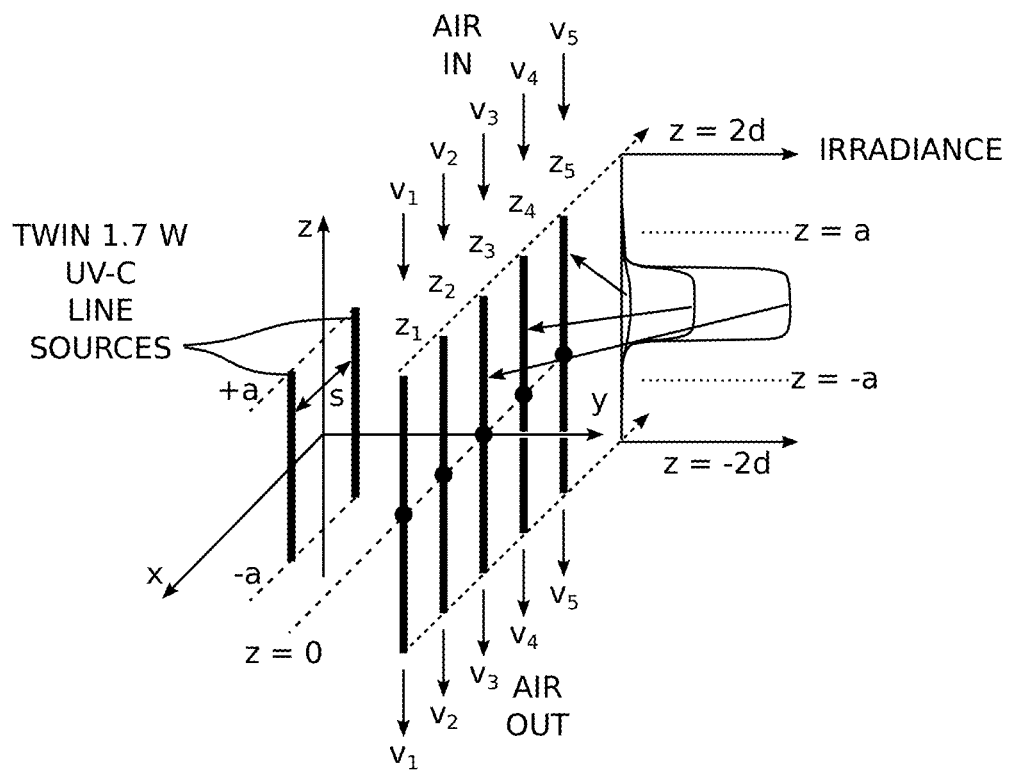
FIG. 39 is a perspective view depicting two-filament geometric representation of the TUV PL-S 13 W/2P UV-C lamp with 5 air filaments.

FIG. 39 is a perspective view depicting two-filament geometric representation of the TUV PL-S 13 W/2P UV-C lamp with 5 air filaments. As can be seen in both cases the UV-C light filament runs between −a≤z≤+a, where $$a = \frac{d}{2},$$

and where a=69.75 mm. The $z_1$ to $z_5$ lines represent "airflow filaments", where air is flowing along these filaments with a constant velocity v, parallel to the z axes. One can think of these airflow filaments as small diameter pipes or streamlines where air flows in them with a constant velocity v. It is assumed that the length of the airflow filaments is between −u≤z≤+u and that they are longer than the light filament, u>a. In the simulation example u is taken as 2d as shown in FIGS. 37 and 39. The centers of the $z_1$-$z_5$ airflow filaments are placed at z=0. As can be seen, the structures are symmetric reference to xy plane at z=0.

It is assumed that the incoming air is entering the airflow filaments from the top marked as "IN" with velocity v and maintaining the same velocity along the airflow filament, and coming out from the bottom, marked as "OUT". For this scenario, the exposure time; $E_t$ calculation is straightforward and is, $$E_t = \frac{2u}{v} = \frac{4d}{v} \quad (6.3)$$

Where 2u is simply the length of the airflow filament. As can be seen, if the UV-C intensity along the airflow filament is uniform, the dose calculation is simply given in (6.3).

However, the UV-C intensity is non-uniform along any airflow filament, and it is represented by I(z). Then, the dose D can be calculated by an integral relation rather than length given as, $$D = \int_{-u}^{u} I(z)\frac{dz}{v} = \frac{1}{v}\int_{-u}^{u} I(z)dz = \frac{1}{v}P_I \quad (6.4)$$

As can be seen, dz/v in (6.4) in the first part is the time dt, which is the time for the airflow to traverse the distance dz in FIGS. 37 and 39. This integral is referred to herein as the "irradiation integral". Moving v, which is assumed to be constant in the airflow filament, outside the integral gives the second term in the relation (6.4). If v is not constant and is a function of z, then the integral becomes, $$D = \int_{-u}^{u} \frac{I(z)}{v(z)}dz \quad (6.5)$$

Therefore, dose can still be calculated in any given path. Relation (6.5) is never the case because the assumption of a streamline or airflow filament requires that v be constant along a streamline.

Since $D=D_{KILL}$, the kill dose is already known, solving v from (6.4) gives the maximum airflow velocity $v_{MAX}$ that can be allowed to achieve the kill dose for the given UV-C power intensity integral on the streamline under consideration. $v_{MAX}$ can be calculated by solving v from (6.4) giving, $$v_{MAX} = \frac{1}{D_{KILL}}\int_{-u}^{u} I(z)dz \quad (6.6)$$

The $v_{MAX}$ defined in relation (6.6) is referred to herein as the "velocity equivalent of irradiation integral". For any arbitrary geometry airflow path where the airflow velocity can be approximated as a constant v in the entire airflow geometry, the power intensity integral $P_I$ can be generalized as, $$P_I = \int_{l_s}^{l_f} I(r)dl \quad (6.7)$$

The airflow path and the UV-C irradiation integral $P_I$ can be tailored to satisfy the kill dose requirement. Using (6.6) one can also calculate the needed value of the irradiation integral $P_I$ from a given $v_{MAX}$ to achieve a specified kill dose $D_{KILL}$ as, $$P_I = \int_{-u}^{u} I(z)dz = D_{KILL} \cdot v_{MAX} \quad (6.8)$$

Relations (6.6) and (6.8) are employed in two different design examples given below. The relation (6.6) is applied in the design example of a mercury vapor UV-C discharge lamp-based reactor design. As the second example, the UV-C LED based reactor design is based upon relation (6.8). Generalization of the Airflow Filament Concept to Non-Uniform Velocity Profile Flow regions.

Consider a circular cross-section pipe or a tube with a diameter D to be taken as the airflow path. The fluid velocity profiles in a tube or a pipe have been explained in detail above for laminar and turbulent flow conditions. From the required volumetric fluid-flow relation (2.10) one can simply calculate the average flow rate by dividing the fluid flow rate by cross-sectional area. Then, using the average volumetric fluid flow value with the relations given in (2.4-2.9) for laminar flow and (2.11-2.19) turbulent flow conditions, the cross-sectional fluid velocity profile in the tube can be calculated by finding the maximum value as a function of radius. By taking the minimum value of the calculated irradiation integral as given in (6.6) across the cross-section of the tube, the $v_{MAX}$ value of the calculated velocity profile can be determined in that cross-section. Thus, the design of the UV-C irradiation reactor becomes a combination of fluid dynamics relations and UV-C irradiation related calculations.

The next section gives a detailed methodology of how to calculate the UV-C irradiance analytically at any point as a function of any given UV-C source geometry and power.
Numerical Integration of the Irradiation Integral on the Airflow Filament or More Generally on any Arbitrarily Defined Airflow Path Most of the mathematical operations described herein are based on evaluating a complex integral. The irradiance calculation at a given point for any UV-C source requires an integration performed on the UV-C source. This integral for irradiance at any given point for all UV-C sources (e.g., the sources listed in Table 4) can be analytically calculated. This is due to the fact that they are all geometrically simple structures and they all can be approximated very closely with a line, point, or a cylindrical structure, where the desired integral can be evaluated analytically. Using coordinate transformations and the super-position principle, irradiance from arbitrarily placed and configured combinations of line, cylindrical, and point sources can also be analytically calculated. This is a difficult, laborious, and error-prone task for hand calculations, but it is a straightforward task for the UVGI Designer program. As described above, the dose calculation requires the irradiance integral on a straight line which is referred to herein as an airflow filament. This air-flow filament can be generalized as a path like a constant air velocity streamline, so the irradiance integral needs to be calculated on this path. Analytical calculation of the irradiation integral in general becomes impossible or non-practical. Therefore, all the irradiation integrals described herein are evaluated numerically.

The numerical integration task used in UVGI Designer is a very general adaptive numerical integration routine applied to any selected airflow filament or path. The major steps of the adaptive-iterative numerical integration algorithm employed in this work can be summarized as;

i) The airflow filament or path is sampled with equally spaced n points. This process is called mesh generation. This is iteration counted until k=1,
ii) Calculate irradiance values for all n mesh points analytically,
iii) Since the spacing between the mesh points is known, one can use one of the many well-known numerical integration methods. Use the specified integration method from trapezoidal rule, Simpson's rule, Newton-Cote's, or Romberg's method to calculate the irradiation integral needed given in (6.4)-(6.7),
iv) Store the integral value $P_I$ (k) at iteration k,
v) If k=1, go to vii,
vi) Compare the integral value with the previous integral value obtained with the previous mesh. If the difference is larger than specified, Go to viii,
vii) Numerically calculate second order derivatives at each mesh point and refine the mesh by halving the spacing accordingly at needed mesh intervals having a larger number of "new n" mesh points and keeping the adjacent mesh spacing ratio between 2 and 3. Go to ii, This step is only performed once, at the first pass when k=1 to find the intervals where the higher derivatives are large. In the linear regions increasing the mesh points will not increase the accuracy, vii) Return.

This numerical integration flow is used in all numerical integrations employed herein. It is also applicable for evaluating the irradiation at any given point from a complex geometry UV-C source numerically, where an analytical integration is not possible or too difficult.

Mathematical Derivations of UV-C Irradiance from Cylindrical Sources.

As can be seen in Table 4, all the UV-C mercury discharge lamps, except the first one (TUV PL-S 13 W/2P UV-C), have cylindrical geometries. On the other hand, the TUV PL-S 13 W/2P UV-C discharge lamp is made up of two "connected" cylindrical UV-C sources.

It is known that one can calculate irradiance at a given point on a surface from a cylindrical source by approximating it with an infinitely thin filament, radiating a uniform radiant power density along its length analytically. Lumen, candela, and lux calculations for standard fluorescent tube lighting can be derived using this method.

The TUV PL-S 13 W/2P UV-C discharge lamp is geometrically the most complicated structure in Table 4. However, due to its compact size, it is suitable for use in a portable/wearable safe face shield application. Therefore, formulations are performed for the TUV PL-S 13 W/2P UV-C discharge lamp, which can also be generalized for any number of cylindrical sources configured in any orientation.

Figure 40:
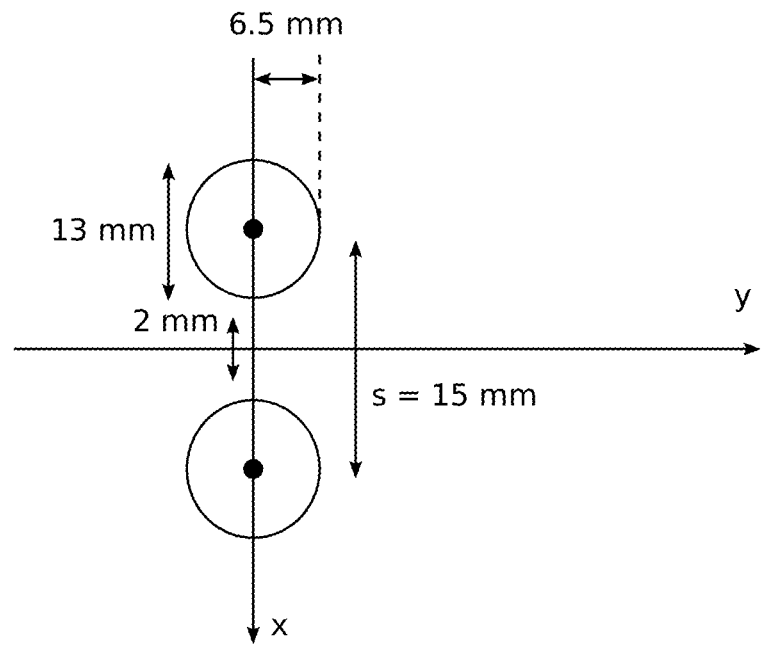
FIG. 40 is a plan view of the TUV PL-S 13 W/2P UV-C lamp.

FIG. 40 is a plan view of the TUV PL-S 13 W/2P UV-C lamp. The lamp is d=139.5 mm long, with side-by=side 2 cylindrical tubes, each having a diameter of 13 mm, and separated by a 2 mm gap. It is fair to assume that each tube generates the same amount of UV-C power and the radiation is uniformly distributed along the length of each tube. As a result of this assumption, each of the cylindrical tube generates 3.4/2=1.7 Watts. The UV-C radiation power density per unit length in each UV-C tube then becomes σ=1.7/0.1395=12.195 W/m or 12.195 mW/mm. Since the length-to-diameter ratio of the TUV PL-S 13 W/2P is large (139.5/13>10.73), this radiating geometry can be approximated very accurately with 2 parallel infinitely thin radiating filaments separated by a spacing s=13+2=15 mm, each radiating 253.7 nm wavelength UV-C radiation with a 12.195 W/m power density.

Since the separation s, between the tubes is small compared to their lengths, one can further approximate them as a single filament having the same length filament placed at a Z axis with twice the radiative power density, as compared to the twin filament approximation, given as σ=3.4/0.1395=24.39 [W/m] or 24.39 mW/mm. This geometrical single filament approximation gives accurate enough irradiance calculations for distances larger than the spacing between the tubes. This is r>2 mm radial distance from the z axis, and is a small dimension with respect to the irradiance reactor dimensions. The comparative simulations which are given from this approximation are valid for irradiance calculations of distances larger than spacings between the tubes for the TUV PL-S 13 W/2P UV-C lamp geometry.

Mathematical Derivation of the UV-C Irradiance from a Filament Source at a Given Point on a Non-Transparent Surface In the filament or line method [37, 40, 41], the cylindrical source is approximated by an infinitely thin line segment or, in other words, a filament having a uniform UV-C radiating power density of σ W/m given as, $$\sigma = \frac{P_{UV-C}}{d} \quad (7.1)$$

Where $P_{UV-C}$ and d are the total radiative UV-C power in Watts, and length of the filament in meters, respectively.

Figure 41:
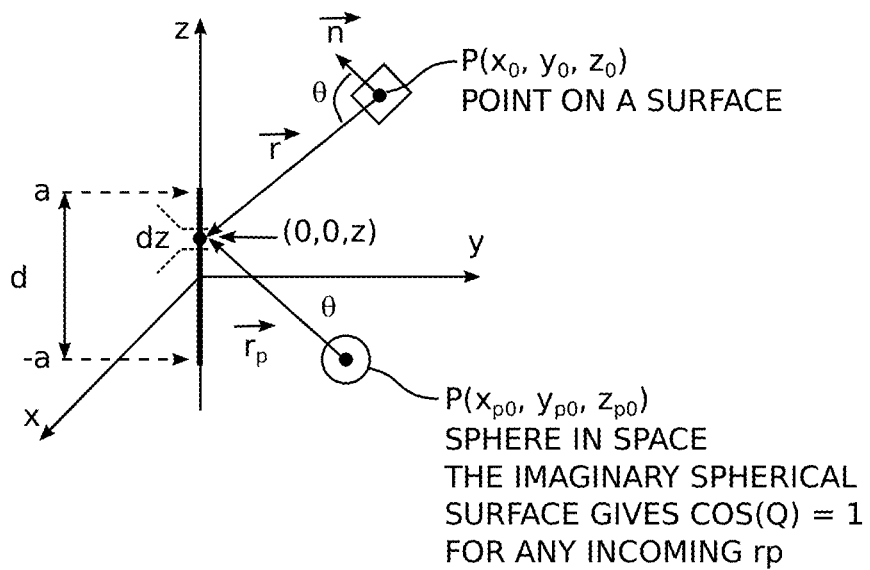
FIG. 41 depicts the basis for the analytical derivation of the irradiance calculations for a single filament UV-C source on a surface and a point in space.

FIG. 41 depicts the basis for the analytical derivation of the irradiance calculations for a single filament UV-C source on a surface and a point in space. The UV-C radiating filament is placed on the z axis between z=−a and z=+a, and it has a uniform power density of σ W/m as given in (7.1), which corresponds to σ=3.4/0.1395=24.37 W/m. The symbol "a" is the half the length (d) of the UV-C lamp. In the case of the TUV PL-S 13 W/2P where a=d/2=139.5/2=69.75 mm, this is the same length as the twin tube filament approximation shown in FIG. 39.

One needs to be able to calculate the irradiance produced by the UV-C lamp at a surface with a given normal vector n at arbitrary point $x_0$, y, $z_0$ coordinates selected on the air flow path.

Let r be a vector joining to an arbitrary point on the selected surface $x_0$, y, $z_0$ to an arbitrarily selected coordinate (0,0,z) on the lamp filament which can be represented as, $$r = x_0 i + y_0 j + (z_0 - z) k \quad (7.2)$$

The i, j, k are the unit vectors along x, y and z axes, respectively. Let the unit outward normal vector in the proper direction to the surface where the irradiance flux calculation is done be represented as, $$n = x_n i + y_n j + z_n k \quad (7.2)$$

As an example, if the surface that where the power density flux calculation is selected as the spherical surface centered at the origin, its outward unit normal vector is simply, $$n = \frac{x_0 i + y_0 j + z_0 k}{\sqrt{x_0^2 + y_0^2 + y_0^2}} \quad (7.3)$$

Dot product of n·r gives, $$n \cdot r = x_n x_0 + y_n y_0 + z_n (z_0 - z) \quad (7.4)$$

Irradiance at the point $x_0$, $y_0$, $z_0$ in the direction of the n vector can be calculated with the integral on the UV-C filament placed at the z axis from z=−a to z=+a as, $$I = \frac{\sigma}{4\pi} \int_{-a}^{+a} \frac{n \cdot r}{|r|^3} dz \quad (7.5)$$

The integral (7.5) I represents irradiance, which includes the "cosine effect" as it is known in engineering and science. As can be seen, a is the half of the length of the UV-C lamp and it appears in the lower and upper integral limits, and σ is the UV-C radiation power density. The integral (7.5) explicitly becomes, $$I = \frac{\sigma}{4\pi} \int_{-a}^{+a} \frac{x_n x_0 + y_n y_0 + z_n (z_0 - z)}{[x_0^2 + y_0^2 + (z_0 - z)^2]^{\frac{3}{2}}} dz \quad (7.6)$$

Integral (7.6) can be written as the sum of basically three integrals as, $$I_1 = \sigma \frac{x_n x_0}{4\pi} \int_{-a}^{+a} \frac{1}{[x_0^2 + y_0^2 + (z_0 - z)^2]^{\frac{3}{2}}} dz \quad (7.7)$$

$$I_2 = \sigma \frac{y_n y_0}{4\pi} \int_{-a}^{+a} \frac{1}{[x_0^2 + y_0^2 + (z_0 - z)^2]^{\frac{3}{2}}} dz \quad (7.8)$$

$$I_3 = \sigma \frac{1}{4\pi} \int_{-a}^{+a} \frac{z_n(z_0 - z)}{[x_0^2 + y_0^2 + (z_0 - z)^2]^{\frac{3}{2}}} dz \quad (7.9)$$

$I_3$ integral could be split into two different components as, $$I_{31} = \sigma \frac{z_n z_0}{4\pi} \int_{-a}^{+a} \frac{1}{[x_0^2 + y_0^2 + (z_0 - z)^2]^{\frac{3}{2}}} dz \quad (7.10)$$

$$I_{32} = -\sigma \frac{z_n}{4\pi} \int_{-a}^{+a} \frac{z}{[x_0^2 + y_0^2 + (z_0 - z)^2]^{\frac{3}{2}}} dz \quad (7.11)$$

Integrals $I_1$, $I_2$, $I_{31}$ in expressions (7.7), (7.8), and (7.10) are the same type of integrals having their indefinite integrals form as [29-31], $$\int \frac{dz}{(t^2 + z^2)^{\frac{3}{2}}} = \frac{z}{t^2 \sqrt{(t^2 + z^2)}} \quad (7.12)$$

On the other hand, $I_{32}$ (7.11) can calculated using the form [29-31], $$\int \frac{z dz}{(t^2 + z^2)^{\frac{3}{2}}} = -\frac{1}{\sqrt{(t^2 + z^2)}} \quad (7.13)$$

Using the form (7.12) for the integrals in $I_1$, $I_2$, $I_{31}$ gives, $$\int \frac{1}{[x_0^2 + y_0^2 + (z_0 - z)^2]^{\frac{3}{2}}} dz = -\frac{z_0 - z}{(x_0^2 + y_0^2)\sqrt{[x_0^2 + y_0^2 + (z_0 - z)^2]}} \quad (7.14)$$

Using the form (7.13) for the integral $I_{32}$ gives, $$\int \frac{z dz}{[x_0^2 + y_0^2 + (z_0 - z)^2]^{\frac{3}{2}}} = -\frac{1}{\sqrt{[x_0^2 + y_0^2 + (z_0 - z)^2]}} \quad (7.15)$$

Analytical derivation for the 2 filament approximation of the TUV PL-S 13 W/2P UV-C lamp can be done using superposition and coordinate transformation principles applied to the derivation given above. The UVGI Designer program also can calculate any number of arbitrarily placed filaments with arbitrary orientations using general superposition and coordinate transformation principles using "surface irradiance" formulation as a user input.

Later, in the simulation results section, one and two filament results are compared with one and two filament results of irradiance formulation and UV-C LED simulation results. To make the comparison clear, the derivation for one-filament surface irradiance calculation is denoted as, $$I_{1,1FIL}(r) = \frac{\sigma}{4\pi} \int_{-a}^{+a} \frac{n \cdot r}{|r|^3} dz \quad (7.16)$$

The two-filament "surface irradiance" formulation is denoted as, $$I_{1,2FIL}(r) = \frac{\sigma}{4\pi} \int_{-a}^{+a} \frac{n \cdot r}{|r|^3} dz \quad (7.17)$$

The first subscript "1" in (7.16) and (7.17) represents the first formulation corresponding to surface irradiance and the second subscript "1FIL" and "2FIL" represent 1 and 2 filament approximations for the TUV PL-S 13 W/2P.

Figure 42:
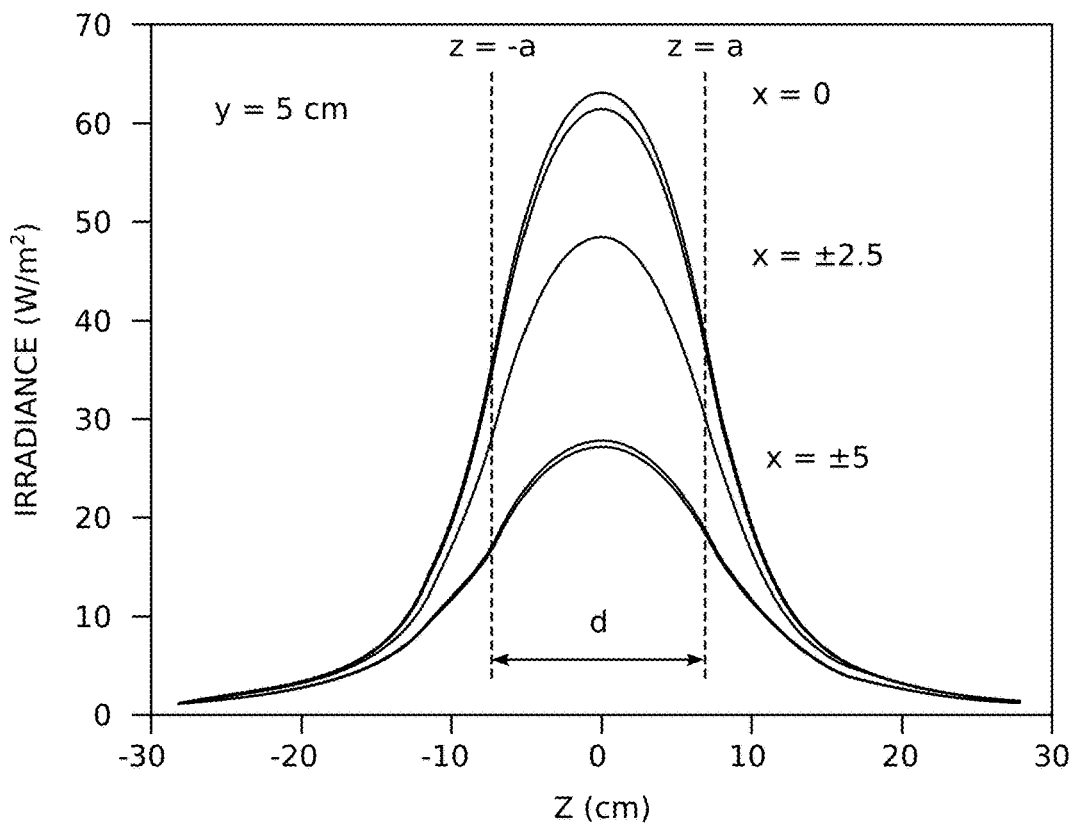
FIG. 42 illustrates $I_{1,1FIL}$ and $I_{1,2FIL}$ irradiation integrals as given in (7.16) and (7.17) along an airflow filament oriented parallel to the z axes at y=5 cm and at five x coordinates given as x=0, ±2.5, and ±5 cm as a function of z.

FIG. 42 illustrates $I_{1,1FIL}$ and $I_{1,2FIL}$ irradiation integrals as given in (7.16) and (7.17) along an airflow filament oriented parallel to the z axes at y=5 cm and at 5 x coordinates given as x=0, +2.5, and ±5 cm as a function of z.

Figure 43:
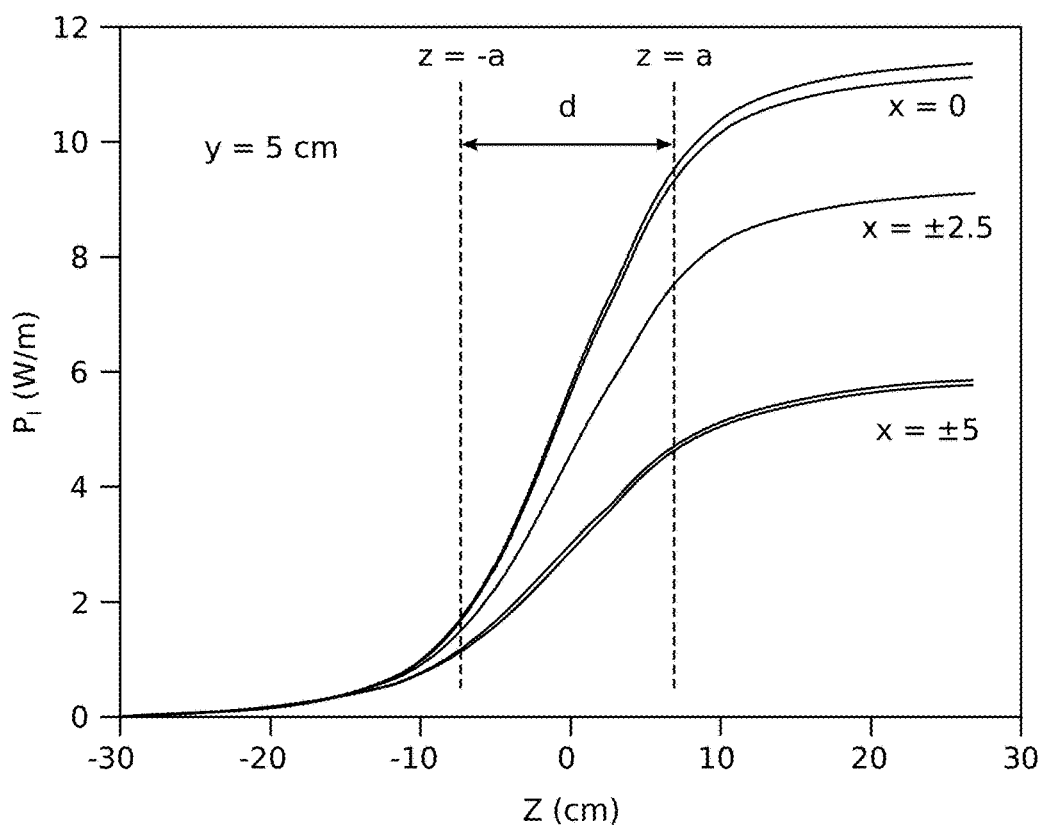
FIG. 43 depicts the integrals of $I_{1,1FIL}$ and $I_{1,2FIL}$ shown in FIG. 42, which are denoted as $P_{1,1FIL}$ and $P_{1,2FIL}$ integrals with respect to z, as defined in its most general form given in (6.7).

FIG. 43 depicts the integrals of $I_{1,1FIL}$ and $I_{1,2FIL}$ shown in FIG. 42, which are denoted as $P_{1,1FIL}$ and $P_{1,2FIL}$ integrals with respect to z, as defined in its most general form given in (6.7). The numerical value of the integrals divided by the given kill dose defines the maximum air velocity $v_{MAX}$ to achieve that kill dose as given at relation (6.6).

Figure 44:
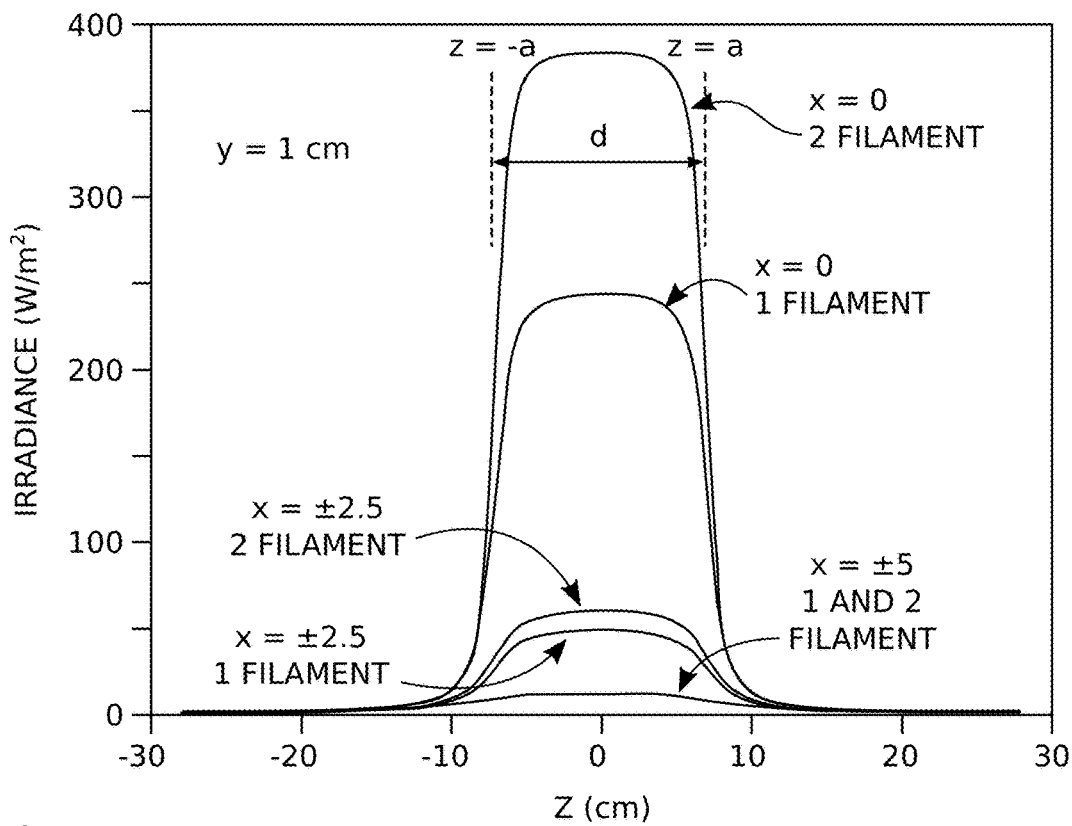
FIG. 44 illustrates $I_{1,1FIL}$ and $I_{1,2FIL}$ irradiation integrals as given in (7.16) and (7.17) along an airflow filament oriented parallel to the z axes at y=1 cm and at 5 x coordinates given as x=0, ±2.5, and ±5 cm.

FIG. 44 illustrates $I_{1,1FIL}$ and $I_{1,2FIL}$ irradiation integrals as given in (7.16) and (7.17) along an airflow filament oriented parallel to the z axes at y=1 cm and at 5 x coordinates given as z=0, +2.5, and ±5 cm.

Figure 45:
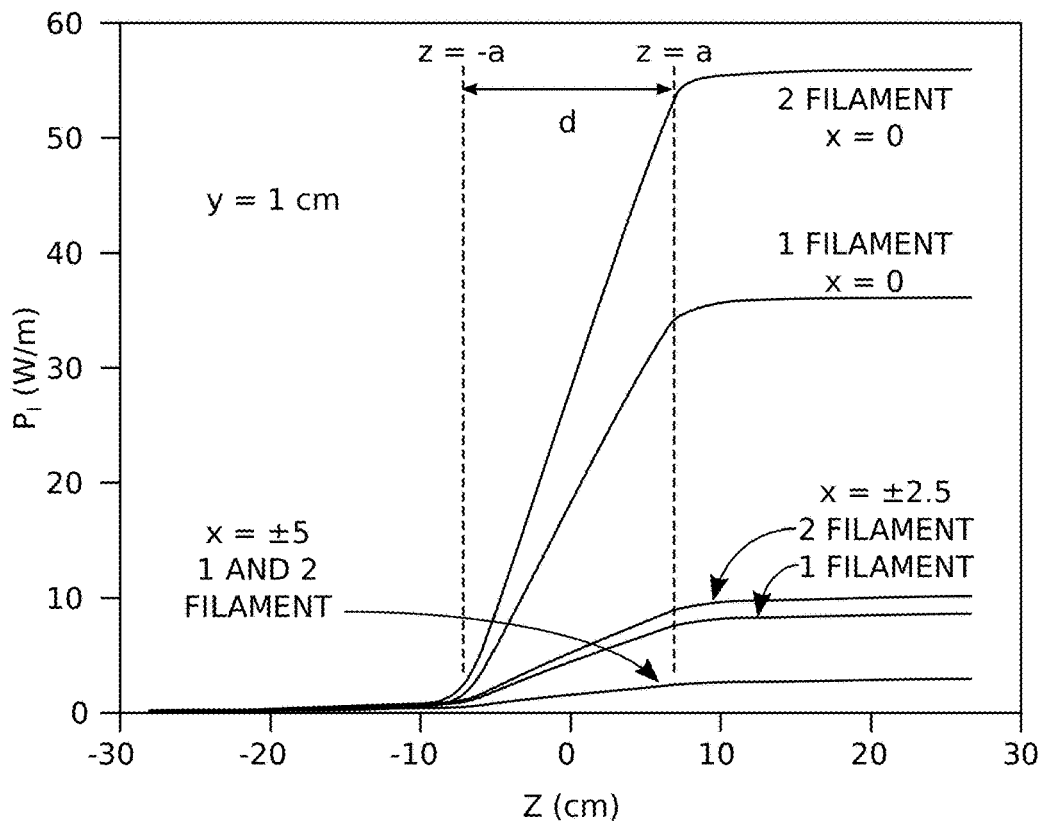
FIG. 45 show the integrals of $I_{1,1FIL}$ and $I_{1,2FIL}$ shown in FIG. 44, which are denoted as $P_{1,1FIL}$ and $P_{1,2FIL}$ integrals with respect to z, as defined in its most general form given as in (6.7).

FIG. 45 show the integrals of $I_{1,1FIL}$ and $I_{1,2FIL}$ shown in FIG. 44, which are denoted as $P_{1,1FIL}$ and $P_{1,2FIL}$ integrals with respect to z, as defined in its most general form given as in (6.7). The numerical value of the integrals divided by the given kill dose defines the maximum air velocity $v_{MAX}$ to achieve that kill dose as given at relation (6.6).

Mathematical Derivation of the UV-C Irradiance from a Filament Source at a Spherical Object at a Given Point in Space, the $I_{2,2FIL}$, $P_{2,2FIL}$ the UVGI Case The derivation of irradiance above is for a surface, not for a point or a spherical surface floating in air. Irradiance derivation for Corona virus or any kind of virus or bacteria floating in air depends on the perpendicular cross-sectional area exposed to the UV-C radiation direction. A virus like Coronavirus, due to its spherical symmetry, captures or absorbs a photon or radiation of any sort independent of the direction of radiation, therefore the cosine law in the irradiation formula cannot be valid.

On the other hand, for UVGI application to a *Tuberculosis bacillus*, which is a rod shape bacterium having a diameter of 2-4 μm and 200-500 nm length, the perpendicular cross-sectional area which is exposed in the direction of radiation is very dependent to its relative orientation with respect to the propagation direction. UVGI Designer handles this problem by applying Monte-Carlo simulation defining these non-symmetric structures with two uniformly distributed statistically independent random numbers in the θ and φ directions in spherical coordinates.

In the end, the kill, or more properly, the deactivation of a virus is an irreversible damage to its molecular structure due to a photon-molecule interaction resulting in a bond breaking, just like in the photo-electric phenomena experimentally shown by Phillip Lenard in 1900 and formulated by Einstein in 1905, which was the subject of his Nobel prize in physics in 1921. A bond breaking action can only occur if the photon energy is greater than a certain threshold level. A large photon flux with energies less than a threshold energy level will not generate any bond breaking damage. Only photon flux having an energy level above a threshold energy causes damage to the bacteria or virus. The exact photon energy for deactivation of Covid-19 virus is not known at this date. Studies in this area only state that UV-C range of radiation effective for Covid-19 is in the 100<λ<280 nm wavelength band, which corresponds to 4.428 to 12.399 eV of photon energies.

As a result, removing the "cosine effect" from the irradiance integral (7.5) for a single filament becomes, $$I = \frac{\sigma}{4\pi} \int_{-a}^{+a} \frac{1}{|r|^2} dz \tag{7.19}$$

Explicitly (7.19) becomes, $$I = \frac{\sigma}{4\pi} \int_{-a}^{+a} \frac{dz}{[x_0^2 + y_0^2 + (z_0 - z)^2]} \tag{7.20}$$

As can be seen, it is a simpler integration and gives higher values for a point with the same distances to the filament, as compared to the integral (7.5) with the cosine effect.

With variable transformations, $$t^2 = x_0^2 + y_0^2 \text{ or } t = \sqrt{x_0^2 + y_0^2} \tag{7.21}$$

And, $$v = (z_0 - z) \tag{7.22}$$

The indefinite integral can be transformed into a well-known integral form [29, 30, 31], $$-\int \frac{dv}{(t^2 + v^2)} = -\frac{1}{t} \tan^{-1}\left(\frac{v}{t}\right) \tag{7.23}$$

Giving, $$\int \frac{dz}{[x_0^2 + y_0^2 + (z_0 - z)^2]} = -\frac{1}{\sqrt{x_0^2 + y_0^2}} \tan^{-1}\left[\frac{(z_0 - z)}{\sqrt{x_0^2 + y_0^2}}\right] \tag{7.24}$$

As a result, the definite integral (4.2) by applying its upper and lower integration limits the irradiance explicitly becomes a simpler expression as, $$I = \frac{\sigma}{4\pi} \frac{1}{\sqrt{x_0^2 + y_0^2}} \left\{ \tan^{-1}\left[\frac{(z_0 + a)}{\sqrt{x_0^2 + y_0^2}}\right] - \tan^{-1}\left[\frac{(z_0 - a)}{\sqrt{x_0^2 + y_0^2}}\right] \right\} \tag{7.25}$$

Analytical derivation for the 2 filament approximation of the TUV PL-S 13 W/2P UV-C lamp can be done using superposition and coordinate transformation principles applied to the derivation given as well.

To make the comparison clear in the simulation results section, the derivation for one filament point irradiance calculation is denoted as, $$I_{2,1FIL}(r) = \frac{\sigma}{4\pi} \int_{-a}^{+a} \frac{1}{|r|^2} dz \tag{7.26}$$

The two-filament "point irradiance" formulation is denoted as, $$I_{2,2FIL}(r) = \frac{\sigma}{4\pi} \int_{-a}^{+a} \frac{1}{|r|^2} dz \tag{7.27}$$

The first subscript "2" in (7.26) and (7.27) represents the second formulation corresponding to point irradiance and the second subscript "1FIL" and "2FIL" represent 1 and 2 filament approximations for the TUV PL-S 13 W/2P.

The UVGI Designer program also can calculate any number of arbitrarily placed filaments with arbitrary orientations using general superposition and coordinate transformation principles using the point irradiance formulation as a user input.

Figure 46:
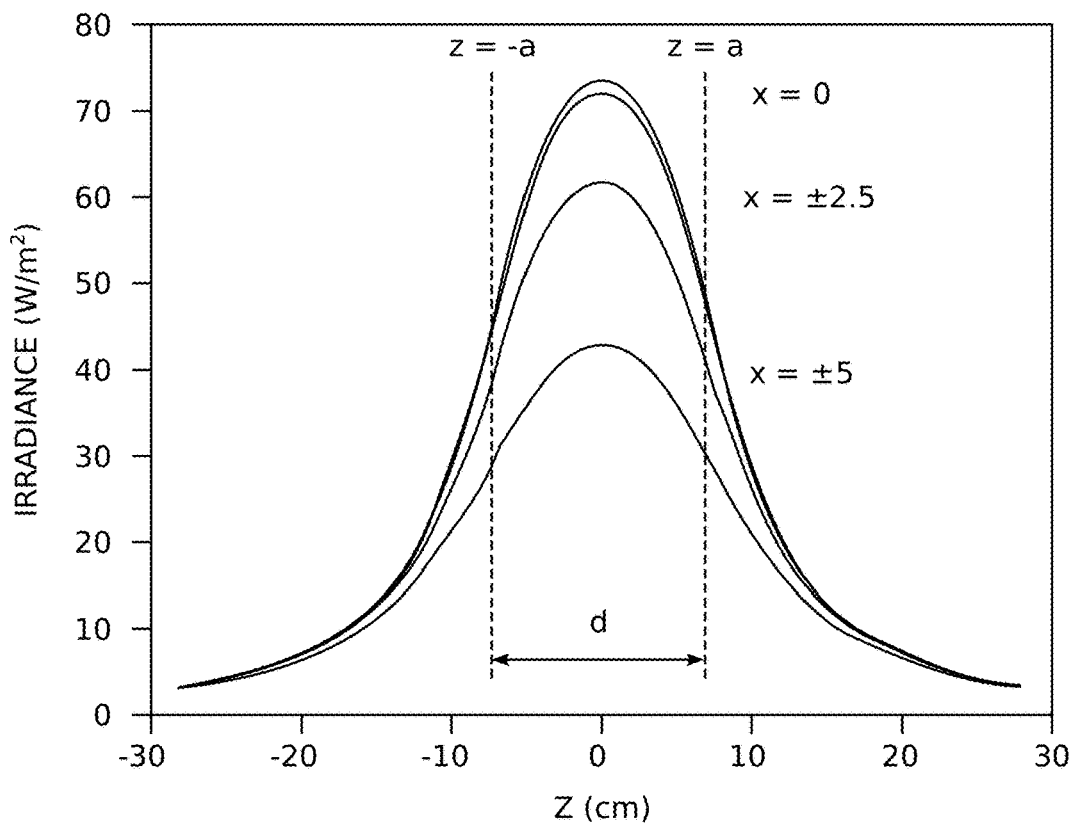
FIG. 46 illustrates $I_{2,1FIL}$ and $I_{2,2FIL}$ irradiation integrals as given in (7.26) and (7.27) along an airflow filament oriented parallel to the z axis at y=5 cm and at 5 x coordinates given as x=0, ±2.5, and ±5 cm.

FIG. 46 illustrates $I_{2,1FIL}$ and $I_{2,2FIL}$ irradiation integrals as given in (7.26) and (7.27) along an airflow filament oriented parallel to the z axis at y=5 cm and at 5 x coordinates given as x=0, ±2.5, and ±5 cm.

Figure 47:
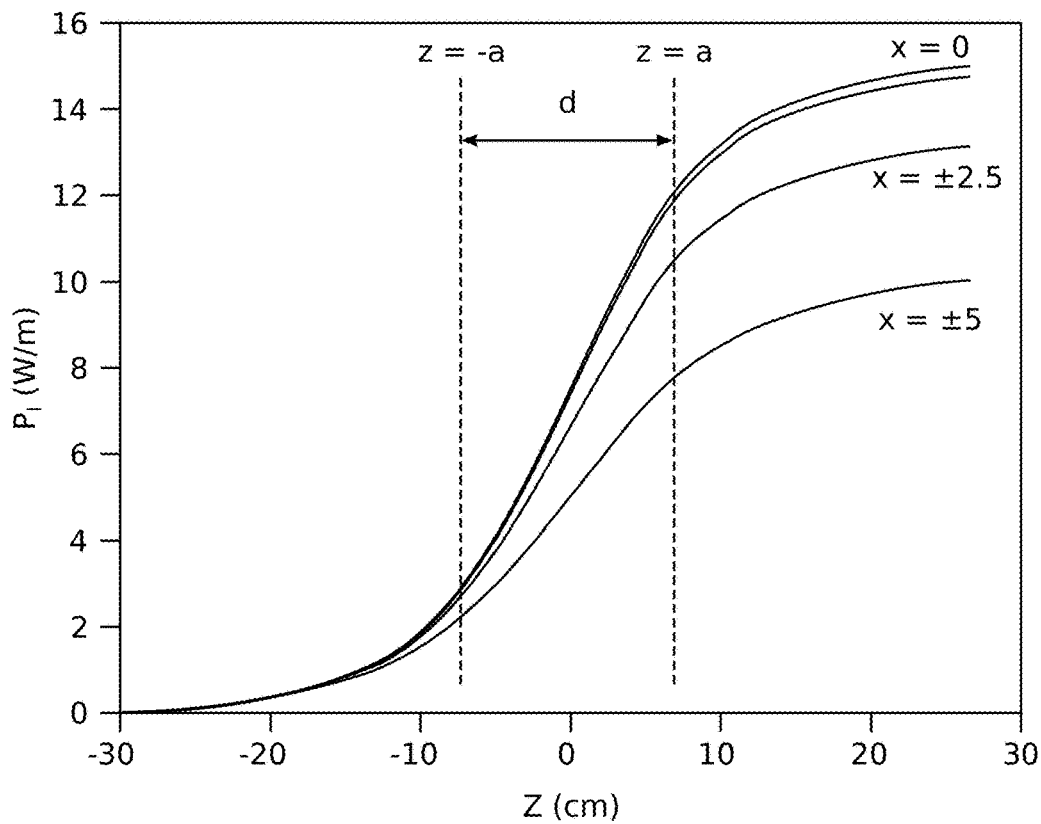
FIG. 47 show the integrals $I_{2,1FIL}$ and $I_{2,2FIL}$ from FIG. 46, which are denoted as $P_{2,1FIL}$ and $P_{2,2FIL}$ integrals with respect to z defined in its most general form in (6.7).

FIG. 47 show the integrals $I_{2,1FIL}$ and $I_{2,2FIL}$ from FIG. 46, which are denoted as $P_{2,1FIL}$ and $P_{2,2FIL}$ integrals with respect to z defined in its most general form in (6.7). The numerical value of the integrals divided by the given kill dose defines the maximum air velocity $v_{MAX}v_{MAX}$ to achieve that kill dose as given in relation (6.6).

Figure 48:
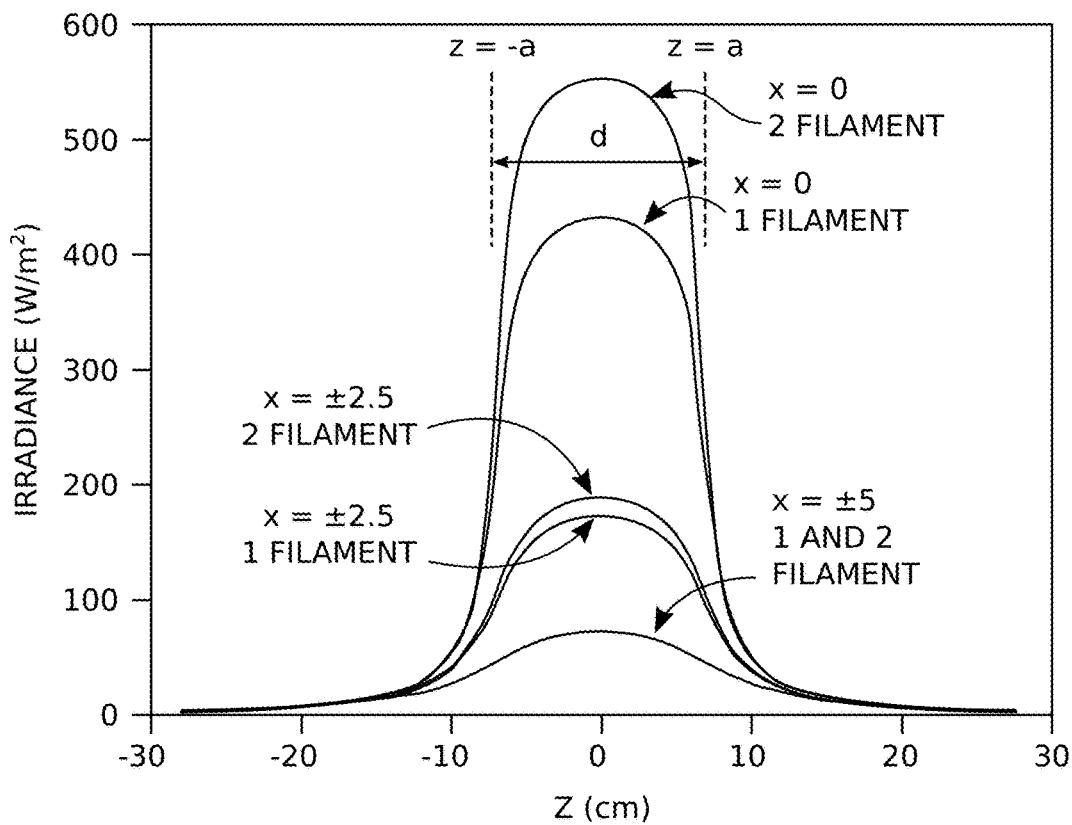
FIG. 48 illustrates $I_{2,1FIL}$ and $I_{2,2FIL}$ irradiation integrals as given in (7.26) and (7.27) along an airflow filament oriented parallel to the z axis at y=1 cm and at five z coordinates given as x=0, ±2.5, and ±5 cm.

FIG. 48 illustrates $I_{2,1FIL}$ and $I_{2,2FIL}$ irradiation integrals as given in (7.26) and (7.27) along an airflow filament oriented parallel to the z axis at y=1 cm and at 5 x coordinates given as x=0, ±2.5, and ±5 cm.

Figure 49:
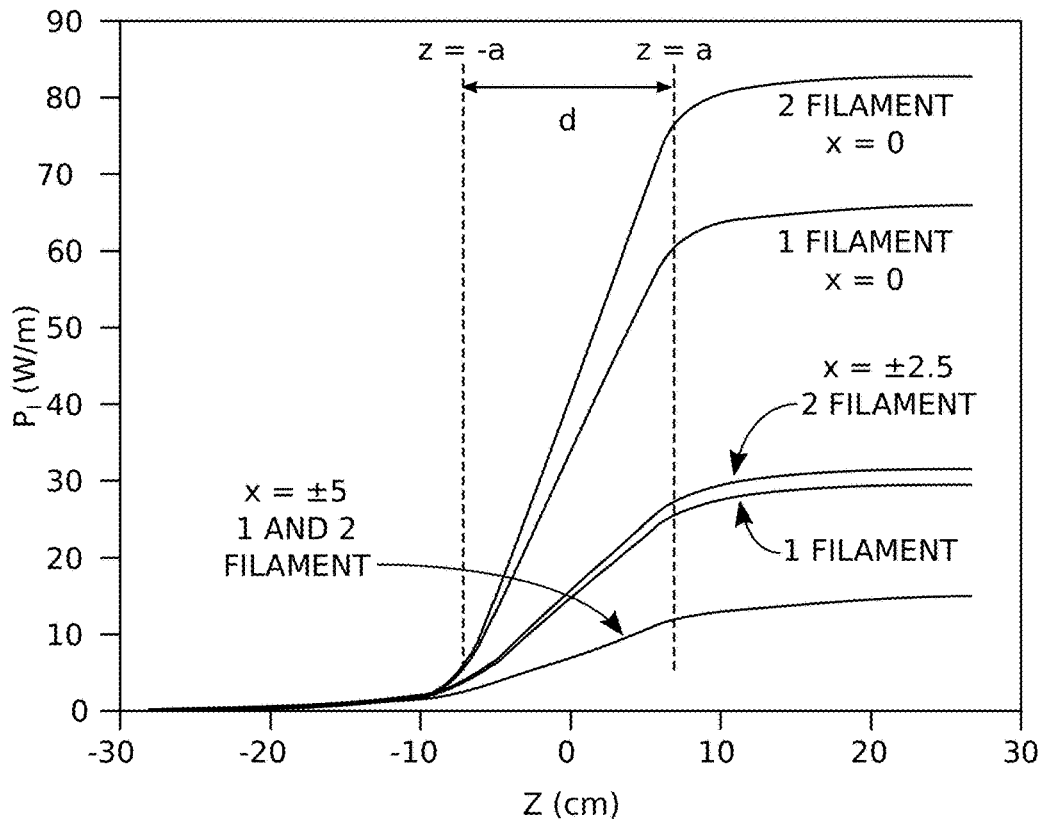
FIG. 49 shows the integrals $I_{2,1FIL}$ and $I_{2,2FIL}$ from FIG. 48. which are denoted as $P_{2,1FIL}$ and $P_{2,2FIL}$ integrals with respect to z defined in its most general form in (6.7).

FIG. 49 shows the integrals $I_{2,1FIL}$ and $I_{2,2FIL}$ from FIG. 48, which are denoted as $P_{2,1FIL}$ and $P_{2,2FIL}$ integrals with respect to z defined in its most general form in (6.7). The numerical value of the integrals divided by the given kill dose defines the maximum air velocity $v_{MAX}$ to achieve that kill dose as given in relation (6.6).

Figure 50:
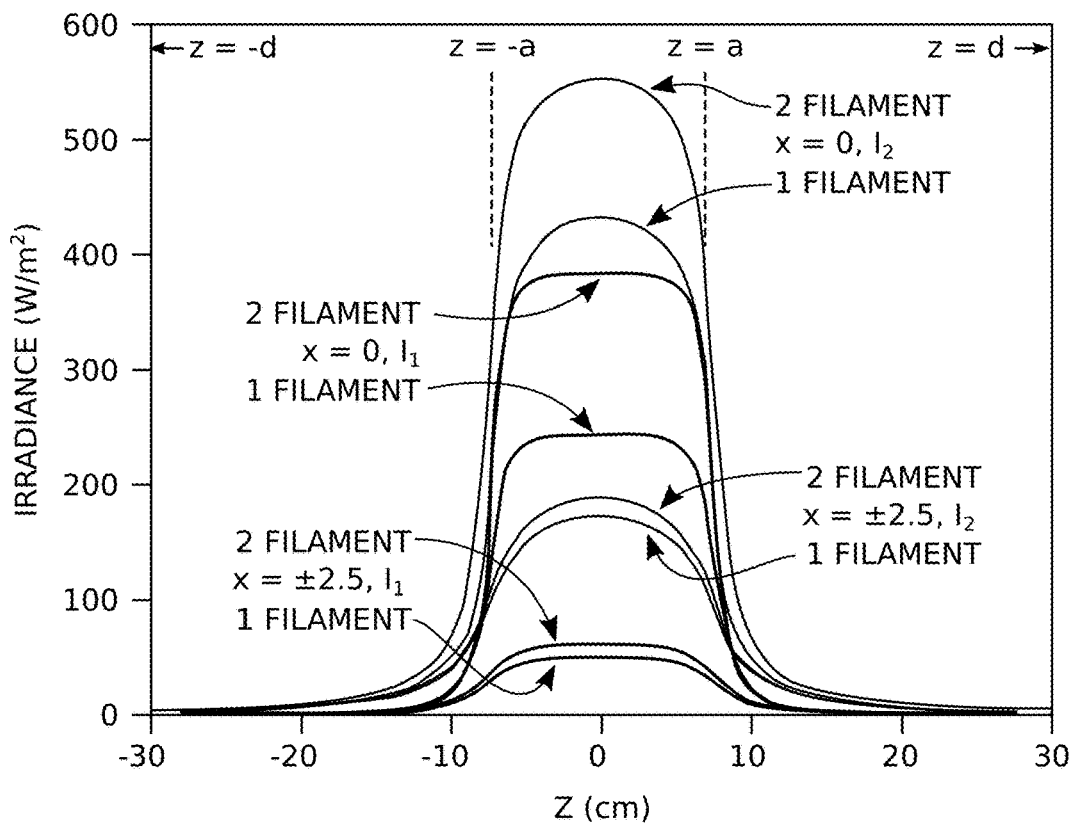
FIG. 50 depicts irradiance curves at y=1 cm to show how $I_{1,1FIL}$ and $I_{1,2FIL}$ compare to $I_{2,1FIL}$ and $I_{2,2FIL}$, which are the surface versus point integration formulations.

FIG. 50 depicts irradiance curves at y=1 cm to show how $I_{1,1FIL}$ and $I_{1,2FIL}$ compare to $I_{2,1FIL}$ and $I_{2,2FIL}$, which are the surface versus point integration formulations.

Figure 51:
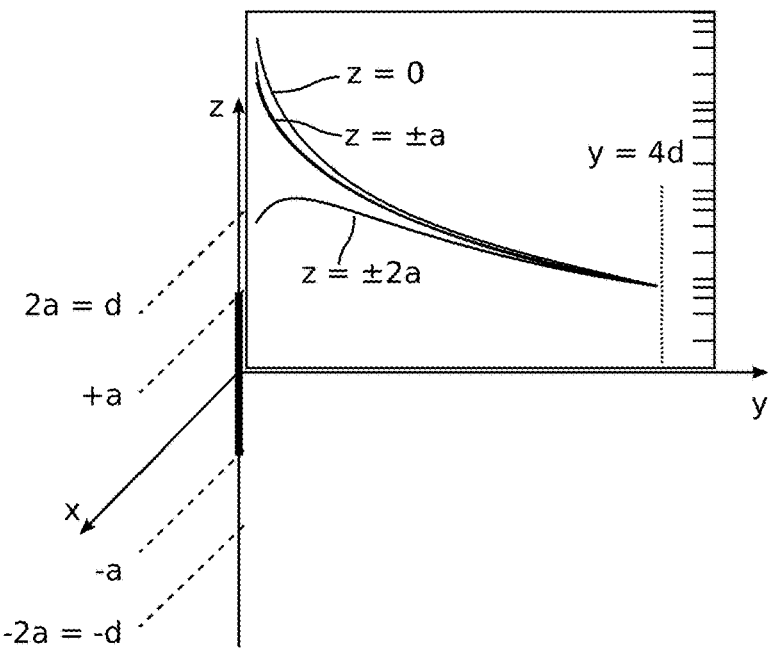
FIG. 51 illustrates radial directional irradiance calculation setup.

FIG. 51 illustrates radial directional irradiance calculation setup. The goal is to see how irradiance varies as distance varies radially at different z coordinates taken as z=0, ±a, and ±2a. The radial dimension r varies between the radius of the tube to r=4d.

Figure 52:
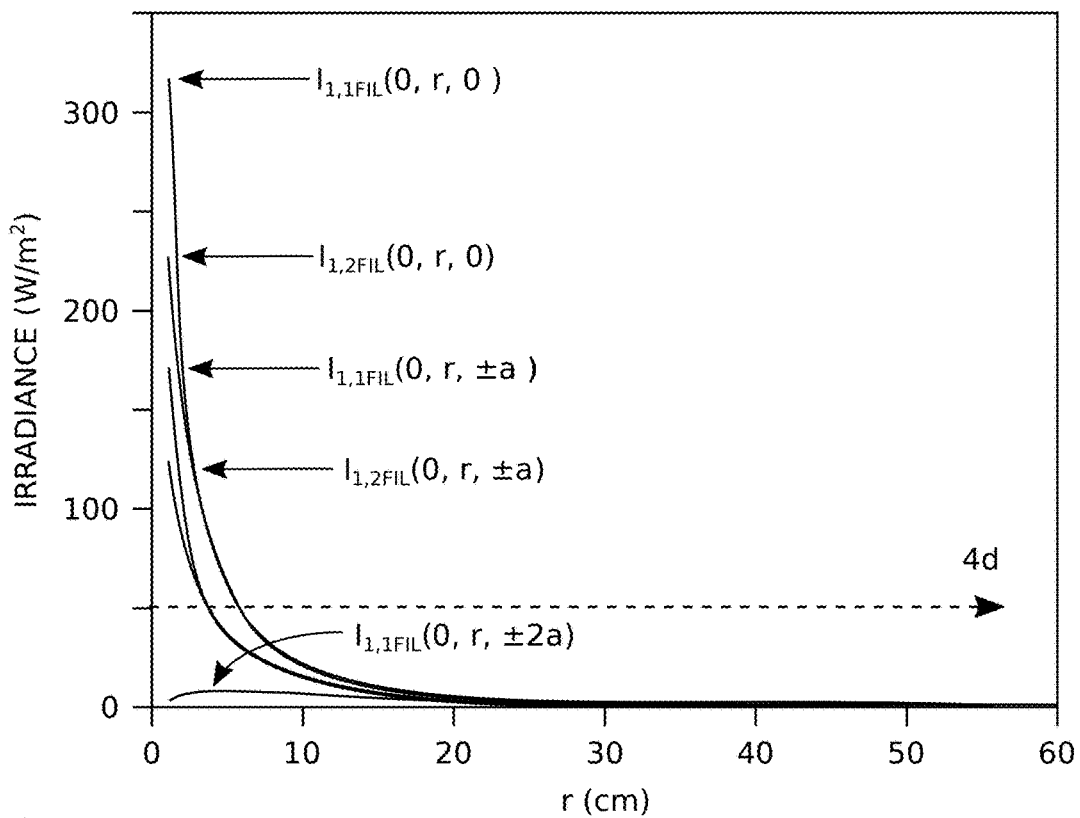

FIG. 52 illustrates $I_{1,1FIL}$ and $I_{1,2FIL}$ irradiation integrals as given in (7.16) and (7.17) along the radial direction at z=0, ±a, and ±2a.

Figure 53:
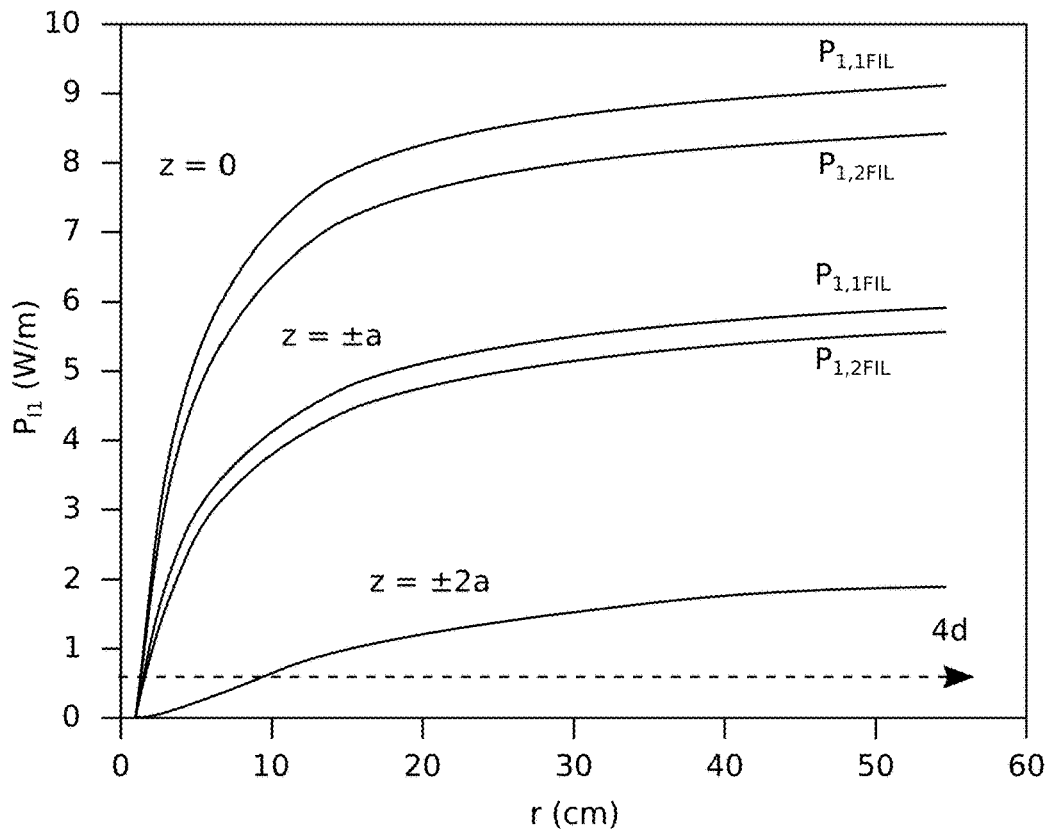
FIG. 53 illustrates integrals $I_{1,1FIL}$ and $I_{1,2FIL}$ with respect to z, which sets the radial airflow velocity maximum in the UV-C irradiance reactor design.

FIG. 53 illustrates integrals $I_{1,1FIL}$ and $I_{1,2FIL}$ with respect to z, which sets the radial airflow velocity maximum in the UV-C irradiance reactor design.

Figure 54:
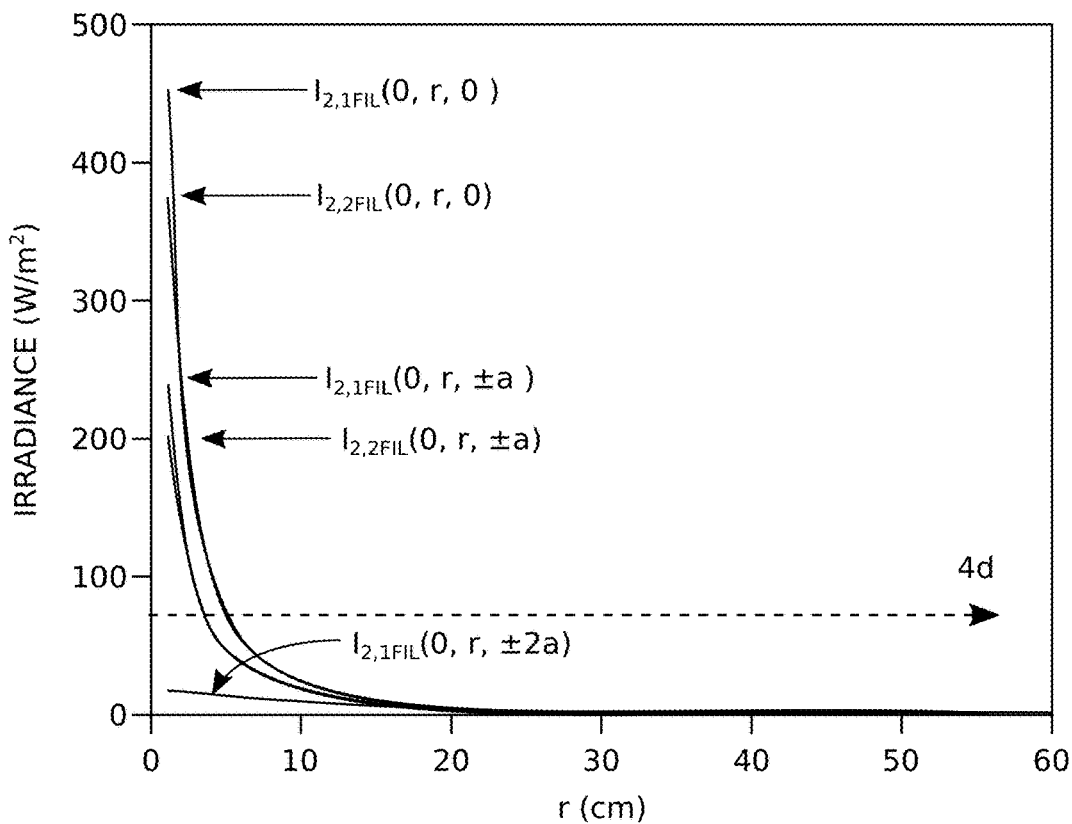

FIG. 54 illustrates $I_{2,1FIL}$ and $I_{2,2FIL}$ irradiation integrals as given in (7.26) and (7.27) along the radial direction at z=0, ±a, and ±2a.

Figure 55:
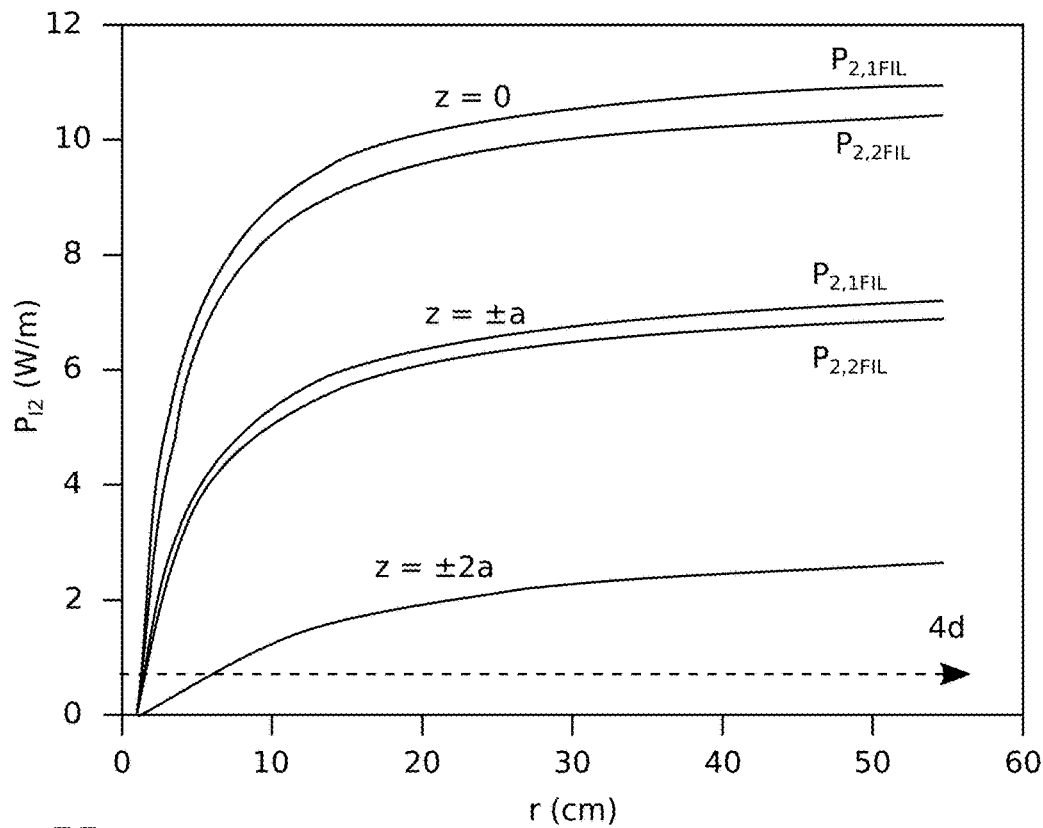
FIG. 55 illustrates integrals $I_{2,1FIL}$ and $I_{2,2FIL}$ with respect to z, which sets the radial airflow velocity maximum in the UV-C irradiance reactor design.
Figure 56:
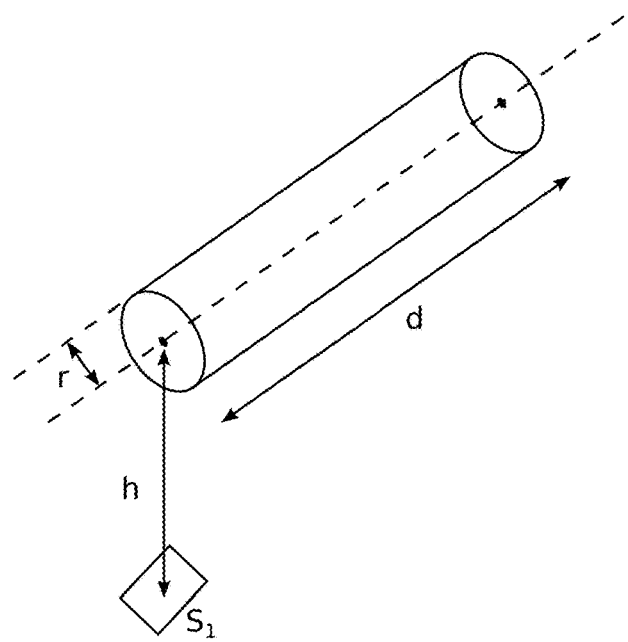
FIG. 56 depicts the fraction of the radiative intensity leaving a cylindrical surface and a differential surface area of $S_1$.
Figure 57:
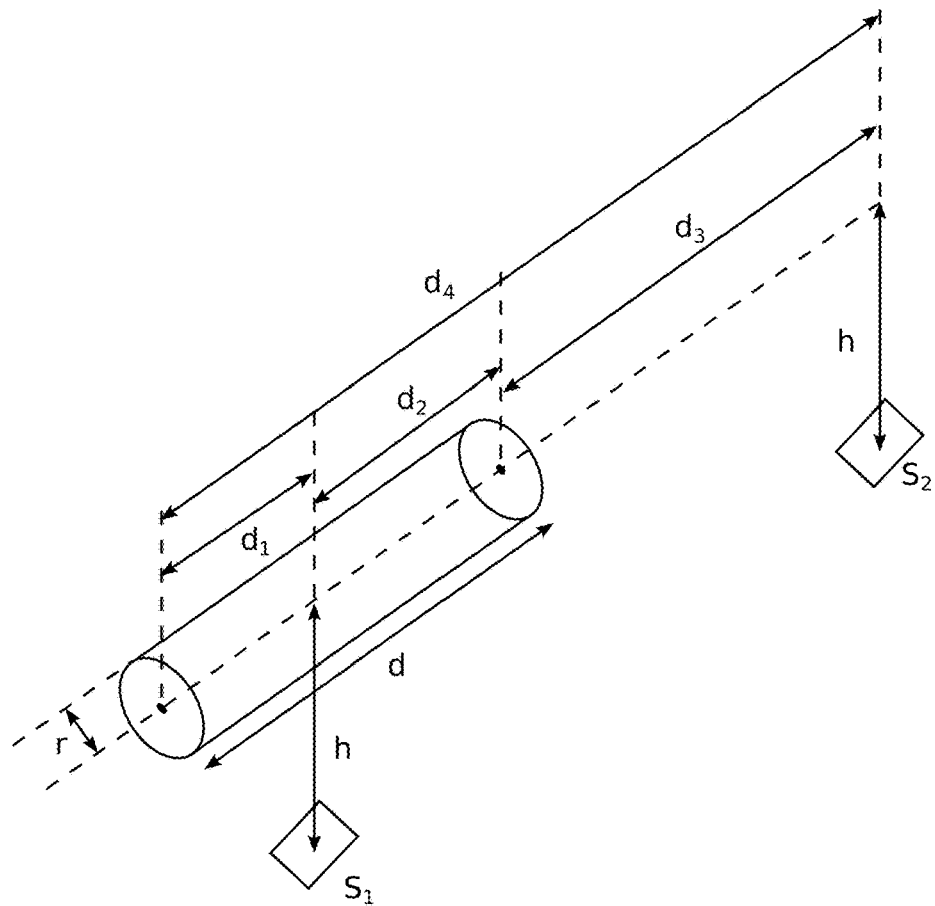
FIG. 57 depicts the view factor from the middle of a UV-C lamp.
Figure 58:
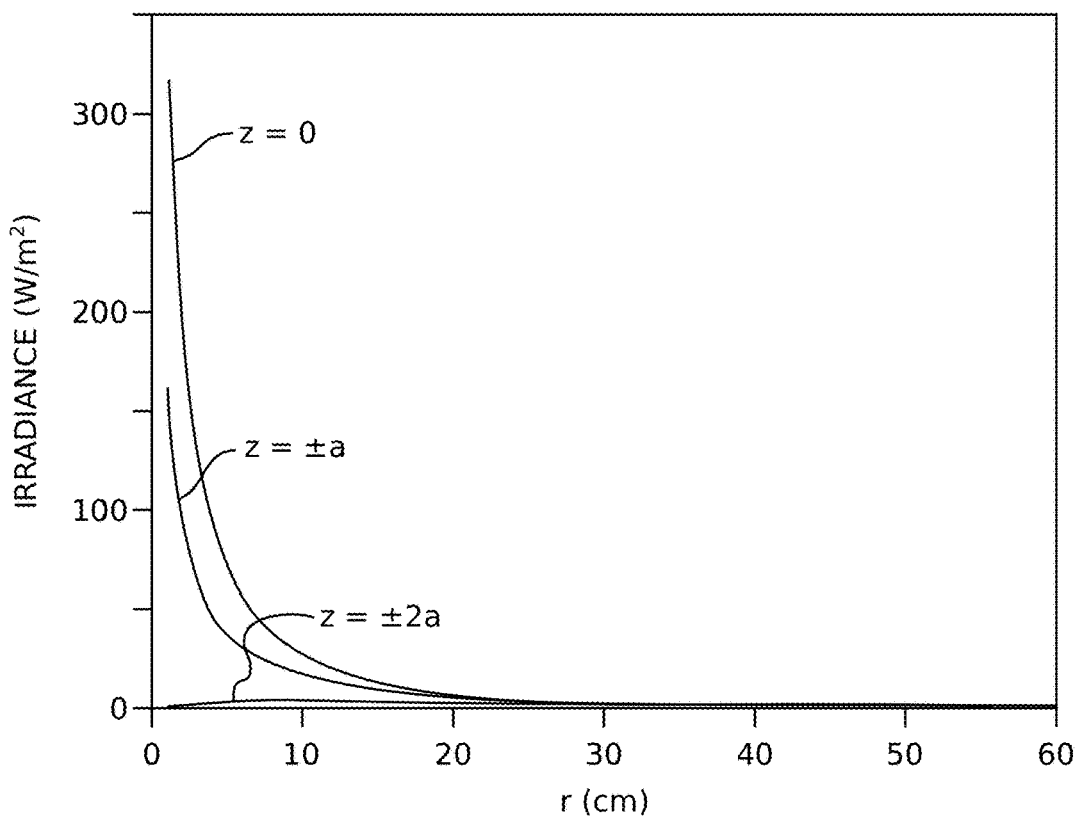
FIG. 58 illustrates irradiation calculations based on view factor method in the radial direction at z=0, ±a, and ±d.
Figure 59A:
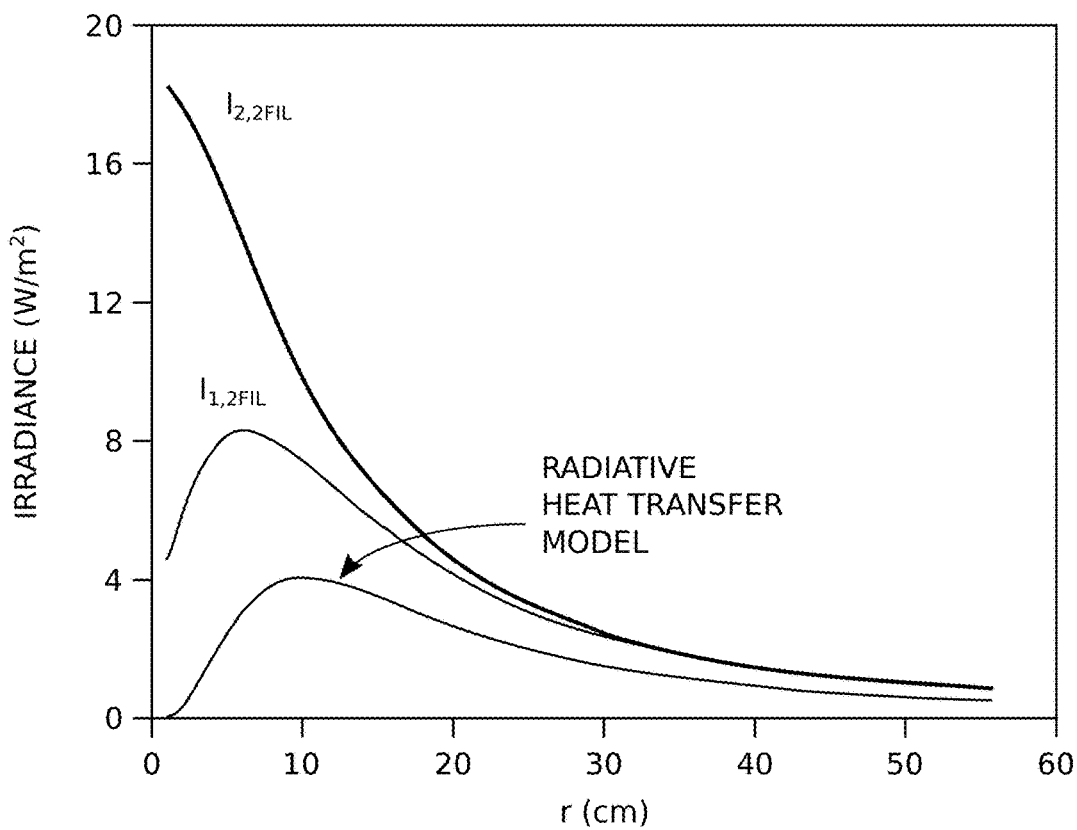
FIGS. 59A through 59C illustrate the differences between radial models at, respectively, z=±d, z=0, and z=0 (log scale).
Figure 59B:
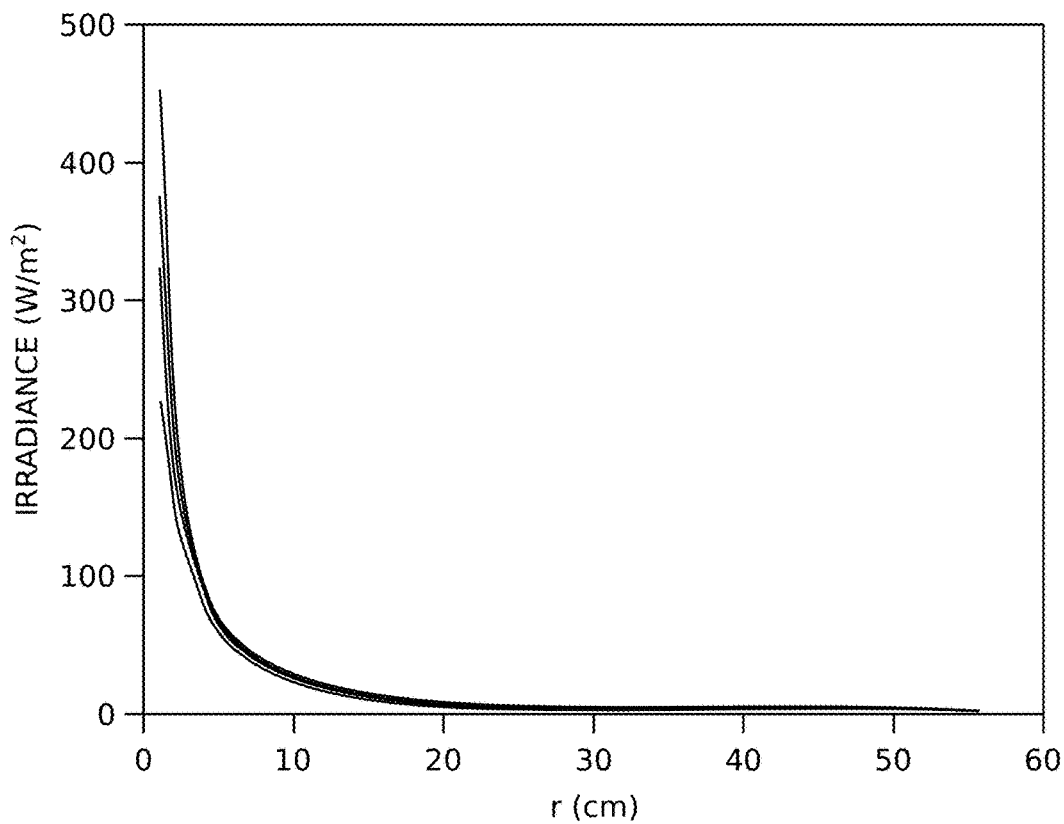
Figure 59C:
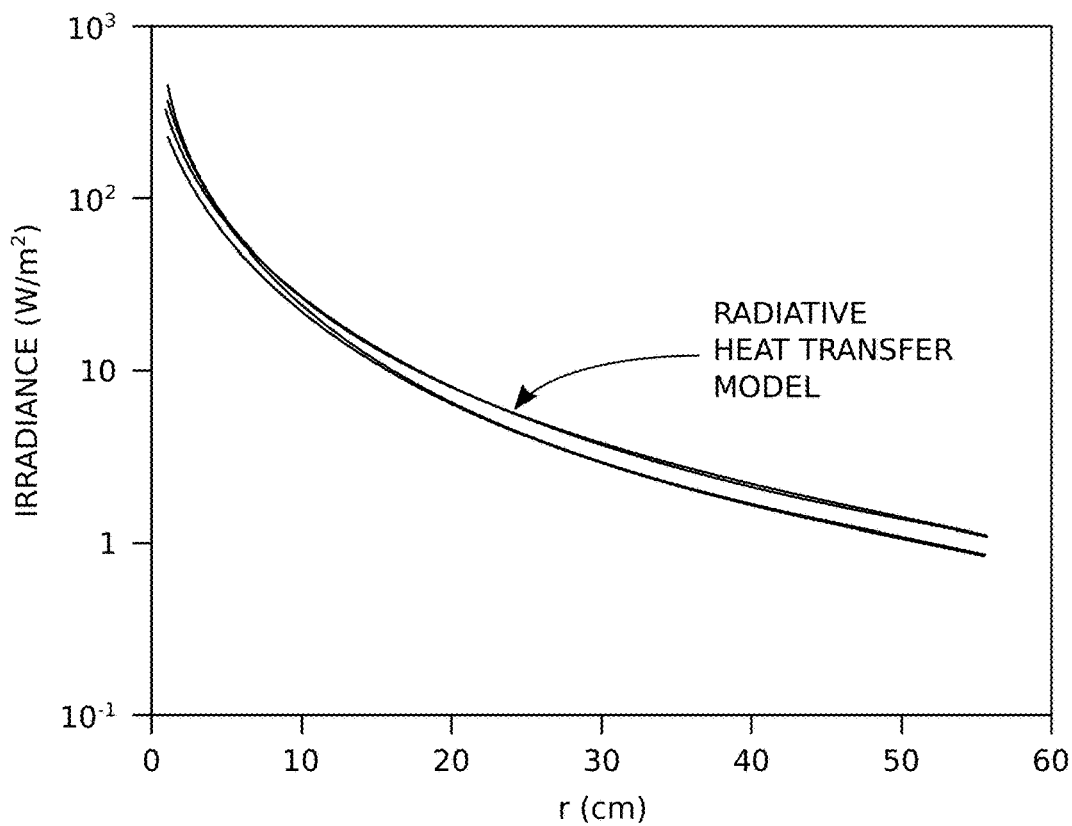
Figure 60:
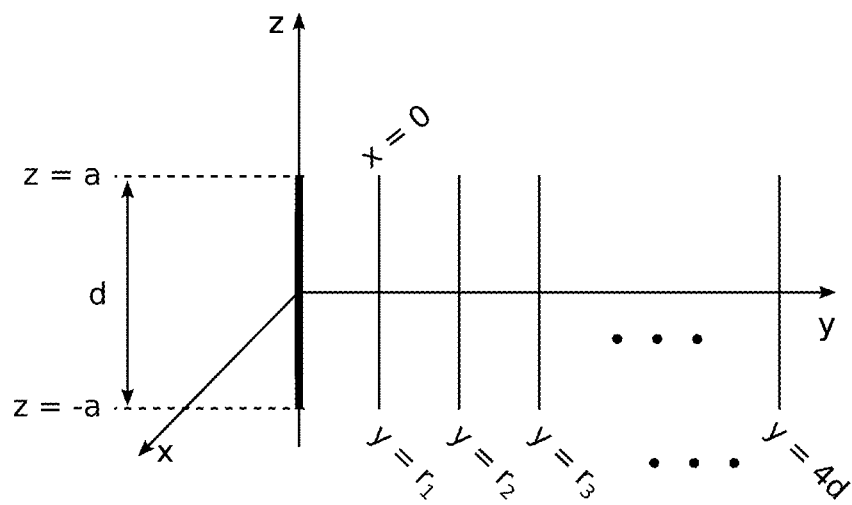
FIG. 60 shows the airflow filament arrangements where the irradiation function along z axes is calculated and integrated with respect to z for single UV-C filament.
Figure 61:
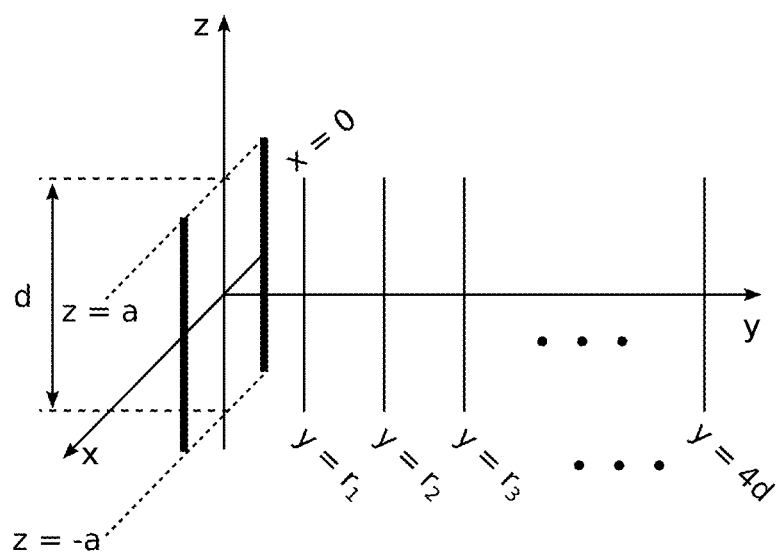
FIG. 61 shows the airflow filament arrangements where the irradiation function along z axes is calculated and integrated with respect to z for two UV-C filaments.
Figure 62:
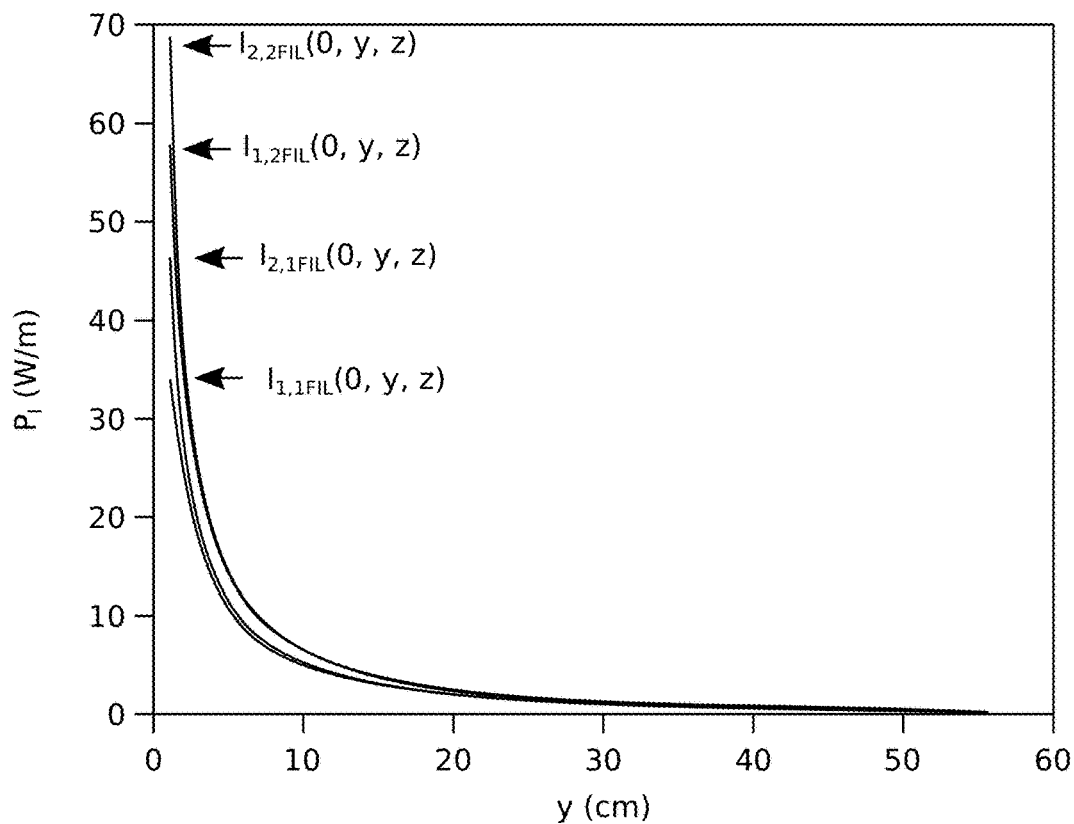
FIG. 62 shows the $P_f(z)$ integral of the irradiation along z axes from z=−a to +a, which sets the airflow rate on the airflow filament with the desired dose.
Figure 63:
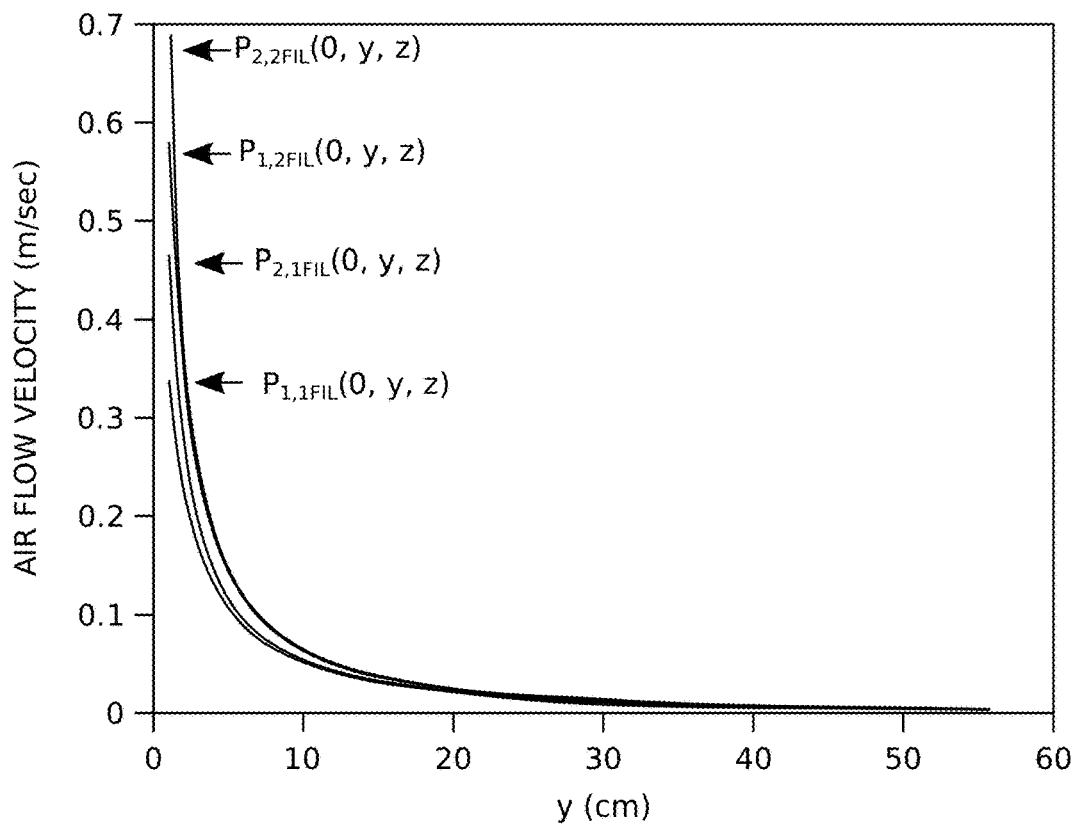
FIG. 63 shows the related airflow velocity as a function of radius for airflow filaments achieving a dose value of 10,000 $\rho W \cdot sec/cm^2$ for the TUV PL-S 13W/2P at the center of the radial UV-C irradiance reactor.
Figure 64:
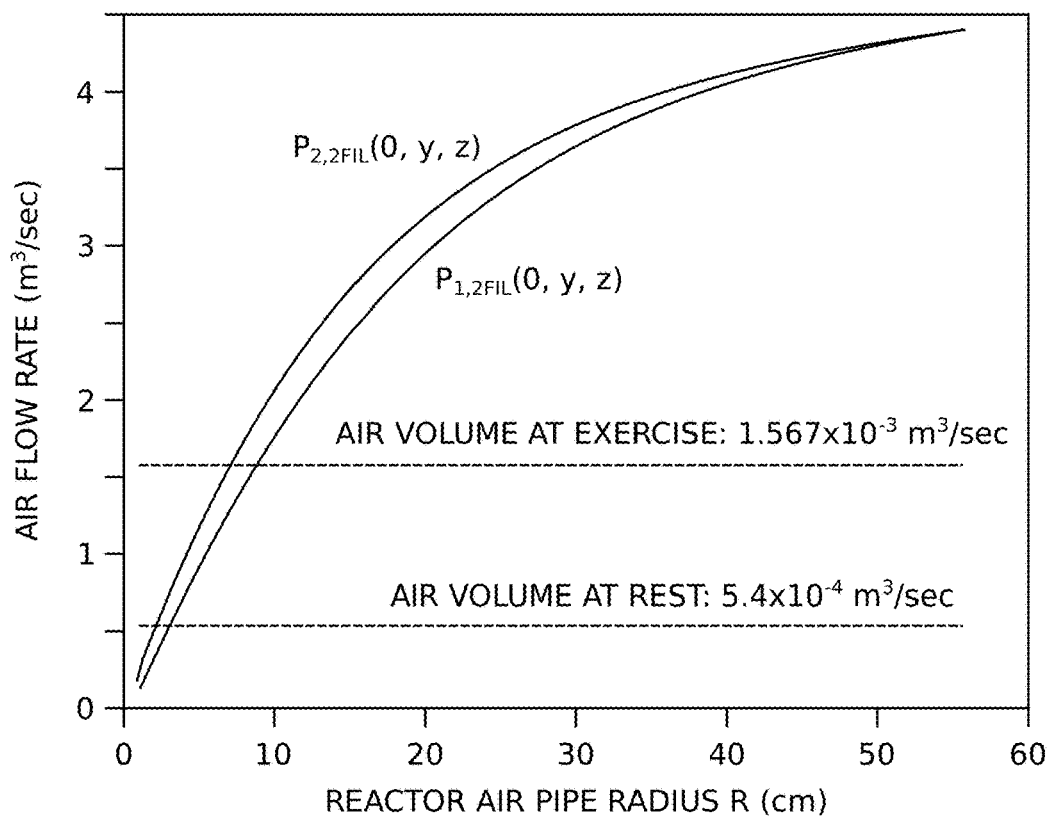
FIG. 64 is the final design guide for the tailoring the airflow velocity guideline using TUV PL-S 13 W/2P at the center of the radial UV-C irradiance reactor.

FIG. 55 illustrates integrals $I_{2,1FIL}$ and $I_{2,2FIL}$ with respect to Z, which sets the radial airflow velocity maximum in the UV-C irradiance reactor design.

Blocking Effect of a Non-Transparent Surface

The dominator of the irradiance integral (7.5) can take negative values. This means geometrically that the orientation of the point P on the surface S is not visible from the source point (0,0,z). In this situation, since the surface is not transparent, point P cannot receive any incoming radiation from the source point at (0,0,z). Before performing the irradiance integrals $I_{1,1FIL}$, $I_{1,2FIL}$, $I_{2,1FIL}$, $I_{2,2FIL}$ analytically, UVGI designer checks if the point (0,0,z), where $-a<z<a$ is visible from point $P(x_0,y_0,z_0)$. This check can be done very easily by evaluating the condition, $$n\cdot r=x_n x_0+y_n y_0+z_n(z_0-z)>0$$

for $$z=-a \text{ and } z=+a \tag{7.28}$$

If n·r<0 for both of the points, then there is no need for calculating the integral. All the irradiance integral values are zero, meaning that point P cannot receive any incoming radiation from any source point (0,0,z) where $-a<z<a$. Another way of interpreting this situation geometrically is by stating that the angles between the outward normal vector of the plane and the vectors from $P(x_0,y_0,z_0)$ to (0,0, −a) and to (0,0, +a), and any point on the z axis in-between, are 900 or larger.

If (7.28) is positive for one point, then the filament is partially visible and the irradiation integral has to be performed between the $z_{MIN}$ or $z_{MAX}$ values which is obtained by solving, $$n\cdot r=x_n x_0+y_n y_0+z_n(z_0-z_{MIN\ or\ MAX})=0 \tag{7.29}$$

UV-C Irradiance Calculation Based on View Factor Method as in the Radiative Heat Transfer, $I_{3,2FIL}$ and $P_{3,2FIL}$ In the earlier two models, the radius of the UV-C lamp is assumed to be small compared to distances where the irradiance is calculated. Therefore, irradiance calculations based on filament methods close to the cylindrical lamp radius can be questionable and need to be verified with more accurate methods. For more accurate calculations a more complicated integral formulation known as the view factor method may be more appropriate, as it has been the workhorse in radiative heat transfer calculations for some time [35, 36]. This is basically a very general quadruple integral formulation that models radiative energy exchange between two surfaces [35, 36]. An excellent reference to the subject is "Radiative Heat Transfer", by Modest [35]. In its appendix D, pp. 762-773, there are 51 analytically derived formulas of view factors for very general surfaces to different surfaces, and to a differential surface element, one of which is a cylindrical source radiator to a given differential element as shown in FIG. 1C of the reference. Based on reference [35], there are other excellent references that cover UVGI application aspects, and more are presented by Kowalski, Bahnfleth, and Beggs et al., [37-42].

FIG. 56 depicts the fraction of the radiative intensity leaving a cylindrical surface and a differential surface area of $S_1$. The formula is given as [35-42], $$F(d,r,h)=\frac{D}{\pi H}\left\{\frac{1}{D}\tan^{-1}\left[\frac{D}{\sqrt{H^2-1}}\right]-\tan^{-1}[M]+\frac{X-2H}{\sqrt{XY}}\tan^{-1}\left[M\sqrt{\frac{X}{Y}}\right]\right\} \tag{7.30}$$

-continued

Where, $$H=\frac{h}{r} \text{ and } D=\frac{d}{r} \tag{7.31}$$

$$X=[(1+H)^2+D^2] \tag{7.32}$$

$$Y=[(1-H)^2+D^2] \text{ and } M=\sqrt{\frac{H-1}{H+1}} \tag{7.33}$$

FIG. 57 depicts the view factor from the middle of a UV-C lamp. Using (7.30)-(7.33) multiple times and with the superposition of (7.28) one can calculate any relative configuration of differential surface with respect to the cylindrical source. As an example, the view factor for $S_1$ surface in FIG. 57 can be calculated as the sum of two view factors as, $$F_{S1}=F(d_1,r,h)+F(d_2,r,h) \tag{7.34}$$

As FIG. 57 illustrates, it is clear that $d_1+d_2=d$ and it corresponds to (7.30) displayed in FIG. 56. Similarly, a differential area, such as the $S_2$ surface shown in FIG. 57, can be calculated as the difference of two view factors as, $$F_{S2}=F(d_4,r,h)-F(d_3,r,h) \tag{7.35}$$

The negative portion is named the "ghost" portion of the lamp.

As can be seen the view factor is a dimensionless quantity. The irradiance can be simply calculated as, $$I=\frac{P_{UV-C}}{2\pi rd}F_S \tag{7.36}$$

Where $F_S$, $P_{UV-C}$, r, and d are the equivalent view factor calculated with the super-position methods shown in (7.33) and (7.34), representing radiant UV-C power, UV-C lamp radius, and UV-C lamp length respectively. The denominator in (7.36) basically gives the side radiation area of the UV-C lamp.

FIG. 58 illustrates irradiation calculations based on view factor method in the radial direction at z=0, ±a, and ±d.

FIGS. 59A through 59C illustrate the differences between radial models at, respectively, z=±d, z=0, and z=0 (log scale). Calculations between the radial models at z=0 show close agreement and the differences in irradiation at r less than 5 cm are practically nonexistent.

FIG. 60 shows the airflow filament arrangements where the irradiation function along z axes is calculated and integrated with respect to z for a single UV-C filament.

FIG. 61 shows the airflow filament arrangements where the irradiation function along z axes is calculated and integrated with respect to z for two UV-C filaments.

FIG. 62 shows the $P_I(z)$ integral of the irradiation along z axes from z=−a to +a, which sets the airflow rate on the airflow filament with the desired dose.

FIG. 63 shows the related airflow velocity as a function of radius for airflow filaments achieving a dose value of 10,000 μW·sec/cm² for the TUV PL-S 13 W/2P at the center of the radial UV-C irradiance reactor.

FIG. 64 is the final design guide for the tailoring the airflow velocity guideline using TUV PL-S 13 W/2P at the center of the radial UV-C irradiance reactor. As can be seen, the TUV PL-S it is feasible choice and even exceeds the Covid-19 disinfection goals.

Tables 5.1-5.4 show the numerical values in all the figures along with the numerical values of the velocity equivalent of the irradiation integral.

TABLE 5.1

One Filament Approximation of the UV-C Source
(TUV PL-S 13W/2P UV-C lamp)

| Airflow Filament z Coordinates<br>$-2a \leq z \leq 2a$, $a = 69.5$ mm | Irradiance Integral<br>[W/m]<br>$P_I = \int_{-2d}^{2d} I(z)dz$ | Maximum Airflow Velocity<br>[m/sec] to give 10,000<br>[$\mu$W·s/cm$^2$] kill dose<br>$v_{MAX} = \dfrac{1}{D_{KILL}} \int_{-u}^{u} I(z)dz$ |
|---|---|---|
| y = 5 cm, x = 5 cm and −5 cm | 5.823 | $V_1$ = 0.05823 |
| y = 5 cm, x = 2.5 cm and −2.5 cm | 9.183 | $V_2$ = 0.09183 |
| y = 5 cm, x = 0 cm | 11.4 | $V_3$ = 0.114 |
| y = 1 cm, x = 5 cm and −5 cm | 2.796 | $V_1$ = 0.02796 |
| y = 1 cm, x = 2.5 cm and −2.5 cm | 8.513 | $V_2$ = 0.08513 |
| y = 1 cm, x = 0 | 55.69 | $V_3$ = 0.5569 |

TABLE 5.2

Two Filament Approximation of the UV-C Source
(TUV PL-S 13W/2P UV-C)

| Airflow Filament z Coordinates<br>$-2a \leq z \leq 2a$, $a = 69.5$ mm | Irradiance Integral<br>[W/m]<br>$P_I = \int_{-2d}^{2d} I(z)dz$ | Maximum Airflow Velocity<br>[m/sec] to give 10,000<br>[$\mu$W·s/cm$^2$] kill dose<br>$v_{MAX} = \dfrac{1}{D_{KILL}} \int_{-u}^{u} I(z)dz$ |
|---|---|---|
| y = 5 cm, x = 5 cm and −5 cm | 5.883 | $V_1$ = 0.05883 |
| y = 5 cm, x = 2.5 cm and −2.5 cm | 9.147 | $V_2$ = 0.09147 |
| y = 5 cm, x = 0 cm | 11.16 | $V_3$ = 0.1116 |
| y = 1 cm, x = cm and −5 cm | 2.934 | $V_1$ = 0.02934 |
| y = 1 cm, x = 2.5 cm and −2.5 cm | 10.06 | $V_2$ = 0.1006 |
| y = 1 cm, x = 0 | 36.09 | $V_3$ = 0.3609 |

TABLE 5.3

One Filament Approximation of the UV-C Source ATAN
(TUV PL-S 13W/2P UV-C lamp)

| Airflow Filament z Coordinates<br>$-2a \leq z \leq 2a$, $a = 69.5$ mm | Irradiance Integral<br>[W/m]<br>$P_I = \int_{-2d}^{2d} I(z)dz$ | Maximum Airflow Velocity<br>[m/sec] to give 10,000<br>[$\mu$W·s/cm$^2$] kill dose<br>$v_{MAX} = \dfrac{1}{D_{KILL}} \int_{-u}^{u} I(z)dz$ |
|---|---|---|
| y = 5 cm, x = 5 cm and −5 cm | 10.08 | $V_1$ = 0.1008 |
| y = 5 cm, x = 2.5 cm and −2.5 cm | 13.25 | $V_2$ = 0.1325 |
| y = 5 cm, x = 0 cm | 15.04 | $V_3$ = 0.1504 |
| y = 1 cm, x = 5 cm and −5 cm | 14.71 | $V_1$ = 0.1471 |
| y = 1 cm, x = 2.5 cm and −2.5 cm | 29.59 | $V_2$ = 0.2959 |
| y = 1 cm, x = 0 | 83.02 | $V_3$ = 0.8302 |

TABLE 5.4

Two Filament Approximation of the UV-C Source
(TUV PL-S 13W/2P UV-C)

| Airflow Filament z Coordinates<br>$-2a \leq z \leq 2a$, $a = 69.5$ mm | Irradiance Integral<br>[W/m]<br>$P_I = \int_{-2d}^{2d} I(z)dz$ | Maximum Airflow Velocity<br>[m/sec] to give 10,000<br>[$\mu$W·s/cm$^2$] kill dose<br>$v_{MAX} = \dfrac{1}{D_{KILL}} \int_{-u}^{u} I(z)dz$ |
|---|---|---|
| y = 5 cm, x = 5 cm and −5 cm | 10.12 | $V_1$ = 0.1012 |
| y = 5 cm, x = 2.5 cm and −2.5 cm | 13.20 | $V_2$ = 0.1320 |
| y = 5 cm, x = 0 cm | 14.85 | $V_3$ = 0.1485 |

TABLE 5.4-continued

Two Filament Approximation of the UV-C Source
(TUV PL-S 13W/2P UV-C)

| Airflow Filament z Coordinates<br>$-2a \leq z \leq 2a$, $a = 69.5$ mm | Irradiance Integral<br>[W/m]<br>$P_I = \int_{-2d}^{2d} I(z)dz$ | Maximum Airflow Velocity<br>[m/sec] to give 10,000<br>[µW·s/cm²] kill dose<br>$v_{MAX} = \dfrac{1}{D_{KILL}} \int_{-u}^{u} I(z)dz$ |
|---|---|---|
| y = 1 cm, x = 5 cm and −5 cm | 15.06 | $V_1 = 0.1506$ |
| y = 1 cm, x = 2.5 cm and −2.5 cm | 31.61 | $V_2 = 0.3161$ |
| y = 1 cm, x = 0 | 66.02 | $V_3 = 0.6602$ |

Radial Flow Irradiance Reactor Design Using UV-C Mercury Discharge Lamp Fluid Mechanics The building block of the radial flow irradiance reactor as shown in FIG. 33 has the cylindrical UV-C mercury vapor discharge lamp in the center to support a coaxial airflow flow geometry. Therefore, the airflow fluid dynamics cannot be represented with the tubular flow case presented above. The airflow velocity profile in a coaxial flow can be calculated by solving the Navier-Stokes equation [42].

The Navier-Stokes equation in the case of incompressible parallel permanent flux fluid flow condition can be written as, $$\mu \nabla 2v - \nabla p = 0 \quad (8.1)$$

Where $\mu$, $v$, and $p$ are viscosity, fluid velocity, and pressure respectively. Since we are interested in fluid flow in a tube, velocity and pressure only have z components. Therefore (8.1) can be converted into its scalar form as, $$\mu \nabla^2 v - \frac{\partial p}{\partial z} = 0 \quad (8.2)$$

Moreover, since we are also interested in cylindrical tubular structures, it is convenient to write (8.2) in cylindrical coordinates as, $$\mu\left(\frac{\partial^2 v}{\partial r^2} + \frac{1}{r}\frac{\partial v}{\partial r}\right) - \frac{\partial p}{\partial z} = 0 \quad (8.3)$$

Assuming a linear pressure drop along z direction, the differential equation (8.3) become an ordinary differential equation, where the z directional fluid velocity distribution has only r dependency and can be represented as, $$\mu\left(\frac{d^2 v}{dr^2} + \frac{1}{r}\frac{dv}{dr}\right) - \frac{\Delta p}{L} = 0 \quad (8.4)$$

Where $\Delta p$ is the pressure drop along the length L of the tube. Equation (8.4) has a solution in the form of, $$v(r) = \frac{\Delta p}{4L\mu}r^2 + C_1 \ln(r) + C_2 \quad (8.5)$$

Where $C_1$ and $C_2$ are integration constants to be determined by the two boundary conditions related to laminar flow as, $$v(R_1) = v(R_2) = 0 \quad (8.6)$$

The solution of $C_1$ and $C_2$ with the boundary conditions given in (8.6) gives, $$v(r) = -\Delta p \frac{(R_2^2 - R_1^2)\ln(r) + (r^2 - R_2^2)\ln(R_1) + (R_1^2 - r^2)\ln(R_2)}{4L\mu \cdot \ln\left(\frac{R_1}{R_2}\right)} \quad (8.7)$$

The solution has a maximum at $r = r_{MAX}$ which is given as, $$r_{MAX} = \sqrt{\frac{(R_2^2 - R_1^2)}{2\ln\left(\frac{R_2}{R_1}\right)}} \quad (8.8)$$

Figure 65:
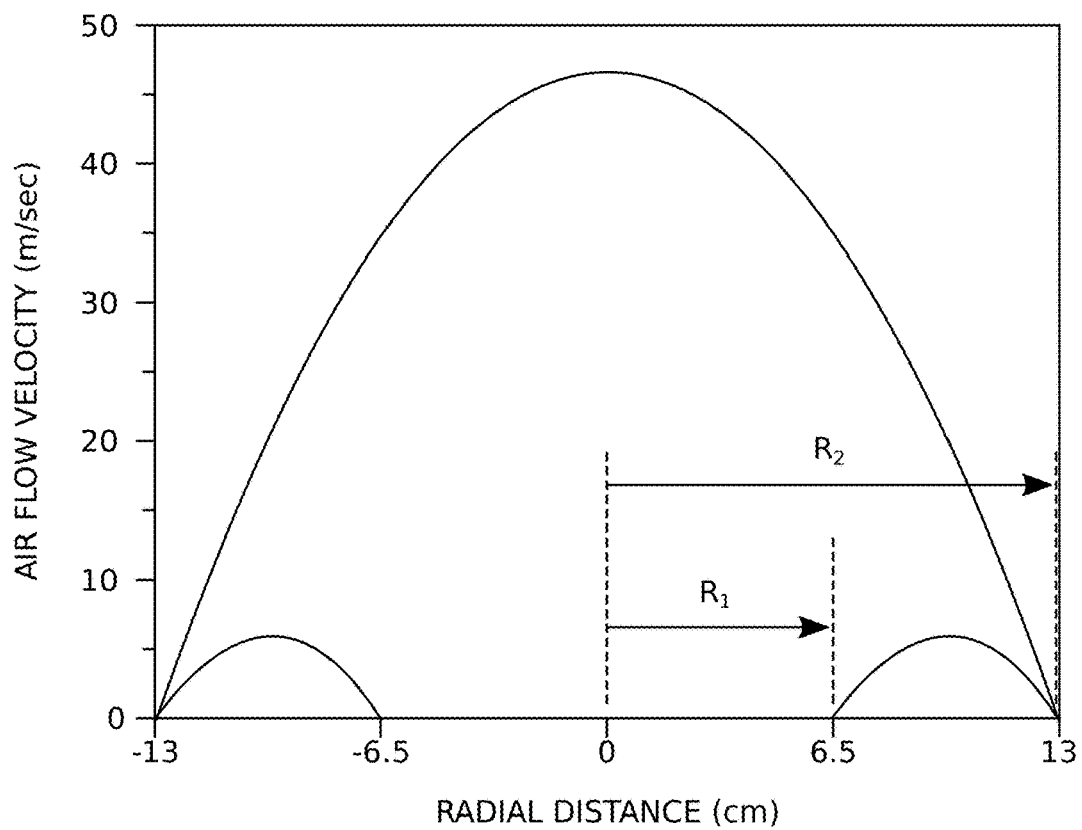
FIG. 65 illustrates the radial fluid velocity profile as a function of radius of the coaxial tube structure with inner radius of $R_1$ and outer radius of $R_2$ as it is formulated in (8.7).

FIG. 65 illustrates the radial fluid velocity profile as a function of radius of the coaxial tube structure with inner radius of $R_1$ and outer radius of $R_2$ as it is formulated in (8.7). The center parabolic distribution is the laminar fluid velocity profile in the tube with a radius of $R_2$ with the same length and pressure difference along z axes. The velocity profile maximum points $r_{MAX}$ as formulated in (8.8) along r axes are shown. As can be seen, the 2 identical peak values of the velocity profile of the coaxial tube are much less than the parabolic velocity profile of the tube with the same outer radius and with the same pressure difference.

Figure 66:
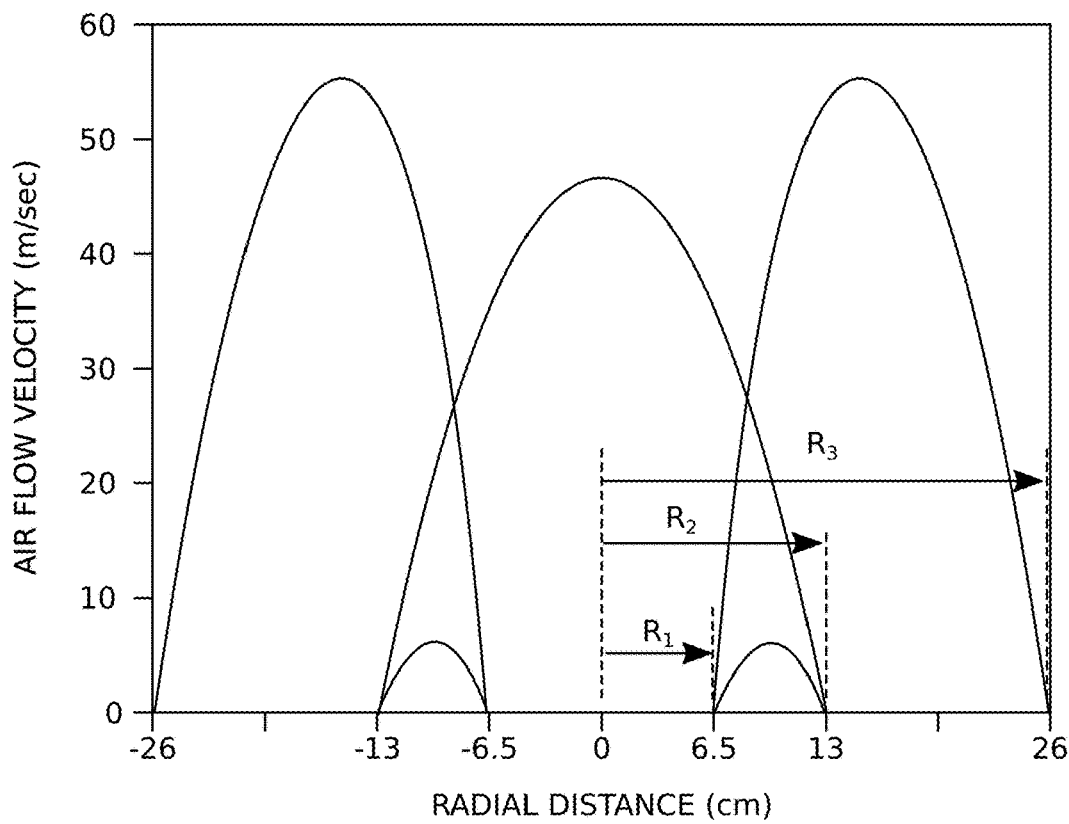
FIG. 66 illustrates the laminar radial distribution of the fluid velocity profile as a function of radius of the coaxial tube structure with inner radius of $R_1$ and outer radius of $R_2$, superimposed on a second coaxial tube having its outer radius $R_3=2 \times R_2$ with the same pressure difference applied as before.

FIG. 66 illustrates the laminar radial distribution of the fluid velocity profile as a function of radius of the coaxial tube structure with inner radius of $R_1$ and outer radius of $R_2$, superimposed on a second coaxial tube having its outer radius $R_3 = 2 \times R_2$ with the same pressure difference applied as before. The center parabolic distribution in FIG. 66 is the same laminar fluid velocity profile in the tube with a radius of $R_2$ as presented in FIG. 65. The new velocity profile peak locations are indicated as $r_{MAX2}$.

Figure 67:
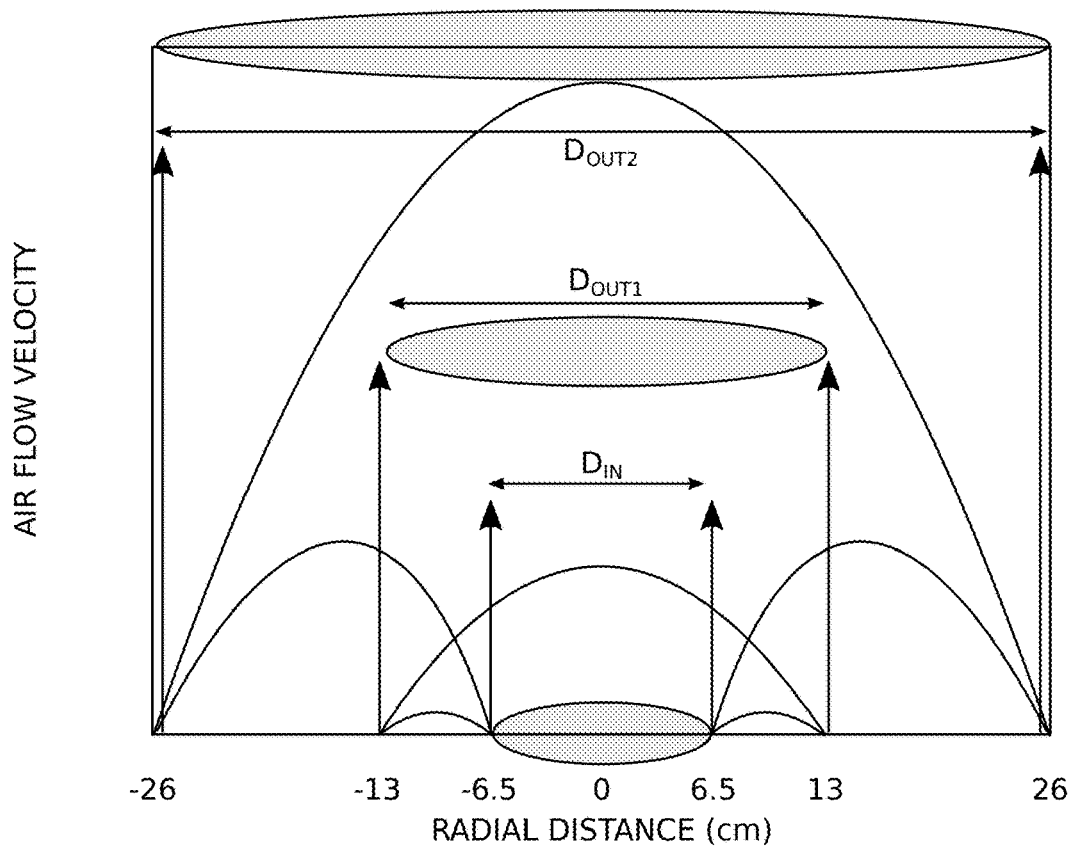
FIG. 67 is the same as FIG. 66 with the parabolic distribution in a tube with a radius of $R_3=2 \times R_2$ and some perspective views of the 2 cases shown in FIG. 65 and FIG. 67.
Figure 68:
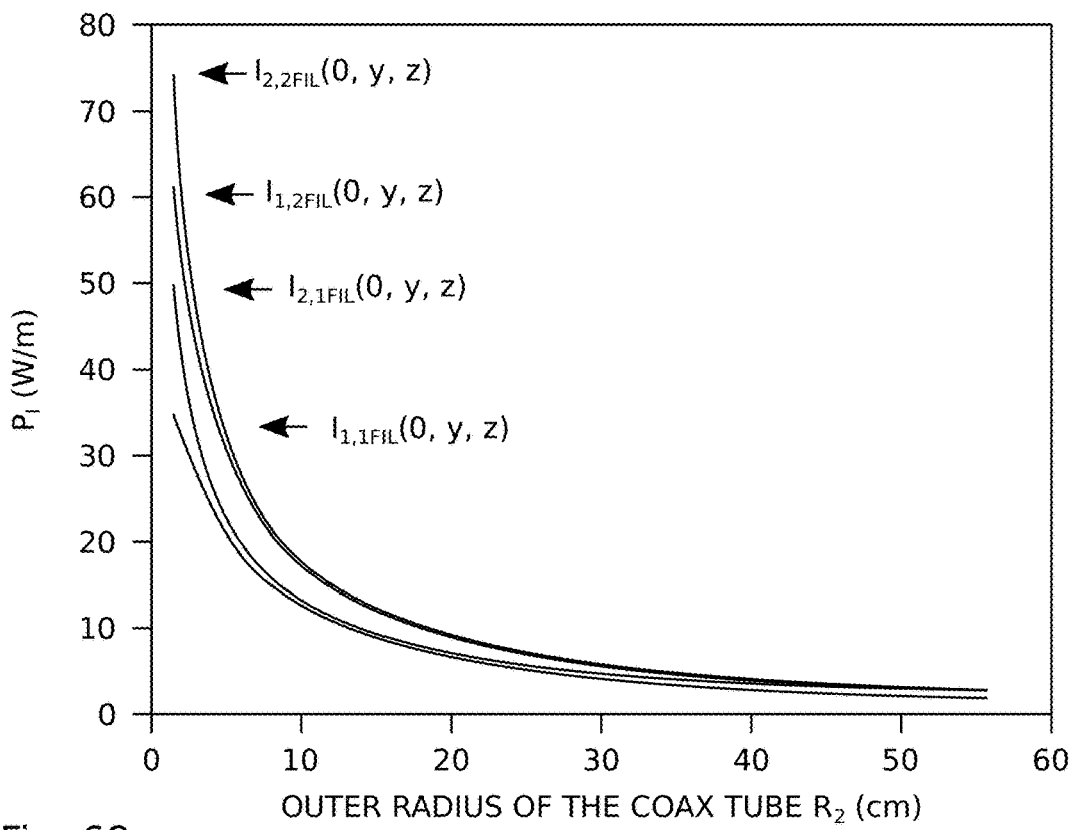
FIG. 68 shows the irradiation integral $P_f(r)$'s performed using all 5 irradiation calculations, namely the $P_{1,1FIL}$, $P_{1,2FIL}$, $P_{2,1FIL}$, $P_{2,2FIL}$, and $P_{3,2FIL}$ methods explained in 7.1, 7.2, and 7.4.

FIG. 67 is the same as FIG. 66 with the parabolic distribution in a tube with a radius of $R_3 = 2 \times R_2$ and some perspective views of the 2 cases shown in FIG. 65 and FIG. 67.

The fluid flux Q can be calculated analytically by integrating the velocity profile given in (8.7), $$Q = \int_{R_1}^{R_2} 2\pi r \cdot v(r) dr \quad (8.9)$$

The velocity profile relation (8.7), which is to be integrated in the coaxial cross-section represented by the integral (8.9), has 3 terms that can be written as, $$\int 2\pi r \cdot v(r) dr = F_1(r) + F_2(r) + F_3(r) \quad (8.10)$$

Explicitly, each term is written as, $$F_1(r) = \frac{2\pi\Delta p}{4L\mu \cdot \ln\left(\frac{R_1}{R_2}\right)} \int r(R_2^2 - R_1^2)\ln(r)dr \quad (8.11)$$

$$F_2(r) = \frac{2\pi\Delta p \ln(R_1)}{4L\mu \cdot \ln\left(\frac{R_1}{R_2}\right)} \int r(r^2 - R_2^2)dr \quad (8.12)$$

$$F_3(r) = \frac{2\pi\Delta p \ln(R_2)}{4L\mu \cdot \ln\left(\frac{R_1}{R_2}\right)} \int r(R_1^2 - r^2)dr \quad (8.13)$$

Using the integration form, $$\int x \ln(x) dx = \frac{x^2}{2}\ln(x) - \frac{x^2}{4} \quad (8.14)$$

And the basic elementary integration rule of, $$\int x^n dx = \frac{x^{n+1}}{n+1} \quad (8.15)$$

The indefinite integrals (8.11)-(8.13) can be explicitly given as, $$F_1(r) = \Delta p \cdot C(R_2^2 - R_1^2)\frac{r^2}{2}\left[\ln(r) - \frac{1}{2}\right] \quad (8.16)$$

$$F_2(r) = \Delta p \cdot C \cdot \ln(R_1)\frac{r^2}{2}\left[\frac{r^2}{2} - R_2^2\right] \quad (8.17)$$

$$F_3(r) = \Delta p \cdot C \cdot \ln(R_2)\frac{r^2}{2}\left[R_1^2 - \frac{r^2}{2}\right] \quad (8.18)$$

Where the multiplier C is, $$C = \frac{\pi}{2L\mu \cdot \ln\left(\frac{R_2}{R_1}\right)} \quad (8.19)$$

The fluid flux Q which are defined by the definite integral (8.9) can then be simply calculated by substituting $R_2$ and $R_1$ in r in the expressions (8.16)-(8.18) as, $$Q=[F_1(R_2)-F_1(R_1)]+[F_2(R_2)-F_2(R_1)]+[F_3(R_2)-F_3(R_1)] \quad (8.20)$$

One can easily calculate the required pressure differential $\Delta p$ needed to be applied to get the desired fluid flux Q as well by solving it from (8.20) where $\Delta p$ appears as multipliers as shown in the (8.16)-(8.18) giving, $$\Delta p = \frac{Q}{[F_1(R_2) - F_1(R_1)] + [F_2(R_2) - F_2(R_1)] + [F_3(R_2) - F_3(R_1)]} \quad (8.21)$$

Relation (8.21) is the last relation that is needed to formulate the laminar fluid flow in a coaxial tube needed to be able to design the irradiance reactor using a UV-C mercury discharge tube.

UV-C Mercury Discharge Lamp Based Radial Flow Irradiance Reactor Design.

Figure 69:
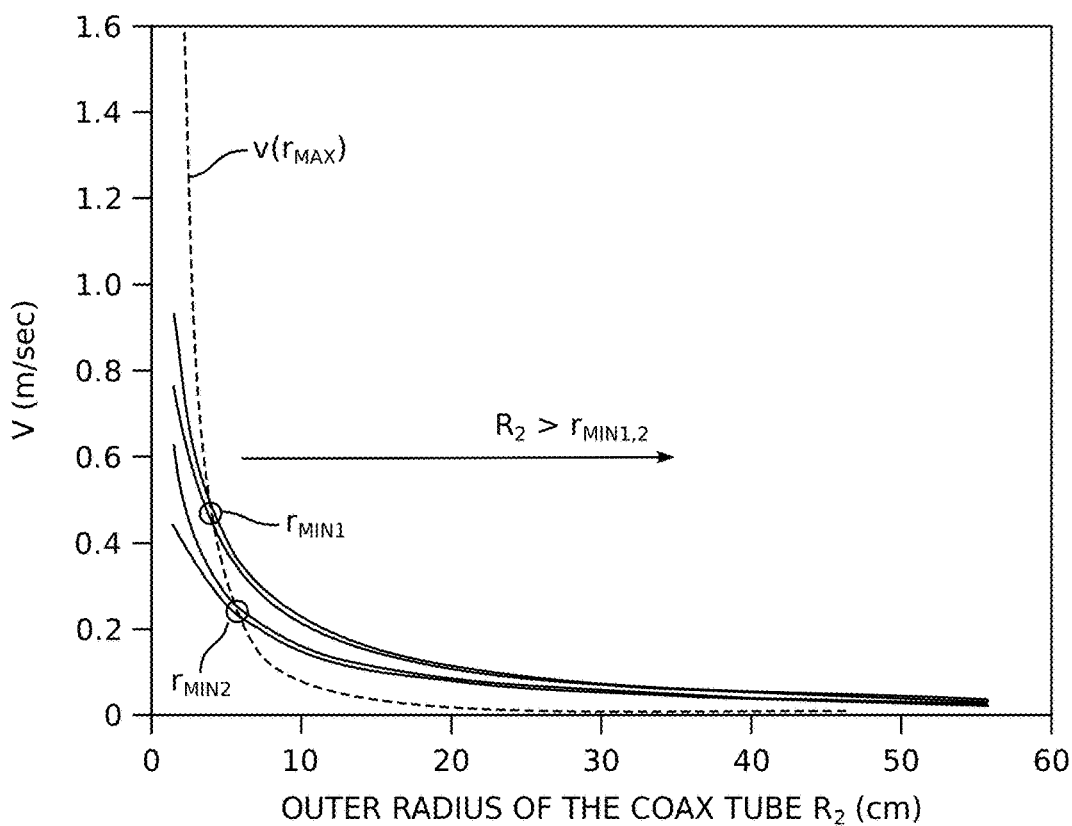
FIG. 69 depicts the peak airflow velocity as a function of $R_2$, calculated by the $v(r_{MAX})$ relation given in (8.7) where $r_{MAX}(R_1, R_2)$ is calculated by the expression (8.8) for the maximum volumetric airflow rate $Q_{MAX}$ for the reactor.

The construction of the radial flow UV-C Mercury discharge lamp reactor design is very simple and also very easy to manufacture. As shown in FIG. 33, a cylindrical UV-C mercury discharge lamp at the center and a cylindrical airflow pipe coaxially enclosing the lamp with a fan at one end which sucks air from one end and lets it out from other end. This design supplies a UV-C irradiated air supply with viruses and bacteria deactivated in the flow.

The interior of the enclosure is a reflective surface to increase the irradiance in the coaxial air flow region. As an example, the reflectivity of polished aluminum is in the order of 72.5%-77.5% in the UV-C band. Titanium oxide ($TiO_2$) is 93% reflective at the 500 nm of wavelength, but is lower than 50% in the UV-C band. Porex PMR15 is 97.5% reflective in the UV-C band [21, 22].

For a face shield application the length of the UV-C mercury discharge lamp is an important consideration. A suitable lamp for portable applications is the first one listed in Table 4, the model TUV PL-S 13 W/2P. It is a twin tube compact lamp with a length of 13.95 cm, providing 3.4 Watts of UV-C radiant power, and consuming 13 W of electrical power. Other UV-C discharge tubes in Table 4 are 21.21 to 54.89 cm long, which are less suitable for portable application. The TUV 4 W FAM10X25CC in the 7th row is shorter than the TUV PL-S 13 W/2P (13.59 cm), but only has 0.9 Watts of UV-C radiant power.

The length of the reactor is slightly longer than the UV-C Mercury discharge lamp that is employed. Simulations show that making the length of the reactor more than 10-20% longer that the UV-C discharge lamp does not improve the irradiance integral $P_I$ along the airflow path in the reactor. Therefore, making the reactor more than 10-20% longer than the UV-C discharge lamp does not significantly benefit the UVGI characteristics, and so justify the added length and weight increase.

FIG. 68 shows the irradiation integral $P_I(r)$'s performed using all 5 irradiation calculations, namely the $P_{1,1FIL}$, $P_{1,2FIL}$, $P_{2,1FIL}$, $P_{2,2FIL}$ and $P_{3,2FIL}$ methods explained in 7.1, 7.2, and 7.4.

As given by the relation (6.6) in the dose calculation part above, dividing $P_{1,1FIL}$, $P_{1,2FIL}$, $P_{2,1FIL}$, $P_{2,2FIL}$, and $P_{3,2FIL}$ by the kill dose of 8,000 μW·sec/cm² for the Coronavirus gives the 5 equivalent maximum velocity curves $v_{max}$ for each irradiance calculation method. One of these assumptions has to be picked, but here to show all the cases together, all 5 are selected and are indicated as $V_{1,1FIL}$, $V_{1,2FIL}$, $V_{2,1FIL}$, $V_{2,2FIL}$, and $V_3$,2FIL in FIG. 28.2. These equivalent 5 $v_{max}$ curves are referred to as "V" curves.

FIG. 69 depicts the peak airflow velocity as a function of $R_2$ calculated by the $v(r_{MAX})$ relation given in (8.7) where $r_{MAX}(R_1, R_2)$ is calculated by the expression (8.8) for the maximum volumetric airflow rate $Q_{MAX}$ for the reactor. For a given $Q_{MAX}$, increasing the $R_2$ in the coaxial tube for a fixed $R_1$, which is the UV-C tube radius in the center, gives a lower $v_{max}$. The selected v curves have to be higher than the dotted $v(r_{MAX})$ curve in the entire cross-section $R_1 \le r \le R_2$. If the $v(r_{MAX})$ curve indicates larger values than the V curves in the cross-section, the airflow will not satisfy the kill dose. The marked portion as $r > R_2$ gives the minimum radius for a possible design which satisfies the kill dose.

The irradiance integral $P_I$ and the corresponding V curves are descending curves as a function of increasing radius r as can be seen in FIG. 69. Even if its corresponding $v_{max}$ at $r_{MAX}$ is equal to or larger than the airflow velocity $v(r_{MAX})$, it is not a guarantee that it will be larger than the airflow at every point in the coaxial air flow cross section.

Figure 70:
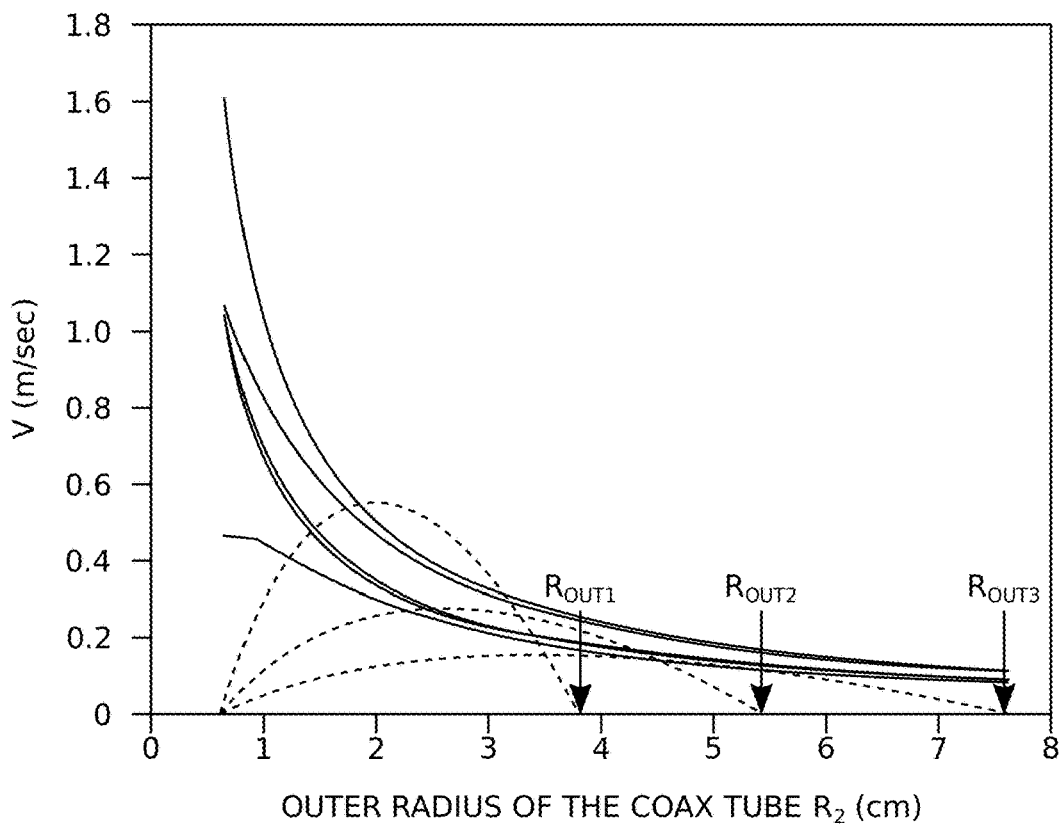
FIG. 70 illustrates airflow velocity distributions as a function of radius for three outer radiuses $R_2=R_{OUT1}$, $R_{OUT2}$, and $R_{OUT3}$ along with the $V_{1,1FIL}$, $V_{1,2FIL}$ $V_{2,1FIL}$, $V_{2,2FIL}$, and $V_{3,2FIL}$ functions showing that $R_{OUT1}$ does not satisfy kill dose requirement for all irradiation formulations.
Figure 71:
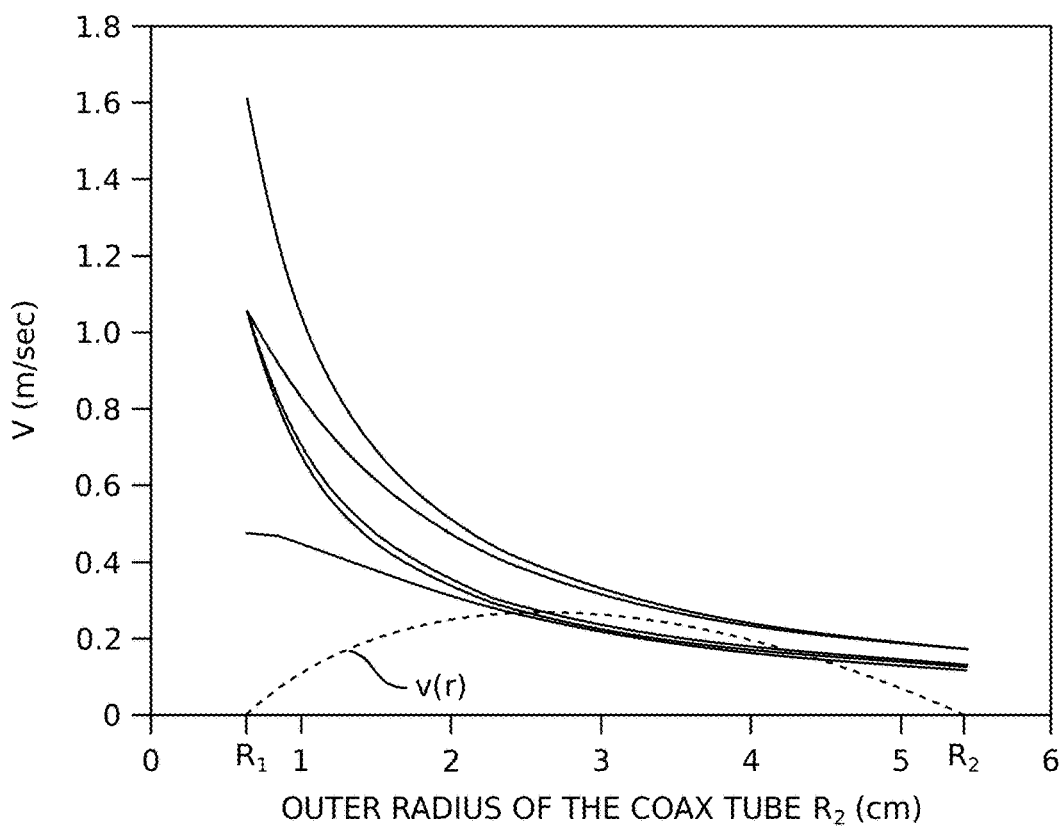
FIG. 71 illustrates the issue for only one coax tube structure having $R_2=R design of the Ultra-Violet Germicidal Irradiation Designer (UVGI) devices explained in this work.

FIG. 70 illustrates airflow velocity distributions as a function of radius for three outer radiuses $R_2=R_{OUT1}$, $R_{OUT2}$, and $R_{OUT3}$ along with the $V_{1,1FIL}$, $V_{1,2FIL}$, $V_{2,1FIL}$, $V_{2,2FIL}$, and $V_{3,2FIL}$ functions showing that $R_{OUT1}$ does not satisfy kill dose requirement for all irradiation formulations. The $R_{OUT2}$ satisfies the kill dose condition for 3 out of 5 irradiation formulations and ONLY $R_{OUT3}$ satisfies the kill dose condition for all 5 irradiation formulations.

FIG. 71 illustrates the issue for only one coax tube structure having $R_2=R_{OUT2}$ shown in FIG. 70 to give a clearer picture for the outer radius $R_2$ selection algorithm. As can be seen, $V_{1,1FIL}$, $V_{1,2FIL}$, and $V_{2,1FIL}$ are partially below the calculated airflow velocity profile v(r) in the coax tube, which is calculated by relation (8.7) and is shown with dotted line. This graphically illustrates that the coax tube has airflow velocities higher than the equivalent airflow velocities $V_{1,1FIL}$, $V_{1,2FIL}$, and $V_{2,1FIL}$ that are calculated by dividing the irradiation integral to the kill dose.

The design goal is to find out what is the correct $R_2$, which is the outer radius of the hollow tube or coax tube, the UV-C irradiation reactor satisfying a given kill dose for a given reactor length L, the UV-C discharge tube radius of $R_1$, and the specified UV-C radiative power for a given airflow volumetric flow rate Q. To be compatible with the earlier sections, the airflow and the UV-C lamp orientation is along the z axis and the reactor is defined in $z_{min}\le z\le z_{max}$.

i) Pick up an irradiation calculation method from $I_{1,1FIL}$, $I_{1,2FIL}$, $I_{2,1FIL}$, $I_{2,2FIL}$, and $I_{3,2FIL}$, ii) Construct the irradiance and irradiance integral calculation interval for from to UV-C tube diameter, $R_1\le r\le R_{2MAX}$, $R_1$ being the radius of the UV-C discharge tube being used and $R_{2MAX}$ being the upper limit of the search radius for outer radius of the hollow tube radial reactor, iii) Calculate irradiance I(r,z) at the radius interval $R_1\le r\le R_{2MAX}$ and the reactor height interval along z axes. As shown in FIG. 33, the reactor height L is greater than the UV-C tube length d=2a.

iv) Calculate the irradiance integral, $$P_I(r) = \int_{z_{min}}^{z_{max}} I(r, z)dz,$$

v) Calculate the velocity equivalent of irradiation integral, $v_{MAX}(r)$ from the kill dose and store it in a kill dose velocity array $P_I$, $$v_{MAX}(r) = \frac{P_I(r)}{D_{KILL}} \text{ for } R_1 \le r \le R_{2MAX}$$

vi) Calculate the air pressure difference Δp from the desired volumetric flow rate using (8.21) which appears in the air velocity profile flow in the hollow tube at a given $R_2$, $$\Delta p = \frac{Q}{[F_1(R_2) - F_1(R_1)] + [F_2(R_2) - F_2(R_1)] + [F_3(R_2) - F_3(R_1)]}$$

vii) Calculate the peak airflow velocity point $r_{MAX}$ and $v(r_{MAX})$ in the airflow velocity profile relation as given in (8.7) and (8.8), $$v(r) = -\Delta p \frac{(R_2^2 - R_1^2)\ln(r) + (r^2 - R_2^2)\ln(R_1) + (R_1^2 - r^2)\ln(R_2)}{4L\mu \cdot \ln\left(\frac{R_1}{R_2}\right)}$$

For $$r_{MAX} = \sqrt{\frac{(R_2^2 - R_1^2)}{2\ln\left(\frac{R_2}{R_1}\right)}}$$

viii) Calculate the velocity equivalent of the irradiation integral at $r_{MAX}$ $$v_{MAX}(r_{MAX}) = \frac{P_I(r_{MAX})}{D_{KILL}}$$

If $$v_{MAX}(r_{MAX}) = \frac{P_I(r_{MAX})}{D_{KILL}} > v(r_{MAX})$$

This condition is the necessary condition that needs to be satisfied, but it does not guarantee that the velocity equivalent of the irradiation integral is greater than the velocity in the velocity profile of the actual flow in the entire cross-section. Therefore, there is a need to check if the entire cross-section of the airflow in the hollow tube satisfies the condition, $$v_{MAX}(r) > v(r) \text{ for } R_1 \le r \le R_2$$

This check is named the kill dose check and is the sufficient condition to meet the kill dose in the reactor. If it is satisfied, the airflow in the reactor with outer diameter of $R_2$ satisfies the kill dose. If not, either an increase in power of the UV-C tube satisfying the condition has to be found, or the outer tube radius $R_2$ must be increased until the kill dose check is satisfied. This helps guarantee that the new value of $R_2$ satisfies the kill dose in the entire cross-section of the airflow in the hollow tube. Since the kill dose velocity array is formed, the calculations need not be iteratively repeated to find the $R_2$ satisfying the velocity equivalent of irradiation integral. Both processes require solution of non-linear equations solved using discretizes Newton's method [47].

FIG. 72 is a flowchart illustrating a method for designing a radial ultraviolet-C (UV-C) mercury discharge tube airflow irradiator. Although the method is depicted as a sequence of numbered steps for clarity, the numbering does not necessarily dictate the order of the steps. It should be understood that some of these steps may be skipped, performed in parallel, or performed without the requirement of maintaining a strict order of sequence. Generally however, the method follows the numeric order of the depicted steps. The method starts at Step 7200.

Step 7202 selects the irradiation reactor unit chamber and mercury discharge tube cross-sectional dimensions. In more detail, Step 7202*a* selects a mercury discharge tube radius ($R_1$), and Step 7202*b* selects an irradiation reactor unit cylinder interior radius ($R_2$), where $R_1 \leq r \leq R_2$. Typically, the irradiation reactor unit cylinder interior surface is reflective. Step 7204 calculates an irradiation integral ($I_P$). Step 7206 determines a deactivation dosage ($D_{kill}$). For example, the step may determine a deactivation dosage of at least 8,000 micro-Watt seconds per square centimeter ($\mu W \cdot sec/cm^2$) for a COVID-19 pathogen. Step 7208 calculates a maximum airflow velocity ($V_{MAX}$) in response to the irradiation integral, cross-sectional dimensions, and deactivation dosage. Step 7210 selects the irradiation reactor unit chamber length (L). In one aspect, the irradiation reactor unit chamber length (L) is selected to be in the range of 10 to 25 percent greater than mercury discharge tube length d.

In one aspect, Step 7203 selects an irradiation calculation from the group comprising surface irradiation ($I_1$), point irradiation ($I_2$), or view factor ($I_3$), and the calculation of the irradiation integral in Step 7204 is responsive to the selected irradiation calculation.

If Step 7203 selects either the surface irradiation or point irradiation calculation, this step also selects the number of discharge tube filaments to be modeled. In more detail, Step 7203 calculates irradiance I(r, z) along a length (L) of the irradiation reactor unit cylinder, where $z_{min} \leq z < z_{max}$;
where $d < z_{max} - z_{min}$; and,
where d is the length of the mercury discharge tube.

Step 7203a calculates I(r,z) for surface irradiance as follows:

$$I_1(r) = \frac{\sigma}{4\pi} \int_{-a}^{+a} \frac{n \cdot r}{|r|^3} dz$$

where $\sigma$ is the UV-C mercury discharge tube UV-C radiating power density in watts per meter (W/m);
where a is the UV-C mercury discharge tube half-length (a=d/2); and,
where n is a normal vector.

Step 7203b calculates I(r,z) for point irradiance as follows:

$$I_2(r) = \frac{\sigma}{4\pi} \int_{-a}^{+a} \frac{1}{|r|^2} dz.$$

where $\sigma$ is the UV-C mercury discharge tube UV-C radiating power density in (W/m); and,
where a is the UV-C mercury discharge tube half-length (a=d/2).

Step 7203c calculates I(r,z) for view factor as follows:

$$I_3 = \frac{P_{UV-C}}{2\pi R_1 d} F_S;$$

where $F_S$ is a calculation based upon the view factor model between two coaxial mercury discharge tube cylinders; and,
where $P_{UV-C}$ is the total UV-C radiative power.

Regardless of the irradiance calculation method selected, Step 7204 calculates the irradiation integral as follows:

$$P_I(r) = \int_{z_{min}}^{z_{max}} I(r, z) dz.$$

Then, Step 7205a calculates a velocity equivalent of the irradiation integral in the form of the deactivation dose as follows:

$$v_{MAX}(r) = \frac{P_I(r)}{D_{KILL}} \text{ for } R_1 \leq r \leq R_{2MAX}.$$

Step 7205b calculates the differential air pressure between irradiation reactor unit cylinder input and output as follows:

$$\Delta p = \frac{Q}{[F_1(R_2) - F_1(R_1)] + [F_2(R_2) - F_2(R_1)] + [F_3(R_2) - F_3(R_1)]}$$

where $\Delta p$ is the pressure differential along length L of the irradiation reactor unit cylinder with a mercury discharge tube length of d;
where Q is the volumetric airflow rate;

where $$F_1(r) = \Delta p \cdot C(R_2^2 - R_1^2)\frac{r^2}{2}\left[\ln(r) - \frac{1}{2}\right]$$

$$F_2(r) = \Delta p \cdot C \cdot \ln(R_1)\frac{r^2}{2}\left[\frac{r^2}{2} - R_2^2\right]$$

$$F_3(r) = \Delta p \cdot C \cdot \ln(R_2)\frac{r^2}{2}\left[R_1^2 - \frac{r^2}{2}\right] \text{ and,}$$

where the multiplier C is;

$$C = \frac{\pi}{2L\mu \cdot \ln\left(\frac{R_2}{R_1}\right)}.$$

Step 7205*c* calculates the peak airflow velocity point $r_{MAX}$ and $v(r_{MAX})$ in the airflow velocity as follows:

$$v(r) = -\Delta p\frac{(R_2^2 - R_1^2)\ln(r) + (r^2 - R_2^2)\ln(R_1) + (R_1^2 - r^2)\ln(R_2)}{4L\mu \cdot \ln\left(\frac{R_1}{R_2}\right)}$$

for $$r_{MAX} = \sqrt{\frac{(R_2^2 - R_1^2)}{2ln\left(\frac{R_2}{R_1}\right)}}.$$

Then, calculating the maximum airflow velocity (v) in Step 7208 includes calculating a necessary condition irradiation integral at $r_{MAX}$ as follows:

$$v_{MAX}(r_{MAX}) = \frac{P_I(r_{MAX})}{D_{KILL}}$$

if $$v_{MAX}(r_{MAX}) = \frac{P_l(r_{MAX})}{D_{KILL}} > v(r_{MAX}).$$

Further, Step 7208 calculates a sufficient condition irradiation integral at $r_{MAX}$ as follows:

$$v_{MAX}(r_{MAX}) > v(r) \text{ for } R_1 \leq r \leq R_2.$$

Figure 72:
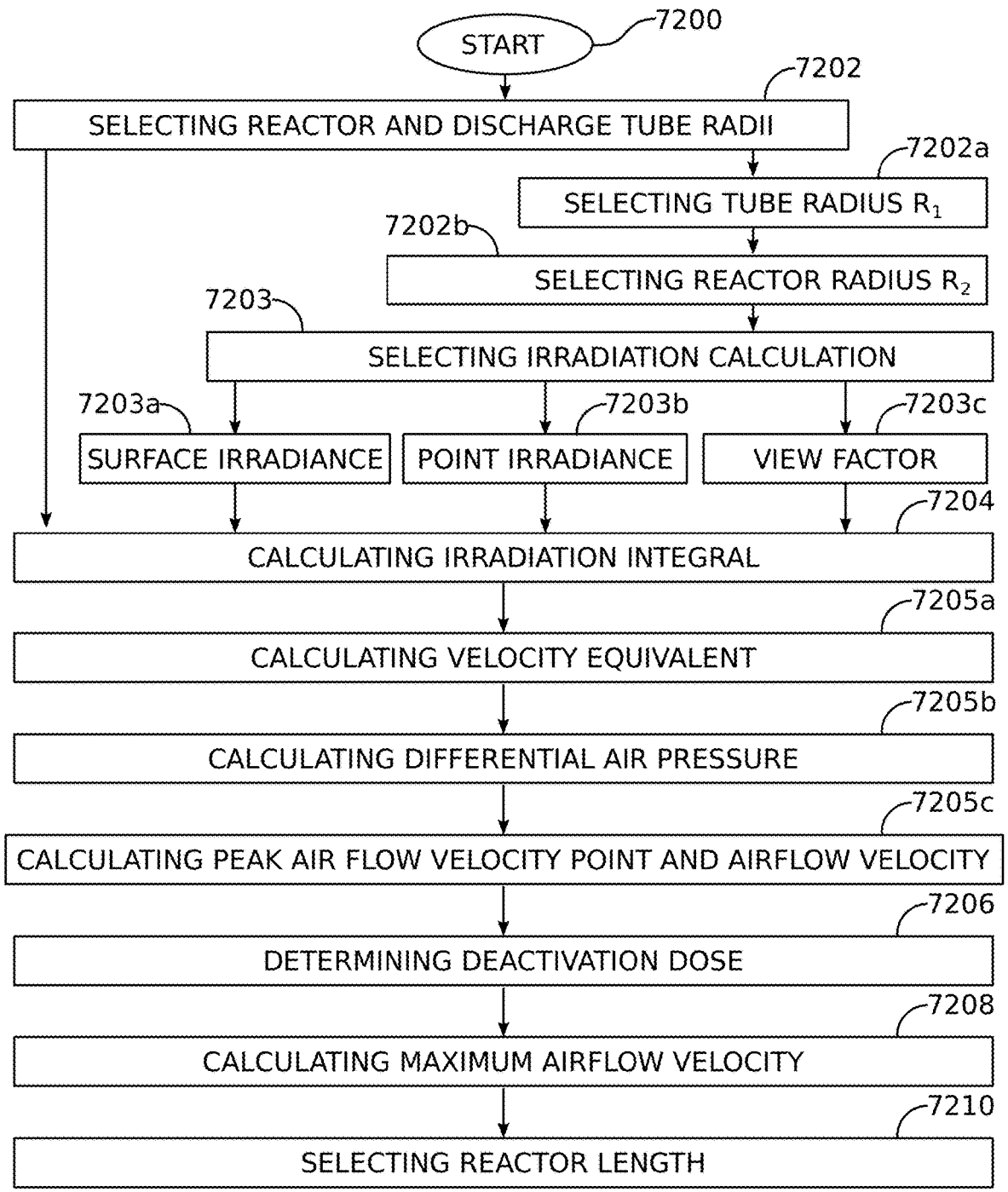
Figure 73:
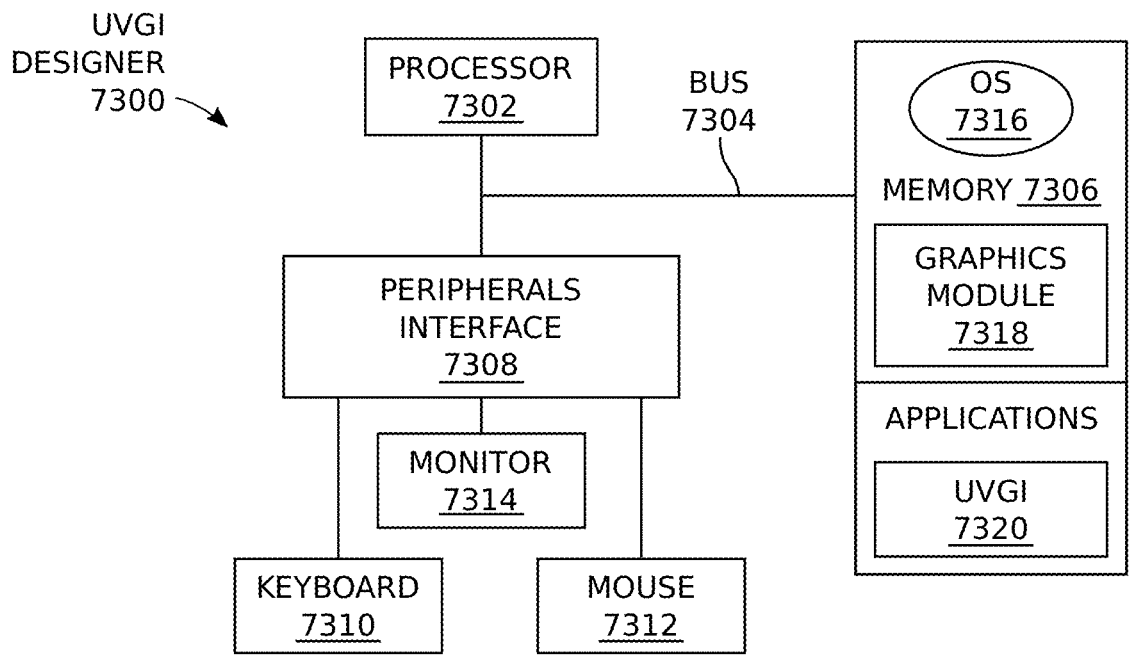

FIG. 73 depicts an exemplary computer system capable of enabling the ultraviolet germicidal irradiation designer (UVGI) program summarized in FIG. 72. It should be understood that the steps described in FIG. 72 may be enabled as a set of processor instructions for designing a radial ultraviolet-C(UV-C) mercury discharge tube airflow irradiator, which can be stored in a non-transitory memory. It is also understood that the steps described below can be formulated into code in a number of computer languages by a person of ordinary skill in the art. As such, the UVGI designer system 7300 of FIG. 73 depicts a processor 7302 connected by bus 7304 to a non-transitory memory 7306 and a peripherals interface 7308. The peripherals interface 7308 is connected, for example, to a keyboard 7310, mouse 7312, and monitor 7314. As is conventional, the memory 7306 may store an operating system (OS) 7316 and modules, such as graphics module 7318. The memory 7306 would conventionally store several applications. In this case only the UVGI designer application 7320 is shown.

The computing system 7300 broadly represents any type or form of electrical load, including a single or multi-processor computing device or system capable of executing computer-readable instructions. Examples of computing systems include, without limitation, workstations, laptops, client-side terminals, servers, distributed computing systems, mobile devices, network switches, network routers (e.g., backbone routers, edge routers, core routers, mobile service routers, broadband routers, etc.), network appliances (e.g., network security appliances, network control appliances, network timing appliances, SSL VPN (Secure Sockets Layer Virtual Private Network) appliances, etc.), network controllers, gateways (e.g., service gateways, mobile packet gateways, multi-access gateways, security gateways, etc.), and/or any other type or form of computing system or device. Memory 7306 generally represents any type or form of storage device or medium capable of storing data and/or other computer-readable instructions. Examples of system memory include, without limitation, Read Only Memory (ROM), flash memory, thumb drives, hard drives, CD disks, or any other suitable memory device.

The UVGI designer code performs the calculations described above. However, the program requires human interaction to select variables such a lamp and reactor lengths and radii and explicit irradiator components. The various formulas presented above are widely known in the art. At least part of the novelty of the method of FIG. 72 and software of FIG. 73 is in arranging the formulas so that variables found aid in the design of a portable irradiator. Further, a step-by-step linkage is created between the formulas for the particular purpose of the portable irradiator design. Perhaps most important, the linkage between formulas permits variables to submitted, via a user interface (UI) for example, that permit the design to be customized for particular purposes, based upon variables such as power consumption, size, weight, and the deactivation dose required for a pathogen of interest.

UV-C LED Source Based Irradiance Reactor Design

The size, power consumption, and irradiation related calculations of UV-C LEDs are very different as compared to the mercury discharge lamp related calculations, which leads into a very different design style for a of UV-C LED irradiance reactor. Before going into the UV-C LED based irradiance reactor design, it will be helpful to go over the irradiance related calculations for a UV-C LED system.

Mathematical Derivation of the UV-C Irradiance Calculations from UV-C LED Source UV-C LEDs are becoming a preferred source of UV-C radiation. They are much smaller and lighter than discharge lamps, with an exemplary size of 3.5×3.5 mm in a surface mount package approximately 1 mm in height. They have smaller power and conversion efficiencies, but since their radiation is focused, they can supply a surprisingly higher irradiance at the same distances away from the source, as compared to mercury discharge UV-C tubes with much higher radiative power outputs.

The UV-C LED supplies a focused UV-C radiation. The UV-C LED radiation pattern is defined by two methods. The first and the easiest method being as simple as a half apex angle $\theta_{APEX}$, like 60° in the case of CL7003C2. When the radiation pattern is defined only by a half apex angle it means that the radiation is confined in a solid angle and it is assumed that the radiation is uniformly confined in the given half apex angle of the cone, which it is referred to as the light cone. As a result, there is no radiation outside the cone with a half apex angle defined.

In this situation the irradiance at the center line of the UV-C LED at a distance r away from it can be calculated as, $$I_{LED}(r) = \frac{P_{UV-C}}{2\pi r^2[1 - \cos(\theta_{APEX})]} \quad (9.1)$$

Where $\theta_{APEX}$ is the half apex angle of the cone and $P_{UV-C}$ is the UV-C radiative power of the UV-C LED. The denominator of (9.1) is basically the area of a spherical cap and it basically states Gauss law. If radiation is uniformly distributed in all directions (9.1) would be $$I_{LED}(r) = \frac{P_{UV-C}}{4\pi r^2} \quad (9.2)$$

A more accurate approach of calculating the UV-C irradiation at a given coordinate is using the supplied polar radiation pattern given for the UV-C LED.

The UVGI Designer program takes the datasheet information of the UV-C LEDs and their placement x, y, z coordinates with their orientation vector. The orientation vector is a unit vector defining where the LED is pointing in reference to the coordinate system where the LED placement x, y, z coordinates are given. With this information the UVGI Designer can numerically calculate the total irradiance at any given coordinate for any number of arbitrarily placed and oriented UV-C LEDs.

Figure 74:
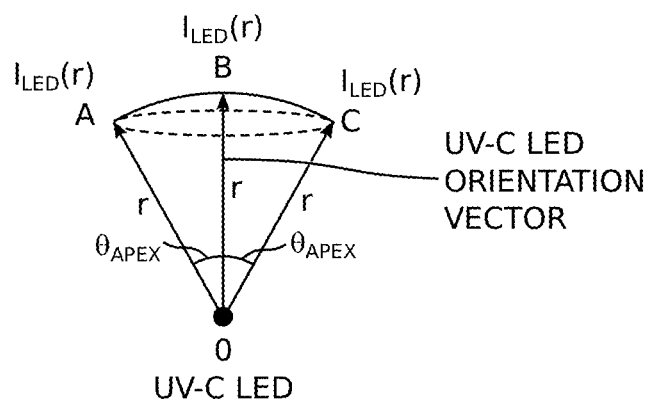

FIG. 74 illustrates of the irradiance relation given at (9.1) showing the light cone and its parameters.

Figure 75:
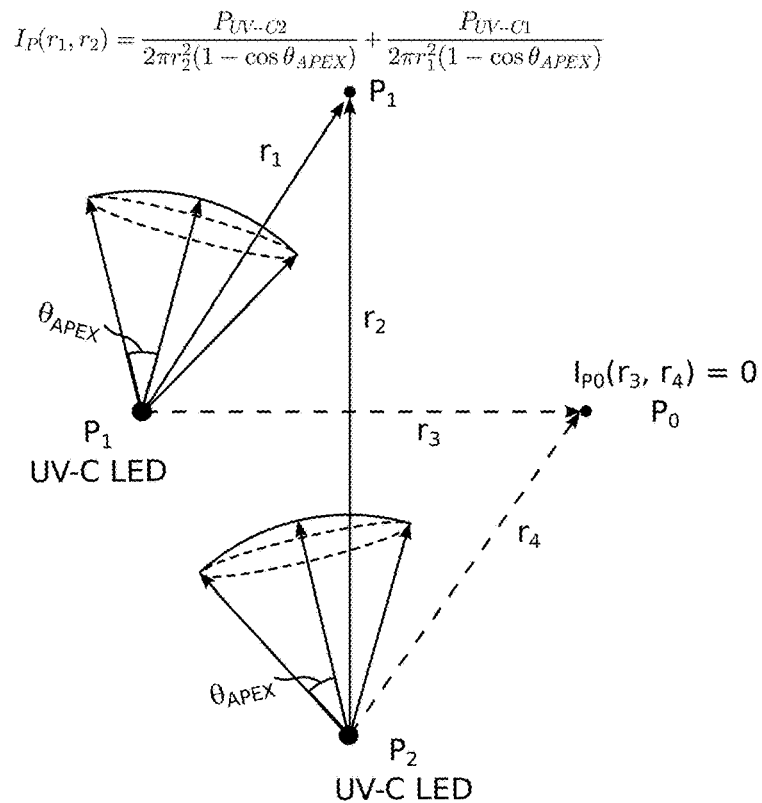

FIG. 75 shows irradiance formulations generalized for placing UV-C LEDs with arbitrary orientation vectors.

Figure 76:
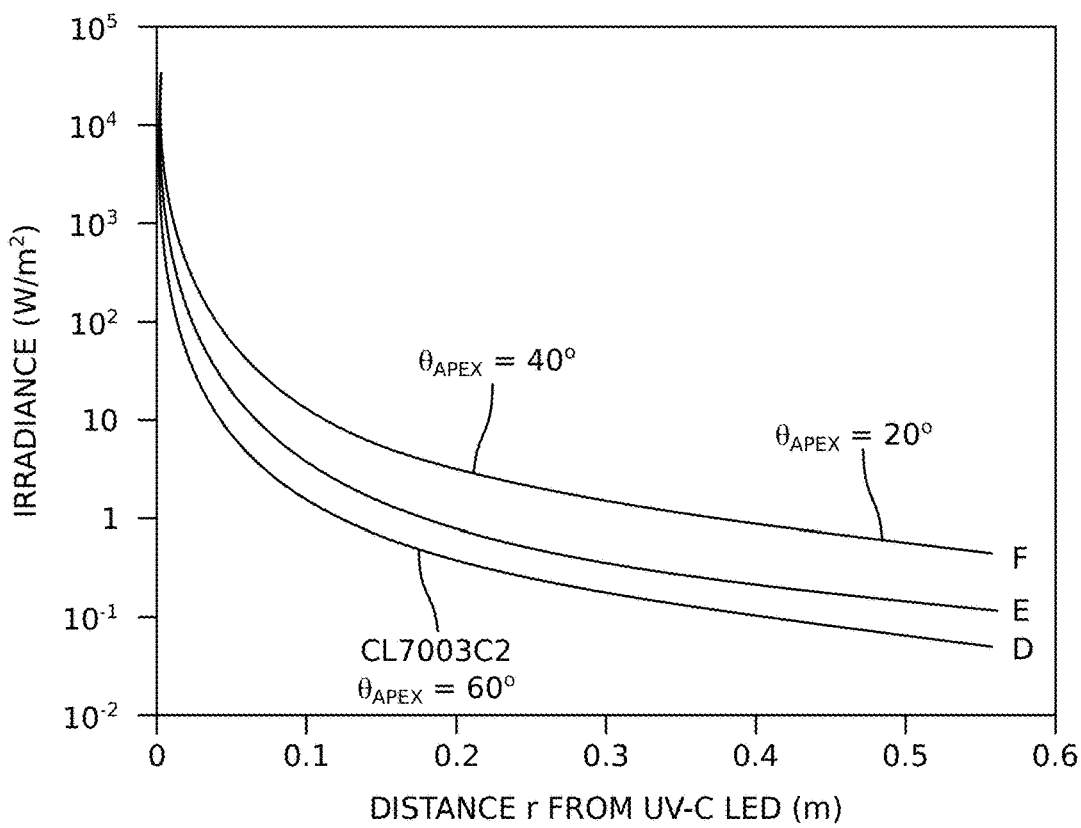

FIG. 76 depicts the calculated irradiance from a UV-C LED as a function of distance for $\theta_{APEX}$ half apex angles of 20°, 40°, and 60°. The 60° curve corresponds to the CL7003C2 UV-C LED supplying 50 mW of UV-C radiative power.

Since the UV-C mercury discharge lamps are geometrically very different as compared to the UV-C LEDs, a direct comparison is difficult. To make a fair comparison, a linear array of 40 CL7003C2 UV-C LEDs are placed side-by-side with the same length of 13.95 cm as the TUV PL-S 13 W/2P mercury discharge lamp. The total UV-C radiative power for this linear array is 50 mW×40=2 W giving σ=14.34 mW/mm of UV-C power density, and consuming 3.3 W×40=132 W of electrical power. Comparing this result to the TUV PL-S 13 W/2P mercury discharge lamp figures of 3.4 W, 24.39 mW/mm, and 13 W, it clearly shows the need for a larger electrical power to be comparable.

UV-C LED Airflow Irradiance Reactor Design.

Figure 77:
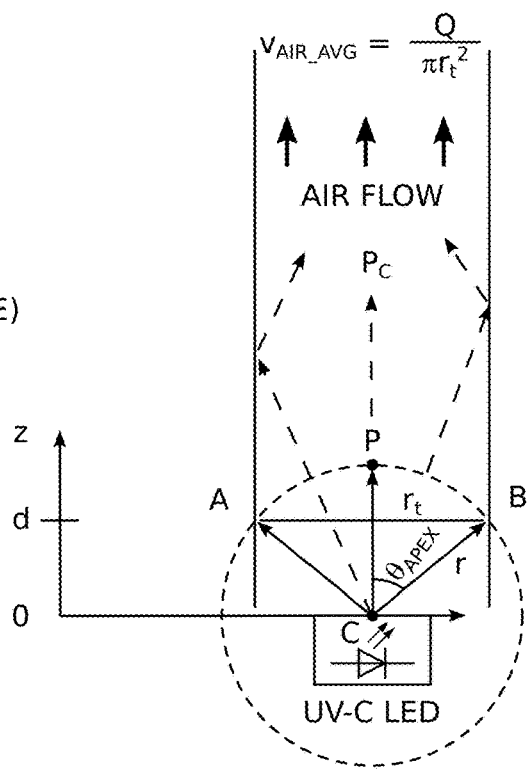

FIG. 77 depicts a UV-C LED based reactor design based upon a tubular structure. The UV-C LED, like the CL7003C2, is placed at the center of the tube at z=0 and radiates in a cone that has a half apex angle θ of 60° along the length of the tube z axis. As shown, the LED orientation vector direction is along the center line of the airflow guide.

The airflow guide has a radius of $r_t$ and the airflow is in the direction or the opposing direction of the central axis of the tube. The average flow velocity $v_{AVG}$ of the airflow is given as a function of the volumetric airflow rate Q. The airflow velocity profile in the tube is preferably set to laminar, rather than the turbulent flow condition. As it is done in the mercury discharge UV-C reactor, the air velocity profile in the tube is tailored to meet the desired kill dose for a given volumetric airflow rate for a calculated length of the periodic arrangement of the light guide structures. The cross-sectional geometry of the tube can be any shape, such as a rectangular or square. However, having a cross-section circular shape has advantages, because it matches the radiation pattern of the LED better.

The arc shown with dotted line as APB is the intersection of the spherical cap of the sphere with its center at C and with a radius of r. The r can be calculated as a function of tube radius $r_t$ and the half apex angle $\theta_{APEX}$ related to the LED focus angle as, $$r = \frac{r_t}{\sin(\theta_{APEX})} \quad (9.3)$$

The distance d from the LED to the middle of the chord APB of the circle radius given by (9.3) and is defined by the half apex angle $\theta_{APEX}$ related to the LED focus angle as, $$d = \frac{r_t}{\tan(\theta_{APEX})} \quad (9.4)$$

Since the LED's radiation pattern is defined by the half apex angle θ related to the LED focus angle, d is the length of the dark region on the inner tube surface of the light guide from the LED. In other words, LED illuminates the inner surface of the light guide with UV-C radiation at a distance d further away from the LED, which corresponds to coordinate Z=d in FIG. 77.

Figure 78:
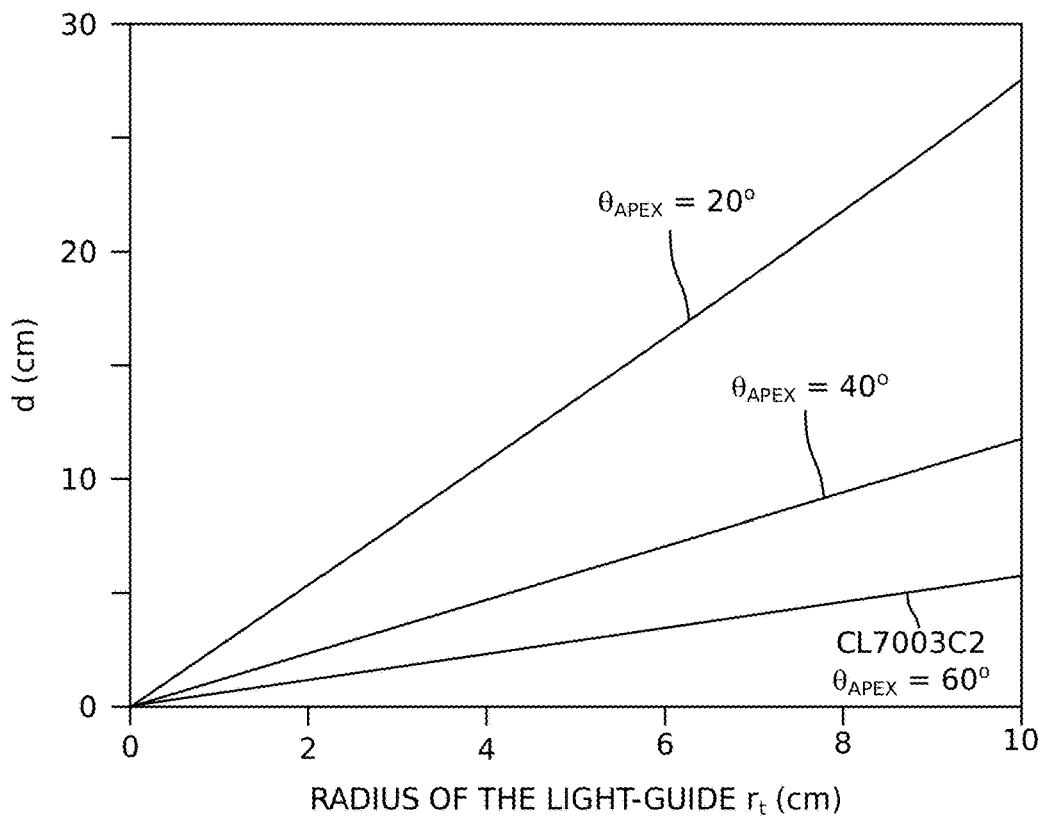

FIG. 78 depicts d as a function of the radius r of the light guide for θ=20°, 40°, and 60° half apex angle $\theta A_{PEX}$, as related to the LED focus angle.

Figure 79:
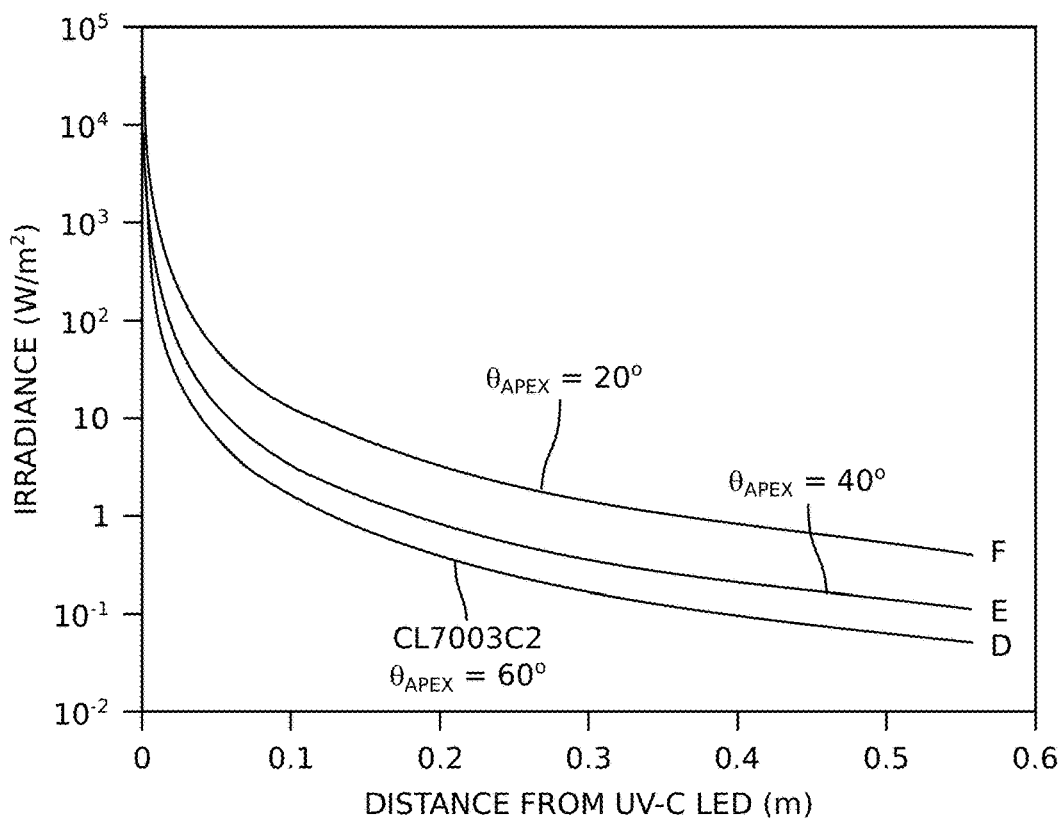

FIG. 79 depicts the UV-C irradiance along the orientation vector direction of the LED for $\theta_{APEX}$=20°, 40° and 60° half apex angle. The LED radiative power is 50 mW for all of the cases (CL7003C2 UV-C LED). If there was no light guide, at a distance r along the center axes $CPP_C$ (FIG. 77) from the LED, the irradiation provided by the LED can be given with the relation (9.1).

The inner surface of the LED airflow irradiator, which may also be referred to as a light guide, can be made of a material highly reflective to UV-C. If the tube itself is made from Aluminum and polished, its reflectivity is on the order of 72.5%-77.5% in the UV-C band. A Porex PMR15 coating is 97.5% reflective in the UV-C band [21, 22]. For z>d the radiated UV-C from the LED is reflected from the inner surface of the light guide and so not attenuated inversely proportional with z. Therefore, most of the UV-C attenuation is reached at z=d in the light guide with less attenuation along the light guide after >d. The attenuation for a given $r_t$ are calculated using the view factor model [35, 36].

Figure 80:
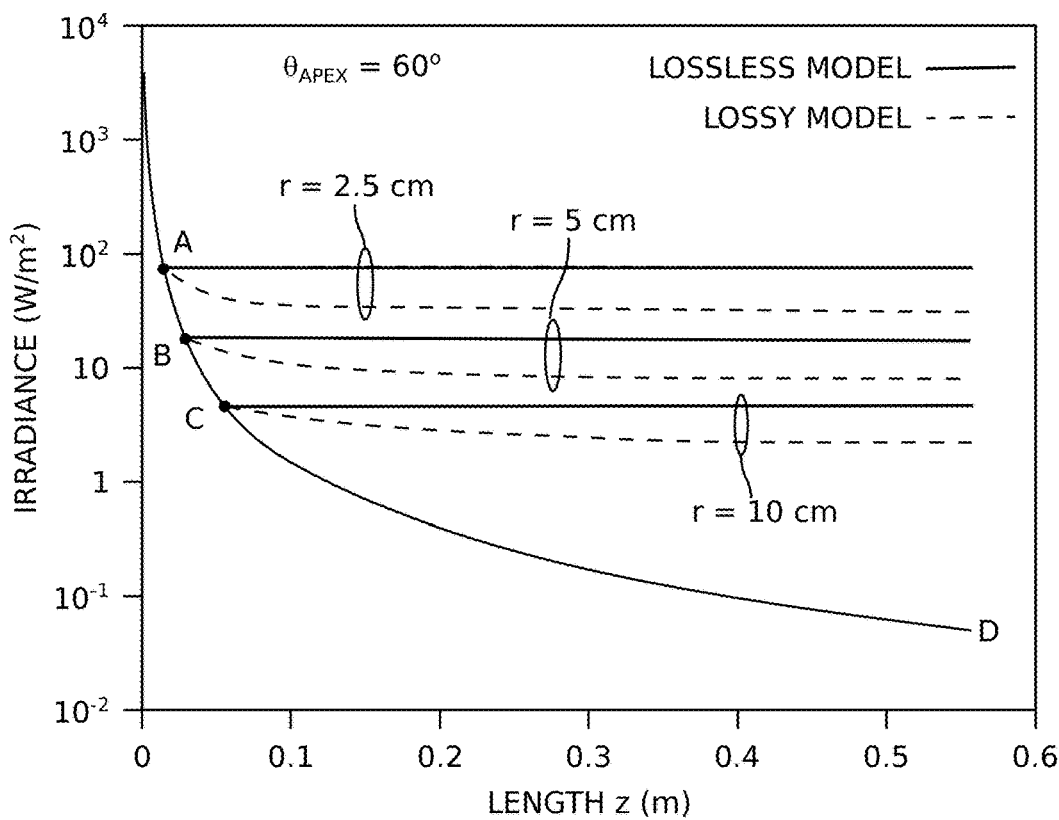

FIG. 80 illustrates UV-C irradiation $I(z,r_t)$ for $r_t$=2.5, 5, and 10 cm of light guide radii with and without attenuation for the half apex angle $\theta_{APEX}$=60°. Curve D shows the attenuation of the LED if not in a light guide.

Figure 81:
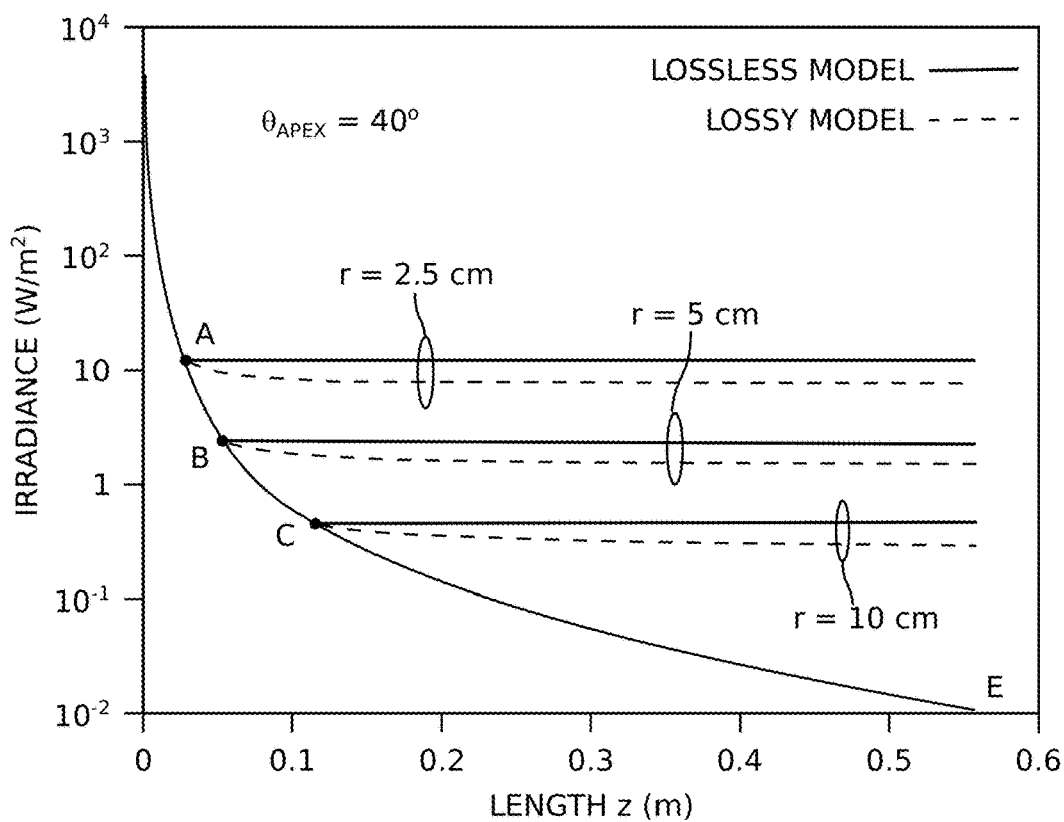

FIG. 81 illustrates UV-C irradiation $I(z,r_t)$ for $r_t$=2.5, 5, and 10 cm of light guide radii with and without attenuation for the half apex angle $\theta_{APEX}$=40°. Curve E shows the attenuation of the LED if not in a light guide.

Figure 82:
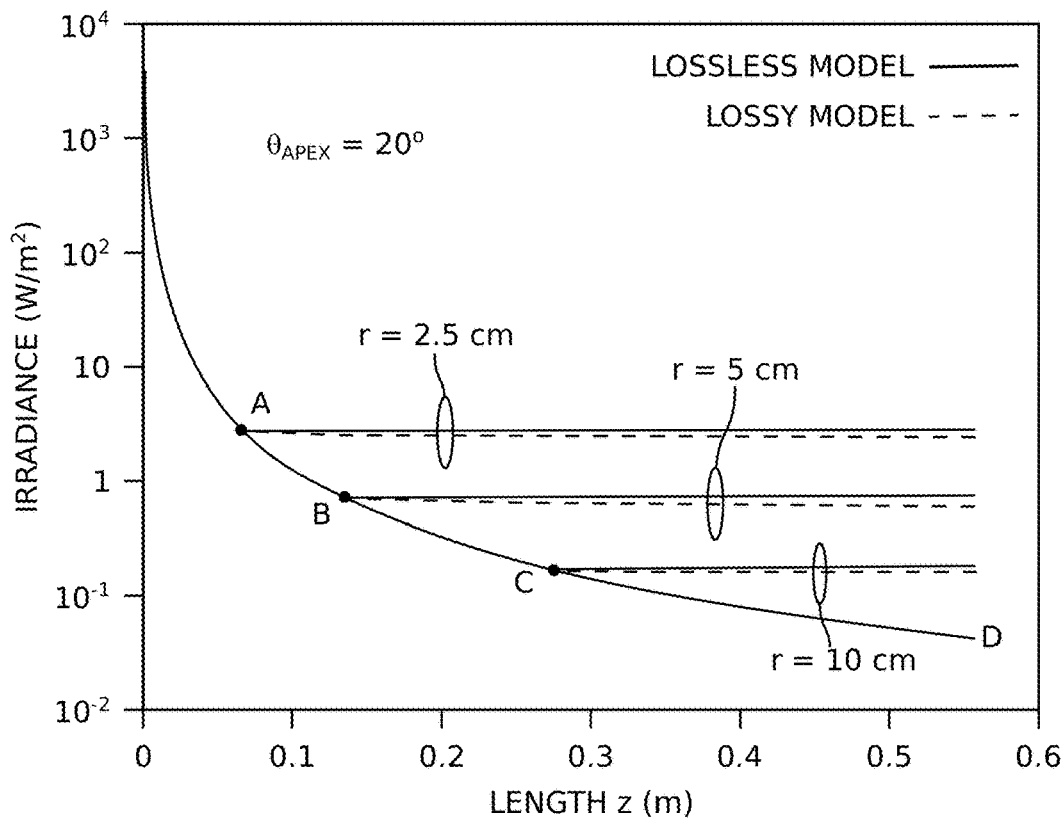

FIG. 82 illustrates UV-C irradiation $I(z, r_t)$ for $r_t$=2.5, 5, and 10 cm of light guide radii with and without attenuation for the half apex angle $\theta_{APEX}$=20°. Curve F shows the attenuation of the LED if not in a light guide. The d($r_t$, $\theta_{APEX}$) given in (9.4) and the attenuation for z>d are different for all the cases shown in FIGS. 80-82.

Figure 83:
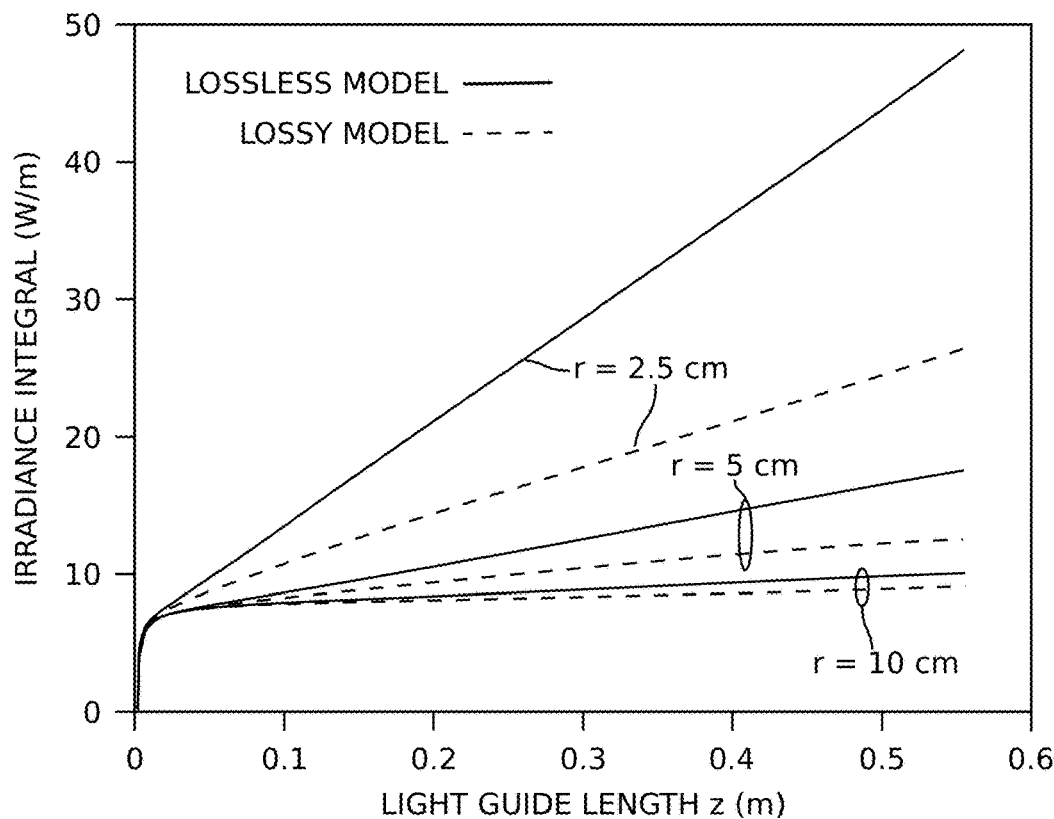

FIG. 83 depicts the irradiance integral $P_I(z, r_t)$ as a function of z in the light guide for $r_t$=2.5, 5, and 10 cm. The relation is given as, $$P_I(z, r_t) = \int_0^z I(z', r_t)dz' \quad (9.5)$$

Where the plot of the irradiation function in the integral (9.5) is shown in FIG. 80. As can be seen for all the radii $P_I(z,r_t)$ the irradiation integral increases rapidly 0<z<d and the increase is more like a linear rate due to the irradiation function $I(z,r_t)$.

Figure 84:
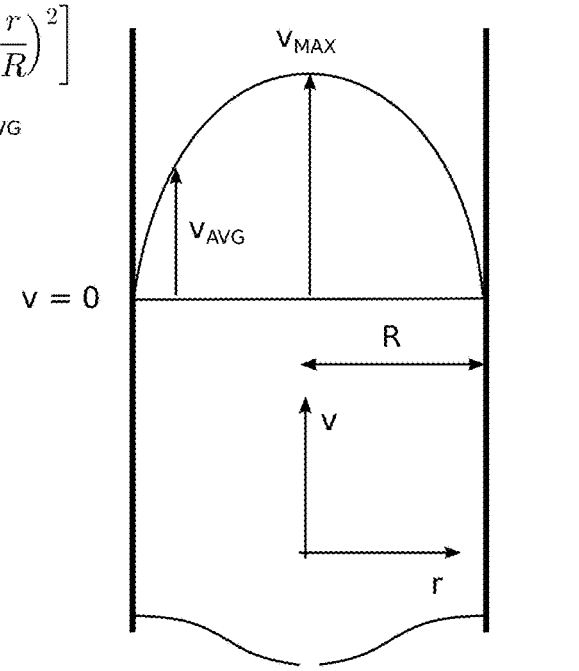

FIG. 84 shows the parabolic velocity profile of airflow under laminar flow conditions. Since the airflow velocity is maximum at the center of the tube and it is known as a function of the volumetric flow rate Q. The corresponding relation between the kill dose and maximum velocity for a given radius $r_t$ and length can be calculated and is also related to the irradiation integral in the light guide as, $$v_{MAX}(z, r_t) = \frac{2Q}{\pi r_t^2} = \frac{1}{D_{KILL}} \int_0^z I(z', r_t)dz' \quad (9.6)$$

Figure 85:
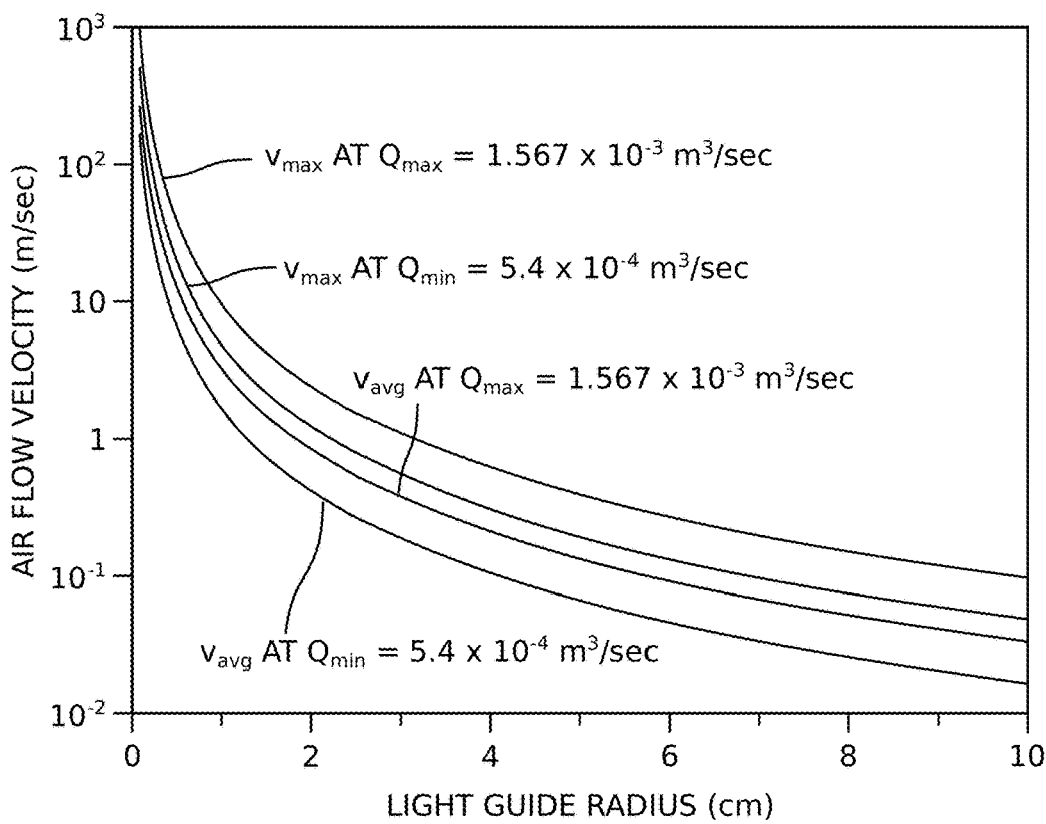

FIG. 85 depicts $v_{AVG}$ and $v_{MAX}$ for a light guide having a length of 55 cm for radii $r_t$=2.5, 5, and 10 cm.

Solving (9.6) for $P_I(z,r_t)$ gives, $$P_I(z, r_t) = \int_0^z I(z', r_t)dz' = \frac{2Q}{\pi r_t^2} D_{KILL} \quad (9.7)$$

(9.7) gives the numerical value of irradiance integral $P_I(z,r_t)$ needed to meet the desired kill dose. On the other hand, by solving (9.6) the equivalent dose value $D_{EQ}$ of the irradiation integral is, $$D_{EQ} = \frac{\pi r_t^2}{2Q} P_I(z, r_t) = \frac{\pi r_t^2}{2Q} \int_0^z I(z', r_t) dz' \qquad (9.8)$$

Figure 86:
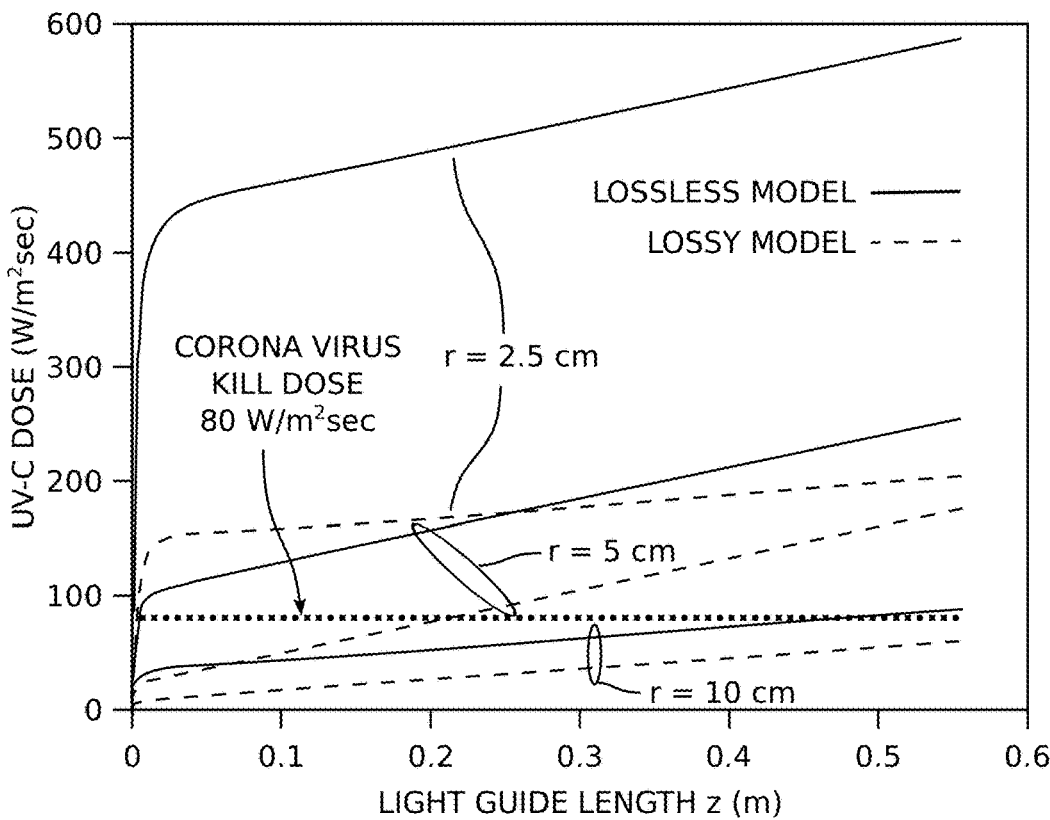

FIG. 86 shows the equivalent dose value $D_{EQ}$ of the irradiation integral for light guide radii of $r_t$=2.5, 5, and 10 cm, as function of z along the length of the light guide using a single 50 mW CL7003C2 UV-C LED. The kill dose of 8,000 $\mu$W·sec·cm$^{-2}$ for Coronavirus is also shown as a reference. As can be seen here, an opposite approach is applied as compared to the UV-C lamp based reactor design.

Figure 87:
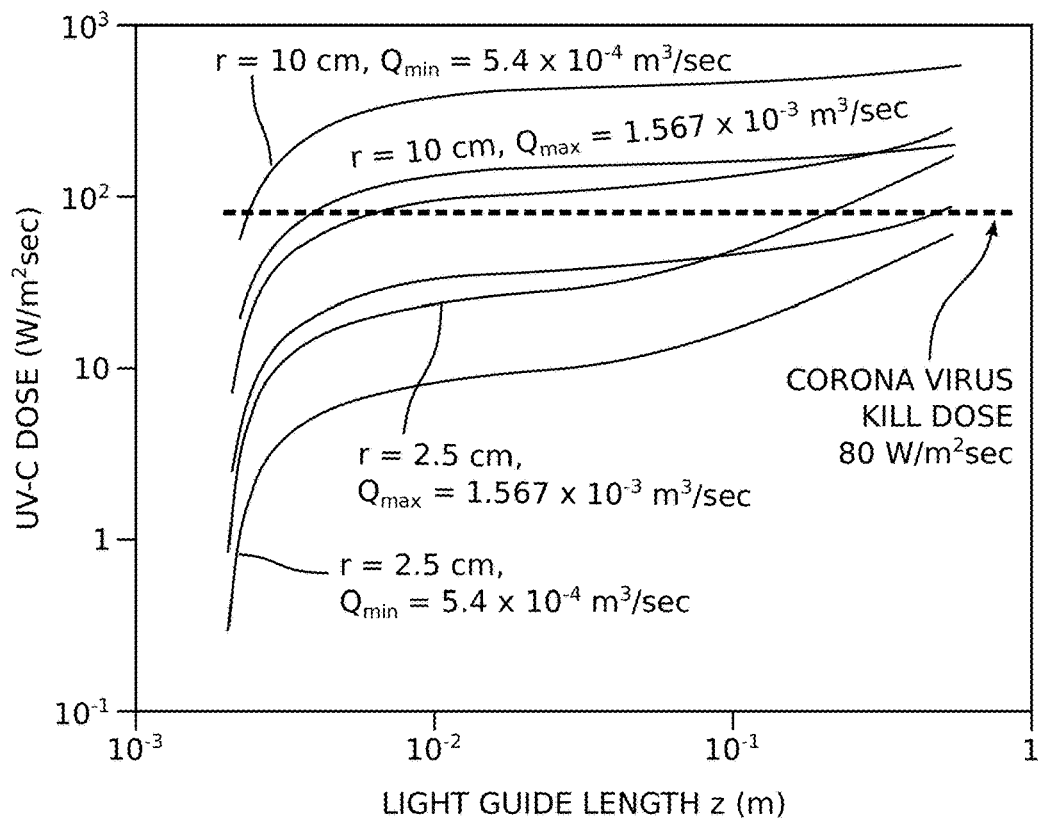

FIG. 87 is log-log presentation of the same data shown in FIG. 86, which more clearly depicts smaller z values. FIGS. 86 and 87 show that the deactivation of Coronavirus is possible by using even a single CL7003C2 UV-C LED in a light guide structure. The problem becomes the radius $r_t$ and the lengths becoming large for a portable application like in the safe face shield irradiation reactor. By using cascaded multiple UV-C LEDs with properly selected lengths in series, a practical length and radius with minimum power consumption can be achieved.

Figure 88:
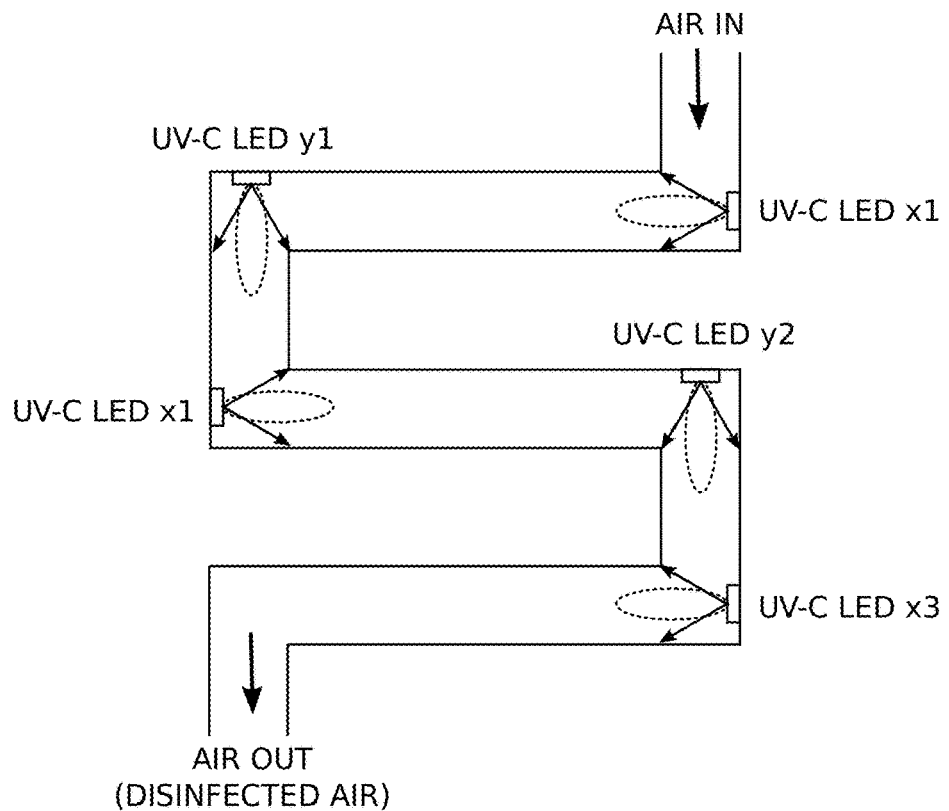

FIG. 88 depicts a serpentine arrangement of UV-C LED segments. To be determined is the optimum length of each straight segment for achieving a minimum total length and power needed to satisfy a given dose requirement for a desired volumetric airflow rate Q.

Optimal Periodic Division of the Light Guide for Achieving a Given Dose Requirement.

A key functional relation in the algorithm can be seen in FIGS. 86 and 87. Since the kill dose is known, the ratio of the kill dose to $D_{EQ}$ gives the number of equal segments that is needed as a function of z.

Figure 89:
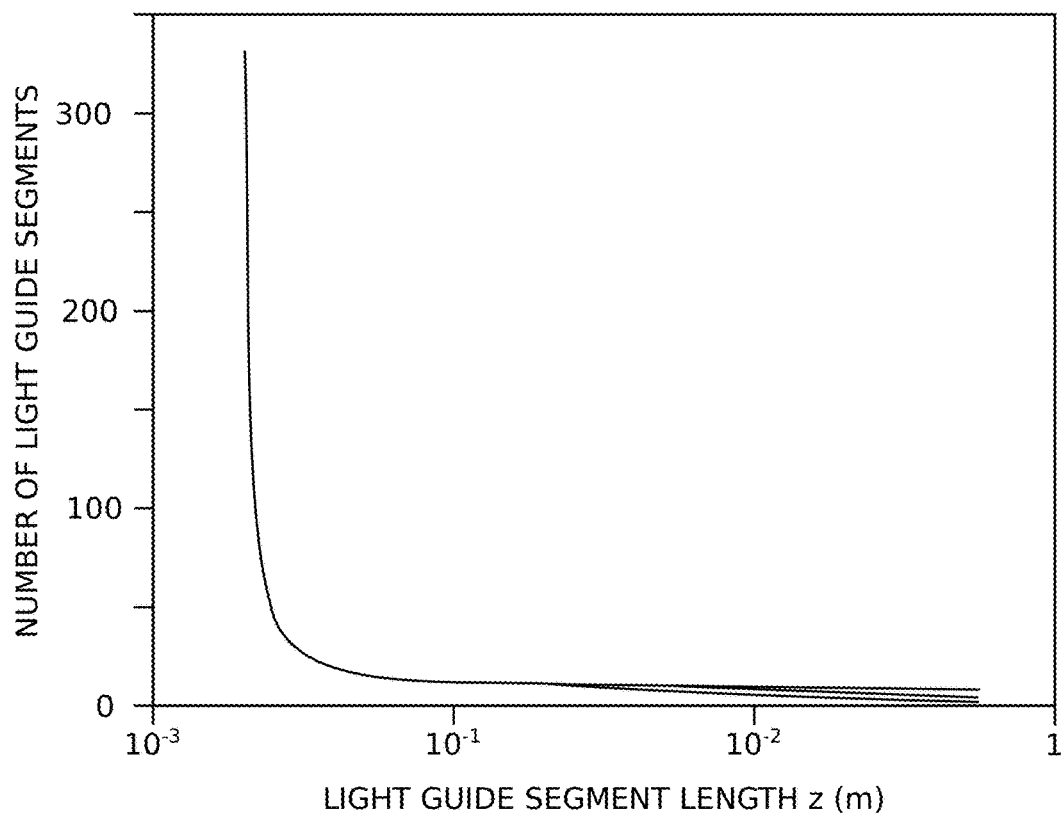

FIG. 89 illustrates the number of segments as a function of segment length. This value is basically z in the upper integral boundary as illustrated in FIGS. 86 and 87, and can be written as, $$n(z, r_t) = \frac{D_{KILL}}{D_{EQ}} = \frac{2QD_{KILL}}{\pi r_t^2 \int_0^z I(z', r_t) dz'} \qquad (9.9)$$

Figure 90:
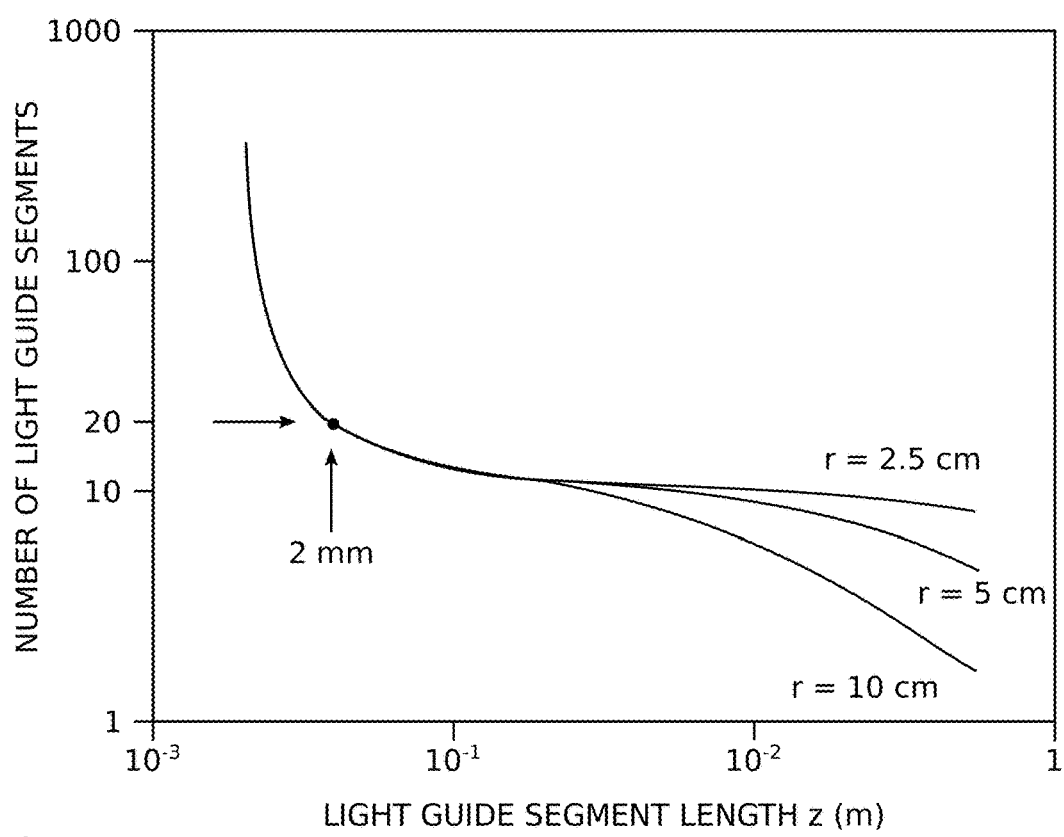

FIG. 90 is the log-log presentation of the FIG. 89 showing lower and upper end dependency of the number of segments needed to achieve the kill dose for $r_t$=2.5, 5, and 10 cm. It is clearly seen that as the segment length, which is the z parameter, increases, the number of segments needed for achieving the kill dose decreases. The more important parameter is the overall length of the reactor which can be calculated as multiplying (9.9) by the length of each segment Z.

Figure 91:
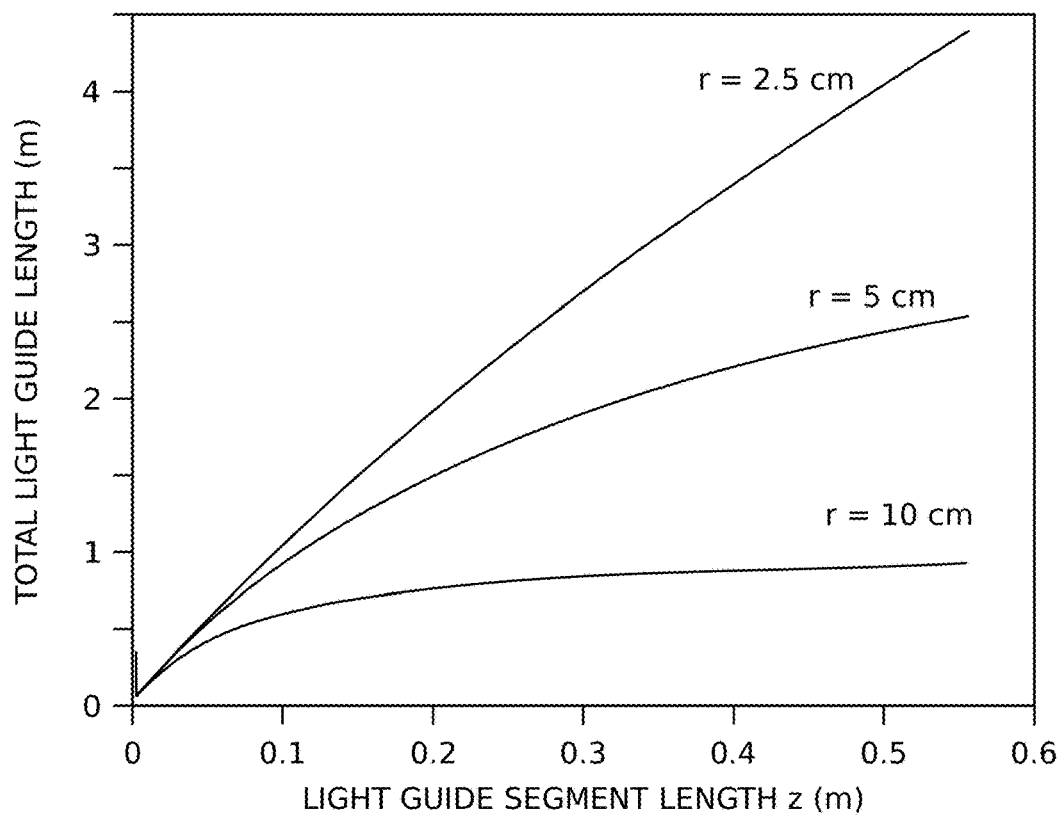

FIG. 91 depicts the total reactor length as a function of z for $r_t$=2.5, 5, and 10 cm.

Figure 92:
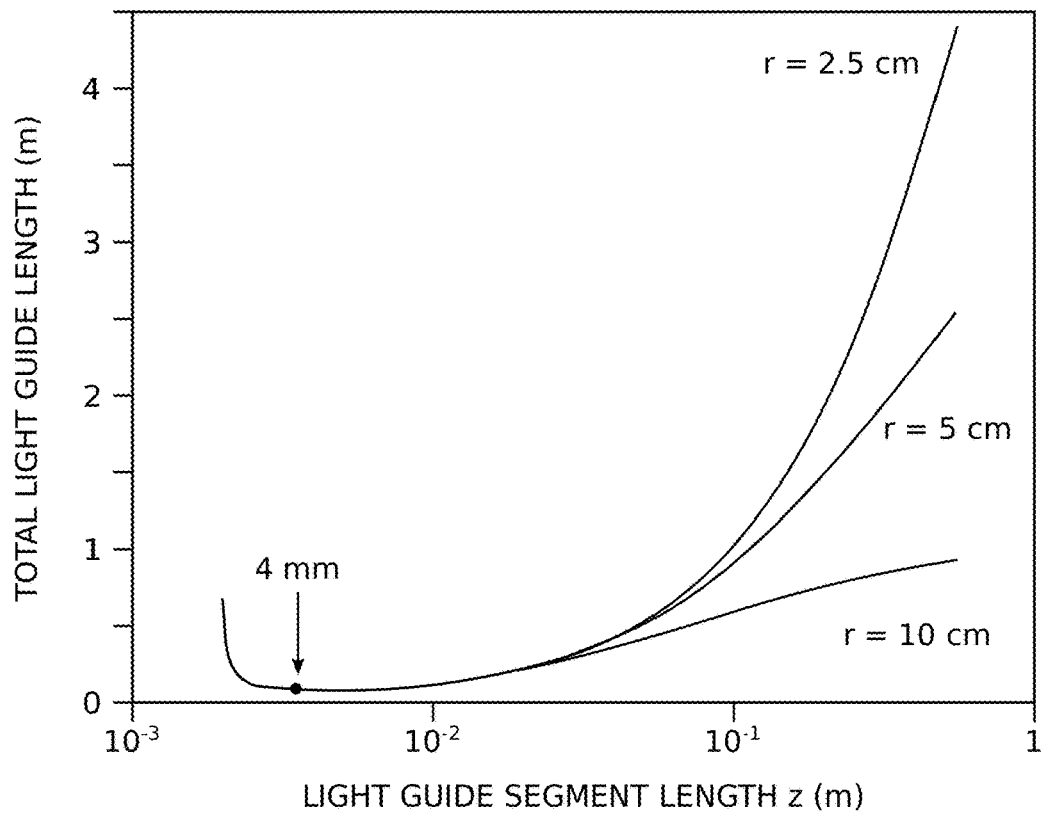

FIG. 92 depicts minimum z values as a log function for greater clarity.

Figure 93:
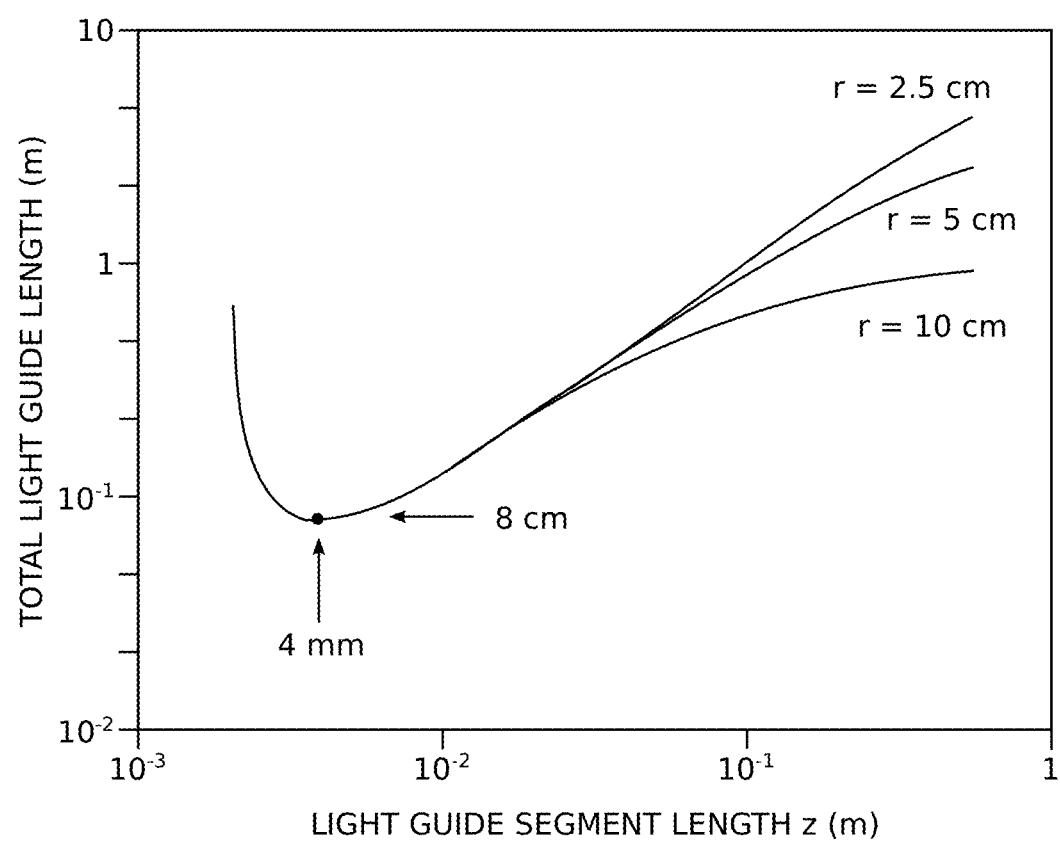

FIG. 93 depicts the same data as in FIG. 92 as a log-log plot. It is interesting to note that the minimum length is not a strong function of the light guide radius $r_t$, which adds design flexibility to the problem.

According to FIG. 90 and FIG. 93, the minimum light guide length can be built using 20×2 mm segments. This is physically not possible because of the size of the LEDs, but it can be also built using 12×1 cm segments. The solution is not unique, as multiple solutions exist and FIG. 90 and FIG. 93 merely serve as design guideline charts. The design of the UV-C irradiation reactor is simpler than the UV-C discharge lamp design due to the simpler fluid dynamics associated with the airflow, which leads to simpler linear equations.

The following is the listing of the design steps of the UV-C LED based irradiance reactor.

i) Generate a fine enough mesh along the light guide with different radii of interest, such as $r_t$=1, 2, 3, . . . , k [cm]. Using the numerical UV-C LED irradiation routine perform irradiation calculations $I(z_i)$ for all mesh points i=1, 2, . . . n along the light guide tube. Store the calculated irradiance values for each mesh point $I(z_i)$ along the light guide, ii) Calculate the numerical integration of $I(z_i)$ for all $r_t$=1, 2, 3, . . . , k. There will be $P_I(z_i)$ integral values at each mesh point which the process analytically represents as, $$P_I(z, r_t) = \int_0^z I(z', r_t) dz'$$

iii) Calculate the number of reactor segments needed for the selected segment length using the generated mesh to achieve the desired kill dose $D_{KILL}$, for a given volumetric airflow rate Q for all $r_t$=1, 2, 3, . . . , k. The process is analytically represented as, $$n(z_i, r_t) = \frac{2QD_{KILL}}{\pi r_t^2 \int_0^{z_i} I(z', r_t) dz'} \quad \text{for } i = 1, 2, \ldots n$$

iv) Calculate the total length of the light guide made up of the number of identical segment lengths calculated in iii).

$$l(z_i, r_t) = n(z_i, r_t) \cdot z_i \text{ for } = 1, 2, \ldots n$$

v) Plot the $n(z_i, r_t)$ and $l(z_i, r_t)$ functions. The $l(z_i, r_t)$ function will have a minimum point which gives the minimum total light guide length with the minimal number of UV-C LEDs in each segment. Select the desired solution from the $l(z_i, r_t)$ plot which meets the kill dose requirement. Another solution might have multiple LEDs in all or some segments. As can be seen, there is no single unique design, the process only guides the design activity.

Figure 94:
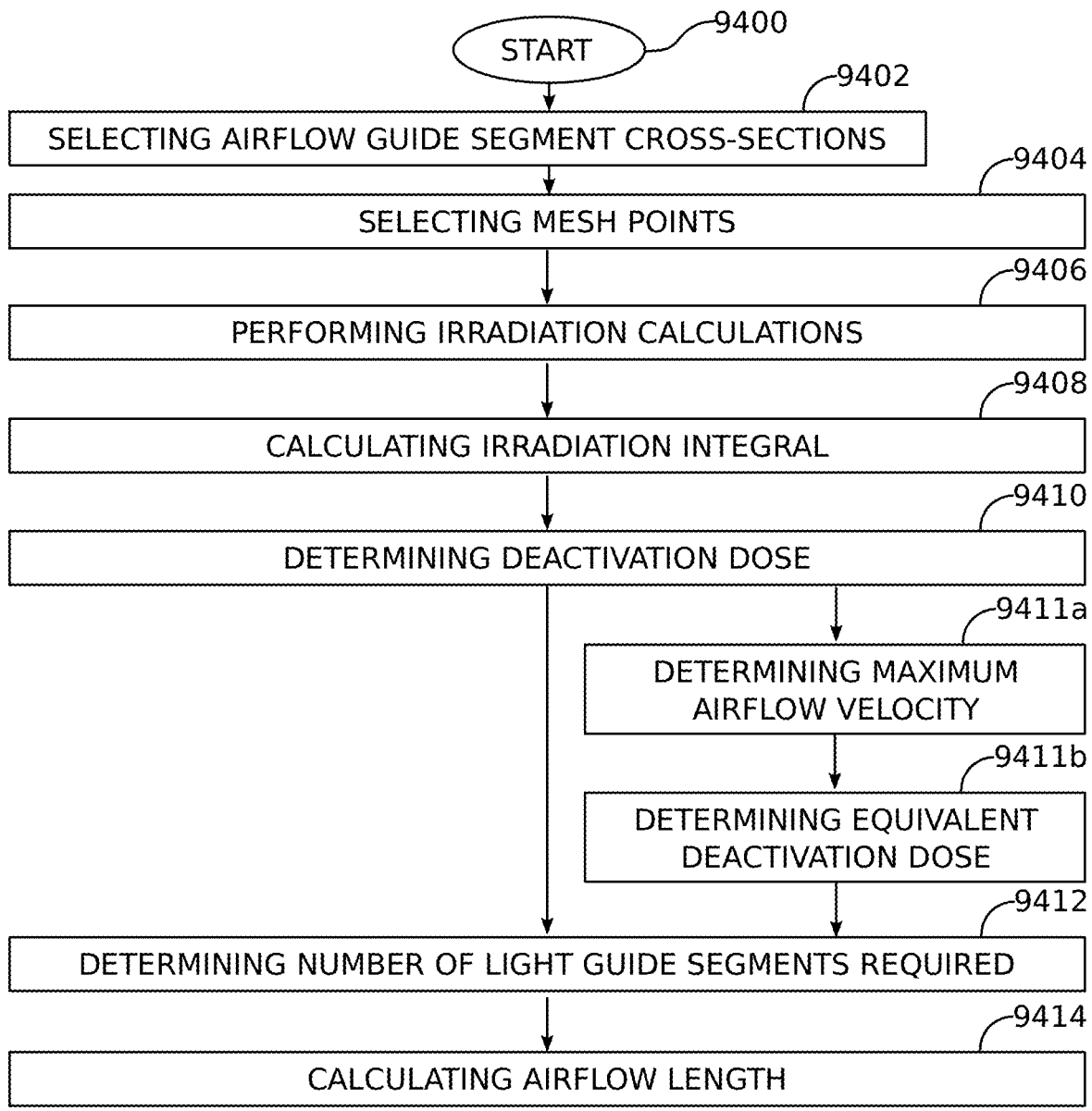

FIG. 94 is a flowchart Illustrating a method for designing a radial ultraviolet-C(UV-C) LED airflow irradiator. The method begins at Step 9400. Step 9402 selects a plurality of cross-sections ($r_t$) for an airflow guide segment. In one aspect, radii for an airflow guide segments are selected having a reflective interior surface. Step 9404 selects a plurality of mesh points ($z_i$) along the length of the airflow guide segment. Step 9406 performs irradiation calculations (I(z,$r_t$)) for each mesh point. For each mesh point irradiation calculation, Step 9408 calculates an irradiation integral ($P_I(z,r_t)$) for each radius. Step 9410 determines a deactivation dosage ($D_{KILL}$). For example, a deactivation dosage of at least 8,000 micro-Watt seconds per square centimeter $\mu$W·sec/cm$^2$ for the COVID-19 pathogen. Step 9412 determines the number of light guide segments (n) required to achieve $D_{KILL}$ for volumetric airflow rate (Q) for each radius. In response to determining the number of airflow guide segments, Step 9414 calculates a total airflow (light guide) length (L).

Typically, the airflow guide segments selected in Step 9402 have a circular cross-section with a radius $r_t$. Then, performing irradiation calculations (I(z, $r_t$)) for each mesh point in Step 9406 includes calculating irradiance (with loss) as follows:

$$I(z, r_t) = \frac{P_{UV-C}}{2\pi z^2[1 - \text{Cos}(\theta_{APEX})]} \text{ for } 0 \leq z \leq d(r_t),$$

and for a lossless case, $$I(z, r_t) = \frac{P_{UV-C}}{2\pi d^2[1 - \text{Cos}(\theta_{APEX})]} \text{ for } z \geq d(r_t)$$

where $$d(r_t) = \frac{r_t}{\text{Cos}(\theta_{APEX})}$$

where $P_{UV-C}$ is the radiative power of the UV-C LED; and, where $\theta_{APEX}$ is a half apex angle of a cone associated with the UV-C LED. It should be noted that increasing the value of $P_{UV-C}$ decreases the number of segments (n) needed in Step 9412.

In more detail, Step 9402 selecting a circular cross-section as follows:

$$d = \frac{r_t}{\tan(\theta_{APEX})};$$

where d is a length bisecting a cord formed by the spherical cap.

In one aspect, Step 9408 calculates the irradiation integral as follows:

$$P_I(z, r_t) = \int_0^z I(z', r_t)dz'$$

where Z' is a light guide segment length.

Step 9411a determines a maximum airflow velocity ($V_{MAX}$) as follows:

$$v_{MAX}(z, r_t) = \frac{2Q}{\pi r_t^2} = \frac{1}{D_{KILL}} \int_0^z I(z', r_t)dz'$$

where Q is a volumetric flow rate. In one aspect, Q≥4.7× $10^{-3}$ cubic meters per second m³/sec.

Step 9411b determines an equivalent deactivation dose ($D_{EQ}$) of the irradiation integral as follows:

$$D_{EQ} = \frac{\pi r_t^2}{2Q} P_I(z, r_t) = \frac{\pi r_t^2}{2Q} \int_0^z I(z', r_t)dz'.$$

Then, determining the number of light guide segments (n) required to achieve $D_{KILL}$ for volumetric airflow rate (Q) for each radius in Step 9412 includes calculating as follows:

$$n(z, r_t) = \frac{D_{KILL}}{D_{EQ}} = \frac{2QD_{KILL}}{\pi r_t^2 \int_0^z I(z', r_t)dz'}.$$

Thus, calculating the total airflow (light guide) length (L) in Step 9414 includes calculating:

$$L(z_i, r_t) = n(z_i, r_t) \cdot z_i \text{ for } i=1,2,\ldots n.$$

Referring again to FIG. 73, it should again be understood that the steps described in FIG. 94 may be enabled as a set of processor instructions for designing a UV-C LED airflow irradiator, which can be stored in a non-transitory memory. It is also understood that the steps described below can be formulated into code in a number of computer languages by a person of ordinary skill in the art. As such, the UVGI designer system 7300 of FIG. 73 depicts a UVGI designer application 7320 performs the calculations described above after receiving input selections from the user interface to select variables such reactor length, the number of segments, radii, and explicit LED components. The various formulas presented above are widely known in the art. As is the case with the mercury discharge tube design, at least part of the novelty of the method of FIG. 94 and associated software is in arranging the formulas so that variables found aid in the design of a portable irradiator. Further, a step-by-step linkage is created between the formulas for the particular purpose of the portable irradiator design. Perhaps most important, the linkage between formulas permits variables to submitted, via a user interface for example, that permit the design to be customized for particular purposes, based upon variables such as power consumption, size, weight, and the deactivation does required for a pathogen of interest.

Figure 95A:
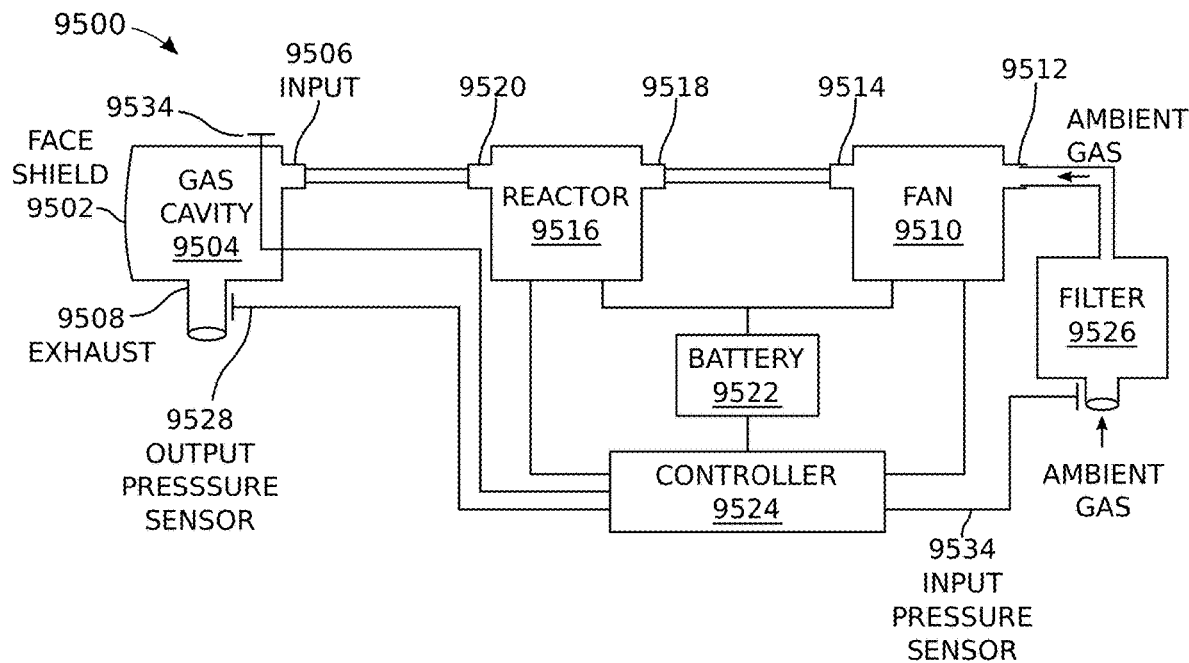
Figure 95B:
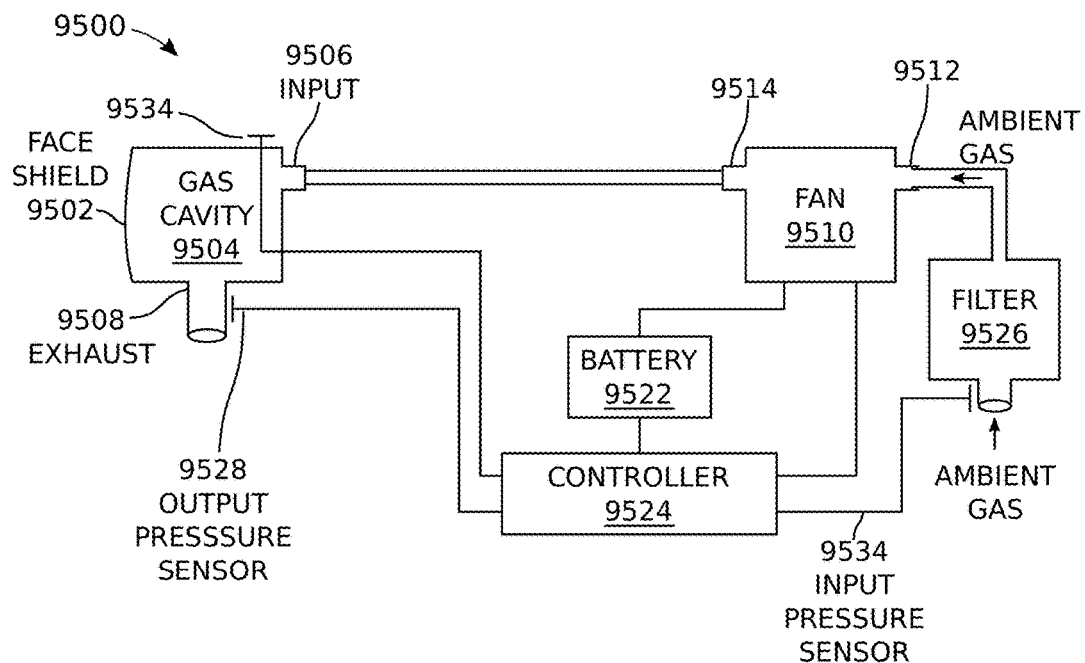

FIGS. 95A and 95B are schematic block diagrams respectively depicting a personal airflow safe shield irradiation system and positive airflow pressure filter system. The system 9500 comprises a face shield 9502 having a back surface, a gas cavity 9504 formed between the back surface and a human face, a gas input aperture 9506, and a gas exhaust aperture 9508. A fan 9510 has an input interface 9512 to accept an ambient gas at an ambient pressure and an output interface 9514 to supply the ambient gas at a positive pressure. For most cases the "ambient gas" would be the air surrounding the system 9500, and this, a human user of the system. An ultraviolet C (UV-C) irradiator reactor 9516 has an input interface 9518 to accept the ambient gas and an output interface 9520 to supply irradiated ambient gas at a positive pressure. Thus, the face shield gas exhaust aperture 9508 emits irradiated gas at a positive pressure greater than the ambient gas pressure. Here, the reactor 9516 is shown interposed between the face shield 9502 and the fan 9510, but alternatively (not shown), the fan may be serially connected between the reactor and the face shield, or fans may be serially connected both before and after the reactor 9516, in which case two fans are required. The system may optionally include a battery 9522 to power the fan 9510 and the irradiator reactor 9516.

In one aspect, the fan 9510 accepts air as the ambient gas, at an ambient pressure of 1 Bar, and the gas exhaust aperture 9508 emits irradiated air at a positive pressure of greater than about 4.7×$10^{-3}$ cubic meters per second m³/sec. More generally, the gas exhaust aperture 9508 emits irradiated air at a positive pressure. In one aspect the positive pressure is greater than about $4.7 \times 10^{-3}$ m³/sec.

The pressure difference between the ambient input and the space behind the face shield may be monitored and the fan control is adjusted with the control system to maintain positive pressure in the air cavity, for example, to maintain a volumetric airflow greater than about $4.7 \times 10^{-3}$ m³/sec. Likewise, if the positive pressure needs to be adjusted due to a change in pressure behind the face shield, the irradiation reactor may also need to be adjusted to maintain the proper radiation dosage. This way the safety of the safe mask is always maintained regardless in the air pressure changes in the ambient environment due to altitude or windy conditions. As mentioned above, the irradiator reactor used may supply radiation at a dose of at least 8,000 µW·sec/cm², capable of deactivating pathogens in the gas.

Optionally, the system 9500 may include a controller 9524 for adjusting the outputs of the fan 9510 and the irradiator reactor 9516. In one aspect, the system 9500 includes a filter 9526 to accept the ambient gas and supply filtered ambient air. The filter 9526 may be a particulate filter or an electrostatic filter. The system 9500 may further comprise at least one output pressure sensor 9528 to measure gas pressure at the exhaust output 9508. The controller 9524 accepts the pressure measurements and supplies fan speed signals on line 9530 to adjust the fan and so maintain a positive pressure at the face shield exhaust 9508. In addition, the controller may supply dosage signals to the reactor on line 9532 to adjust the reactor in response to changes in the fan speed and gas pressure. In some aspects the controller includes aspects that are enabled as a wirelessly connected (e.g., Bluetooth) smartphone application. Besides establishing control parameters, the smartphone application may track and display historical data. As an alternative to hard wiring, the controller may be in wireless communication with the reactor, fan, battery, and pressure sensors. Otherwise, the controller 9528 is embedded in the same chassis with the fan 9510 and reactor 9516. The controller 9524 may perform functions related to battery charging, pressure/airflow monitoring, pressure/airflow control, power monitoring, and reactor control. In other aspects, the system further comprises at least one input pressure sensor 9534 which supplies ambient gas pressure measurements to the controller 9524. Alternatively, gas flow meters may be used in place of the pressure sensors, or in addition to the pressure sensors.

The positive airflow pressure filter system of FIG. 95B is essentially the same system as shown in FIG. 95A except that the filter 9526 is no longer optional, but the reactor is not used. This system typically has use in protecting the user from relatively large particles in an ambient gas environment, especially if the particles are not biological pathogens, or the biological pathogens are relatively large. As is the case with the irradiation system of FIG. 95A, in the positive airflow pressure system of FIG. 95B, the positive output exhaust gas pressure is typically at least three times greater than the input ambient gas pressure.

Figure 96A:
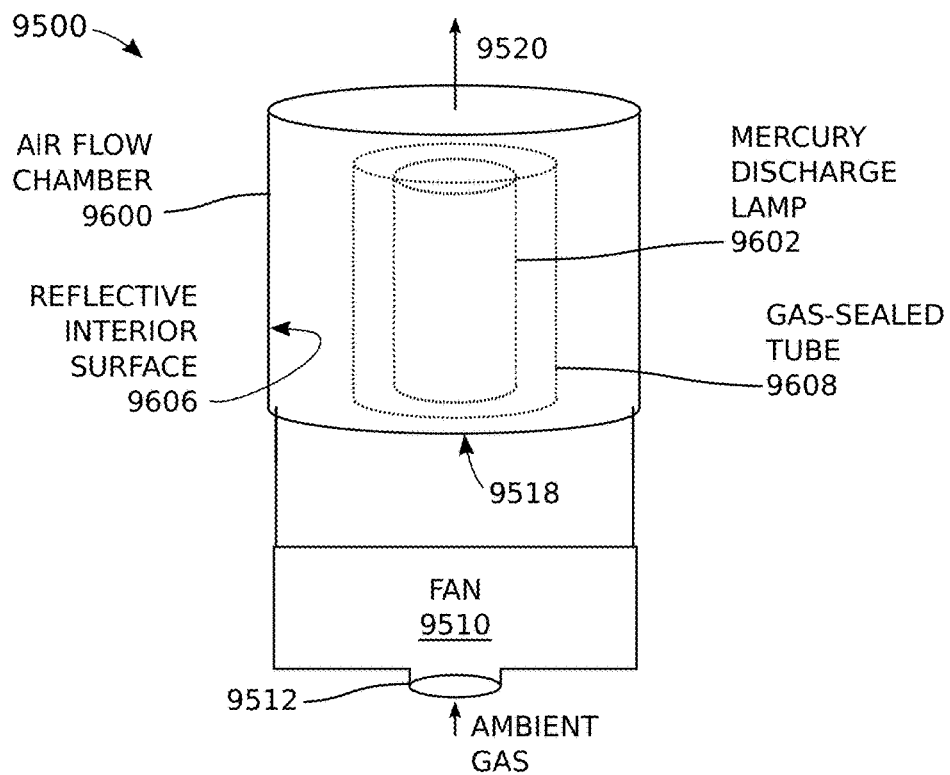
Figure 96B:
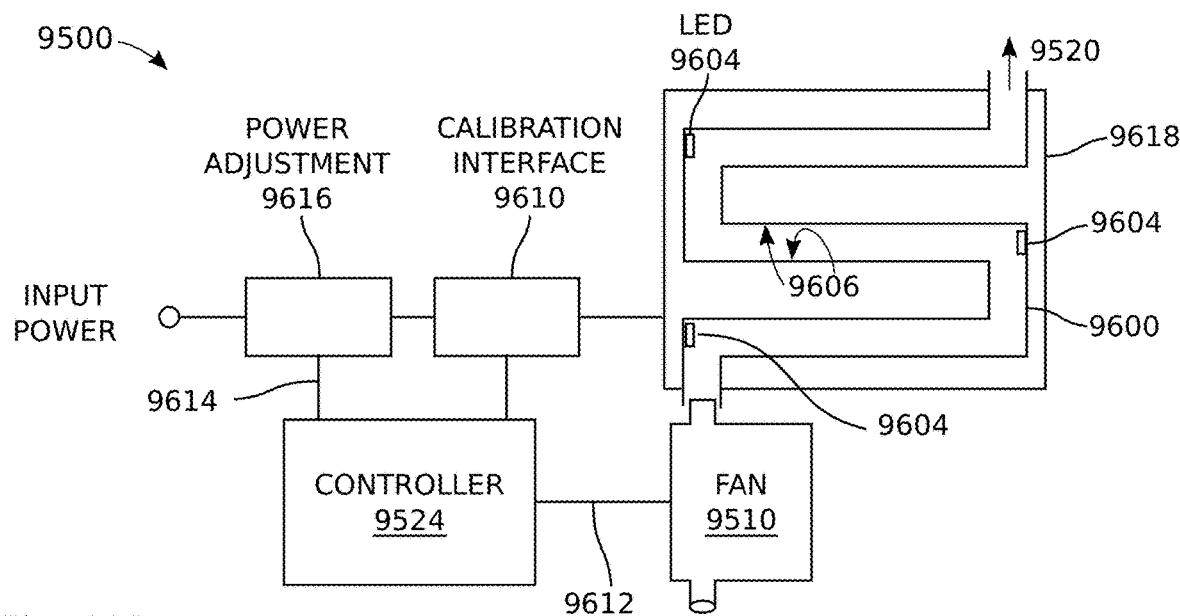

FIGS. 96A and 96B are schematic block diagrams, respectively, of exemplary mercury discharge tube and UV-C LED radiators. As is typical for both designs, the radiator reactor 9500 comprises a cylindrical airflow chamber 9600. In FIG. 96A the radiator 9602 is a mercury discharge lamp (in phantom). Optionally the mercury discharge tube 9602 is encased in a gas-sealed tube structure 9608, made from a material such as quartz glass, to protect the user from inhaling mercury gas in case of the mercury tube accidently breaking. In FIG. 96B the radiator 9604 is a UV-C light emitting diode (LED). The airflow chamber of FIG. 96B is a serial collection of segments with a serpentine shape in chassis 9618, comprising an LED for each segment. While airflow chamber cross-section shapes other than cylindrical are possible, the mathematics presented above is more convenient cylinders having a uniform radius along their length. In one aspect, the airflow chambers 9600 have interior surfaces 9606 (e.g., Porex or Al) that are reflective in the wavelengths between 100 and 280 nanometers.

Also shown in FIG. 96B is a controller 9524 has a calibration interface 9610 for measuring power supplied to the UV-C LED radiator and an interface on line 9612 to adjust the output interfaces of the fan, and an interface on line 9614 to power adjust mechanism 9616 to adjust the UV-C LED radiator 9602 in response to power measurements. The advantage to this approach is that if one of the LEDs becomes defective, the power to the working LEDs can be increased to compensate.

Figure 97A:
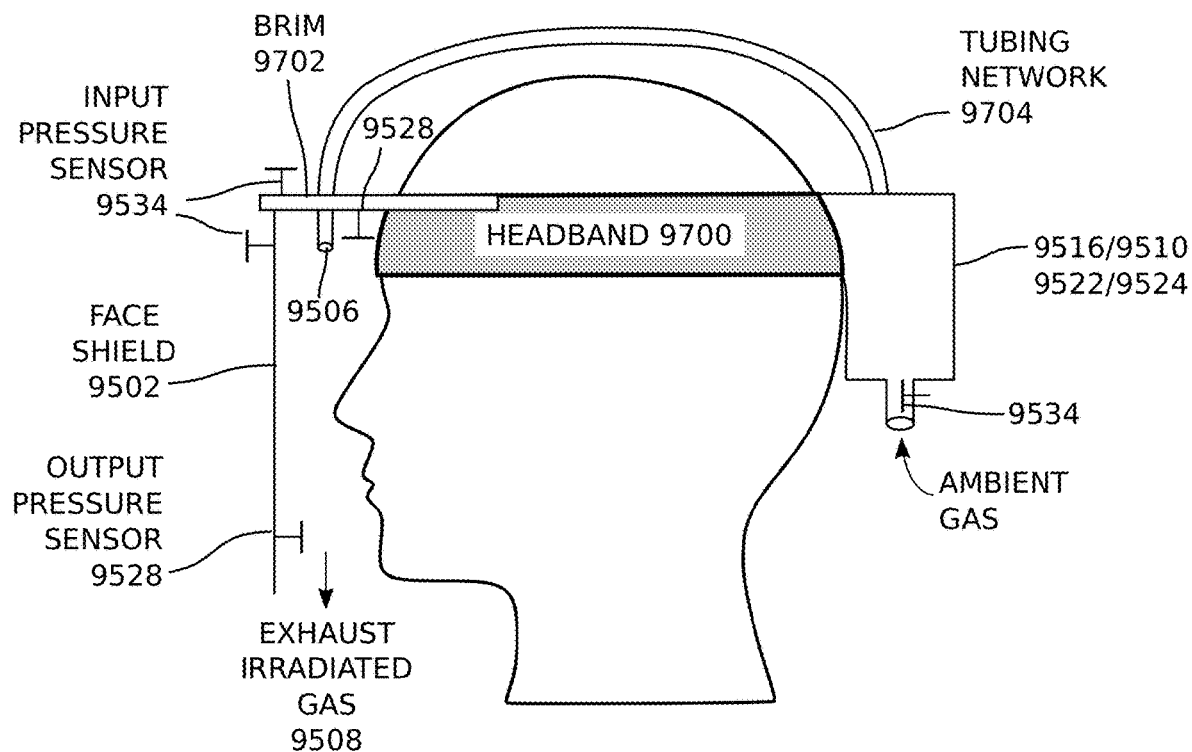
Figure 97B:
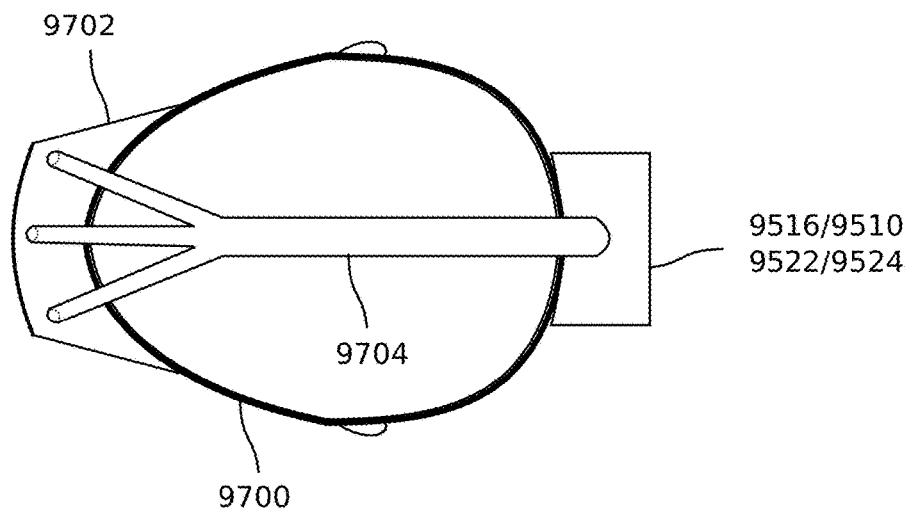

FIGS. 97A and 97B are, respectively, partial cross-sectional and plan views depicting an exemplary implementation of the system of FIGS. 95A and 95B. Shown here is a headband 9700 configured to fit around the circumference of a human head. A brim or sunshade 9702 is connecting between the face shield 9502 and a forward section of the headband. The gas input aperture 9506 is formed in the brim 9702. A tubing network 9704 supplies the irradiated gas to the gas input aperture 9506. As shown, the fan 9510, irradiator reactor 9516, and optionally the battery 9522 and controller 9524 are attached to a rear section of the headband. Alternatively but not shown, the fan 9510, irradiator reactor 9516, and optionally the battery 9522 and controller 9524 are configured for attachment to a belt or to the top of the head. The face shield exhaust aperture 9508 is formed from a spacing between side edges of the face shield and the sides of a human head, and between a face shield bottom edge and a human chin. Optionally, one or more output pressure sensors 9528 are attached to the back of the face shield 9502 to measure the pressure of the irradiated exhaust gas. The pressure sensors 9528 may be connected to the controller 9524 via a hardwired or wireless connection. As another option, one or more input pressure sensors 9534 are attached to the front of the face shield 9502, and/or on the brim (outside the shield), and/or near the ambient gas input to measure the pressure of the ambient input gas. The pressure sensors 9534 may be connected to the controller 9524 via a hardwired or wireless connection. Although not explicitly shown, the positive airflow pressure filter system of FIG. 95B could be enabled in a manner similar as shown in FIGS. 97A and 97B.

Figure 98:
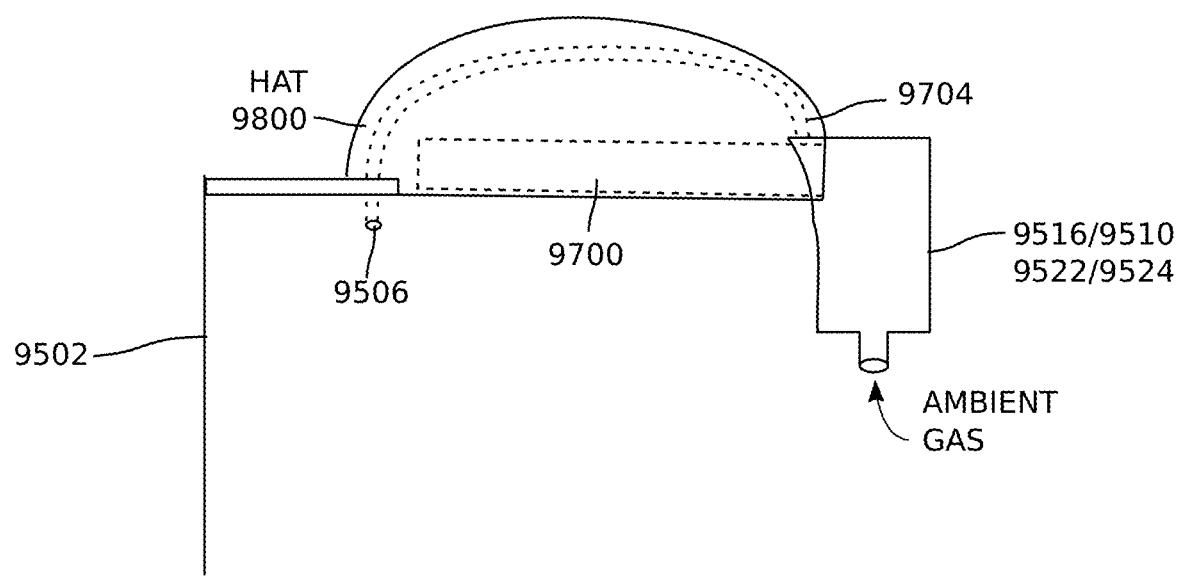

FIG. 98 depicts the safe shield implementation of FIG. 97A with the addition of a head covering. As shown, a hat 9800 covers the headband 9700. In one aspect, headband 9700 may be conventional hat headband, and is therefore attached to the hat. In this aspect, the brim 9702 is also part of, and so attached, to the hat 9800. In the case of a hat style that does not include a brim, the brim may be formed as a upper horizontal component of the face shield. The safe shield can be implemented to work with a number of hat styles. Alternatively, the implementation of FIG. 98 is compact enough that may hats may simply be worn to cover the above-mentioned components, without being attached to the components.

Figure 99:
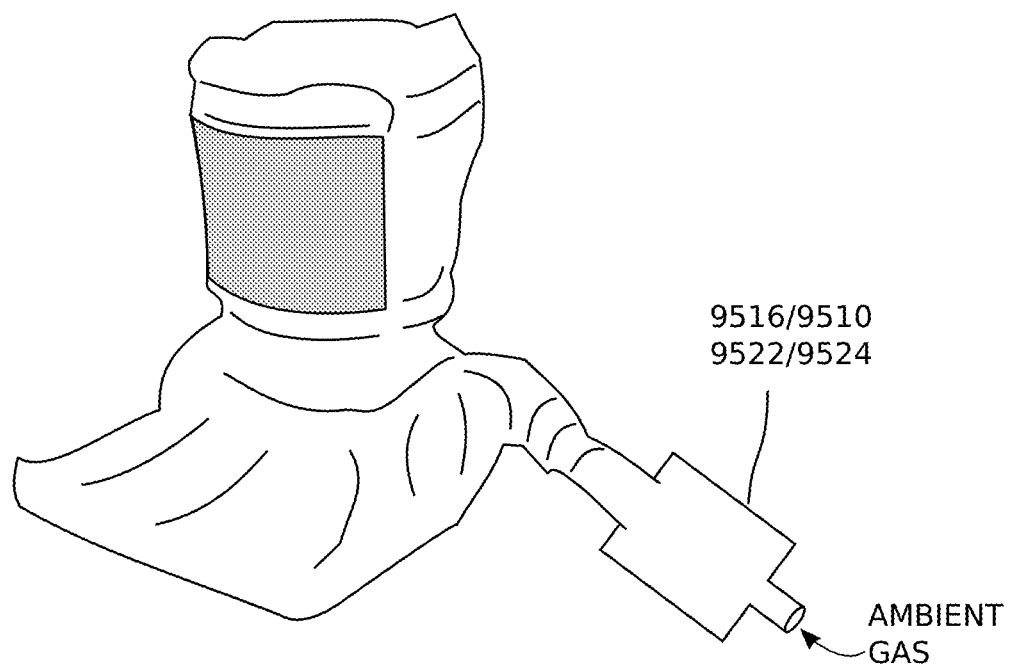

FIG. 99 depicts the safe shield implemented as a respirator hood.

Figure 100:
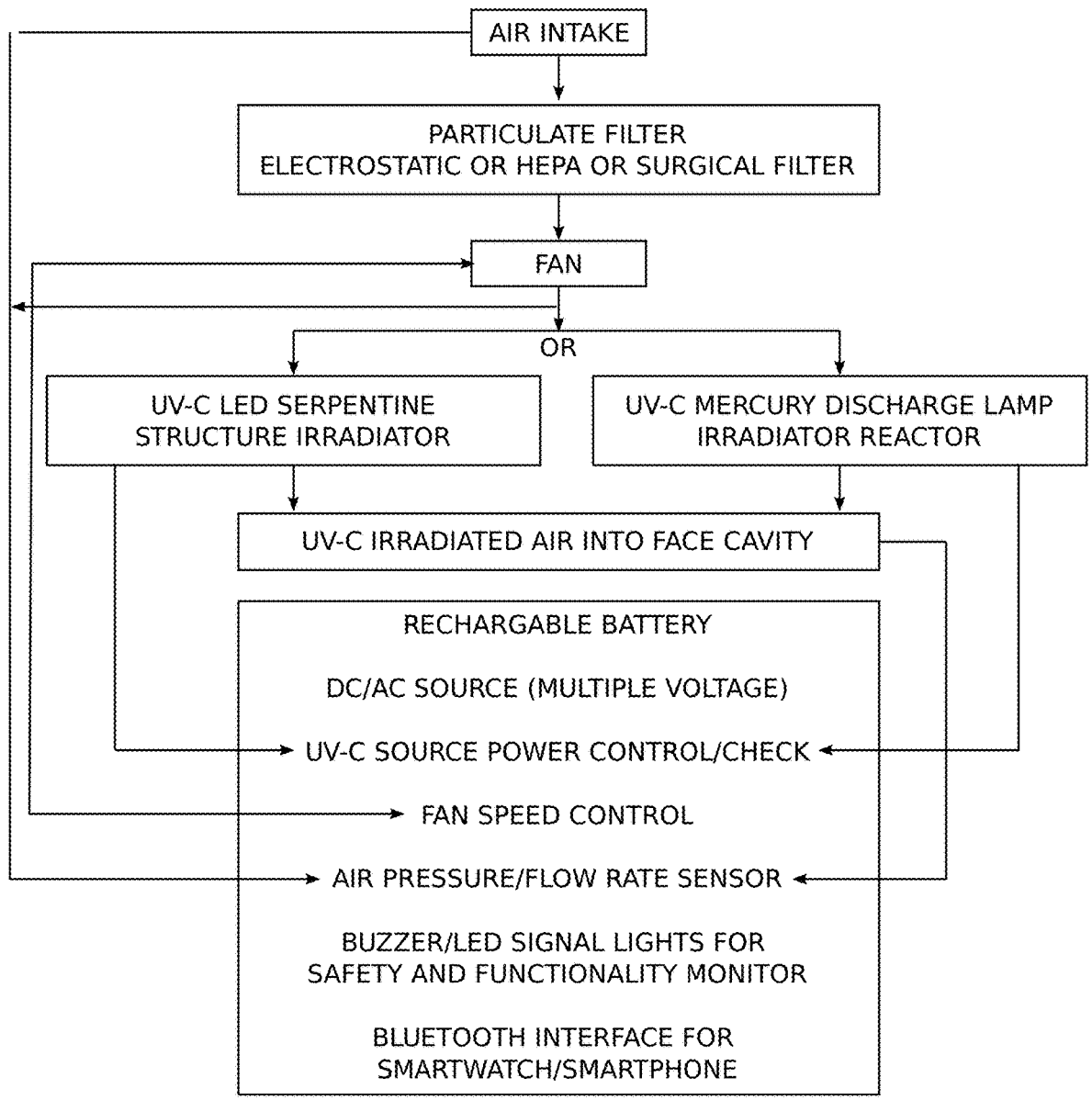

FIG. 100 is a drawing depicting the safe shield system as a functional block diagram.

Figure 101:
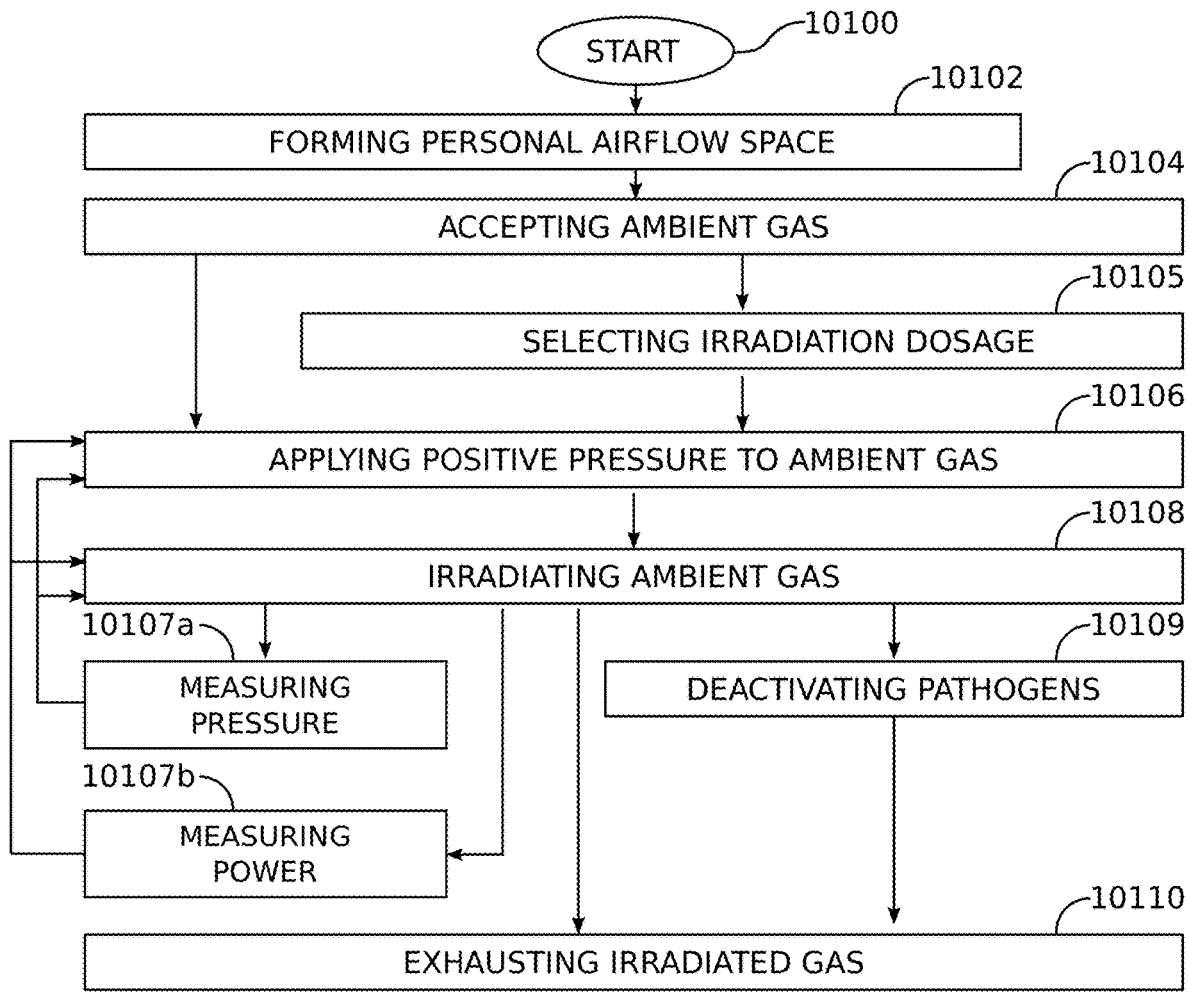

FIG. 101 is a flowchart illustrating a method for personal airflow irradiation. The method begins at Step 10100. Step 10102 forms a personal airflow space shielding a human mouth and nose. Typically, a face shield forms a spacing between side edges of the face shield and the sides of a human head, and between a face shield bottom edge and a human chin. Step 10104 accepts an ambient gas at an ambient pressure. Step 10106 applies a positive pressure to the gas. Step 10108 irradiates the gas with ultraviolet C (UV-C) radiation. The radiation source may be either a UV-C LED or a mercury (or some other gas) vapor discharge lamp.

As noted above, the application of positive pressure to the ambient may be the result of using a fan to prior to introduction of the ambient gas to an irradiation reactor, after the introduction of the ambient gas to the irradiation reactor, or both prior to and after the introduction of the ambient gas to the irradiation reactor. Step 10110 exhausts the irradiated gas from the personal airflow space at the positive pressure. In one aspect, Step 10104 accepts (ambient) air at an ambient pressure of 1 Bar, and Step 10110 exhausts irradiated air at a positive pressure of greater than about $4.7 \times 10^{-3}$ cubic meters per second ($m^3$/sec).

If the ambient gas accepted in Step 10104 includes pathogens, Step 10109 deactivates the pathogens in the ambient gas in response the irradiation of Step 10108. More generally, if Step 10104 accepts air with first pathogens, Step 10105 selects a first irradiation dosage associated with the first pathogen, and in response to irradiating the air in Step 10108, Step 10109 deactivates the first pathogens. If the first pathogen is Covid 19, the first irradiation dose may be at least 8,000 micro-Watt seconds per square centimeter $\mu W \cdot sec/cm^2$.

In one aspect, Step 10107a measures the gas pressure in the personal airflow space and then Step 10106 adjusts the applied pressure in response to the gas pressure measurements in the personal airflow space. Optionally, Step 10108 adjusts the dosage of the UV-C radiation in response to adjustments in the applied pressure. In the case of an LED radiator, Step 10107b may measure the power supplied to the UV-C LED radiator and Steps 10106 and 10108 respectively adjust the applied pressure and current to the LED radiator in response to power measurements.

Comparing the Calculated UV-C Irradiance to Solar Radiation at Sea Level and its effectiveness for Covid-19 Disinfection Since the beginning of the Covid-19 pandemic there were and still are large number of TV broadcasts, social media publications and articles based upon unfounded misleading claims and wrong information. One of these and probably the one potentially less damaging claim related to public health safety was made several times, even by health experts claiming that leaving items thought of being subject to Coronavirus contamination in the sun light for effective means of disinfection. The claim originated from a well-known fact that the UV spectrum produced by the sun has disinfection properties, which is true in general but not for Covid-19 case. In this section, this assertion is investigated in the light of physics and mathematics rather than on unfounded statements.

Figure 102:
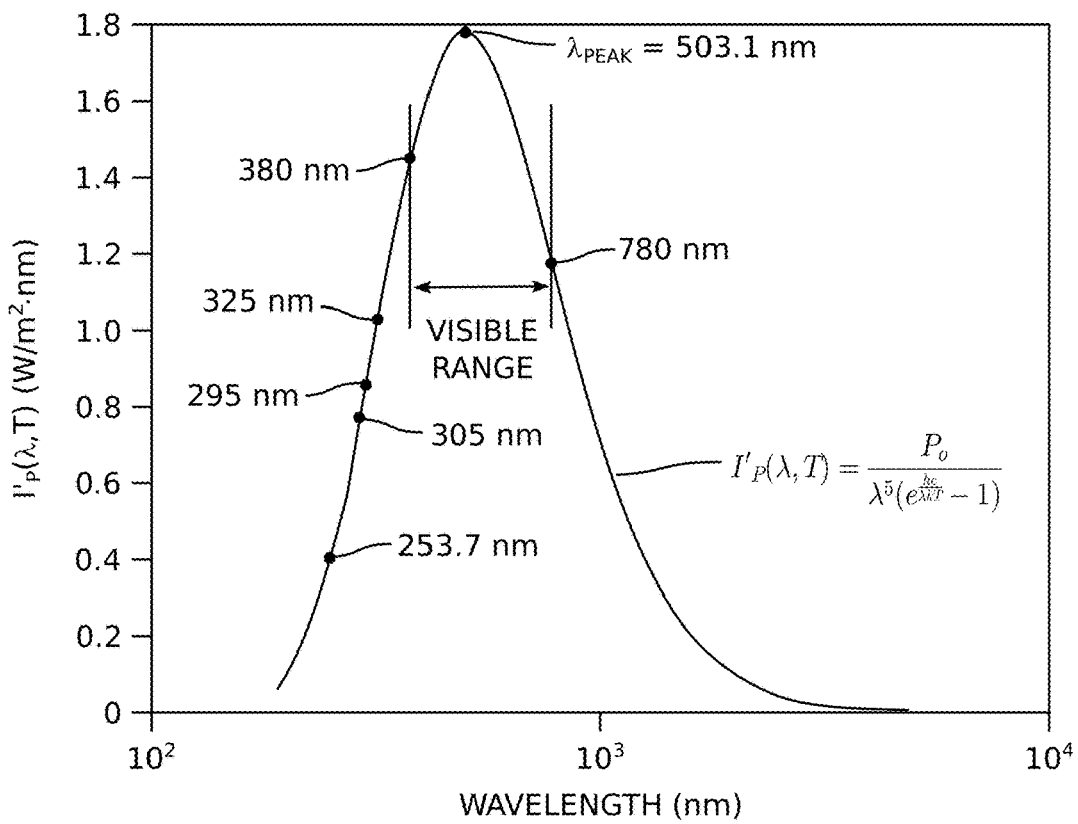

FIG. 102 depicts the solar spectrum power density. The UV spectrum that earth receives makes up 5% of the total power of received radiation and is divided into three wavelength bands known as UV-A, UV-B, and UV-C as shown in Table 3 and in the figure. These wavelength bands are $315 < \lambda < 400$ nm, $280 < \lambda < 315$ nm, and $100 < \lambda < 280$ nm for UV-A, UV-B, and UV-C respectively. The ozone producing UV light wavelength range is in the 100-240 nm interval and it is at the shorter wavelength region of the UV-C spectrum. It has to be noted that the 253.7 nm wavelength peak produced by the mercury vapor UV-C lamp is greater than this range of ozone producing radiation and therefore does not produce ozone. The literature indicates that UV-C band, which is in the wavelength interval of $100 < \lambda < 280$ nm, and which is a 180 nm wide wavelength bandwidth, is the only wavelengths effective for Covid-19 disinfection purposes. To quantify the effectiveness of the solar radiation at the UV-C band that we receive on the surface of the earth one needs to know the measured irradiance at this UV-C wavelength band of $100 < \lambda < 280$ nm, which is not available in the literature for a good reason, it is below detection level. Therefore, in this section a theoretical effort is given to at least approximate the maximum possible irradiance in this UV-C wavelength band that is received at sea level on earth.

The UV irradiation levels received at the earth surface is a function of many things and can change frequently. Most of the factors effecting UV radiation are the surface temperature of the sun, which can be assumed constant at 5,780° K, the ozone layer thickness in the upper atmosphere, solar flare conditions, air quality, atmospheric thickness variations, altitude, date, latitude, and temperature. Therefore, having an exact number which is constant at all times is not realistic, but a maximum value can be estimated.

The measured incident spectral power density in midday Equatorial summer sunlight at some selected wavelengths is something which can serve the purpose as a "high" value. These measured values are 0.6 $mW/m^2 \cdot nm$ at 295 nm, 74 $mW/m^2 \cdot nm$ at 305 nm, and 478 $mW/m^2 \cdot nm$ at 325 nm spectral power densities, which shows the intense attenuation of the atmosphere as the wavelength degreases [11-14]. As can be noticed, none of these measured values are in the $100 < \lambda < 280$ nm UV-C band effective for Covid-19 disinfection.

As can be seen, the measured data are in units of spectral power density units of $mW/m^2$ nm, different than the dose units of $\mu W$ 19 $sec/cm^2$. One needs to perform an integration with respect to the wavelength and the result can be multiplied by the exposure time to calculate the dose, and compared to 8000 $\mu W \cdot sec/cm^2$ of the kill dose of the Coronavirus.

The lack of measured spectral power density data is due to the power densities at the earth surface at UV-C band being less than the sensitivity of the measuring instrument for following reasons:

i) The high absorption rate of the UV-B and UV-C band in the ozone layer greatly attenuates the UV-B and UV-C bands, which is also the source of the existence of the ozone layer in first place in the upper atmosphere, ii) The $\lambda^{-4}$ dependency in Rayleigh scattering in the atmosphere [23-26] attenuates the shorter wavelengths with the same $\lambda^{-4}$ wavelength dependency in the atmospheric path down to the sea level, Due to these two reasons, there should be no significant UV-C radiation reaching the earth's surface above the measurement limits at any time or any date even in the Equatorial summer. But this statement doesn't give the dose needed to make a conclusive statement. On the other hand, based on the measured data on the longer wavelengths, along with valid best possible approximations based on physics rather than speculations, one can approximate dose calculations in the UV-C band to find out if a 8000 $\mu W \cdot sec/cm^2$ kill dose can be reached for a given duration of exposure time at sea level during the Equatorial summer.

One thing well known is how to calculate the solar power spectrum density above the ozone layer, in space. Using the Planck black body radiation formula and the Stefan-Boltzmann relation with some math and some basic astronomical knowledge of the solar system, one can calculate the received solar power spectrum power density at these measured wavelengths in the upper atmosphere, above the ozone layer [11-14]. Knowing the sun surface temperature of T=5780° K Planck's black body radiation formula gives the spectral power density relation as a function of wavelength and sun's surface temperature as, $$I'_P(\lambda, T) = \frac{P_0}{\lambda^5 \left(e^{\frac{hc}{\lambda kT}} - 1\right)} \quad (10.1)$$

Where $P_0$, h, C, $\lambda$, k, and T are power density scaling number to be calculated by the integral equation (10.2), Planck constant, speed of light, wavelength, Boltzmann constant, and the sun's surface temperature in Kelvin, respectively. The only unknown here is $P_0$ which can be solved by knowing the total radiation power density coming from the sun, which is $P_S$=1,353 W/m² which gives the integral equation, $$P_S = \int_0^\infty \frac{P_0}{\lambda^5 \left(e^{\frac{hc}{\lambda kT}} - 1\right)} d\lambda = 1,353 \left[\frac{W}{m^2}\right] \quad (10.2)$$

Solving $P_0$ from (10.2) with the use of some variable transformations along with the use of the Riemann-Zeta and Gama functions gives [23], $$P_0 = \frac{15 P_S}{\pi^4} \left(\frac{hc}{kT}\right)^4 \quad (10.3)$$

$$\lambda'_{peak} = \frac{2.8977685 \times 10^{-3}}{T} [m] \quad (10.4)$$

Figure 103:
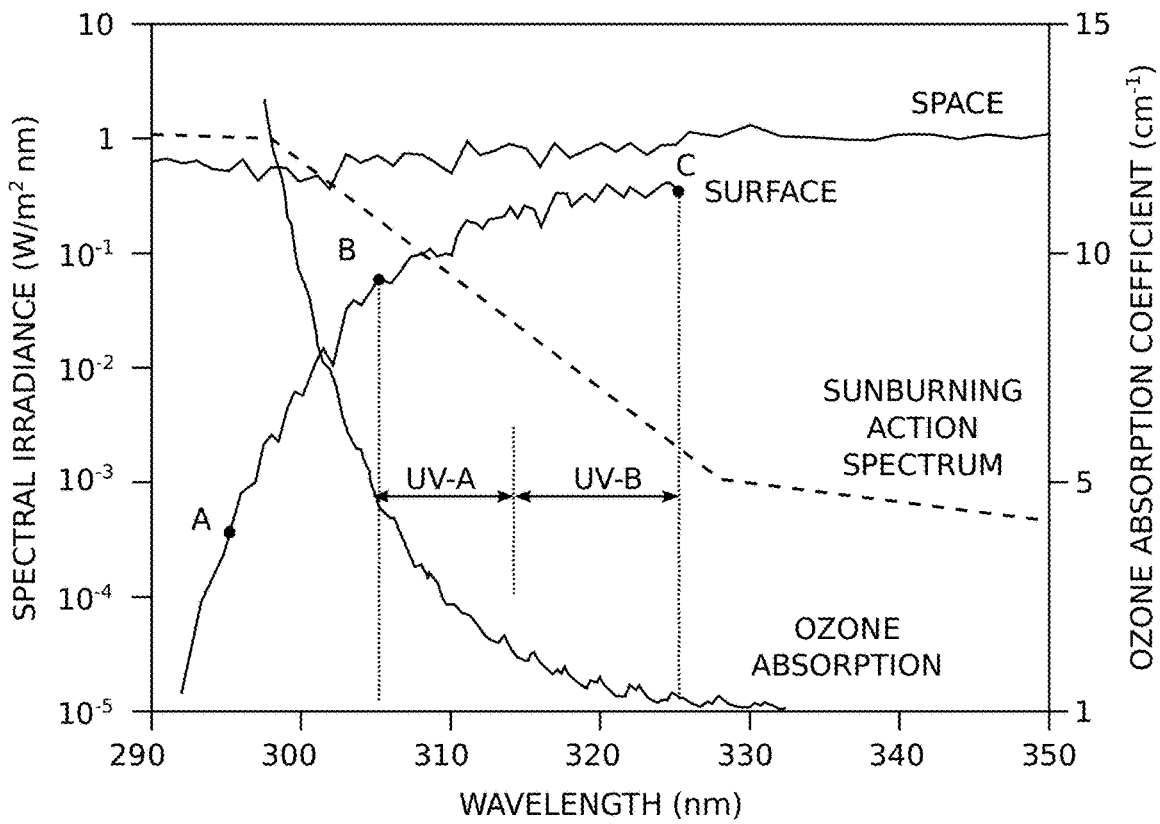

FIG. 103 depicts the numerical values of the spectral power density in space above the ozone layer for the wavelengths of 295, 305, and 325 nm. The wavelengths are calculated by using the relation (10.1) and are presented in column 3 of Table 6. The measured values of spectral power density at sea level in Equatorial summer are given in column 2 for the same wavelengths, which are compiled from the measured data given in FIG. 103. Attenuation for these wavelengths can be calculated simply by dividing their space values to the sea level values as given in column 4.

Figure 104:
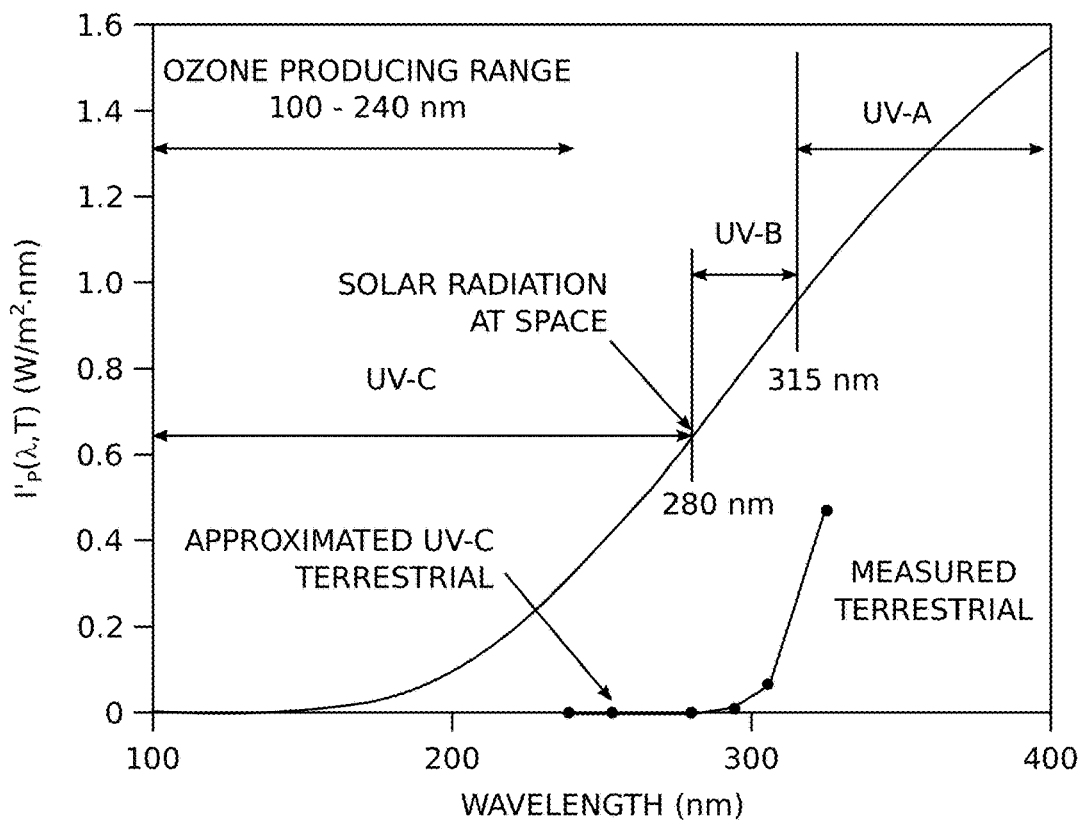

FIG. 104 show the calculated spectral power density using the scaled Planck black body radiation formula (10.2) in the UV band in space, above the atmosphere. Table 6 shows the calculated numerical values at some wavelengths with measured sea level values of spectral power density. The data in Table 6 shows that atmospheric attenuation increases very rapidly with smaller wavelengths. This increase in the attenuation is due to $\lambda^{-4}$ dependency in Rayleigh scattering in the atmosphere. Therefore, the attenuation for the wavelengths shorter than 295 nm is much larger than the attenuation value of 1,292. Since we are interested in finding the highest possible radiation in the UV-C band, taking 1,292 as the "constant" attenuation for all the shorter wavelengths than 295 nm will serve the purpose.

The first wavelength in row 2 of Table 6 is the UV-C mercury lamp radiation wavelength, which has no measured data. Taking the same attenuation value of 1,292 at 253.7 nm as the closest measured wavelength attenuation value to 295 nm wavelength, the calculated spectral power density is 417.14 mW/m²·nm and is calculated to be 0.3228 mW/m²·nm, which can be safely assumed as the highest possible value possible at sea level at Equatorial summer. As is shown in column 2 row 2 in Table 6, this is due to $\lambda^{-4}$ dependency in Rayleigh scattering in the atmosphere. The values in Row 2 are calculated.

TABLE 6

The data in the rows 3,4, and 5 are the measured spectral power density values for 295, 305, and 325 nm wavelengths. The second row is an approximation made by using the same attenuation of 1,292 at 295 nm for the shorter 253.7 nm wavelength.

| Wavelength $\lambda$ [nm] | Solar Radiation at Sea Level at Equatorial summer @ noon $P_{SEALEVEL}$ [mW/(m².nm)] | Solar Radiation in Space $P_{SPACE}$ [mW/(m².nm)] Planck Radiation Formula parameters: P = 1,350 W/m² Sun surface temperature T = 5,780°K | Atmospheric Attenuation A $A = \frac{P_{SPACE}}{P_{SEALEVEL}}$ |
|---|---|---|---|
| 253.7 | 0.3228 (Estimated) | 417.14 | 1,292 (Approximated) |
| 295 | 0.6 | 775.2 | 1,292 |
| 305 | 74 | 865.38 | 11.668 |
| 325 | 478 | 1,041 | 2.1732 |

Figure 105:
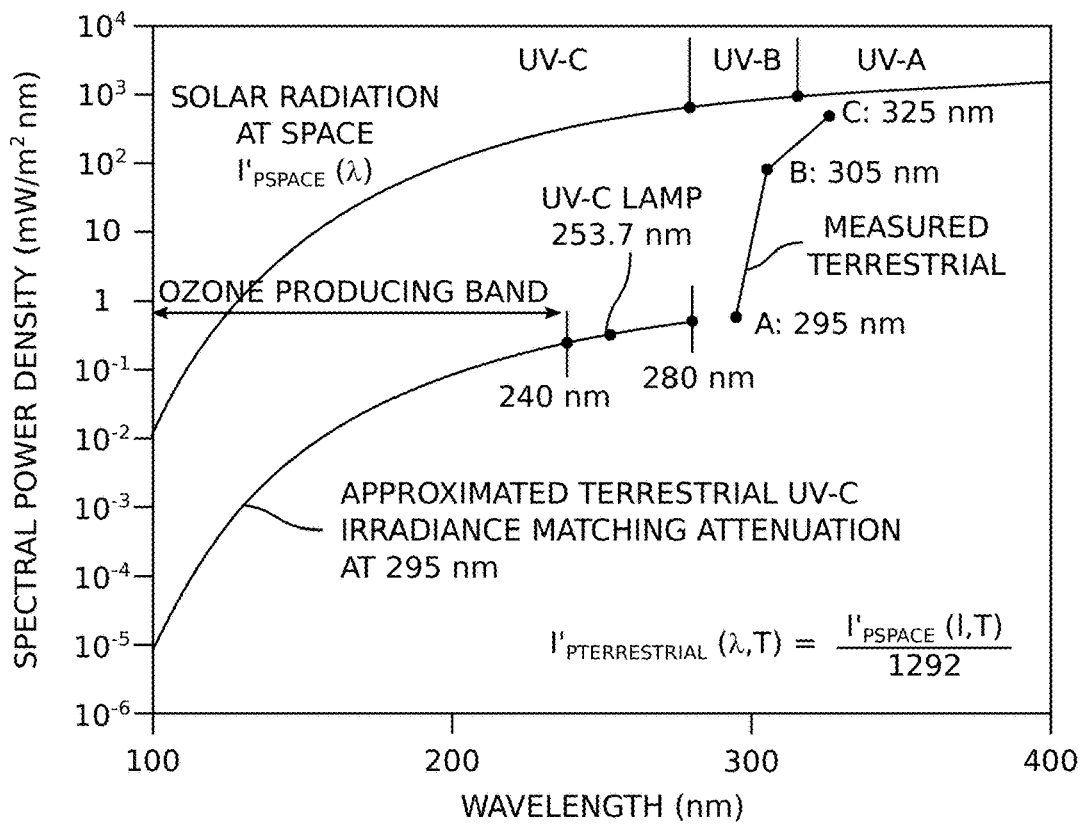

FIG. 102 show the Planck black body spectral power density versus wavelength relation as given by (10.1) with some UV band wavelengths of significance. The wavelength where the maximum of the spectral power density relation (10.1) can be calculated, and it gives well known and surprisingly simple relation, FIG. 105 illustrates the solar radiation power density in the UV-C band in space and approximated radiation power density at sea level in Equatorial summer at sea level curves by dividing the space radiation power density values with the constant attenuation of 1,292. An analytical function in the 180 nm wide UV-C band is obtained that can be numerically integrated to obtain irradiance in the units of W/m² to be used in dose calculation.

Figure 106:
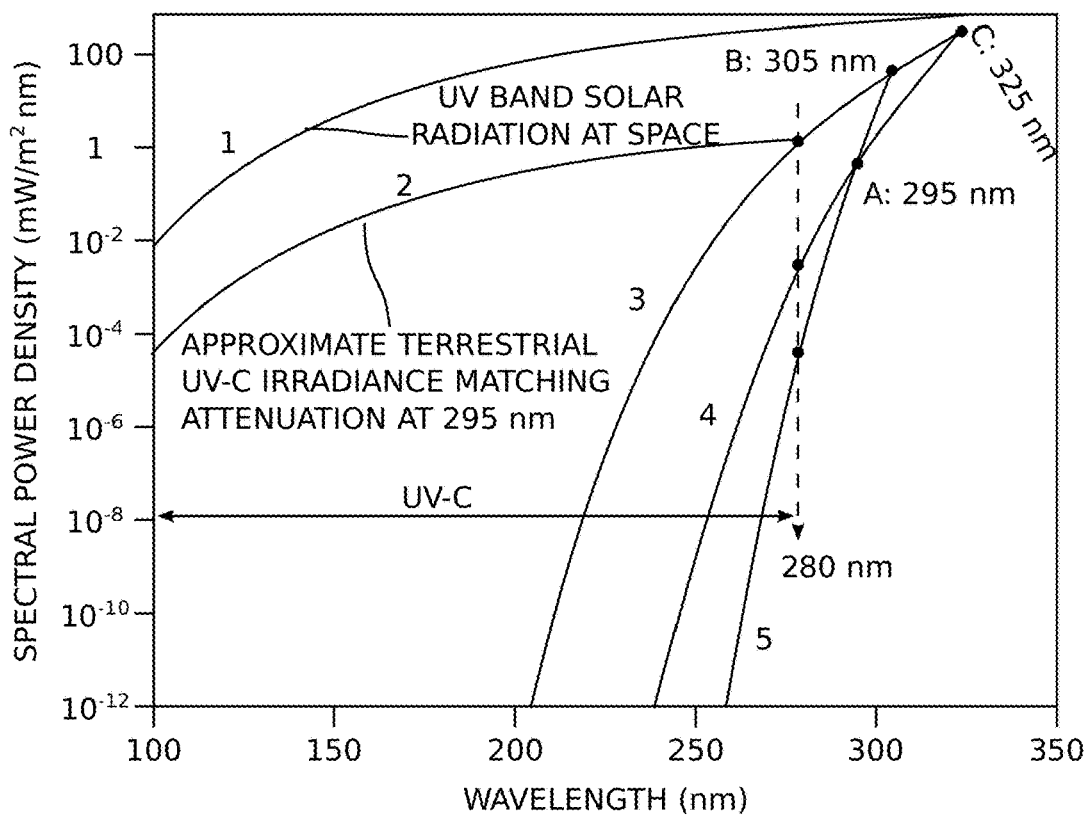

FIG. 106 shows the integral of the spectral power density in space, which can be expressed as, $$P_{SPACE}(\lambda) = \int_{\lambda'=100\ nm}^{\lambda} I'_{pSPACE}(\lambda')d\lambda' \quad (10.5)$$

For $\lambda=280$ nm the numerical integration value of (10.5) is 28,670 mW/m², which can be expressed as, $$P_{SPACE}(UV-C) = \int_{\lambda=100}^{\lambda=280} I'_p(\lambda)d\lambda = 28,670\frac{mW}{m^2} \quad (10.6)$$

This is 2,867 μW/cm² and to meet the 8,000 μW·sec/cm² Covid-19 inactivation kill dose, 2.79 seconds of exposure time is enough to deactivate Covid-19 in space. The integral of the solar power density at sea level in Equatorial summer can be expressed as, $$P_{TERRESTRIAL}(\lambda) = \int_{\lambda'=100\ nm}^{\lambda} I'_{pTERRESTRIAL}(\lambda')d\lambda' \quad (10.7)$$

Where, $$I'_{pTERRESTRIAL}(\lambda') = \frac{I'_{pSPACE}(\lambda')}{1,292} \quad (10.8)$$

For $\lambda=280$ nm the numerical integration value of (10.7) is 21.75 mW/m², which can be expressed as, $$P_{Terrestrial}(UV-C) = \int_{\lambda=100}^{\lambda=280} I'_{pTerrestrial}(\lambda)d\lambda = 21.75\frac{mW}{m^2} \quad (10.9)$$

This is 2.175 μW/cm² and to meet the 8,000 μW·sec/cm² Covid-19 deactivation kill dose, 3,678 seconds or 61.30 minutes of exposure time is needed.

Here, it must be noted again that the UV-C terrestrial power density is over-estimated. A better approximation of the terrestrial UV-C radiation can be obtained by assuming the attenuation is represented with the Beer-Lambert law employing Rayleigh scattering as, $$I'_{PTerrestrial}(\lambda) = I'_{PSpace}(\lambda)e^{-\left(\frac{a}{\lambda^4}+b\right)} \quad (10.11)$$

The 2 unknowns are a and b, and 3 values of calculated space and measured terrestrial spectral power density are known at 3 wavelengths as given in Table 6. Since only 2 of the values are needed to solve the a and b from (10.11) 3 solutions can be calculated with the Table 6 data. The 2 linear equations in a and b to be solved are in the form of, $$I_{PT}(\lambda_1) = I_{PS}(\lambda_1)e^{-\left(\frac{a}{\lambda_1^4}+b\right)} \quad (10.12)$$

$$I_{PT}(\lambda_2) = I_{PS}(\lambda_2)e^{-\left(\frac{a}{\lambda_2^4}+b\right)} \quad (10.13)$$

Taking the log of both sides of (10.12) and (10.13) gives, $$y_1 = \ln\left[\frac{I_{PT}(\lambda_1)}{I_{PS}(\lambda_1)}\right] = -\frac{a}{\lambda_1^4} - b \quad (10.14)$$

$$y_2 = \ln\left[\frac{I_{PT}(\lambda_2)}{I_{PS}(\lambda_2)}\right] = -\frac{a}{\lambda_2^4} - b \quad (10.15)$$

The 2 by 2 matrix equation for solving a and b becomes, $$\begin{bmatrix} \frac{1}{\lambda_1^4} & 1 \\ \frac{1}{\lambda_2^4} & 1 \end{bmatrix}\begin{bmatrix} a \\ b \end{bmatrix} = -\begin{bmatrix} y_1 \\ y_2 \end{bmatrix} \quad (10.16)$$

FIG. 106 illustrates the solar radiation in space and the terrestrial spectral power density curves calculated by solving a and b for the measured terrestrial values shown in Table 6 for $\lambda_1=325$ nm, $\lambda_2=305$ nm, and $\lambda_3=295$ nm wavelengths in 3 pairs and a constant attenuation of 1,292 assumed as shown in Table 7.

TABLE 7

Irradiance and exposure times to deactivate Covid-19 using measured spectral power density values at $\lambda_1$ = 325 nm, $\lambda_2$ = 305 nm, and $\lambda_3$ = 295 nm wavelengths to generate an analytical formulation at sea level for 100 ≤ λ ≤ 280 nm UV-C band.

| Case | Irradiance [mW/m2] $\int_{\lambda=100}^{\lambda=280} I'_{PTerrestrial}(\lambda)d\lambda$ | Exposure time For having kill-dose of $8000\left[\mu W \cdot \frac{sec}{cm^2}\right]$ | Exposure time |
|---|---|---|---|
| 325, 305 [nm] to solve ($a_1$, $b_1$) in (10.11) Curve 3 in FIG. 106 | 14.38 Sea Level | 5,562 | 1.54 hours |
| 325, 295 [nm] to solve ($a_2$, $b_2$) in (10.11) Curve 4 in Fig. 106 | 0.013 Sea Level | $0.95982 \times 10^7$ | 1,662 hours |
| 305, 295 [nm] to solve ($a_3$, $b_3$) in (10.11) Curve 5 in Fig. 106 | $0.127 \times 10^{-3}$ Sea Level | $0.6271 \times 10^9$ | 174,200 hours |
| Attenuate $I'_{PSpace}$ (λ) by 1,292 Curve 2 in FIG. 106 | 22.19 Sea Level | 3,605 | 60.08 minutes |

TABLE 7-continued Irradiance and exposure times to deactivate Covid-19 using measured spectral power density values at $\lambda_1 = 325$ nm, $\lambda_2 = 305$ nm, and $\lambda_3 = 295$ nm wavelengths to generate an analytical formulation at sea level for $100 \le \lambda \le 280$ nm UV-C band.

| Case | Irradiance [mW/m2] $\int_{\lambda=100}^{\lambda=280} I'_{PTerrestrial}(\lambda)d\lambda$ | Exposure time For having kill-dose of $8000\left[\mu W \cdot \dfrac{sec}{cm^2}\right]$ | Exposure time |
|---|---|---|---|
| Black Body Radiation for 5,780K at Upper Atmosphere Curve 1 in FIG. 106 | $\int_{\lambda=100}^{\lambda=280} I'_{PSpace}(\lambda)d\lambda = 28{,}674$ $28{,}674 \dfrac{mW}{m^2}$ | 2.79 | 2.79 seconds |

Figure 107:
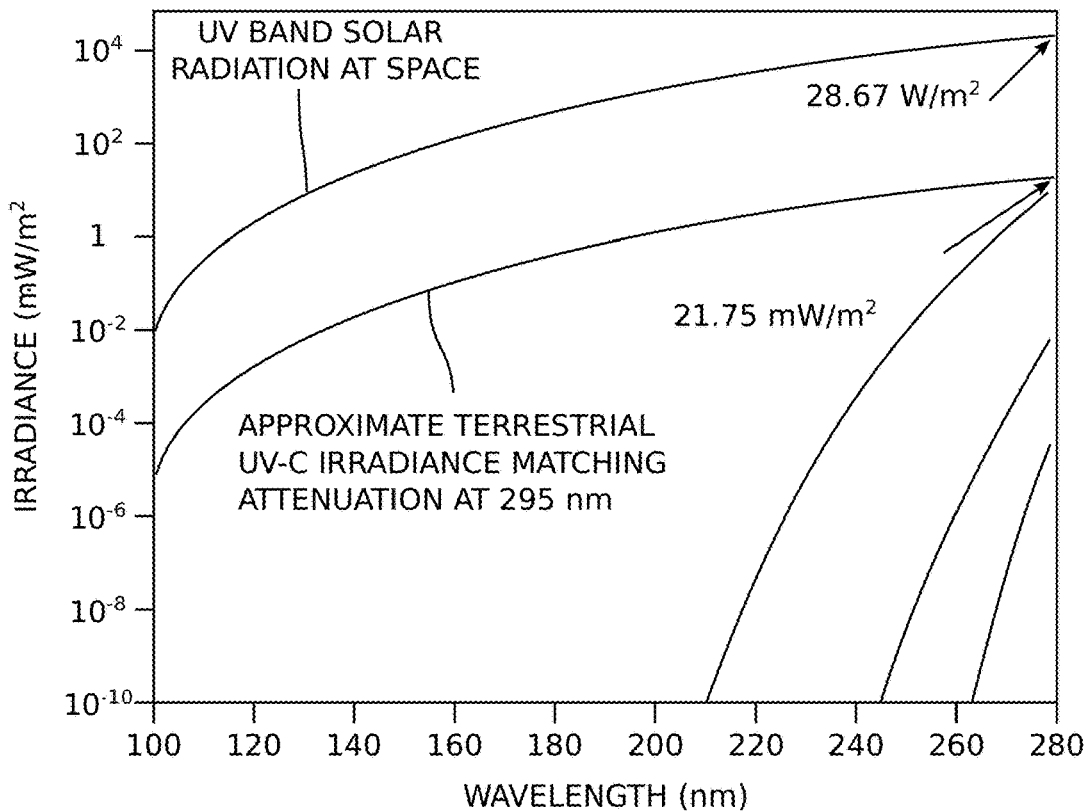

FIG. 107 shows the integral of the calculated solar spectral power density curves which gives irradiance as a function of wavelength between $100 \le \lambda \le 280$ nm UV-C band. Solar irradiance in space above the upper atmosphere along with 3 spectral power density curves is constructed by solving (a,b) Rayleigh scattering and absorption coefficients in (10.11) for pairs of measured data for wavelengths of (325, 305) shown in curve 3, (325, 295) shown in curve 4, and (305, 295) shown in curve 5. Curve 2 is simply generated by relation (10.8).

Figure 108:
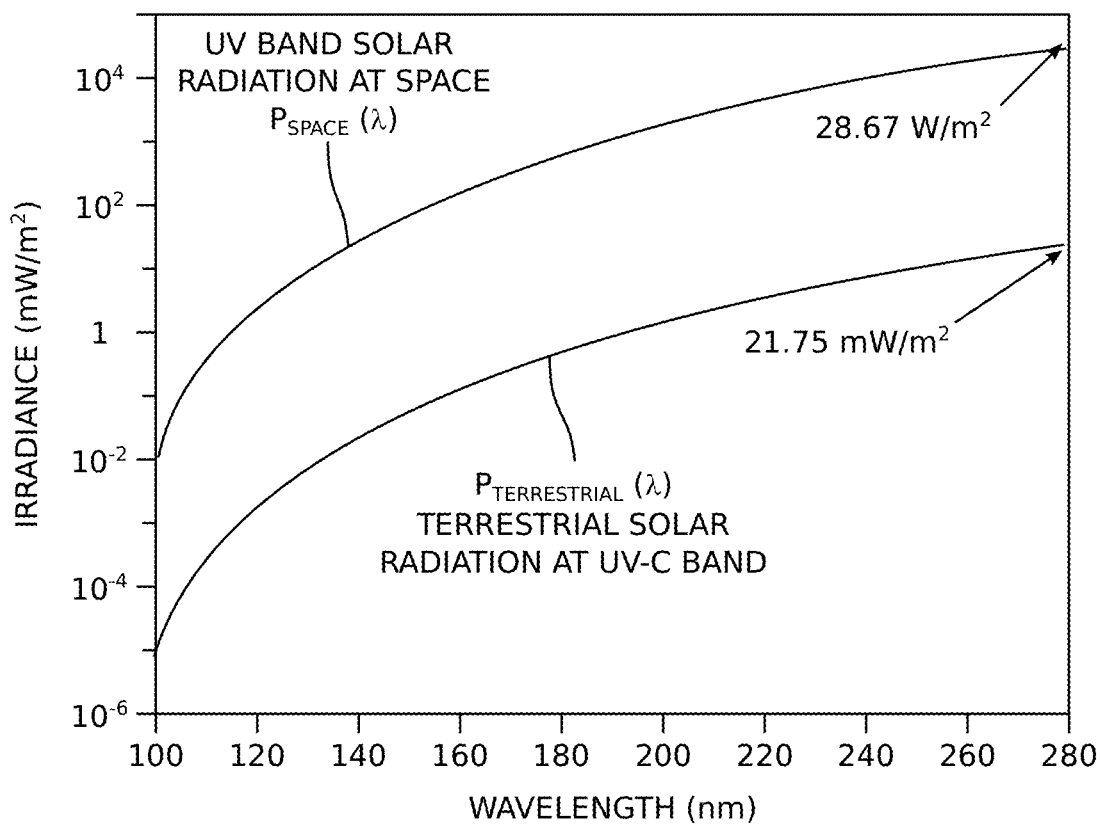

FIG. 108 shows the maximum irradiance as a function of wavelength between $100 \le \lambda \le 280$ nm UV-C band generated by relation 10.8, along with solar irradiance at space above the upper atmosphere.

In conclusion, terrestrial UV-C levels of solar radiation are not an effective means of deactivating the Covid-19 virus. Comparing the irradiation levels calculated earlier such as 60-80 W/m² at 5 cm as shown in FIG. 42 and 400-600 W/m² as shown in FIG. 48 at 1 cm away from the TUV PL-S 13 W/2P UV-C mercury discharge lamps, to the 28 W/m² irradiance values at space and 0.2175 W/m² values at sea level in Equatorial summer, gives a good sense of the UV-C irradiance levels that are used in the UVGI applications as compared to the maximum possible terrestrial solar radiation.

Accurate, Quantitative, and Objective Test Apparatus for the any kind of Face Shield There is a need for an experimental procedure of quantitatively testing the safety of the safe face shield disclosed herein, as well as any other personal device for removing pathogens from the air before they can be put in widespread commercial use. For this safety test, an apparatus is presented to quantitatively test and compare any face shield on the overall inhaled air quality under worst conditions.

Figure 109:
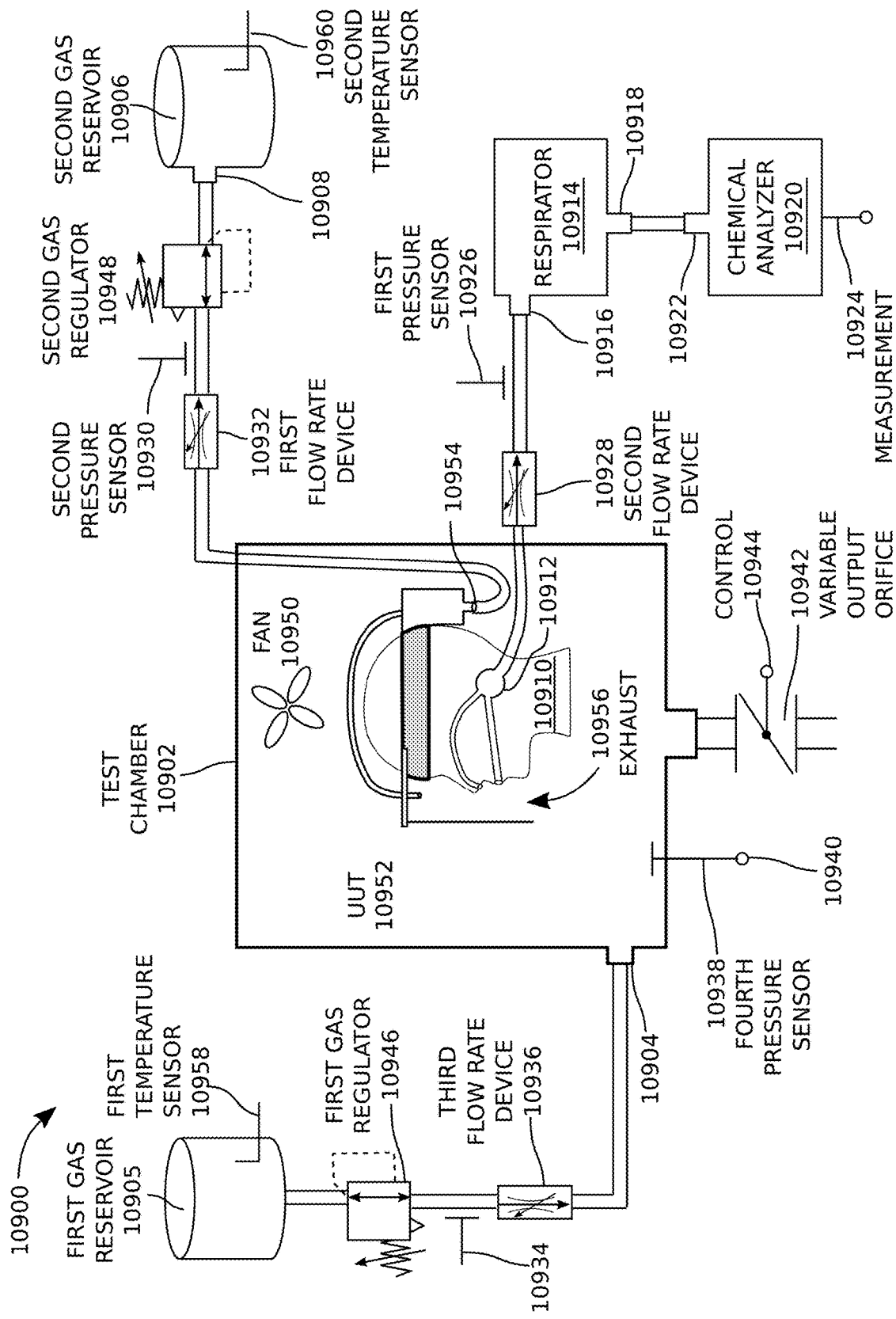

FIG. 109 depicts a personal airflow irradiation testing apparatus. The apparatus 10900 comprises a test chamber 10902 having an input orifice 10904 to accept a first gas (i.e., ambient gas) from first gas reservoir 10905. A reservoir 10906 has an output orifice 10908 to supply a second gas. A mannequin headpiece 10910 is located in the test chamber 10902, comprising an input orifice 10912 to accept a mixed gas comprising the first and second gases. As shown, the mannequin headpiece input orifice 10912 may comprise a mouth orifice and a nasal orifice.

A respirator 10914 has an input 10916 connected to the mannequin headpiece input orifice 10912 to apply an oscillating pressure to the mixed gas, and has an output 10918 to supply the mixed gas. A chemical analyzer 10920 has an input 10922 connected to the respirator output 10918. The chemical analyzer 10920 measures the contents of the mixed gas and has an output on line 10924 to supply a measurement of the first gas content in the mixed gas, as compared to the second gas content. The respirator 10914 creates a periodic selected negative mixed gas pressure, as referenced to a test chamber ambient pressure, followed by a selected positive mixed pressure. The chemical analyzer 10920 supplies measurements of the first and second gas contents in the mixed gas, responsive to the respirator selected periodic mixed gas pressures.

In one aspect, the apparatus 10900 further comprises a first pressure sensor 10926 connected to the respirator input 10916 to measure a respirator input mixed gas pressure. A first flow rate device 10928 is connected to the respirator input 10916 to measure a respirator input mixed gas volumetric flow rate. A second pressure sensor 10930 is connected to the reservoir output 10908 to measure a reservoir output second gas pressure, and a second flow rate device 10932 is connected to the reservoir output 10908 to measure a reservoir output second gas volumetric flow rate. A third pressure sensor 10934 is connected to the test chamber input orifice 10904 to measure a test chamber input first gas pressure, and a third flow rate device 10936 is connected to the test chamber input orifice to measure a test chamber input first gas volumetric flow rate. In one aspect, a fourth pressure sensor 10938 is mounted on an interior surface of the test chamber 10902 having an output on line 10940 to supply a measured test chamber mixed gas pressure. A test chamber variably sized mixed gas output orifice 10942 has a control input on line 10944 to modify its size to maintain a constant first test chamber mixed gas pressure in response to the test chamber mixed gas pressure measurement.

Typically, the third pressure sensor 10934 measures a first test chamber input first gas pressure and the second pressure sensor 10930 measures a reservoir output second gas pressure greater than the first test chamber input first gas pressure. It is also typical that the second flow rate device 10932 measures a first reservoir output second gas volumetric flow rate, while the first flow rate device 10928 measures a respirator input mixed gas volumetric inhale flow rate at negative pressure less than the first reservoir output second gas volumetric flow rate. For example, the first reservoir output second gas volumetric flow rate may be greater than or equal to $4.7 \times 10^{-3}$ m³/sec. In another aspect, the third flow rate device 10936 measures a test chamber input first gas volumetric flow rate of greater than or equal to $14 \times 10^{-3}$ m³/sec.

In one aspect, the apparatus 10900 further comprises a first gas regulator 10946 to supply the first gas at a selected first gas pressure, and the chemical analyzer 10920 supplies measurements of the first and second gas contents in the mixed gas, responsive to the selected first gas pressure. Alternatively or in addition, a second gas regulator 10948 is connected to the reservoir output 10908 to supply the reservoir output second gas at a selected reservoir output second gas pressure, and the chemical analyzer 10920 supplies measurements of the first and second gas contents in the mixed gas, responsive to the selected reservoir output second gas pressure. Alternatively or in addition, the apparatus 10900 further comprises a fan 10950 to create local eddies of the mixed gas in the test chamber in a selected direction and in a selected velocity. The chemical analyzer 10920 supplies a measurement of the first and second gas contents in the respirator output mixed gas, responsive to the direction and velocity of the mixed gas in the test chamber. Further, as noted above, the positive and negative pressures of the respirator 10914 can be selected, and can be combined with adjustments of the above-described variables, and the chemical analyzer 10920 supplies a measurement of the first and second gas contents in the respirator output mixed gas, responsive to the combination of variables. Although not explicitly shown, the various pressure sensors, airflow devices, regulators, and variable orifice may be connected to a controller to record measurements and supply adjustment commands.

A unit under test (UUT) personal airflow irradiation device 10952, such as presented above in FIGS. 95-99 is shown mounted on the mannequin headpiece 10910. The UUT 10952 has a gas input aperture 10954 connected to the reservoir output orifice 10908, at least indirectly, to accept the second gas, and a gas exhaust aperture 10956 exposed to the test chamber. Returning briefly to FIG. 97, the UUT safe shield comprises a face shield forming a cavity overlying the mannequin headpiece input orifice, where the UUT exhaust aperture is formed from a spacing between side edges of the face shield and sides of the mannequin headpiece, and between a face shield bottom edge and a chin of the mannequin headpiece. Optionally, the apparatus 10900 may include a first gas temperature sensor 10958 and a second gas temperature sensor 10960.

As can be seen in FIG. 109, there is a (e.g., stereo-foam or plastic) human mannequin headpiece model with its nose and mouth tied to a respirator mimicking adjustable human inhale and exhale functions. The airways of the headpiece that connect the mouth and are made to scale with human airways and throat/mouth cavity. The gas inhaled by the adjustable respirator is tested for its chemical composition using very accurate chemical analysis apparatus in the accuracy range of parts per million in detecting gas compositions.

The apparatus uses two different gases which can be detected and identified very accurately by the gas detector at the intake of the adjustable respirator. The safe face shield UUT is attached to the headpiece and when it is powered its air intake is fed with a known (second) gas such as $O_2$, $N_2$, $CO_2$, etc. The second gas may be referred to as the intake gas. The whole system is enclosed in a chamber where the first (ambient) gas is supplied, mimicking the environment. Typically, the gasses selected that permit a chemical analysis to be performed with parts per million (PPM) accuracy.

The pressure of the ambient gas can be adjusted along with its flow to measure realistic safe face shield performance. The ambient gas temperature, flow rate, and pressure may be measured as a function of time. Although not explicitly shown, the same measurements may be performed in the face shield cavity, which is the volume between the face and the shield, at the same time. The chemical analysis provides the percentage distribution of the ambient and the intake gas, which objectively and quantitatively gives the effectiveness of the safe face shield. Since the intake and ambient gas molecules are far smaller than any virus, this setup measures the worst possible case.

As an example, assume that the intake gas is 100% $O_2$ and ambient gas is 100% $N_2$. If the chemical analysis of the inhaled gas shows 1% $N_2$ and 99% $O_2$, this result guarantees that the system has a filtration effectiveness better than 99% for any pathogen greater in size than the $O_2$ and $N_2$ molecules.

The recorded percentage of the gas composition of the inhaled gas as a function of time shows the effects of the ambient gas to conditions such as pressure, temperature, direction of the ambient gas flow, as well as the safe face shield operation conditions such as ventilator (fan) speed and intake gas temperature, etc.

Figure 110:
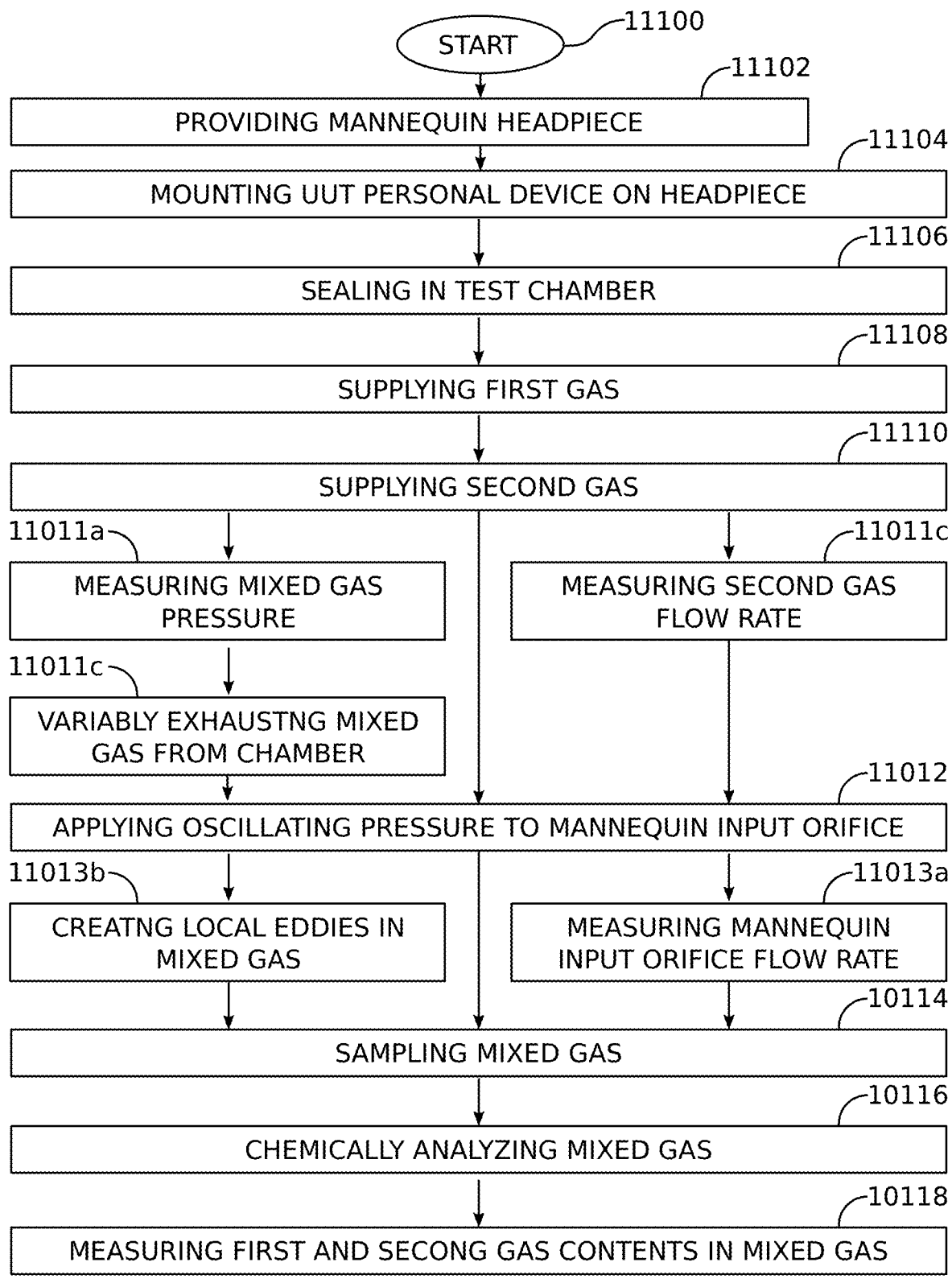

FIG. 110 illustrates a method for testing a personal airflow irradiation apparatus. The method starts at Step 11000. Step 11002 provides a mannequin headpiece having an input orifice. Step 11004 mounts a UUT personal airflow irradiation device on the mannequin headpiece. Step 11006 seals the mannequin headpiece and UUT in a test chamber. Step 11008 supplies a first (ambient) gas to the test chamber. Step 11010 supplies a second gas to a gas input aperture of the UUT. Step 11012 applies an oscillating pressure to the mannequin headpiece input orifice. In response to the oscillating pressure, Step 11014 samples a mixed gas including potential quantities of the first and the second gas. Step 11016 chemically analyzes the contents of the mixed gas. Step 11018 supplies a measurement of the first gas content in the mixed gas, as compared to the second gas content.

In one aspect, Step 11008 supplies the first gas at a variable first gas pressure and Step 11010 supplies the second gas at a variable second gas pressure. Then, Step 11011*a* measures an ambient mixed gas pressure in the test chamber, and Step 11011*b* variably exhausts mixed gas from the test chamber so as to maintain a constant test chamber ambient mixed gas pressure. Typically, the second gas pressure is greater than the first gas pressure.

In another aspect, Step 11011*c* measures a second gas volumetric flow rate, and Step 11013*a* measures a mannequin headpiece input orifice mixed gas volumetric inhale flow rate at negative pressure, less than the second gas volumetric flow rate. Typically, the second gas volumetric flow rate is greater than or equal to $4.7 \times 10^{-3}$ m$^3$/sec, and Step 11009*c* measures a first gas volumetric flow rate of greater than or equal to $14 \times 10^{-3}$ m$^3$/sec.

In one aspect, Step 11012 applies a periodic selected negative mixed gas pressure, as referenced to a test chamber ambient pressure, followed by a selected positive mixed gas pressure. Then, Step 11018 supplies measurements of the first and second gas contents in the mixed gas, responsive to the mannequin headpiece input orifice selected periodic mixed gas pressures.

In another aspect, Step 11010 supplies the second gas at a selected second gas pressure, and Step 11018 supplies measurements of the first and second gas contents in the mixed gas, responsive to the selected second gas pressure. Alternatively or in addition, Step 11008 may supply the first gas at a selected first gas pressure, and Step 11018 supplies measurements of the first and second gas contents in the mixed gas, responsive to the selected first gas pressure. Alternatively or in addition, Step 11013*b* creates local eddies of the mixed gas in the test chamber in a selected direction and in a selected velocity, and Step 11018 supplies measurements of the first and second gas contents in the mixed gas, responsive to the direction and velocity of the mixed gas in the test chamber.

CONCLUSIONS

As a summary this work covers the following,
i) A forced UV-C irradiated air fed face shield for Covid-19 and other pathogen protection,
ii) Mathematical modeling aspects of UV-C irradiation for a given volumetric airflow which meets a given UV-C dose at any UVGI system based on UV-C discharge lamp and/or UV-C LED source,
iii) Design methodology for any given UV-C discharge lamp based UVGI system at a given volumetric airflow which meets a given UV-C dose,
iv) Design methodology for any given UV-C LED based UVGI system at a given volumetric airflow which meets a given UV-C dose,
v) Objective test methodology and apparatus for a safe face shield.
vi) Best case sea level solar UV-C calculations to investigate if solar radiation is an effective means Coronavirus inactivation.

Examples of particular formulas and hardware units have been presented to illustrate the invention. However, the invention is not limited to merely these examples. Other variations and embodiments of the invention will occur to those skilled in the art.

REFERENCES 1. https://en.wikipedia.org/wiki/Ultraviolet_germicidal_irradiation
2. "Design Manual: Municipal Wastewater Disinfection" (https://cfpub.epa.gov/si/si_public_record_Repo rt.cfm?Lab=NRMRL&dirEntryId=49846).
3. UV dose (http://www.americanairandwater.com/uv-definitions/index.htm)
4. "Ultraviolet disinfection guidance manual for the final long term 2 enhanced surface water treatment rule" (http://www.epa.gov/ogwdw000/disinfection/lt2/pdfs/ guide_lt2_uvguidance.pdf) (PDF). Washington, D.C.: United States Environmental Protection Agency. November 2006. Retrieved 30 Jan. 2011.
5. Gadgil, A., 1997, Field-testing UV Disinfection of Drinking Water, Water Engineering Development Center, University of Loughborough, UK: LBNL 40360.
6. "Ultraviolet germicidal irradiation" (https://web.archive.org/web/20160806185506/https://www.liverpool.ac.uk/media/livacuk/radiation/pdf/UV_germicidal.pdf) (PDF). University of Liverpool. p. 3. Archived from the original (https://www.liverpool.ac.uk/media/livacuk/radiation/pdf/UV_germicidal.pdf) (PDF) on 2016 Aug. 6.
7. Nardell, Edward (January-February 2008). "Safety of Upper-Room Ultraviolet Germicidal Air Disinfection for Room Occupants: Results from the Tuberculosis Ultraviolet Shelter Study" (http://www.americanairandwater. com/uv-facts/UV-Safety-Study.pdf) (PDF). UV And People's Health.
8. "Environmental Analysis of Indoor Air Pollution" (http:// www.purifier.org/snapcat/iaq.pdf) (PDF). CaluTech UV Air. Retrieved 2006 Dec. 5.
9. Harm, W., 1980, Biological Effects of Ultraviolet Radiation, International Union of Pure and Applied Biophysics, Biophysics series, Cambridge University Press.
10. "Catskill-Delaware Water Ultraviolet Disinfection Facility" (http://www.nyc.gov/html/dep/html/dep_projects/ cp_ catskill_deleware_uv_plant.shtml).
11. https://en.wikipedia.og/wiki/Ultraviolet_index
12. "Solar and Ultraviolet Radiation", ccbi.nlm.nig.gov/ books/NBK3043
13. "Atmosphere and Ocean", J. B. Kerr and V. E. Fieletov, ISSN 0705-5900 1480-9214, Journal Home page http:/ tandfonline.com/loi/tato.20
14. https://en.wikipedia.org/wiki/Ultraviolet_index
15. AquiSense Technologies, PearlAero UV-C LED Air Treatment.
16. "Ultraviolet Water Purifier", Melvin N. Kosnoff, U.S. Pat. No. 4,184,076, January 1980.
17. "Portable Ultraviolet Water Purifier", Theodor D. Merriam, U.S. Pat. No. 4,755,292, Jul. 5, 1988.
18. "Home Water Purification System with Filter End of Life Monitor", Roy W. Kuennen, Robin M. Dykhouse, Dennis J. Kool, Ronald C. Markham, Bradley J. Pippel, Dennis E. Kid and Merlin G. Tiede, U.S. Pat. No. 5,698,091, Dec. 16, 1997.
19. "UV Water Purification System", Florence Valerie Cossassuce, Itzcoatl Bareno Arce and Oscar Rodrigez Zammudio, U.S. Pat. No. 7,361,904 B2, Apr. 22, 2008
20. Method and Apparatus for Sterilizing and Disinfecting Air and Surfaces and Protecting Zone from External Microbial Contamination", S. Edward Niester, U.S. Pat. No. 9,700,642 B2, Jul. 11, 2017.
21. "Chemical and Biological Protection Mask", Jefery J. Litz, USPTO Publication Number US2010/0132715 A1 Jun. 3, 2010.
22. "Breathing Apparatus with Ultraviolet Light Emitting Diode", Ling Zhu, Fang Hu, USPTO Publication Number US2016/0001108 A1 Jan. 2, 2016.
23. "Photoeradication of Microorganisms with Pulsed Purple or Blue Light", Chukuka S. Enwemeka, John C. Castel, USPTO Publication Number US2020/0222718 A1 Jul. 16, 2020.
21. Porex Electronics and Lighting, Porex LED Reflectors, High Performance Diffuse Reflectors, Data Sheet.
22. Honle Group, RAESCH Quartz GmbH
23. "Method and Apparatus for Controlling Electrical Power Usage Based on exact Sun Elevation Angle and Measured Geographical Location", Osman E. Akcasu, U.S. Pat. No. 9,949,339 B2, Apr. 17, 2018.
24. "Engineering Electromagnetic Fields and Waves," Carl T. A. Johnk, John Willey & Sons, Copyright 1975, ISBN 0-471-44289-5.
25. "Elements of Electromagnetics," Matthew N. O. Sadiku, Oxford University Press, Copyright 2001 Third Edition, 2001, ISBN 0-19-513477-X.
26. "The Feynman Lectures on Physics", Richard P. Feynman, Robert B. Leighton, Matthew L. and Sands, Copyright 1963, 1989 California Institute of Technology, ISBN 0-201-51003-0. Vol. II, pp. 7.9.
27. "Physics of Semiconductor Devices", S. M. Sze, $2^{nd}$ Edition, Copyright 1981, John Willey& Sons, Inc. ISBN 0-471-05661-8.
28. "Wide Energy Bandgap Electronic Devices", Edited by Fan Ren, and John C. Zolper, July 2003, ISBN 978-981-238-246-7.
29. "Mathematical Handbook of Formulas and Tables," Murray R. Spiegel, Schaum's Outline Series, Copyright 1952 by McGraw-Hill, Inc.

30. "Handbook of Mathematical Functions," Edited by Milton Abramowitz and Irene A. Stegun, Dover Publications, Inc., New York, 1972, Library of Congress Catalog Card Number: 65-12253.
31. "Handbook of Chemistry and Physics," 66$^{th}$ Edition, 1985-1986, Copyright Chemical Rubber Publishing Company, ISBN-0-8493-0466-0.
32. Philips TUV TL UV-C "Compact" Mercury UV-C discharge lamp.
33. Philips TUV TL UV-C "Mini" Mercury UV-C discharge lamp.
34. CEL (California Eastern Laboratories) CL7003C2 UV-C Light Emitting Diode Data Sheet.
35. "Radiative Heat Transfer", Michael F. Modest, Second Edition, Academic Press Copyright 2003, 1993 Elsevier Science (USA), ISBN 0-12-503163-7.
36. "A Catalog of Radiation Configuration Factors", Howell, J. R, McGraw-Hill, New York, 1982.
37. "UVGI Design Basics", Kowalski and W. P. Bahnfleth, Heating/Piping/Air Conditioning Transactions, January 2000, pp. 100-110.
38. "An Engineering approach to the Control of *Mycobaterium tuberculosis* and other Airborne Pathogens: A UK Hospital Based Pilot Study", C. B. Beggs, K. G. Kerr, J. K. Donelly, P. A. Sleigh, D. D. Mara, G. Cairns, Transactions of the Royal Society of Tropical Medicine and Hygiene 94, 141-146 (2000).
39. Ultraviolet Germicidial Irradiation Handbook: UVGI for Air and Surface Disinfection", Wladyslaw Kowalski, Springer Science and Business, 2010, ISBN 978-3-642-01998-2, Copyright Springer-Verlag Berlin, Hiedelberg 2009.
40. "Mathematical Modeling of Ultraviolet Germicidial Irradiation for Air Disinfection", W. Kowalski, W. P. Bahnfleth, D. L. Witham, B. F. Severin, T. S. Wittam, Quantitative Microbiology 2, 249-270, 2000, Copyright 2002 Kluwer Academic Publishers.
41. "Mathematical Modeling of UV Disinfection", Wladyslaw J. Kowalski, Ultraviolet Germicidal Irradiation Handbook, 2009, July, 9, pp. 51-72.
42. "Three Approaches to Calculating the Velocity Profile of a Laminar Incompressible Fluid Flow in a Hollow Tube", J. Neipp, A. Hernandez, T. Belendez, J. J. Rodes and A. Belendez, American Journal of Physics, Vol. 71, No: 1 pp. 46-48, 2003.
43. "A Contribution to the Mathematical Theory of Epidemics, I, II, and III", W. O. Kermack and A. G. McKendrick, 1927, 1932, 1933 reprinted at Bulletin of Mathematical Biology 1991.
44. "Fluid Mechanics", L. D. Landau and E. M. Lifshitz, Butterwort-Heinemann, 1995.
45. "Ultraviolet Air and Surface Treatment", Chapter 62, Copyright 2019 ASHRAE (American Society of Heating, Refrigeration and Air-Conditioning Engineers, Inc.
46. Philips 1985 UVGI Catalog and Design Guide, Catalog Number UDC 628.9 Netherlands.
47. O. E. Akcasu, "Convergence Properties of Newton's Method for the Solution of Semiconductor Carrier Transport Equations and Hybrid Solution Techniques for Multidimensional Simulation of VLSI Devices", Solid-State Electron. Vol. 27, pp. 319-328, April 1984.

I claim:

1. A method for designing a radial ultraviolet-C (UV-C) mercury discharge tube airflow irradiator, the method comprising:
    selecting irradiation reactor unit chamber and mercury discharge tube cross-sectional dimensions;
    calculating an irradiation integral ($I_p$)
    determining a deactivation dosage ($D_{kill}$):
    calculating a maximum airflow velocity ($V_{MAX}$) in response to the irradiation integral, cross-sectional dimensions, and deactivation dosage;
    selecting the irradiation reactor unit chamber length (L); and,
    providing a dosage sufficient for deactivation of a COVID-19 pathogen.

2. The method of claim 1 wherein selecting the irradiation reactor unit chamber and mercury discharge tube cross-sectional dimensions includes:
    selecting a mercury discharge tube radius ($R_1$);
    selecting an irradiation reactor unit cylinder interior radius ($R_2$), where the irradiation reactor unit cylinder interior surface is reflective; and, wherein $R_1 \leq r \leq R_2$.

3. The method of claim 2 further comprising:

selecting an irradiation calculation selected from the group consisting of surface irradiation ($I_1$), point irradiation ($I_2$), and view factor ($I_3$); and, wherein calculating the irradiation integral includes calculating the irradiation integral in response to the selected irradiation calculation.

4. The method of claim 3 further comprising:

subsequent to selecting the surface irradiation or point irradiation calculation, selecting the number of discharge tube filaments to be modeled.

5. The method of claim 4 further comprising:

calculating irradiance I(r,z) along a length (L) of the irradiation reactor unit cylinder, where $z_{min} \leq Z \leq z_{max}$;

where $d < z_{max} - z_{min}$; and, where d is the length of the mercury discharge tube.

6. The method of claim 5 wherein calculating I(r,z) includes, for surface irradiance, calculating:

$$I_1(r) = \frac{\sigma}{4\pi} \int_{-a}^{+a} \frac{n \cdot r}{|r|^3} dz$$

where σ is the UV-C mercury discharge tube UV-C radiating power density in watts per meter (W/m);

where a is the UV-C mercury discharge tube half-length (a=d/2); and, where n is a normal vector.

7. The method of claim 5 wherein calculating I(r, z) includes, for point irradiance, calculating:

$$I_2(r) = \frac{\sigma}{4\pi} \int_{-a}^{+a} \frac{1}{|r|^2} dz.$$

where σ is the UV-C mercury discharge tube UV-C radiating power density in (W/m); and, where a is the UV-C mercury discharge tube half-length (a=d/2).

8. The method of claim 3 wherein calculating I(r, z) includes, for view factor, calculating:

$$I_3 = \frac{P_{UV-C}}{2\pi R_1 d} F_S;$$

where $F_S$ is a calculation based upon the view factor model between two coaxial mercury discharge tube cylinders; and, where $P_{UV-C}$ is the total UV-C radiative power.

9. The method of claim 5 wherein calculating the irradiation integral includes calculating as follows:

$$P_I(r) = \int_{z_{min}}^{z_{max}} I(r,z)dz.$$

10. The method of claim 9 further comprising:
calculating a velocity equivalent of the irradiation integral in the form of the deactivation dose as follows:

$$v_{MAX}(r) = \frac{P_I(r)}{D_{KILL}} \text{ for } R_1 \le r \le R_{2MAX}.$$

11. The method of claim 10 further comprising:
calculating the differential air pressure between irradiation reactor unit cylinder input and output as follows:

$$\Delta p = \frac{Q}{[F_1(R_2) - F_1(R_1)] + [F_2(R_2) - F_2(R_1)] + [F_3(R_2) - F_3(R_1)]}$$

where $\Delta p$ is the pressure differential along length L of the irradiation reactor unit cylinder with a mercury discharge tube length of d;
where Q is the volumetric airflow rate;
where $$F_1(r) = \Delta p \cdot C(R_2^2 - R_1^2)\frac{r^2}{2}\left[\ln(r) - \frac{1}{2}\right]$$

$$F_2(r) = \Delta p \cdot C \cdot \ln(R_1)\frac{r^2}{2}\left[\frac{r^2}{2} - R_2^2\right]$$

$$F_3(r) = \Delta p \cdot C \cdot \ln(R_2)\frac{r^2}{2}\left[R_1^2 - \frac{r^2}{2}\right]; \text{ and,}$$

where the multiplier C is;

$$C = \frac{\pi}{2L\mu \cdot \ln\left(\frac{R_2}{R_1}\right)}.$$

12. The method of claim 11 further comprising:
calculating the peak airflow velocity point $r_{MAX}$ and $v(r_{MAX})$ in the airflow velocity as follows:

$$v(r) = -\Delta p \frac{(R_2^2 - R_1^2)\ln(r) + (r^2 - R_2^2)\ln(R_1) + (R_1^2 - r^2)\ln(R_2)}{4L\mu \cdot \ln\left(\frac{R_1}{R_2}\right)}$$

for $$r_{MAX} = \sqrt{\frac{(R_2^2 - R_1^2)}{2\ln\left(\frac{R_2}{R_1}\right)}}.$$

13. The method of claim 12 wherein calculating the maximum airflow velocity (v) includes calculating a necessary condition irradiation integral at $r_{MAX}$ as follows:

$$v_{MAX}(r_{MAX}) = \frac{P_I(r_{MAX})}{D_{KILL}}$$

if $$v_{MAX}(r_{MAX}) = \frac{P_I(r_{MAX})}{D_{KILL}} > v(r_{MAX}).$$

14. The method of claim 13 wherein calculating the maximum airflow velocity ($V_{MAX}$) includes calculating a sufficient condition irradiation integral at $r_{MAX}$ as follows:

$$v_{MAX}(r_{MAX}) > v(r) \text{ for } R_1 \le r \le R_2.$$

15. The method of claim 1 wherein determining the deactivation dosage includes determining a deactivation dosage of at least 8,000 micro-Watt seconds per square centimeter ($\mu W \cdot sec/cm^2$) for a COVID-19 pathogen.

16. The method of claim 1 wherein selecting the irradiation reactor unit chamber length (L) includes selecting L in the range of 10 to 25 percent greater than mercury discharge tube length d.

17. A non-transitory memory device storing a set of processor instructions for designing a radial ultraviolet-C (UV-C) mercury discharge tube airflow irradiator, the instructions comprising:
selecting irradiation reactor unit chamber and mercury discharge tube cross-sectional dimensions;
calculating an irradiation integral ($I_p$)
determining a deactivation dosage ($D_{kill}$):
calculating a maximum airflow velocity ($V_{MAX}$) in response to the irradiation integral, cross-sectional dimensions, and deactivation dosage;
selecting the irradiation reactor unit chamber length (L); and,
providing a dosage sufficient for deactivation of a COVID-19 pathogen.

18. The instructions of claim 17 wherein selecting the irradiation reactor unit chamber and mercury discharge tube cross-sectional dimensions includes:
selecting a mercury discharge tube radius ($R_1$);
selecting an irradiation reactor unit cylinder interior radius ($R_2$), where the irradiation reactor unit cylinder interior surface is reflective; and,
wherein $R_1 \le r \le R_2$.

19. The instructions of claim 18 further comprising:
selecting an irradiation calculation selected from the group consisting of surface irradiation ($I_1$), point irradiation ($I_2$), and view factor ($I_3$); and,
wherein calculating the irradiation integral includes calculating the irradiation integral in response to the selected irradiation calculation.

20. The instructions of claim 19 further comprising:
subsequent to selecting the surface irradiation or point irradiation calculation, selecting the number of discharge tube filaments to be modeled.

21. The instructions of claim 20 further comprising:
calculating irradiance I(r, z) along the length (L) of the irradiation reactor unit cylinder,
where $z_{min} \leq z \leq z_{max}$;
where $d < z_{max} - z_{min}$; and,
where d is the length of the mercury discharge tube.

22. The instructions of claim 21 wherein calculating I(r, z) includes, for surface irradiance, calculating:

$$I_1(r) = \frac{\sigma}{4\pi} \int_{-a}^{+a} \frac{n \cdot r}{|r|^3} dz$$

where σ is the UV-C mercury discharge tube UV-C radiating power density in watts per meter (W/m);
where a is the UV-C mercury discharge tube half-length (a=d/2); and,
where n is a normal vector.

23. The instructions of claim 21 wherein calculating I(r, z) includes, for point irradiance, calculating:

$$I_2(r) = \frac{\sigma}{4\pi} \int_{-a}^{+a} \frac{1}{|r|^2} dz$$

where σ is the UV-C mercury discharge tube UV-C radiating power density in (W/m); and,
where a is the UV-C mercury discharge tube half-length (a=d/2).

24. The instructions of claim 21 wherein calculating I(r, z) includes, for view factor, calculating:

$$I_3 = \frac{P_{UV-C}}{2\pi R_1 d} F_S;$$

where $F_S$ is a calculation based upon the view factor model between two coaxial mercury discharge tube cylinders; and,
where $P_{UV-C}$ is the total UV-C radiative power.

25. The instructions of claim 17 wherein calculating the irradiation integral includes calculating as follows:

$$P_I(r) = \int_{z_{min}}^{z_{max}} I(r, z) dz.$$

26. The instructions of claim 25 further comprising:
calculating a velocity equivalent of the irradiation integral in the form of the deactivation dose as follows:

$$v_{MAX}(r) = \frac{P_I(r)}{D_{KILL}} \text{ for } R_1 \leq r \leq R_{2MAX}.$$

27. The instructions of claim 26 further comprising:
calculating the differential air pressure between irradiation reactor unit cylinder input and output as follows:

$$\Delta p = \frac{Q}{[F_1(R_2) - F_1(R_1)] + [F_2(R_2) - F_2(R_1)] + [F_3(R_2) - F_3(R_1)]}$$

where Δp is the pressure differential along length L of the irradiation reactor unit cylinder with a mercury discharge tube length of d;
where Q is the